United States Patent
Aldhamen et al.

(10) Patent No.: US 11,648,294 B2
(45) Date of Patent: May 16, 2023

(54) COMPOSITIONS OF CRACC FUSIONS AND METHODS FOR MODULATING AN IMMUNE RESPONSE AGAINST CANCERS, INFECTIONS DISEASES AND DISORDERS

(71) Applicants: Yasser A. Aldhamen, East Lansing, MI (US); Andrea Amalfitano, East Lansing, MI (US)

(72) Inventors: Yasser A. Aldhamen, East Lansing, MI (US); Andrea Amalfitano, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 839 days.

(21) Appl. No.: 16/574,397

(22) Filed: Sep. 18, 2019

(65) Prior Publication Data

US 2020/0147171 A1 May 14, 2020

Related U.S. Application Data

(60) Provisional application No. 62/732,975, filed on Sep. 18, 2018.

(51) Int. Cl.
| | | |
|---|---|---|
| *A61K 38/17* | (2006.01) | |
| *C12N 15/86* | (2006.01) | |
| *A61K 45/06* | (2006.01) | |
| *A61P 35/00* | (2006.01) | |

(52) U.S. Cl.
CPC ............ *A61K 38/177* (2013.01); *A61K 45/06* (2013.01); *A61P 35/00* (2018.01); *C12N 15/86* (2013.01); *C12N 2710/10343* (2013.01)

(58) Field of Classification Search
CPC .................................................... A61K 38/177
See application file for complete search history.

(56) References Cited

PUBLICATIONS

Amalfitano et al. (Vaccine 34 (2016) 3109-3118) (Year: 2016).*
Mus musculus SLAM family member 7 (Slamf7), transcript variant 1, mRNA; NCBI Reference Sequence: NM_144539.5. (Year: 2022).*
Appledorn et al. (Gene Therapy (2008) 15, 1606-1617) (Year: 2008).*
Aldhamen et al. (J Immunol 2011; 186:722-732) (Year: 2011).*
Aurisicchio et al. (Expert Opinion on Biological Therapy, 12:8, 1043-1058 [2012]). (Year: 2012).*

* cited by examiner

*Primary Examiner* — Scott Long
(74) *Attorney, Agent, or Firm* — Foley Hoag LLP

(57) ABSTRACT

The present invention relates to compositions and methods for modulating immune responses using at least one CRACC composition comprising an adenoviral vector comprising at least one CRACC fusion. Such CRACC compositions may be combined with a number of other therapeutic agents which target modulating immune responses, as well as, treatments that include immune events.

20 Claims, 38 Drawing Sheets

Specification includes a Sequence Listing.

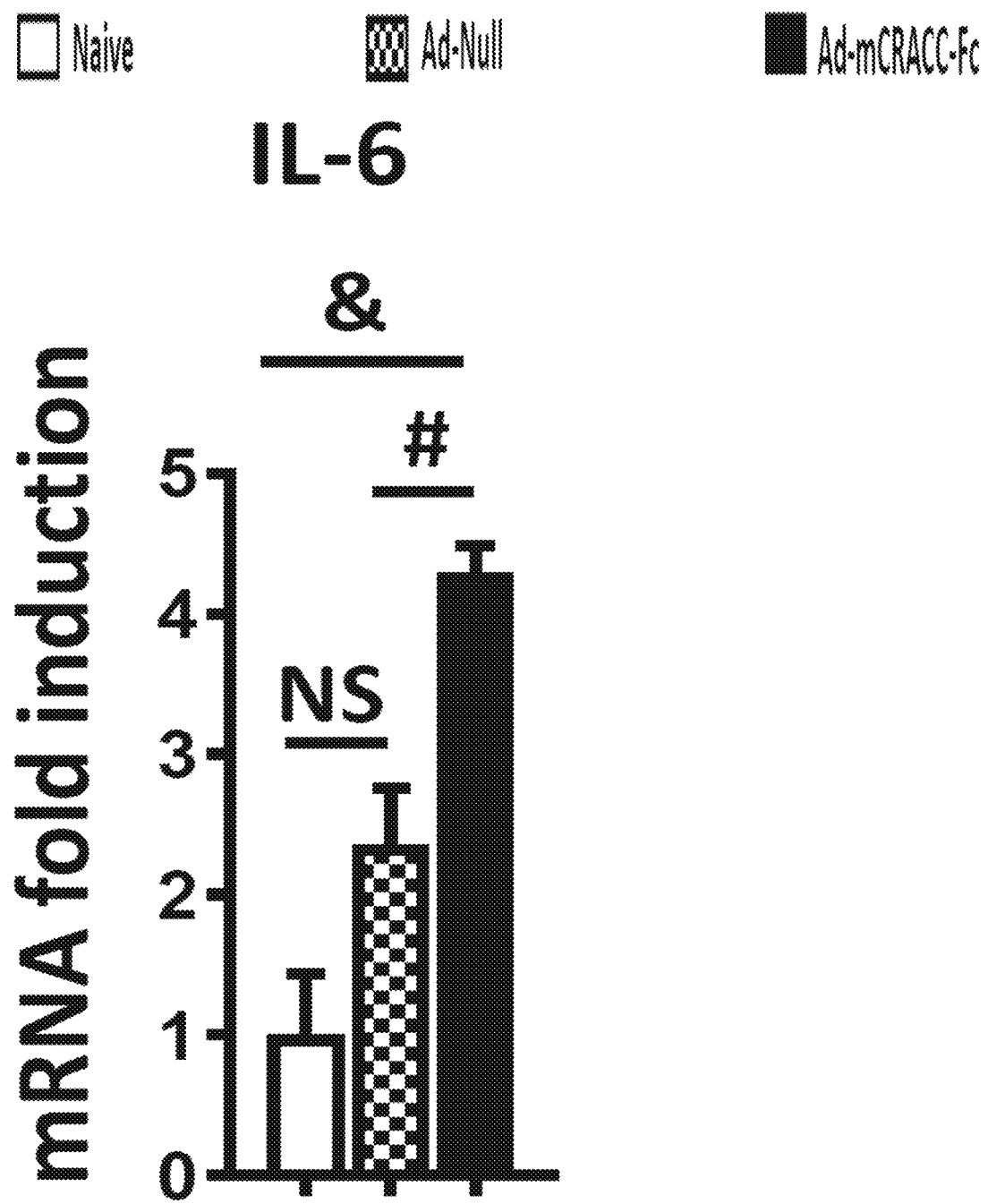

COMPOSITIONS OF CRACC FUSIONS AND METHODS FOR MODULATING AN IMMUNE RESPONSE AGAINST CANCERS, INFECTIONS DISEASES AND DISORDERS

RELATED APPLICATION

This application claims the benefit of priority to U.S. Provisional Patent Application No. 62/732,975, filed Sep. 18, 2018, which is hereby incorporated by reference in its entirety.

GOVERNMENT SUPPORT

This invention was made with government support under AI122808 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jan. 28, 2020, is named MSS-025_01_(31742 02501)_SL.txt and is 61,381 bytes in size.

BACKGROUND

Despite expression of altered oncogenic proteins expressed by tumor cells, which should be recognized by T cell as non-self and thereby induce immune responses, the local tumor immunosuppressive environment can prevent anti-tumor immune activity by inhibition of T cells directly or indirectly via soluble factors or by reduction of co-stimulation signals from antigen presenting cells (APCs) (Adler A J et al. *Curr Cancer Drug Targets* 2007; 7(1):3-14; Gabrilovich D I et al. *Nat Rev Immunol.* 2012; 12(4):253-68; Juneja V R et al. *J Exp Med.* 2017; 214(4):895-904). Immunomodulatory monoclonal antibodies targeting negative T cell receptors, such as CTLA-4 (Hodi F S et al. *N Engl J Med.* 2010; 363(8):711-23), PD-1 (Topalian S L et al. *N Engl J Med.* 2012; 366(26):2443-54), Tim-3 (Anderson A C et al. *Immunity* 2016; 44(5):989-1004), and others, have proven to be effective anti-tumor therapies via blockade of these inhibitory T cell receptors. Furthermore, agonists against co-stimulatory receptors targeting APCs, such as CD134 (OX40) (Weinberg A D et al. *Immunol Rev.* 2011; 244(1):218-31), CD137 (4-1BB) (Ascierto P A et al. *Semin Oncol.* 2010; 37(5):508-16), and CD27 (Roberts D J et al. *J Immunother.* 2010; 33(8):769-79), are promising therapies that will allow for enhanced antigen cross-presentation, T cell activation and increased tumor killing. A combination of multiple immune checkpoint inhibitors has been shown to be superior to using a mono-targeted approach alone (Larkin J et al. *N Engl J Med.* 2015; 373(1):23-34; Moynihan K D et al. *Nat Med.* 2016; 22(12):1402-10; Ryan J M et al. *Cancer Immunol Immunother.* 2018; 67(4):605-13), allowing for a strengthened immune response against tumors and potentially preventing relapse in the future. Therefore, finding additional targets for enhancing anti-tumor responses to use as stand-alone therapies or in combination with others is of interest.

SUMMARY

Numerous embodiments are described herein that can be applied to any aspect of the present invention or embodiment thereof.

One aspect of the invention relates to a method for treating or preventing cancer in a subject in need thereof comprising administering to the subject an effective amount of at least one CRACC composition, said composition comprising a non-naturally occurring vector comprising:

i) a nucleic acid sequence encoding the amino acid sequence of at least one CD2-like receptor activating cytotoxic cell gene (CRACC) fusion, which has at least 50% sequence identity to the amino acid sequence set forth in Table 5;

ii) a nucleic acid sequence of a CRACC fusion, which has at least 50% sequence identity to the nucleotide sequence set forth in Table 6;

iii) a nucleic acid sequence encoding the amino acid sequence of at least one extracellular domain (ECD) of CRACC, which has at least 50% sequence identity to the amino acid set forth in Table 1; said ECD is linked to a nucleic acid sequence encoding the amino acid sequence of at least one Fc constant region or Fc constant domain (Fc), which has 50% sequence identity to the amino acid sequence set forth in Table 3; or iv) a nucleic acid sequence of at least one ECD of CRACC, which has at least 50% sequence identity to the nucleotide sequence set forth in Table 2; said ECD is linked to a nucleic acid sequence of at least one Fc, which has 50% sequence identity to the amino acid sequence set forth in Table 4;

to thereby treat or prevent cancer in the subject.

Another aspect of the invention relates to a method for treating or preventing a pathogenic infection in a subject in need thereof comprising administering to the subject an effective amount of at least one CRACC composition, said composition comprising a non-naturally occurring vector comprising:

i) a nucleic acid sequence encoding the amino acid sequence of at least one CRACC fusion, which has at least 50% sequence identity to the amino acid sequence set forth in Table 5;

ii) a nucleic acid sequence of a CRACC fusion, which has at least 50% sequence identity to the nucleotide sequence set forth in Table 6;

iii) a nucleic acid sequence encoding the amino acid sequence of at least one ECD of CRACC, which has at least 50% sequence identity to the amino acid set forth in Table 1; said ECD is linked to a nucleic acid sequence encoding the amino acid sequence of at least one Fc, which has 50% sequence identity to the amino acid sequence set forth in Table 3; or iv) a nucleic acid sequence of at least one ECD of CRACC, which has at least 50% sequence identity to the nucleotide sequence set forth in Table 2; said ECD is linked to a nucleic acid sequence of at least one Fc, which has 50% sequence identity to the amino acid sequence set forth in Table 4;

to thereby treat or prevent a pathogenic infection in the subject.

Another aspect of the invention relates to a method of modulating an immune response in a subject in need thereof comprising administering to the subject an effective amount of at least one CRACC composition, said composition comprising a non-naturally occurring vector comprising:

i) a nucleic acid sequence encoding the amino acid sequence of at least one CRACC fusion, which has at least 50% sequence identity to the amino acid sequence set forth in Table 5;

ii) a nucleic acid sequence of a CRACC fusion, which has at least 50% sequence identity to the nucleotide sequence set forth in Table 6;

iii) a nucleic acid sequence encoding the amino acid sequence of at least one ECD of CRACC, which has at least 50% sequence identity to the amino acid set forth in Table 1; said ECD is linked to a nucleic acid sequence encoding the amino acid sequence of at least one Fc, which has 50% sequence identity to the amino acid sequence set forth in Table 3; or iv) a nucleic acid sequence of at least one ECD of CRACC, which has at least 50% sequence identity to the nucleotide sequence set forth in Table 2; said ECD is linked to a nucleic acid sequence of at least one Fc, which has 50% sequence identity to the amino acid sequence set forth in Table 4;

to thereby modulate an immune response in the subject.

Another aspect of the invention relates to a method of treating a subject having a condition that would benefit from upregulation of an immune response comprising administering to the subject an effective amount of at least one CRACC composition, said composition comprising a non-naturally occurring vector comprising:

i) a nucleic acid sequence encoding the amino acid sequence of at least one CRACC fusion, which has at least 50% sequence identity to the amino acid sequence set forth in Table 5;

ii) a nucleic acid sequence of a CRACC fusion, which has at least 50% sequence identity to the nucleotide sequence set forth in Table 6;

iii) a nucleic acid sequence encoding the amino acid sequence of at least one ECD of CRACC, which has at least 50% sequence identity to the amino acid set forth in Table 1; said ECD is linked to a nucleic acid sequence encoding the amino acid sequence of at least one Fc, which has 50% sequence identity to the amino acid sequence set forth in Table 3; or iv) a nucleic acid sequence of at least one ECD of CRACC, which has at least 50% sequence identity to the nucleotide sequence set forth in Table 2; said ECD is linked to a nucleic acid sequence of at least one Fc, which has 50% sequence identity to the amino acid sequence set forth in Table 4;

to thereby modulate a CRACC-dependent pathway such that the condition that would benefit from upregulation of an immune response is treated.

In some embodiments, the immune response is induced or enhanced, or stimulated in the mammal.

In some embodiments, any of the aforementioned methods further comprises administering one or more additional compositions or therapies that upregulates an immune response or treats the condition.

In some embodiments, the one or more additional compositions or therapies is selected from the group consisting of anti-viral therapy, immunotherapy, chemotherapy, radiation, and surgery.

In some embodiments, the at least one CRACC fusion set forth in i)-iv) has at least two, three, four, five, six, seven, eight, nine, ten, or more mutations.

In some embodiments, the at least one mutation is a non-naturally occurring mutation.

In some embodiments, the non-naturrally occurring vector is selected from the group consisting of adenovirus, adeno-associated virus (AAV), retrovirus, and lentivirus.

In some embodiments, the non-naturrally occurring vector is a DNA-based vector.

In some embodiments, the non-naturrally occurring vector is an adenoviral vector.

In some embodiments, the non-naturrally occurring vector is a gene-therapy vector.

In some embodiments, the non-naturrally occurring vector is a replication defective adenoviral vector.

In some embodiments, the non-naturrally occurring vector comprises an adenovirus selected from non-human, human adenovirus serotype, or any adenovirus serotype developed as a gene transfer vector.

In some embodiments, the non-human adenovirus comprises an adenovirus selected from chimp, equine, bovine, mouse, chicken, pig, or dog.

In some embodiments, the adenovirus is human adenovirus serotype 5.

In some embodiments, the adenovirus has at least one mutation or deletion in at least one adenoviral gene.

In some embodiments, the adenoviral gene is selected from the group consisting of E1A, E1B, E2A, E2B, E3, E4, L1, L2, L3, L4, and L5.

In some embodiments, the adenovirus has a deletion in E1A, E1B, and E3, or combinations thereof.

In some embodiments, the at least one CRACC fusion is operatively linked to a transcriptional and translational regulatory sequences.

In some embodiments, the at least one CRACC fusion has at least 55%, 60%, 65%, 70%, 75%, 80%, 85%, 90%, or 95% sequence identity to the amino acid or nucleotide sequences set forth in Tables 1-6.

In some embodiments, the CRACC fusion is set forth in SEQ ID NO: 10.

In some embodiments, the CRACC fusion is set forth in SEQ ID NO: 11.

In some embodiments, any of the aforementioned methods further comprises administering in combination at least one therapeutic agent.

In some embodiments, the therapeutic agent is another vaccine, an immunomodulatory drug, a checkpoint inhibitor, or a small molecule inhibitor.

In some embodiments, the checkpoint inhibitor is selected from the group consisting of ant-PD1, anti-CTL4A, anti-VISTA, anti-TIM3, anti-CD47, and anti-LAG3.

In some embodiments, the CRACC composition is a pharmaceutically acceptable composition selected from the group consisting of excipients, diluents, and carriers.

In some embodiments, the pharmaceutical composition comprises the vector at a purity of at least 75%.

In some embodiments, the CRACC composition is an adjuvant.

In some embodiments, any of the aforementioned methods further comprises an antigen.

In some embodiments, the antigen is provide in a second adenoviral vector.

In some embodiments, the antigen is immunogenic.

In some embodiments, the antigen is an extracellular antigen.

In some embodiments, the antigen is a viral-associated antigen, pathogenic-associated antigen, protozoal-associated antigen, bacterial-associated antigen, fungal antigen, or tumor-associated antigen.

In some embodiments, the cancer is selected from the group consisting of acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hypopharyngeal cancer, intraocular melanoma, islet cell tumors (endocrine pancreas), Kaposi sarcoma, Langerhans cell histiocytosis, laryngeal cancer, leukemia, lung cancer, non-small cell lung cancer, small cell lung cancer, Hodgkin lymphoma, lymphoma, medulloblastoma, medulloepithelioma, melanoma, mesothelioma, mouth cancer, multiple myeloma, nasopharyngeal cancer, neuroblastoma, non-Hodgkin lymphoma, oral cancer, oropharyngeal cancer, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm, pleuropulmonary blastoma, primary central nervous system lymphoma, prostate cancer, rectal cancer, renal cell (kidney) cancer, rhabdomyosarcoma, salivary gland cancer, sarcoma, Ewing sarcoma family of tumors, sarcoma, Sezary syndrome, skin cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, the condition that would benefit from upregulation of an immune response is selected from the group consisting septic shock, obesity-related inflammation, Parkinson's Disease, Crohn's Disease, Alzheimer's Disease (AD), cardiovascular disease (CVD), inflammatory bowel disease (IBD), chronic obstructive pulmonary disease, an allergic reaction, an autoimmune disease, blood inflammation, joint inflammation, arthritis, asthma, ulcerative colitis, hepatitis, psoriasis, atopic dermatitis, pemphigus, glomerulonephritis, atherosclerosis, sarcoidosis, rheumatoid arthritis, psoriatic arthritis, ankylosing spondylitis, Wegner's syndrome, Goodpasture's syndrome, giant cell arteritis, polyarteritis nodosa, idiopathic pulmonary fibrosis, acute lung injury, post-influenza pneumonia, SARS, tuberculosis, malaria, sepsis, cerebral malaria, Chagas disease, schistosomiasis, bacteria and viral meningitis, cystic fibrosis, multiple sclerosis, encephalomyelitis, sickle cell anemia, pancreatitis, transplantation, systemic lupus erythematosis, autoimmune diabetes, thyroiditis, and radiation pneumonitis, respiratory inflammation, and pulmonary inflammation.

In some embodiments, the immune response is the innate immune response, adaptive immune response, or humoral immune response.

In some embodiments, the at least one CRACC composition increases or stimulates the secretion of cytokines and chemokines.

In some embodiments, the at least one CRACC composition increases or stimulates an immune response selected from the group consisting of DC maturation, NK cell response, T-cell response, and B-cell response, or combination thereof.

In some embodiments, the subject is a mammal.

In some embodiments, the mammal is an animal model of the condition.

In some embodiments, the mammal is a human.

In some embodiments, the at least one CRACC composition is administered intradermally, intramuscularly, intraperitoneally, intratumorally, peritumoroally, retroorbiatlly, or intravenously via injection.

In some embodiments, the at least one CRACC composition and therapeutic agent is administered concomitantly or conjointly.

In some embodiments, the at least one CRACC composition and therapeutic agent is administered in sequence, one before the other, or one administered subsequent to the other.

In some embodiments, the administration is repeated at least once.

In some embodiments, the effective amount is from about $1\times10^6$ vp to about $5\times10^{11}$ vp.

In some embodiments, the effective amount is from about $1\times10^6$ vp to about $5\times10^9$ vp.

In some embodiments, the effective amount is about $1\times10^6$ vp, about $1\times10^7$ vp, about $1\times10^8$ vp, or about $5\times10^9$ vp.

In some embodiments, the effective amount is about $5\times10^9$ vp.

In some embodiments, the effective amount is about $1\times10^{10}$, about $0.5\times10^{11}$, about $1\times10^{11}$, about $2\times10^{11}$, about $3\times10^{11}$, about $4\times10^{11}$, or about $5\times10^{11}$ viral particles (vp).

In some embodiments, the effective amount is about $2\times10^{11}$ vp.

In some embodiments, the effective amount is about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 125 µg/mL, about 150 µg/mL, about 175 µg/mL, and 200 µg/mL.

In some embodiments, the effective amount is about 100 µg/mL.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE SEQUENCES

```
SEQ ID NO: 1 is an exemplary amino acid sequence for
a full-length, human CRACC polypeptide. (NP_067004.3)
MAGSPTCLTL IYILWQLTGS AASGPVKELV GSVGGAVTFP LKSKVKQVDS

IVWTFNTTPL VTIQPEGGTI IVTQNRNRER VDFPDGGYSL KLSKLKKNDS

GIYYVGIYSS SLQQPSTQEY VLHVYEHLSK PKVTMGLQSN KNGTCVTNLT
```

```
CCMEHGEEDV IYTWKALGQA ANESHNGSIL PISWRWGESD MTFICVARNP

VSRNFSSPIL ARKLCEGAAD DPDSSMVLLC LLLVPLLLSL FVLGLFLWFL

KRERQEEYIE EKKRVDICRE TPNICPHSGE NTEYDTIPHT NRTILKEDPA

NTVYSTVEIP KKMENPHSLL TMPDTPRLFA YENVI

SEQ ID NO: 2 is an exemplary amino acid sequence for the
extracellular domain (ECD) of human CRACC.
SGPVKELVGS VGGAVTFPLK SKVKQVDSIV WTFNTTPLVT IQPEGGTIIV

TQNRNRERVD FPDGGYSLKL SKLKKNDSGI YYVGIYSSSL QQPSTQEYVL

HVYEHLSKPK VTMGLQSNKN GTCVTNLTCC MEHGEEDVIY TWKALGQAAN

ESHNGSILPI SWRWGESDMT FICVARNPVS RNFSSPILAR KLCEGAADDP

DSSMAANESH NGSILPISWR WGESDMTFIC VARNPVSRNF SSPILARKLC

EGAADDPDSS M

SEQ ID NO: 3 is an exemplary amino acid sequence for a
full-length CRACC polypeptide expressed by Rhesus
macaque.
MAGSPTCFTF IYILWQLTGS TASGSVKELV GSIGGAVTFP LKSEVKQVDS

IVWTFNTTTL VTIQPEGGPM IVTQNRNKER VHFPDGGYSL KLSKLKKNDS

GIYNVEIYSS SLQDPFTRKY VLRVYEHLSK PKVTMGLQSN KNGTCVTNLT

CHMEHGEEDV IYTWKALGQA VNESHNGSIL PISWRWGESD MTFICTVRNP

VSSNSSSPIL ARKLCEGAAD DSDSSMVLLC LLLVPLLLSL FVLGLFLWFL

KRETQEESIE EKKRADICRE TPNICPYSGE NTEYDTIPYT NRTIPMEDAA

NTLYSTVEIP KKIENPHSLL TMPDTPRLFA YENVI

SEQ ID NO: 4 is an exemplary amino acid sequence for a
full-length CRACC polypeptide expressed by Chimpanzee.
MAGSPTCLTL IYILWQLTGS AASGPVRELV GSVGGAVTFP LKSKVKQVDS

IVWTFNTTPL VTIQPEGGTI IVTQNRNKER VDFPDGGYSL KLSKLKKNDS

GIYYVGIYSS SLQQPSTQKY VLHVYEHLSK PKVTMGLQSN KNGTCVTNLT

CCMEHGEEDV IYTWKALGQA ANESHNGSIL PISWRWGESD MTFICVARNP

VSSNFSSPIL ARKLCEGAAD DPDSSMVLLC LLLVPLLLSL FVLGLFLWFL

KRERQEESIE EKKRADICRE TPNICPHSGE NTEYDTIPHT NRTILKEDPA

NTVYSTVEIP KKMENPHSLL TMPDTPRLFA YENVI

SEQ ID NO: 5 is an exemplary amino acid sequence for a
full-length, murine CRACC polypeptide.
MARFSTYIIF TSVLCQLTVT AASGTLKKVA GALDGSVTFT LNITEIKVDY

VVWTFNTFFL AMVKKDGVTS QSSNKERIVF PDGLYSMKLS QLKKNDSGAY

RAEIYSTSSQ ASLIQEYVLH VYKHLSRPKV TIDRQSNKNG TCVINLTCST

DQDGENVTYS WKAVGQGDNQ FHDGATLSIA WRSGEKDQAL TCMARNPVSN

SFSTPVFPQK LCEDAATDLT SLRGILYILC FSAVLILFAV LLTIFHTTWI

KKGKGCEEDK KRVDRHQEMP DLCPHLEENA DYDTIPYTEK RRPEEDAPNT

FYSTVQIPKV VKSPSSLPAK PLVPRSLSFE NVI

SEQ ID NO: 6 is an exemplary amino acid sequence for the
extracellular domain of murine CRACC.
SGTLKKVAGA LDGSVTFTLN ITEIKVDYVV WTFNTFFLAM VKKDGVTSQS

SNKERIVFPD GLYSMKLSQL KKNDSGAYRA EIYSTSSQAS LIQEYVLHVY

KHLSRPKVTI DRQSNKNGTC VINLTCSTDQ DGENVTYSWK AVGQGDNQFH

DGATLSIAWR SGEKDQALTC MARNPVSNSF STPVFPQKLC EDAATDLTSL RG
```

SEQ ID NO: 7 is an exemplary amino acid sequence for a full-length, canine CRACC polypeptide. (XP_852458.2)
MLVPPAHFTIFFLLFQLTGPVTSGALKELVGDLGGSVTFPLTLPGIQIDSIVWTFNTT

PLITIQPRTPDRQANVIVTHSHNKKRVDFLHGNYSLKLSKLNKSDSGDYYVVIYSSS

FKEPFSQRYGLRVYEHLSKPKVTMGLQNKENGTCVTNLTCFVDQGGEDVTYSWES

LGQAANKSYNGSILPISWRLGKGGMTFICVARNPISSNSSNPVFAWKLCEGAADDS

ESSVVLYFLGALLFMLTAFTLVPFILFMRRERRKESIEEKKGMDTHQEILNYYPPSG

ETPVYDTISCVNNCIPEENSANTLYFSVQIPPKMEKPHSPPTSPDTPKSFAYENVI

SEQ ID NO: 8 is an exemplary amino acid sequence for a full-length CRACC polypeptide expressed by *bos taurus* (cattle).
MLGAPACFIF LLCQLTGPAA SGIPKKLVGA IGGSVIFPLN LSVNLVDSII

WVFNSTTLVT IQPKTAGKKA LVIVTQKRNL ERVNFPHEGY SLKLSRLKKN

DSGIYRVEIH SSTLQDPLTQ EYELHVYEYL SKPKVVIGLQ ENKNGTCVTN

LTCSMEHGEE DVTYSWKSLD QTTNESHRGS ILPISWRWEK SDMTFICMAS

NPISSNSSNP IFAQNLCEGA AGGQAPYVVL YVLLSFFLLC SLALVLIIFI

IQRERKKEII EEKKELDTHQ KTLPFPPIPE EMPEYDTIST FNGTIPEENP

ANTIYSTVHI APKVTEPYSL PMLSDTPTAS IYNNVM

SEQ ID NO: 9 is an exemplary amino acid sequence for a full-length CRACC polypeptide expressed by rat.
MARFSTHIIF TSVLCQLTVT AASGTPKEVA GALDGSVTFT LNTTEVKVDS

VVWTFKTLFL AIINKNGTIK SQSYEERIVF LDRHSMKLSQ LKKNDSGDYR

AEIHIASNSL SSPFMQEYVL HVHEHLSRPK VNTDSQSSKD GTCILNLTCS

VERGGENVTY SWKAVGQTVD EFHDSANLSI SWRLGEKDKT IICTARNPVS

SSSSTPLLAQ KLCKDAAKDL NSPRVLKYIL CVTLVLVLFC ILLVTILFRW

IPKGKGFEED KKRVDGHQEM SNSCPHLENT DYDTIPYTEK TRPEEDAPNT

LYSTVQIPKV DAGSKSFGAY MMIPHSRMPD TELQGLRLSA RF

SEQ ID NO: 10 is an exemplary amino acid sequence for a fusion protein comprising human CRACC ECD and a human IgG4 Fc constant region.
SGPVKELVGS VGGAVTFPLK SKVKQVDSIV WTFNTTPLVT IQPEGGTIIV

TQNRNRERVD FPDGGYSLKL SKLKKNDSGI YYVGIYSSSL QQPSTQEYVL

HVYEHLSKPK VTMGLQSNKN GTCVTNLTCC MEHGEEDVIY TWKALGQAAN

ESHNGSILPI SWRWGESDMT FICVARNPVS RNFSSPILAR KLCEGAADDP

DSSMESKYGP PCPPCPAPEF EGGPSVFLFP PKPKDTLMIS RTPEVTCVVV

DVSQEDPEVQ FNWYVDGVEV HNAKTKPREE QFNSTYRVVS VLTVLHQDWL

NGKEYKCKVS NKGLPSSIEK TISKAKGQPR EPQVYTLPPS QEEMTKNQVS

LTCLVKGFYP SDIAVEWESN GQPENNYKTT PPVLDSDGSF FLYSRLTVDK

SRWQEGNVFS PSVMHEALHN HYTQKSLSLS LGK

SEQ ID NO: 11 is an exemplary amino acid sequence for a fusion protein comprising murine CRACC ECD and a murine IgG1 Fc constant region.
SGTLKKVAGA LDGSVTFTLN ITEIKVDYVV WTFNTFFLAM VKKDGVTSQS

SNKERIVFPD GLYSMKLSQL KKNDSGAYRA EIYSTSSQAS LIQEYVLHVY

KHLSRPKVTI DRQSNKNGTC VINLTCSTDQ DGENVTYSWK AVGQGDNQFH

DGATLSIAWR SGEKDQALTC MARNPVSNSF STPVFPQKLC EDAATDLTSL

RGGCKPCICT VPEVSSVFIF PPKPKDVLTI TLTPKVTCVV VDISKDDPEV

QFSWFVDDVE VHTAQTQPRE EQFNSTFRSV SELPIMHQDW LNGKEFKCRV

NSAAFPAPIE KTISKTKGRP KAPQVYTIPP PKEQMAKDKV SLTCMITDFF

PEDITVEWQW NGQPAENYKN TQPIMDTDGS YFVYSKLNVQ KSNWEAGNTF

TCSVLHEGLH NHHTEKSLSH SPGK

SEQ ID NO: 12 is an exemplary nucleic acid sequence for a full-length, human CRACC.
atggctggtt ccccaacatg cctcaccctc atctatatcc tttggcagct cacagggtca gcagcctctg gacccgtgaa agagctggtc ggttccgttg gtggggccgt gactttcccc ctgaagtcca agtaaagca agttgactct attgtctgga ccttcaacac aaccccctctt gtcaccatac agccagaagg gggcactatc atagtgaccc aaaatcgtaa tagggagaga gtagacttcc cagatggagg ctactccctg aagctcagca aactgaagaa gaatgactca gggatctact atgtggggat atacagctca tcactccagc agccctccac ccaggagtac gtgctgcatg tctacgagca cctgtcaaag cctaaagtca ccatgggtct gcagagcaat aagaatggca cctgtgtgac caatctgaca tgctgcatgg aacatgggga agaggatgtg atttatacct ggaaggccct ggggcaagca gccaatgagt cccataatgg gtccatcctc cccatctcct ggagatgggg agaaagtgat atgaccttca tctgcgttgc caggaaccct gtcagcagaa acttctcaag ccccatcctt gccaggaagc tctgtgaagg tgctgctgat gacccagatt cctccatggt cctcctgtgt ctcctgttgg tgccctcct gctcagtctc tttgtactgg ggctatttct ttggtttctg aagagagaga gacaagaaga gtacattgaa gagaagaaga gagtggacat ttgtcgggaa actcctaaca tatgccccca ttctggagag aacacagagt acgacacaat ccctcacact aatagaacaa tcctaaagga agatccagca aatacggttt actccactgt ggaaatacccg aaaaagatgg aaaatcccca ctcactgctc acgatgccag acacaccaag gctatttgcc tatgagaatg ttatctag SEQ ID NO: 13 is an exemplary nucleic acid sequence for a full-length, *Rhesus macaque* CRACC.
atggctggtt ccccaacatg cttcaccttc atctatatcc tttggcagct cacagggtca acagcctctg gatccgtgaa agagctggtc ggttccattg gtggggctgt gactttcccc ctgaagtctg aagtaaagca agttgactct attgtctgga ccttcaacac aaccactctt gtcaccatac agccagaagg gggccctatg atagtgaccc aaaatcgtaa taggagaga gtacacttcc cagatggagg ctattccctg aagctcagca aactgaagaa gaatgactca gggatctaca atgtggagat atacagctca tccctccagg atcccttcac ccggaagtat gtgctgcgtg tctacgagca cctgtcaaag cctaaagtca ccatgggtct acagagtaat aagaatggca cctgtgtgac caatctgaca tgccacatgg aacatgggga agaggatgtg atttatacct ggaaggccct ggggcaagca gtcaatgagt cccataatgg gtccatccta cccatctcct ggagatgggg agaaagtgat atgaccttca tctgcactgt caggaaccct gtcagcagca actcctcaag ccccatcctt gccaggaagc tctgtgaagg tgctgctgat gactcagatt cctccatggt cctcctgtgt ctcctgttgg tgccctcct gctcagtctc tttgtactgg ggctatttct ttggtttctg aagagagaga cacaagaaga gtccattgaa gagaagaaga gagcggacat ttgtcgggaa actcctaaca tatgccccta ttctggagag aacacagagt atgacacaat ccttacact aatagaacta tcccaatgga agacgcagca aatacacttt attccactgt ggaaatacca aaaaagattg aaaatcccca ctcactgctc acgatgccag acacaccaag gctatttgcc tatgagaatg ttatctag SEQ ID NO: 14 is an exemplary nucleic acid sequence for a full-length, Chimpanzee CRACC.
atggctggtt ccccaacatg cctcaccctc atctatatcc tttggcagct cacagggtca gcagcctctg gacctgtgag agagctggtc ggttccgttg gtggggccgt gactttcccc ctgaagtcca agtaaagca agttgactct attgtctgga ccttcaacac aaccccctctt gtcaccatac agccggaagg gggcactatc atagtgaccc aaaatcgtaa tagggagaga gtagacttcc cagatggagg ctactccctg aagctcagca aactgaagaa gaatgactca gggatctact atgtggggat atacagctca tcactccagc agccctccac ccagaagtac gtgctgcatg tctacgagca cctgtcaaag cctaaagtca ccatgggtct gcagagcaat aagaatggca cctgtgtgac caatctgaca tgctgcatgg aacatgggga agaggatgtg atttatacct ggaaggccct ggggcaagca gccaacgagt cccataatgg gtccatcctc cccatctcct ggagatgggg agaaagtgat atgaccttca tctgcgttgc caggaaccct gtcagcagca acttctcaag ccccatcctt gccaggaagc

```
tctgtgaagg tgctgctgat gacccagatt cctccatggt cctcctgtgt ctcctgttgg tgccctcct gctcagtctc tttgtactgg ggctatttct ttggtttctg aagagagaga gacaagaaga gtccattgaa gagaagaaga gagcagacat ttgtcgggaa actcctaaca tatgccccca ttctggagag aacacagagt acgacacaat ccctcacact aatagaacaa tcctaaagga agatccagca aatacagttt actccactgt ggaaatacca aaaagatgg aaaatcccca ctcactgctc acgatgccag acacaccaag gctatttgcc tatgagaatg ttatctag
```

SEQ ID NO: 15 is an exemplary nucleic acid sequence for a full-length, murine CRACC.
```
atggctcgtt tctcaacgta catcatcttt acctctgtcc tctgtcagct aacagtcaca gcagcttctg gaactctgaa gaaggtggcc ggtgcccttg atggatctgt gacattcact ctgaatatca ctgaaataaa ggttgactat gttgtatgga cgttcaacac attctttctt gccatggtaa aaaagacgg cgttacatca caagtagta acaaagaaag atagtcttt ccagatggac tctactccat gaagctcagc caattgaaga agaatgactc tggagcctac cgtgcagaga tttacagtac atcgagtcag gcttccttaa tccaggagta tgcgctgcat gtctacaagc atttgtcaag gccaaggtc accatagatc ggcaaagcaa caagaatggc acctgcgtaa tcaatctgac atgttccacg gatcaggacg gggagaatgt aacctacagc tggaaagctg tggggcaggg ggacaatcag tttcatgatg gtgccaccct ctccatcgcc tggagatcag gagagaaaga ccaggcctta acatgcatgg ccaggaatcc agtcagcaac agtttctcaa ccccgtctt tccccagaag ctctgtgaag atgctgccac ggatctaact tcactcaggg gcatcctata catcctgtgc ttctcagcag tgctcatcct atttgctgtc ttgctgacta ttttcatac tatgtggata agaaaggaa aaggatgtga ggaagacaag aagagagtgg acaggcacca ggaaatgccc gacttgtgcc ctcacttaga ggagaacgca gactatgaca caatcccctta cacggaaaaa agaagaccag aagaagatgc accaaacaca tntattcca ctgtgcagat ccccaaagtg gtaagaagct gtccagctga gcatcatctt acttgccaac ccctttccct ggatcatgct cgggctcaga tttcttag
```

SEQ ID NO: 16 is an exemplary nucleic acid sequence for a full-length, canine CRACC.
```
atgcttgttc ccccagcgca cttcaccatt ttctttctcc tcttccagct cacagggcca gtaacctctg gagctctgaa ggagctagtt ggtgaccttg gtgggtctgt gactttccct ctgacgctcc caggaattca gattgacagc attgtctgga ccttcaacac aacccccctc atcaccatac aaccaagaac gccagacaga caagccaatg tcatagtgac ccacagtcat aataagaaaa gggtggattt cctacatgga aactactccc tgaagctcag caaactgaat aagagtgact cgggtgacta ctacgtggtg atatacagct cttccttcaa agagcccttc agccagcggt atgggctgcg tgtctatgag cacctatcaa agcccaaggt taccatgggt ctgcagaaca agagaatgg cacctgtgtg actaatttga cctgcttcgt ggaccaggga ggagaggatg tgacctacag ctgggagtcc ctggggcagg cagccaataa gtcctataat ggctccatcc tccccatatc ctggaggctg gggaaagggg gcatgacctt catctgcgtg gccaggaacc ccatcagcag caattcttca aatcctgtct ttgcctggaa gctctgtgaa ggtgctgctg atgactccga atcctccgtg gtcctgtact tcctggggc gttgctcttc atgctcactg cctttaccct ggtgccattt attctgttta tgcggagaga agaagaaaaa gagtccattg aagagaagaa gggaatggat actcatcagg aaattcttaa ctactatccc ccttctggag agaccccagt gtatgacaca atcagttgtg ttaataactg tattccagaa gaaaattctg caaatacact ttattctct gtgcaaatac ccccaaagat ggagaaaccc cactctcccc ccacatcacc agacacacca aagtcatttg cctatgagaa cgtcatctaa
```

SEQ ID NO: 17 is an exemplary amino acid sequence for a full-length, bos taurus (cattle) CRACC.
```
atgcttggtg ccccagcatg cttcatcttt ctcctctgcc agctcacagg gccagcagcc tctggaatcc caagaagct ggttggtgcc attggtgggt ctgtgatttt ccctctgaat ctctcagtaa atctagttga cagcattatc tgggtcttca attcaaccac tctcgttacc atacagccaa aaacagcagg caaaaaagcc cttgtcatag tgacccaaaa gcgtaacttg gaaagagtga attcccaca tgaaggctac tccctgaagc tcagcagact gaagaagaac gactcaggta tctaccgtgt ggagatacac agctcaaccc tccaggatcc cctcacccag gagtatgagc tgcatgtcta tgagtacctg tcaaagccca aagtcgtcat aggtctgcag gagaataaga atggcacctg tgtaaccaat ctcacatgtt ccatggaaca tggagaagag gatgtaactt acagctggaa gtctctggac cagacaacca atgaatccca caggggctcc attctcccca tatcctggag gtgggagaaa agtgacatga ccttcatctg catggccagt aaccccatca gcagcaactc ctcaaaccct atctttgccc
```

-continued

```
agaatctctg tgaaggtgct gctgggggcc aggctcccta cgtggtcctc tacgtcctgt tgtcgttctt cctgctctgt tccctcgcac tggtgttaat tatttttatc atacaaagag aaagaaaaaa agagatcatt gaagagaaga aggaactgga cactcatcag aaaactcttc ccttccctcc cattcctgaa gagatgcccg agtatgatac aatctctact tttaatggca ctattccaga ggaaaaccca gccaatacca tctattccac tgtgcacata gccccaaagg taacagaacc ctactccctg cccatgttgt cagatacacc aacggcatct atctataaca atgtcatgta a
```

SEQ ID NO: 18 is an exemplary amino acid sequence for a full-length, rat CRACC.
```
atggctcgtt tctcgacaca catcatcttt acctctgtcc tctgccagct aacagtcaca gcagcttctg gaacgccaaa ggaggtggcc ggtgcccttg atggatctgt gacattcact ctgaatacta ctgaagtaaa agttgacagt gttgtatgga ccttcaagac actctttctt gccataataa ataaaaatgg taccatcaaa tcacaaagtt atgaagaaag gatagtcttt ttagatagac actccatgaa gctcagccag ctgaagaaga atgactctgg agactaccgt gcagagattc acattgcgtc aaattcactt tcatctccct tcatgcagga gtacgtgctg catgtccatg agcacctgtc aaggcccaag gtcaacacag attcgcaaag cagcaaggac ggcacctgca tcttaaatct gacatgttcc gtggaacggg gaggagagaa tgtgacatac agctggaaag ctgtgggaca gacagtcgat gagtttcatg acagtgccaa cctctccatc tcctggagac tgggagagaa agacaagacc ataatctgca cagccaggaa tccagtcagc agcagttcct caacccact cctcgcccag aagctctgta aagatgctgc caaggaccta aattcaccca gggtcctcaa atacattctg tgcgtcacac tagtgctcgt cctgttctgt atcctgctgg tgactattct ttttaggtgg ataccgaaag gaaaaggctt tgaggaagac aagaagagag tggacggcca ccaggaaatg tccaactctt gccctcactt ggagaacaca gactatgaca caatccctta cacagaaaaa acgagaccag aagaagatgc gccaaacaca ctttattcca ctgtgcagat ccccaaagtg gatgcagggt ccaaatcctt tggagcttac atgatgatac cacatagcag gatgccagat acggagcttc aaggcttacg tctctctgcc aggttctga
```

Other sequences of interest are set forth in Tables 1-6.

Figure 3B:
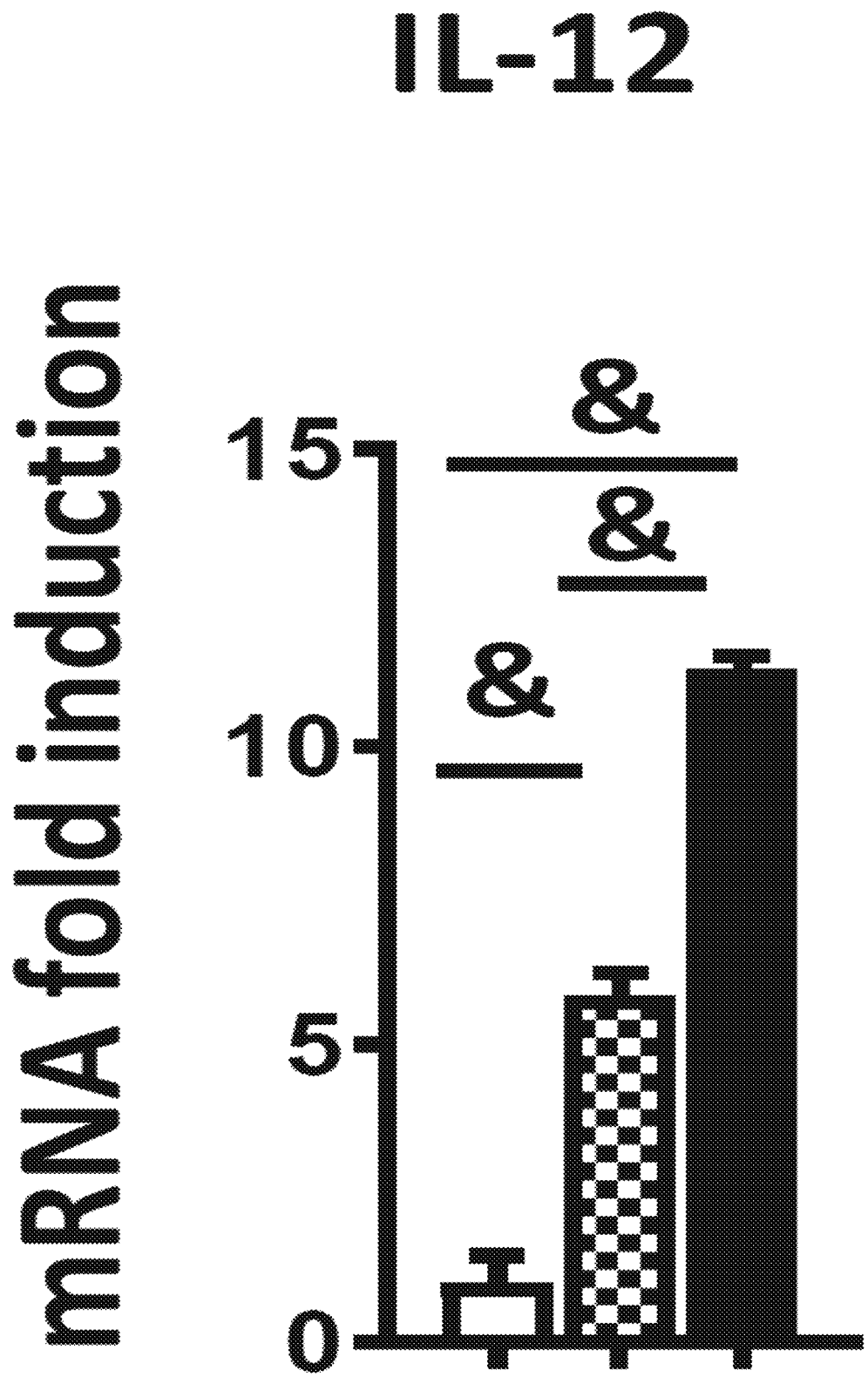
FIG. 3, contains thirteen panels, FIG. 3A-FIG. 3M, depicting cytokine and chemokine responses in Ad-mCRACC treated mice. 6 weeks old Balb/c male mice were injected $10^{10}$ v.p./mouse I.V. (n=6). 6 hours post injection spleens were collected and flesh frozen in liquid nitrogen and stored at −80° C. RNA from spleens was extracted using Trizol reagent. mRNA expression was normalized against GAPDH and expressed as fold over naïve samples. Graphs depicting mRNA fold induction of IL-6 (FIG. 3A), IL-12 (FIG. 3B), IP-10 (FIG. 3C), GM-CSF (FIG. 3D), Socsl (FIG. 3E), IRF7 (FIG. 3F), IRF9 (FIG. 3G).
Figure 3C:
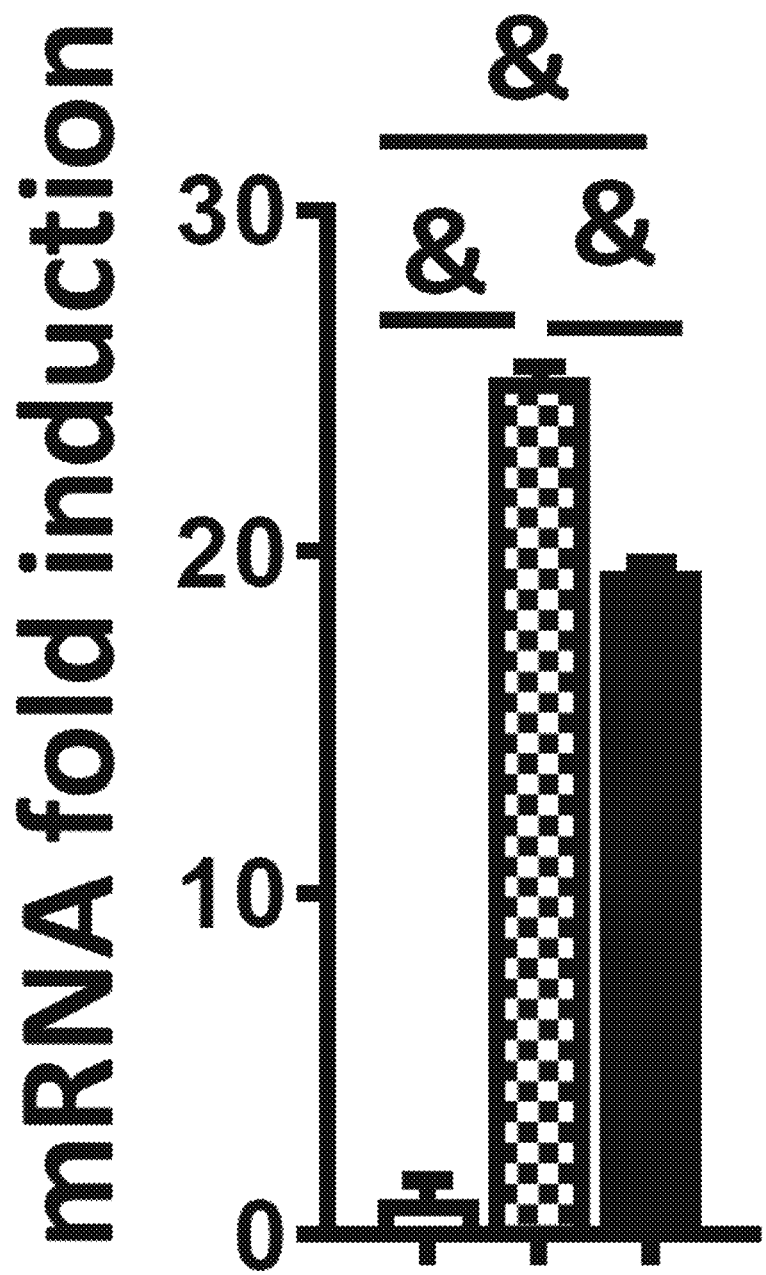
Figure 3D:
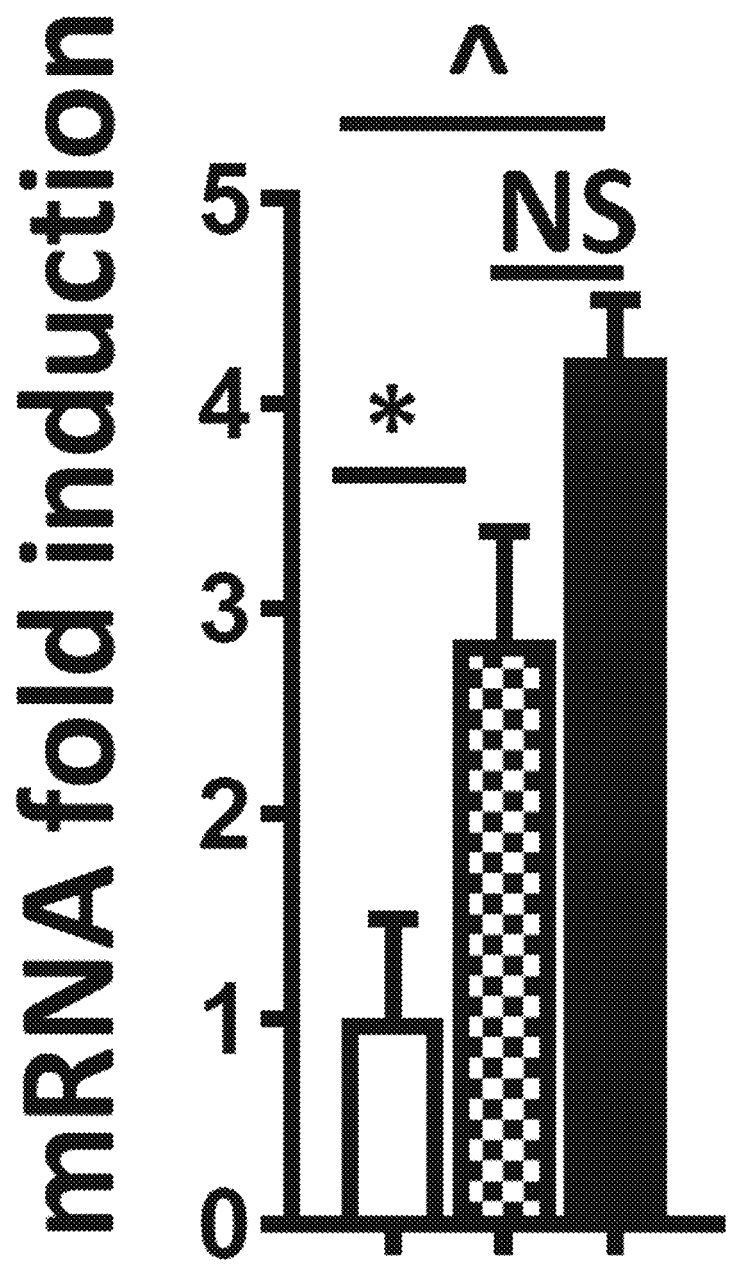
Figure 3E:
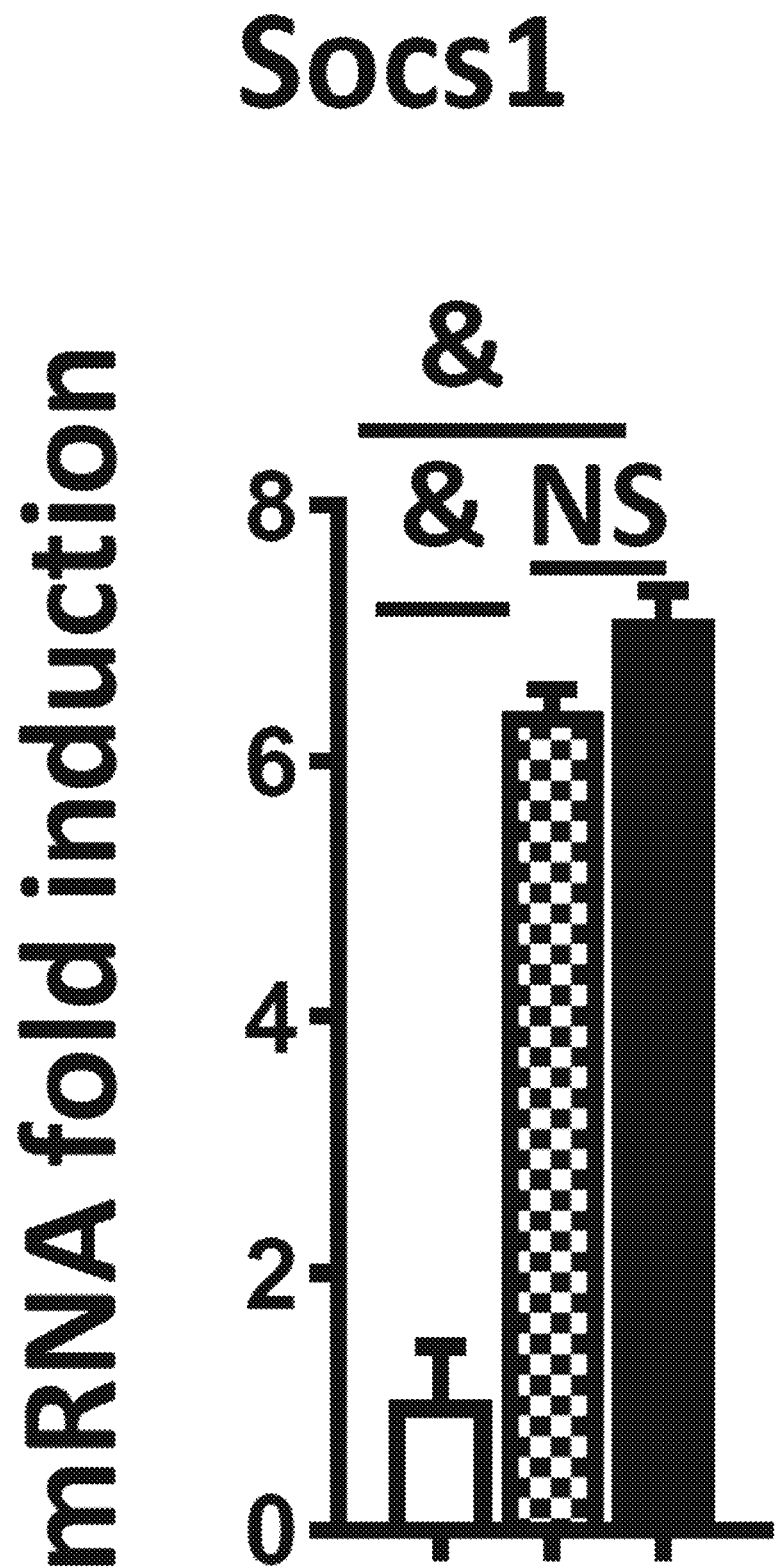
Figure 3F:
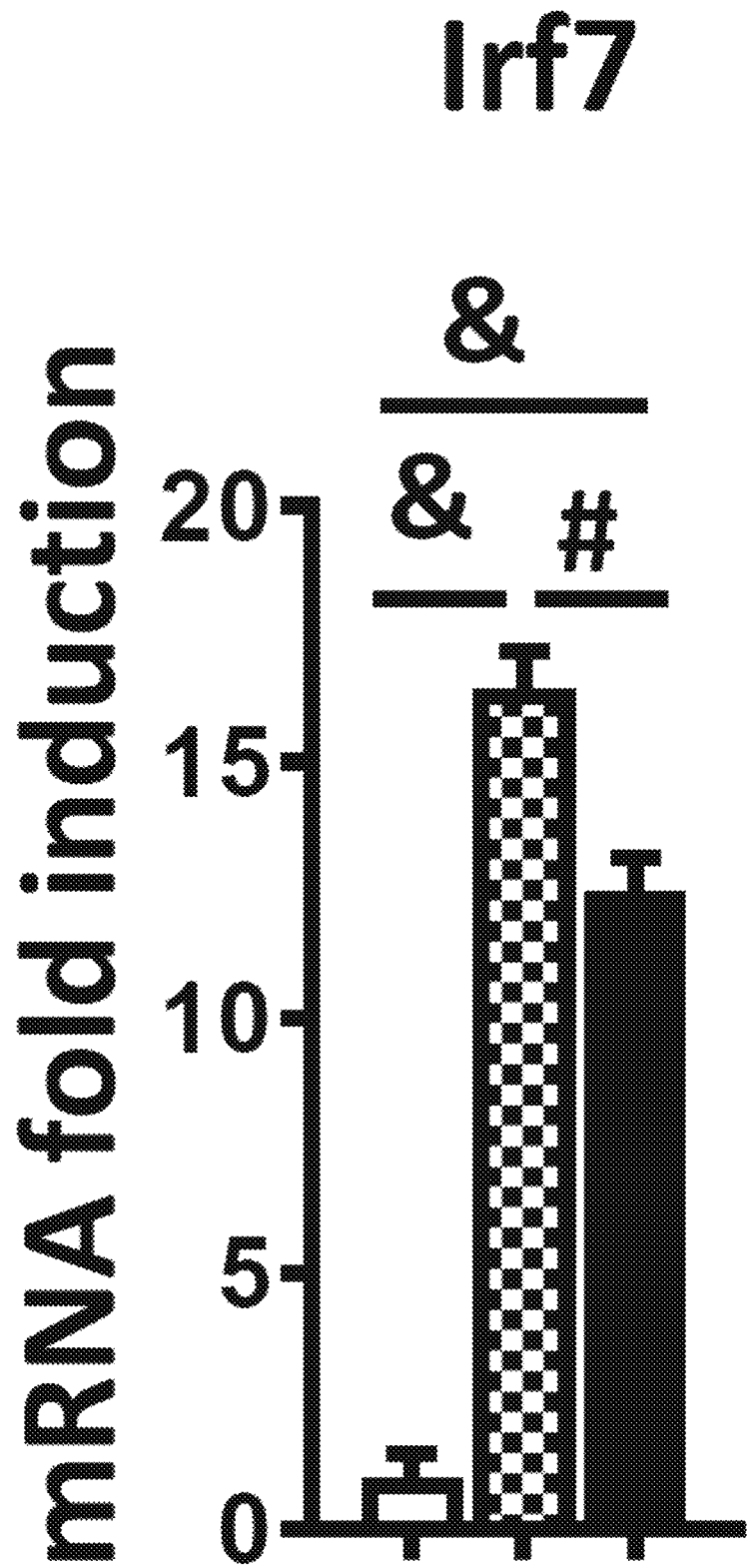
Figure 3G:
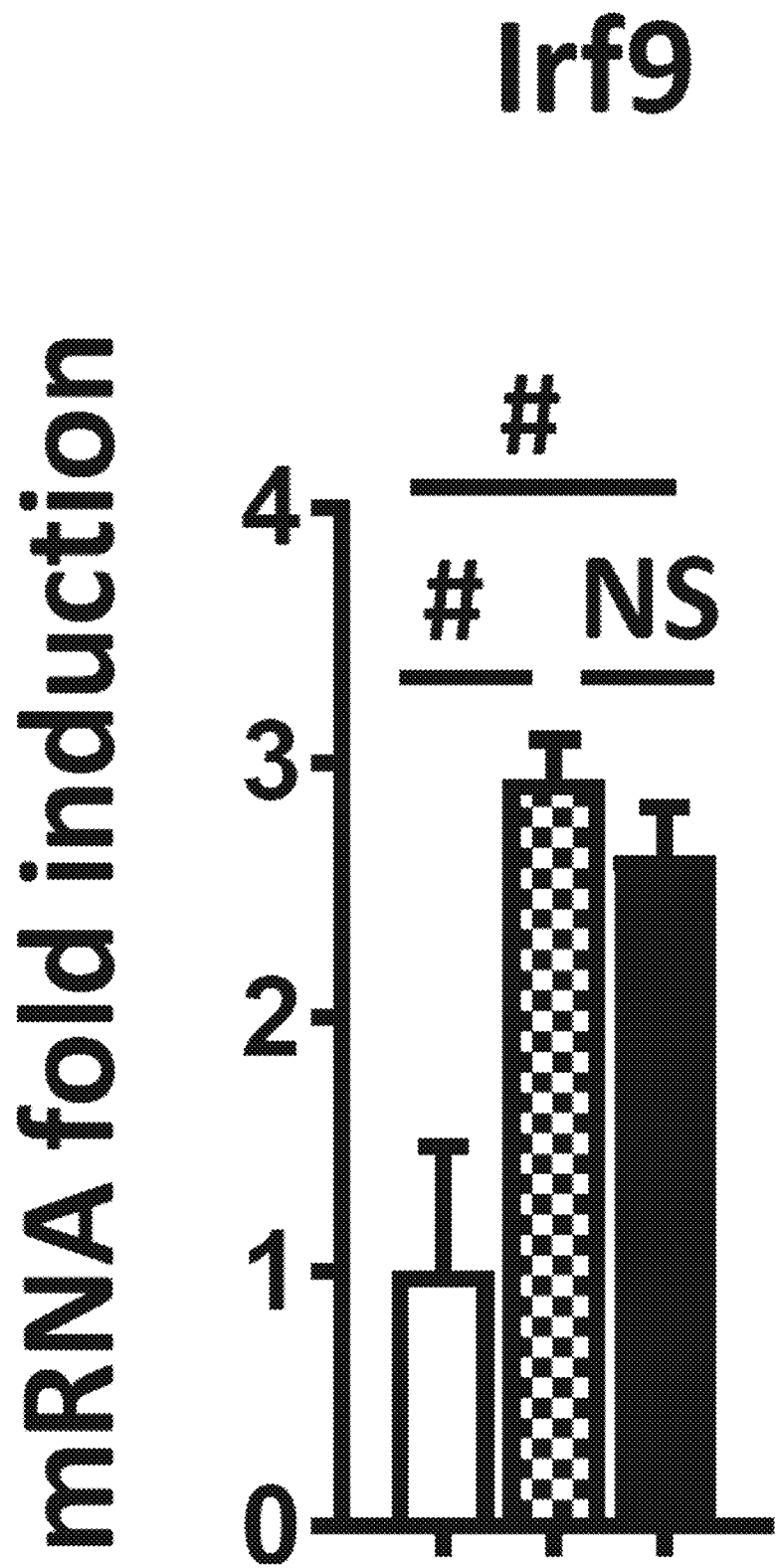
Figure 3H:
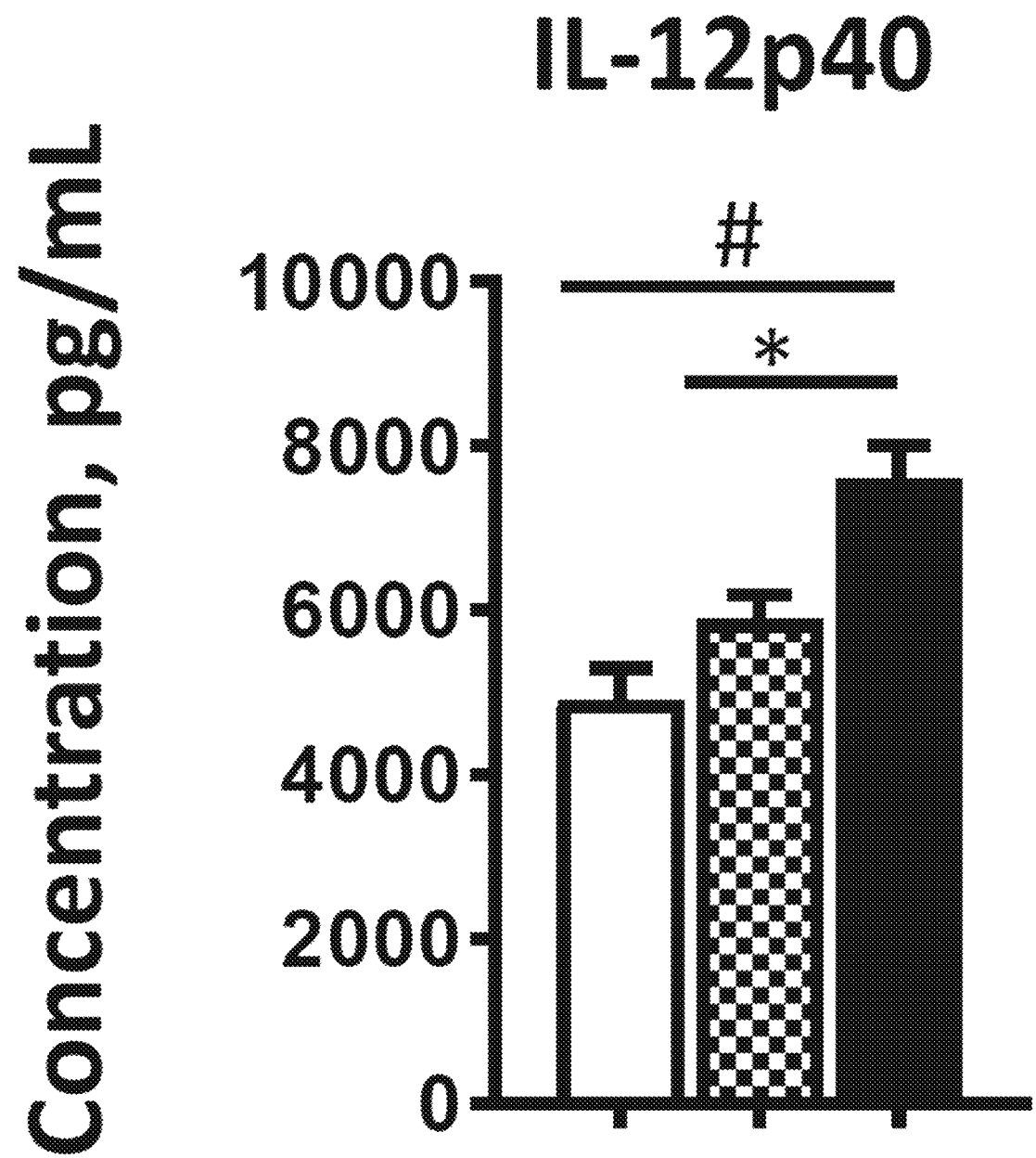
Figure 3I:
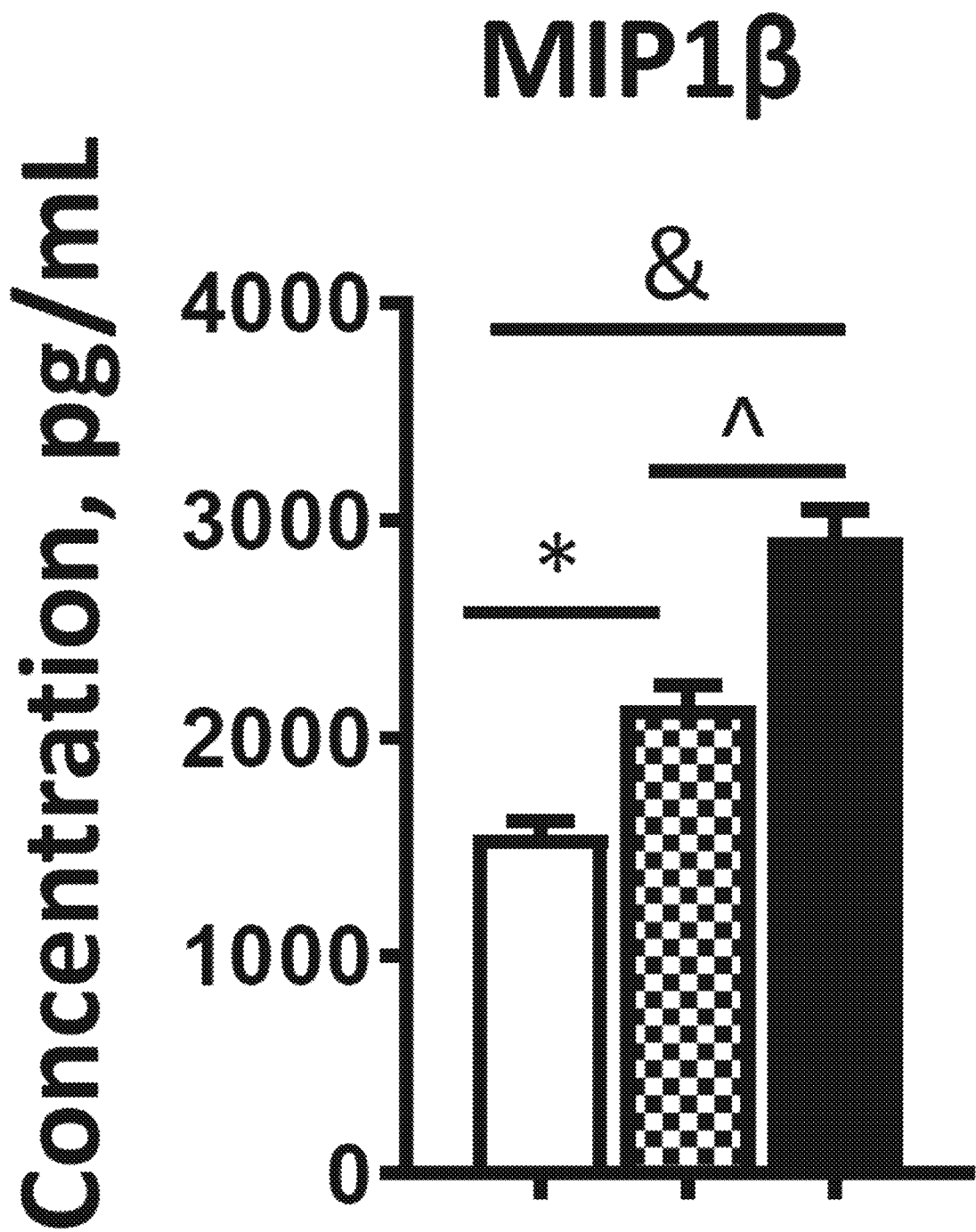
Figure 3J:
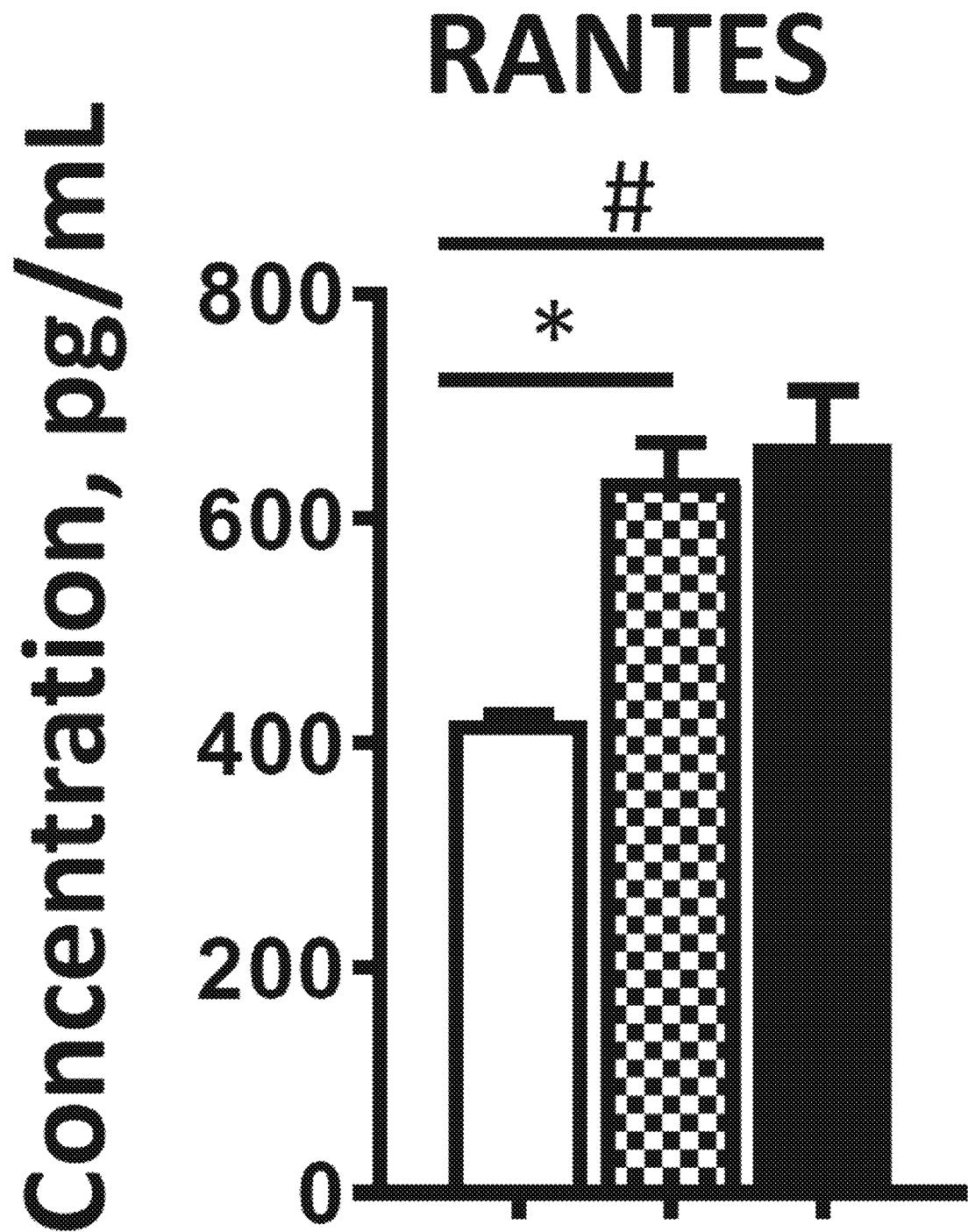
Figure 3K:
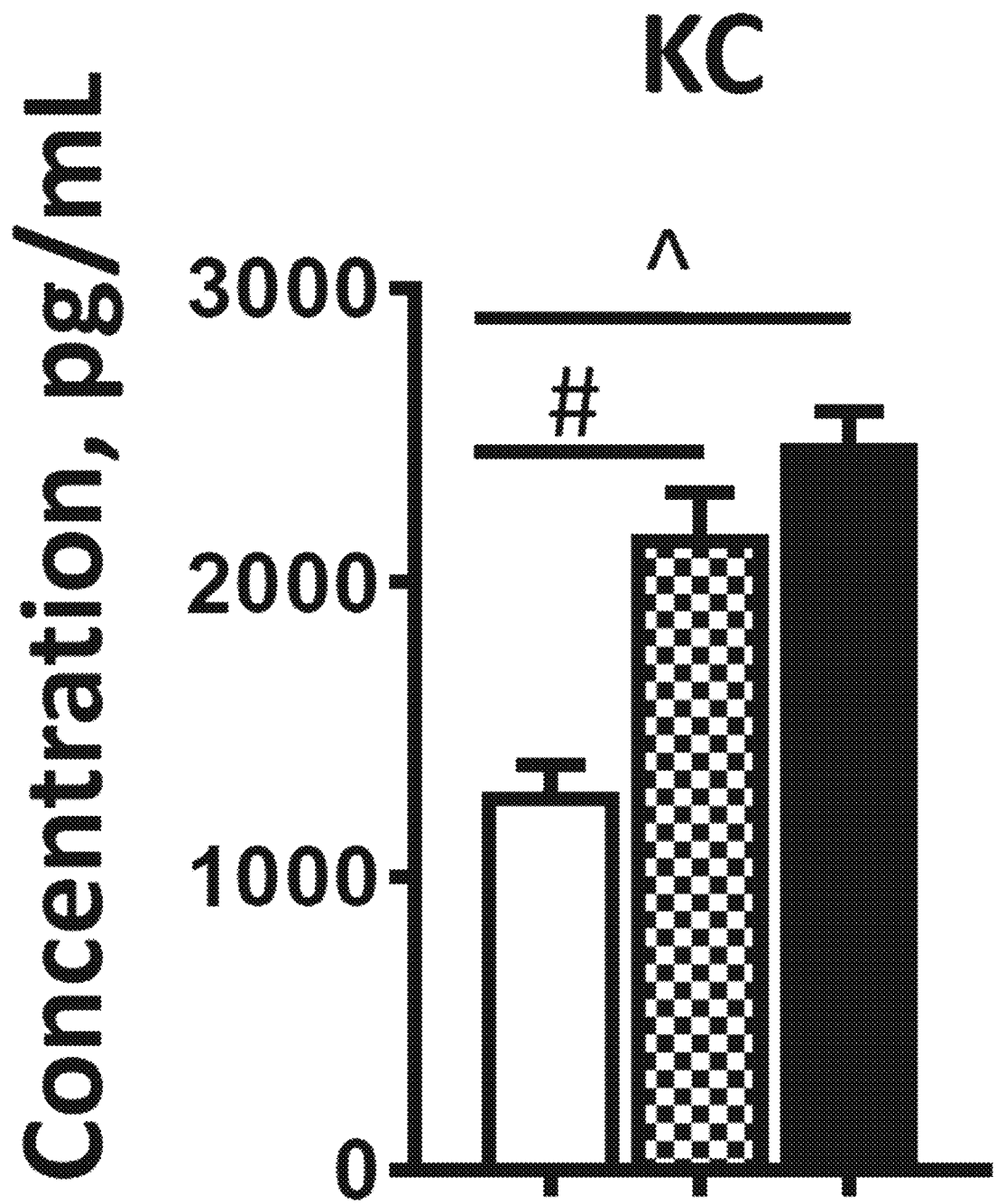
Figure 3L:
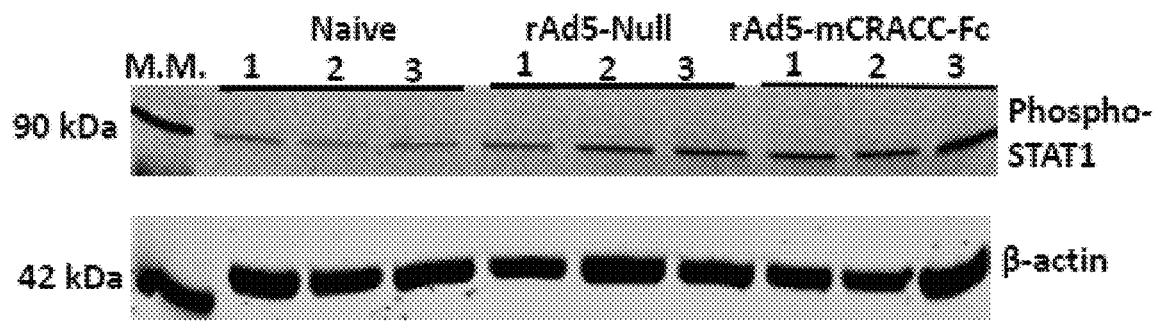
Figure 3M:
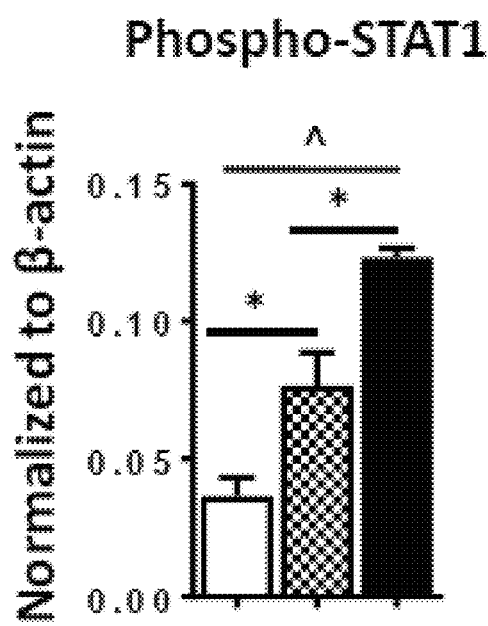

6 weeks old Balb/c male mice (n=6) were injected I.V, with $10^{10}$ v.p. of Ad-null or Ad-mCRACC-Fc. 10 hours post injection, plasma was collected and was analyzed using 27-plex assay on Luminex 100. Graphed concentrations of IL-12p40 (FIG. 3H), MIP1b (FIG. 3I), RANTES (FIG. 3J) and KC (FIG. 3K). Flash Frozen spleens were homogenized for protein analysis 6 hours post injections as described in methods. Images of Western Blots representing phosphorylated STAT-1 and β-actin are depicted in (FIG. 3L) and graphed in (FIG. 3M). Statistical analysis was performed using One-way ANOVA with Tukey's post hoc test, where *—$p<0.05$, #—$p<0.01$, ^—$p<0.001$, & —$p<0.0001$, and NS—not significant.

Figure 4A:
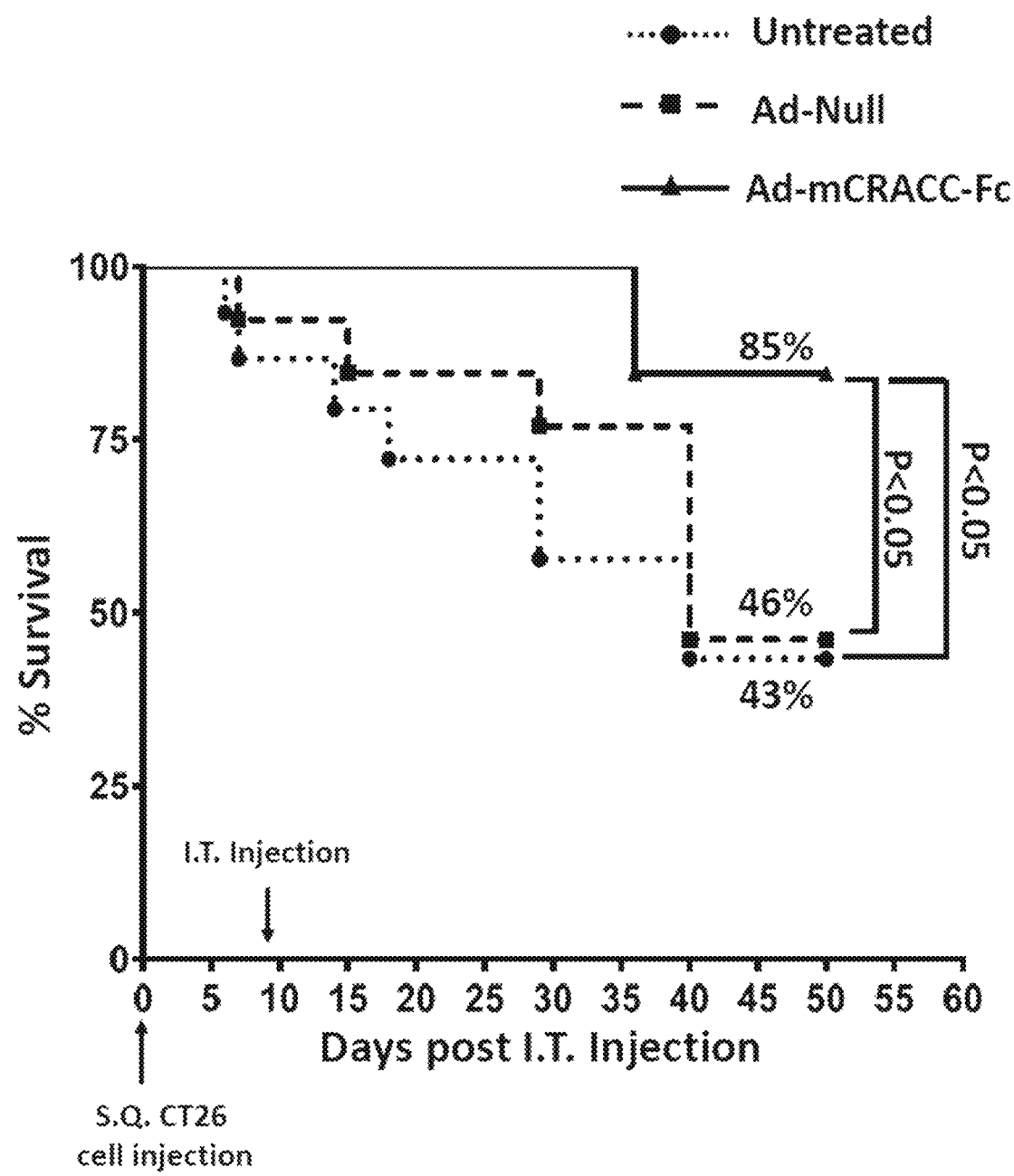
Figure 4B:
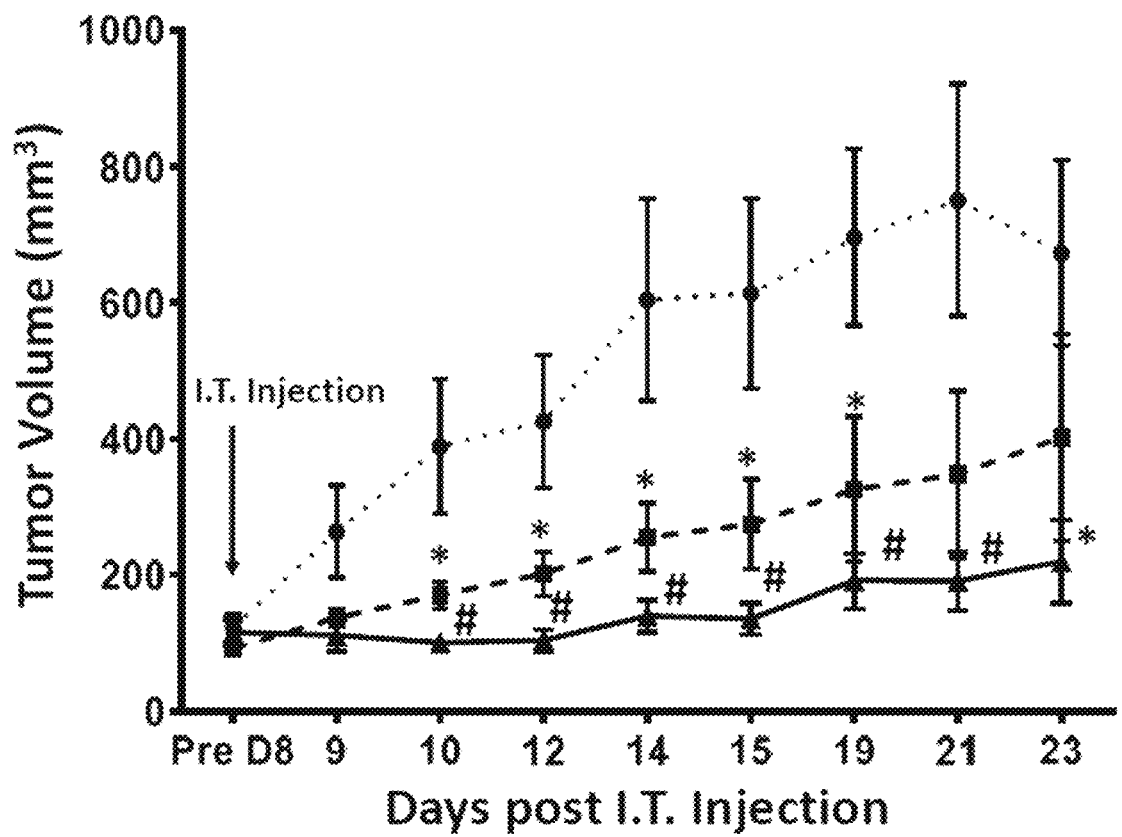
Figure 4C:
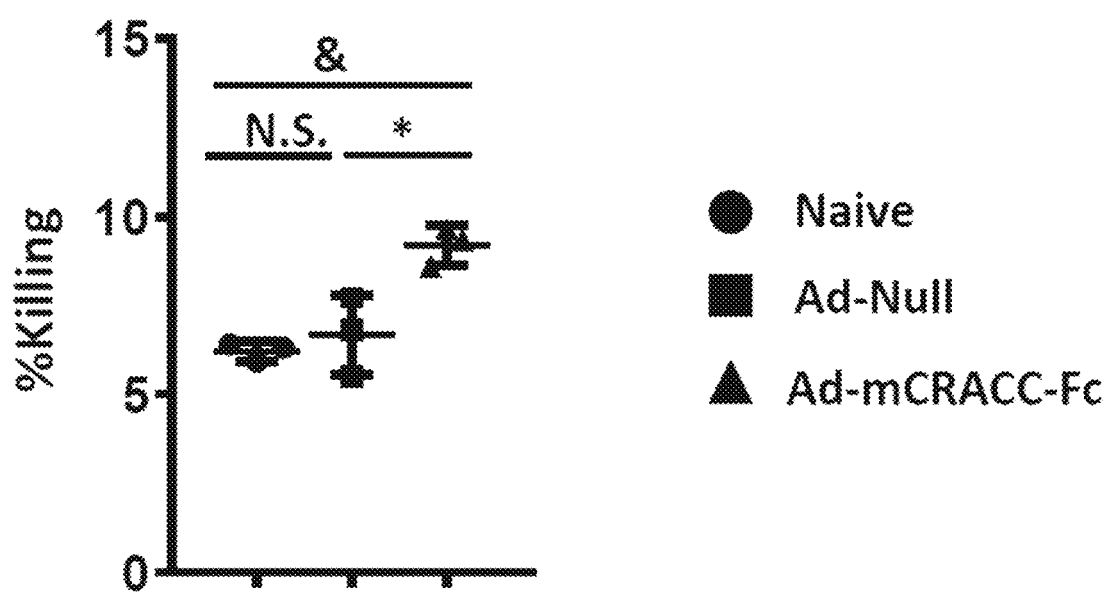

FIG. 4, contains three panels, FIG. 4A-FIG. 4C, depicting the effect of Ad-mCRACC-Fc intratumoral injections on anti-tumor responses. 6 weeks old Balb/c male mice were injected S.Q, with 150,000 CT26 cells. 8 days later, mice were split into 3 groups: injected I.T, with $10^{10}$ v.p. of Ad-Null (n=14), Ad-mCRACC-Fc (n=14), or not injected (n=15). Mice were monitored every 2-3 days starting 5 days post tumor challenge. Tumor volume of 2,000 mm³ was used as the humane end point. FIG. 4A shows graphed percent survival. Statistical analysis was performed using Log-ranked (Mantel-Cox) test. FIG. 4B shows a graph representing tumor volumes over time. Statistical analysis was performed using One-way ANOVA with Tukey's post hoc test. FIG. 4C depicts a killing assay using splenocytes from previously CT26 challenged mice who went into remission was set up as described in methods. Percent killing of CFSE-CT26 cells by splenocytes from naïve, Ad-Null or Ad-mCRACC-Fc treated mice during tumor challenge in presence of Ad-mCRACC virus. Graphs represent mean+/−SEM, where *—$p<0.05$, #—$p<0.01$, ^—$p<0.001$ and & —$p<0.0001$, and NS—not significant.

Figure 5A:
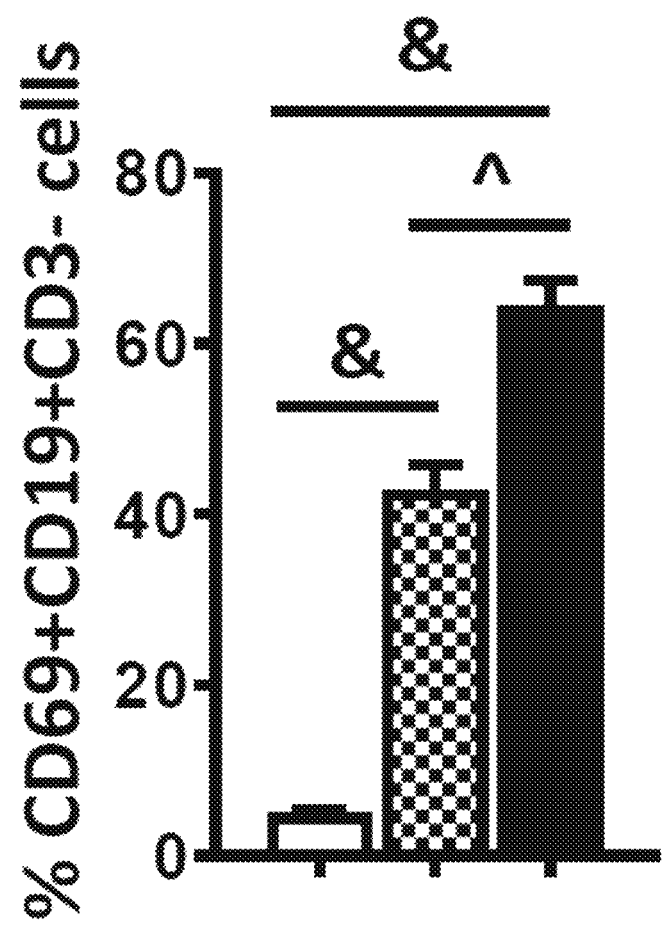
Figure 5B:
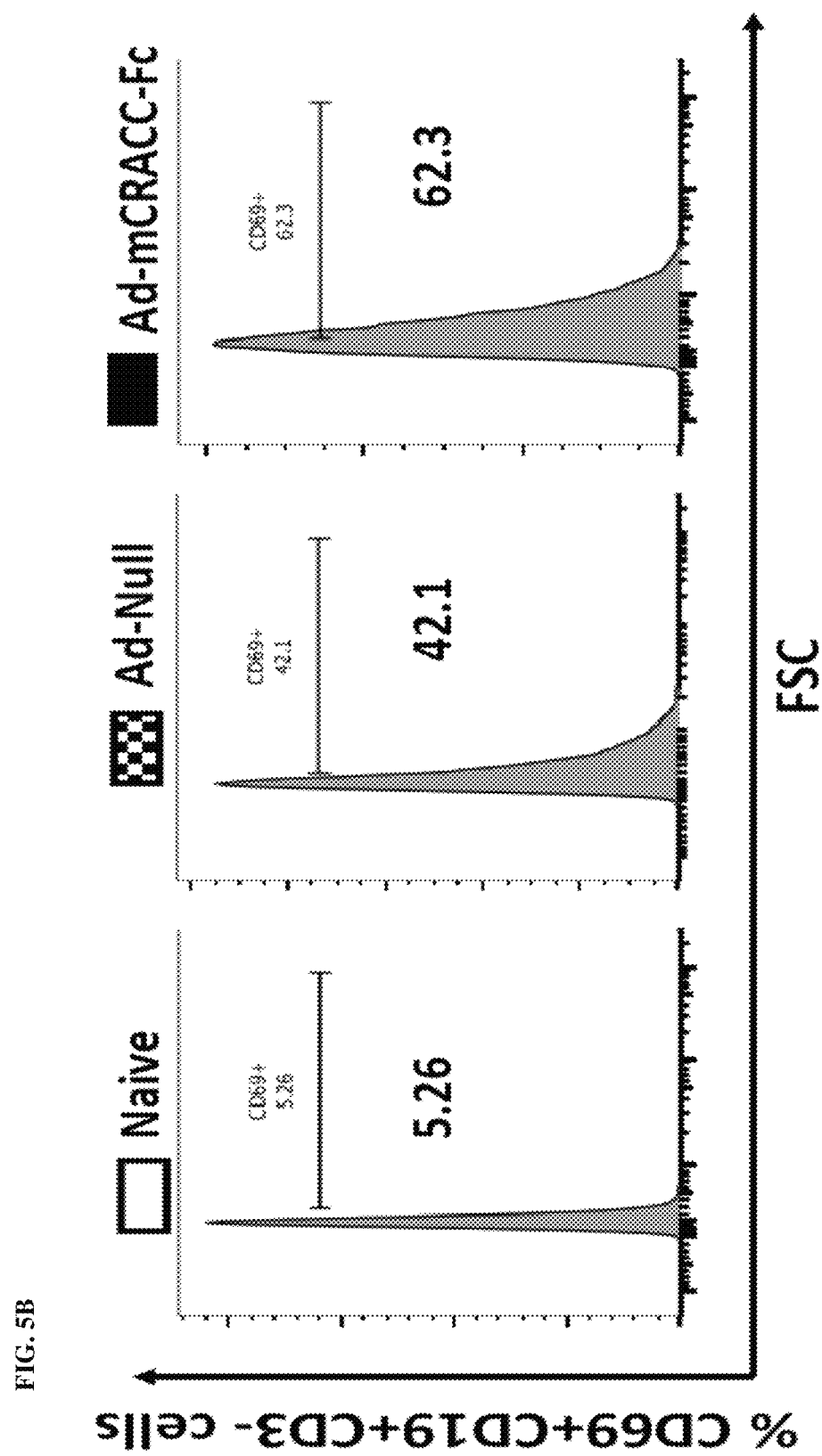
Figure 5C:
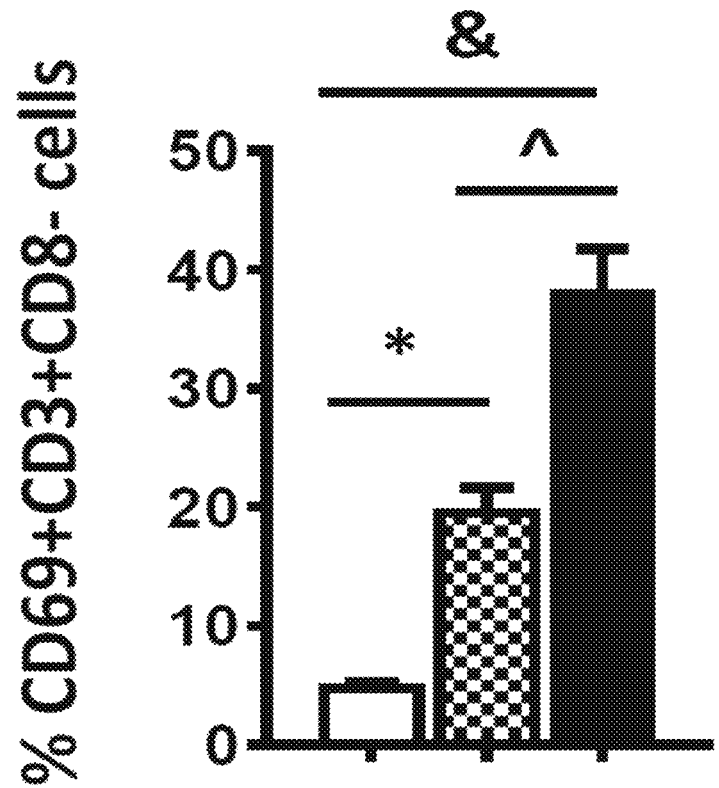
Figure 5D:
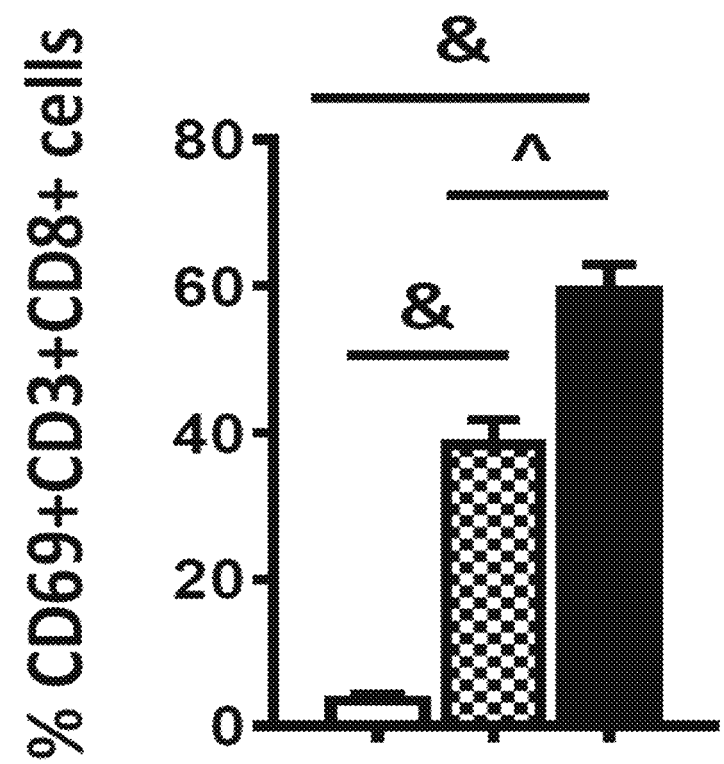
Figure 5E:
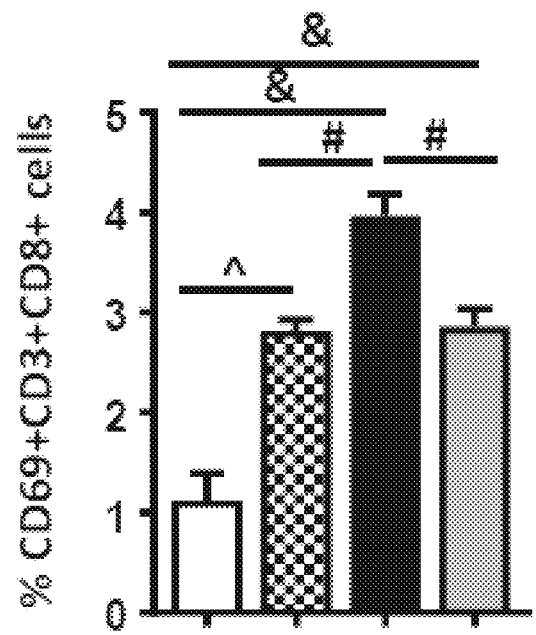
Figure 5F:
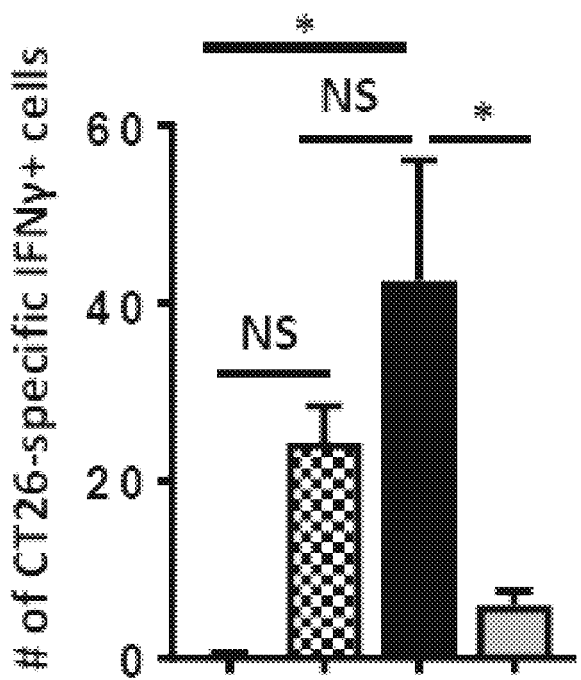
Figure 5G:
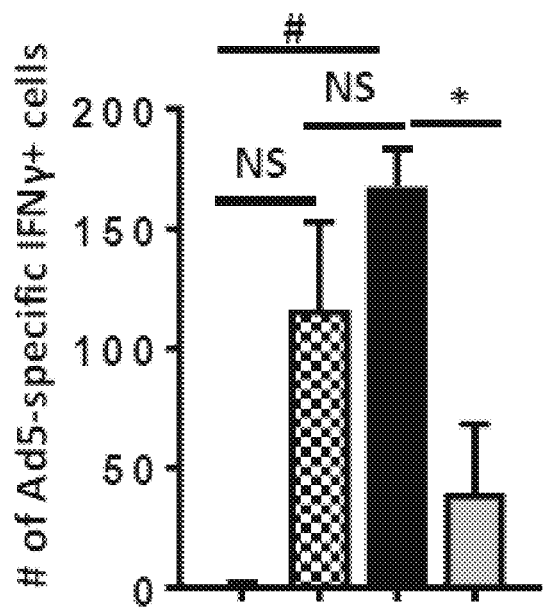

FIG. 5, contains seven panels, FIG. 5A-FIG. 5G, depicting adaptive immune cell activation in Ad-mCRACC-Fc treated mice. 6 weeks old Balb/c male were injected I.V, with $10^{10}$ v.p. of Ad-null or Ad-mCRACC-Fc. 10 hours post injection spleens were collected from injected (n=6) and naïve mice (n=3). Percent CD69+CD19+CD3− B cells analyzed using flow cytometry and graphed in (FIG. 5A), with representative histogram images in (FIG. 5B). Percent CD69+CD3+CD8− T cells (FIG. 5C). Percent CD69+CD3+CD8+ T cells (FIG. 5D). 6-week-old Balb/c mice were injected twice I.M. (n=6) over a period of 1 month (Days 0 and 12) with 200 μg of CT26 tumor lysate, tumor lysate+$10^{10}$ v.p. of rAd5-Null, tumor lysate+$10^{10}$ v.p. of rAd5-mCRACC-Fc, or not injected (unvaccinated, n=4). On Day 27, mice were sacrificed, and their spleens were collected. Splenocytes were cultured in-vitro in the presence of 10 μg/mL of CT26 tumor lysate for 48 hours, after which cells were stained and analyzed by flow cytometry. Percent of CD69+CD3+CD8+ T-cells is graphed in (FIG. 5E). Splenocytes from vaccinated mice were stimulated with 100 μg of CT26 tumor lysate (FIG. 5F) or with $10^{10}$ v.p. of heat inactivated rAd5-Null (FIG. 5G) overnight and subjected to ELISPOT analysis for IFN-γ+ cells. Graphs represent mean+/−SEM, where *—$p<0.05$, #—$p<0.01$, ^—$p<0.001$ and & —$p<0.0001$, and NS—not significant.

Figure 6A:
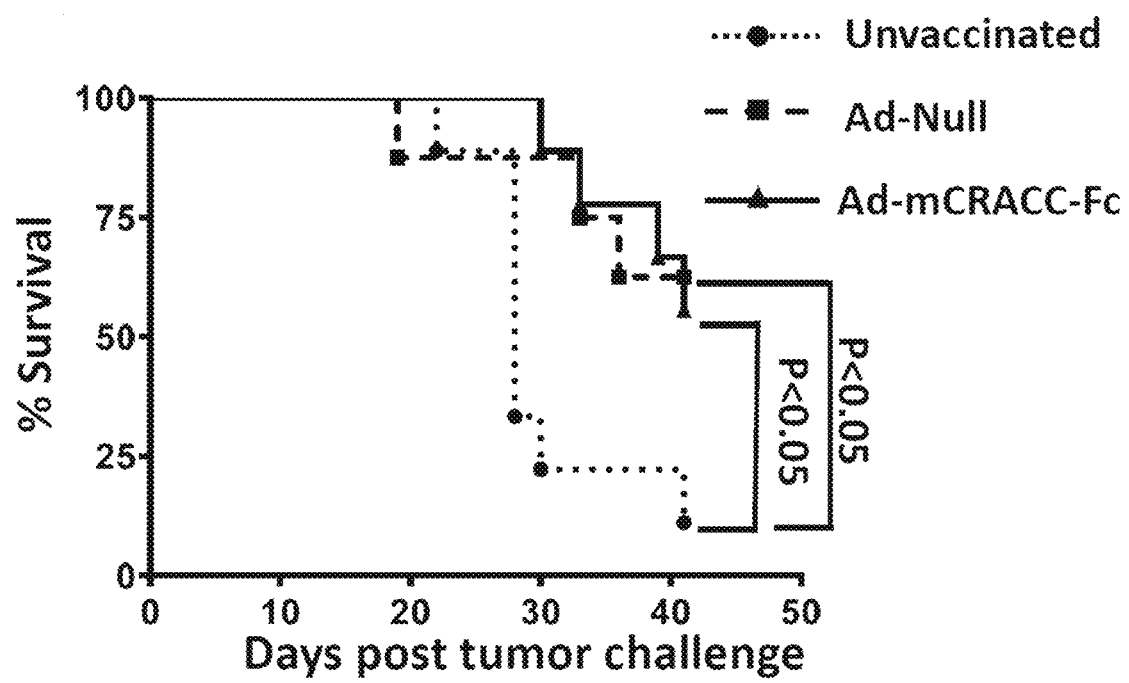
Figure 6B:
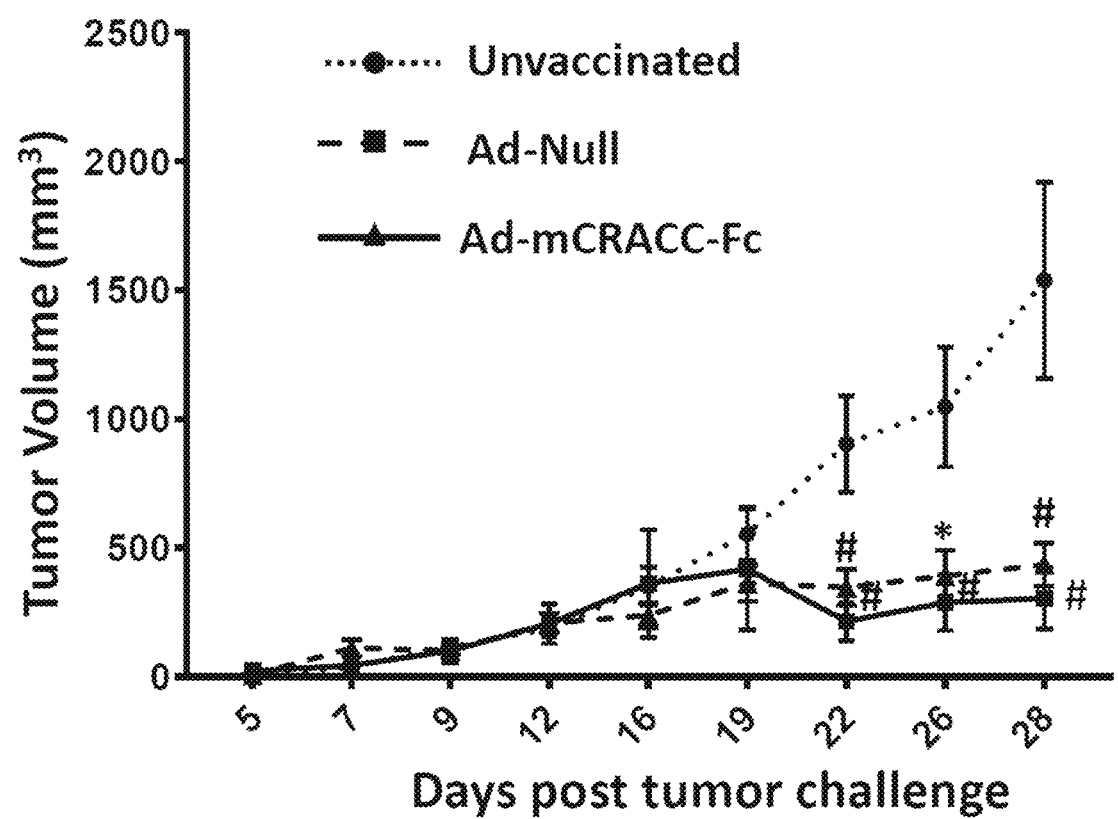
Figure 6C:
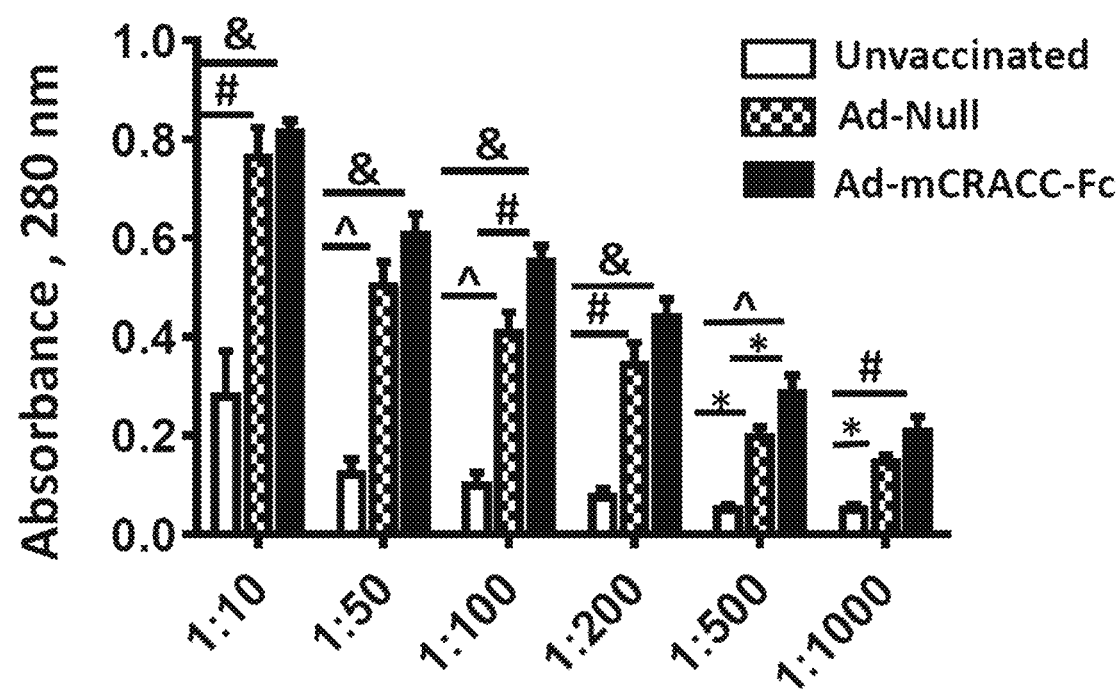
Figure 6D:
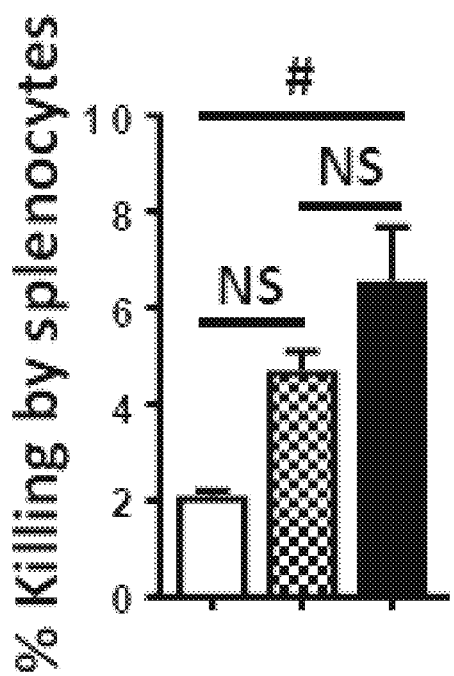
Figure 6E:
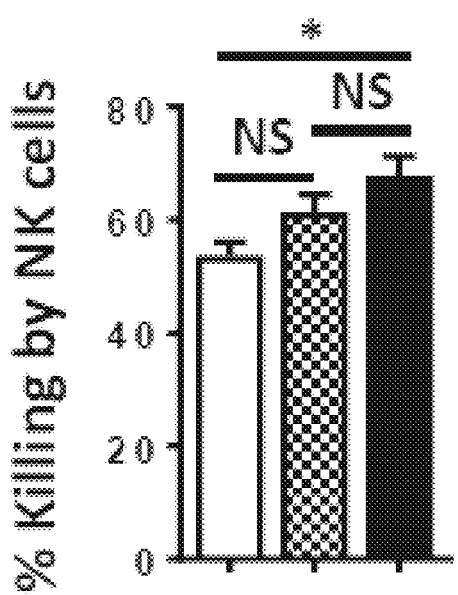

FIG. 6, contains five panels, FIG. 6A-FIG. 6E, depicting efficacy of tumor lysate in combination with Ad-mCRACC-Fc as an anti-tumor vaccine. 6 weeks old Balb/c male mice were injected with 3 doses of 200 μg CT26 tumor lysate and $10^{10}$ v.p. of adeno-virus I.P. over a period of 5 weeks as described in methods. Week 5 post $1^{st}$ injection mice were give the $3^{rd}$ dose of vaccination and were injected S.Q, with 300,000 CT26 tumor cells into flank. Mice were monitored every 2-3 days starting 5 days post tumor challenge. Tumor volume of 2,000 mm³ was used as the humane end point. FIG. 6A shows graphed percent survival. Statistical analysis was performed using Log-ranked test. FIG. 6B depicts a graph representing tumor volumes over time. Statistical analysis was performed using One-way ANOVA with Tukey's post hoc test. FIG. 6C shows relative abundance of tumor specific IgG antibodies in plasma in vaccinated mice compared to naïve on day 41 post tumor cell injection. Each dilution was analyzed using One-way ANOVA with Tukey's post hoc test to determine statistical significance. Splenocytes from naïve mice were incubated with CFSE-CT26 cells (20:1 E:T) and cultured for 18 hours in presence of plasma 1:200 dilution from rAd5-Null/CT26 lysate, rAd5-mCRACC-Fc/CT26 lysate vaccinated, or unvaccinated mice. Cells were stained with CellTrace Violet dye and analyzed by flow cytometry. Percent killing is graphed in FIG. 6D. Percent killing of CFSE-CT26 cells by Dx5+NK cells (1:1 E:T) overnight in presence of plasma (1:50 dilution) from vaccinated mice is graphed in FIG. 6E. Each dilution was analyzed using One-way ANOVA with Tukey's post hoc test to determine statistical significance. Graphs represent mean+/−SEM, where *—$p<0.05$, #—$p<0.01$, ^—$p<0.001$, & —$p<0.0001$, and NS—not significant.

Figure 7A:
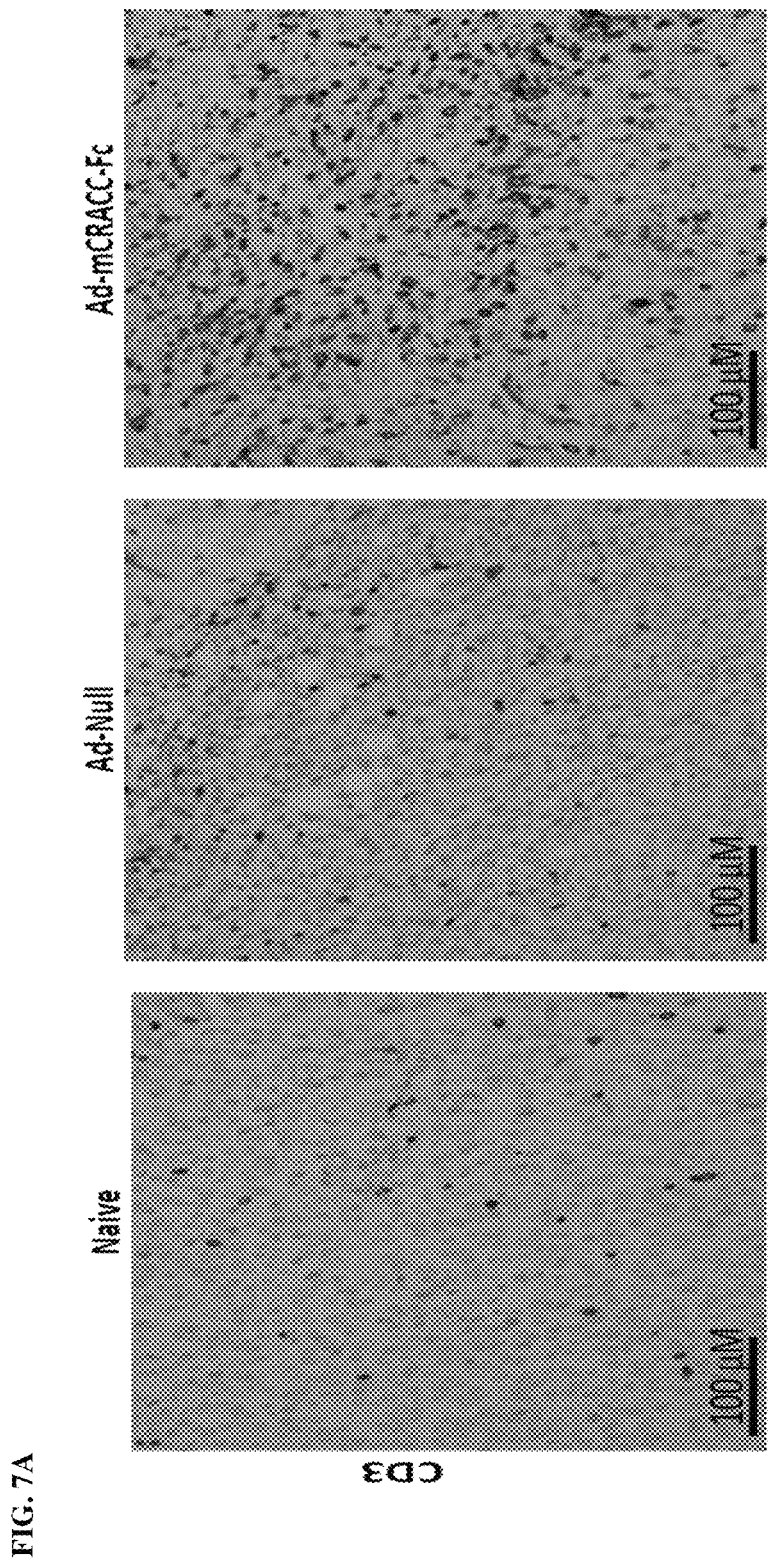
Figure 7B:
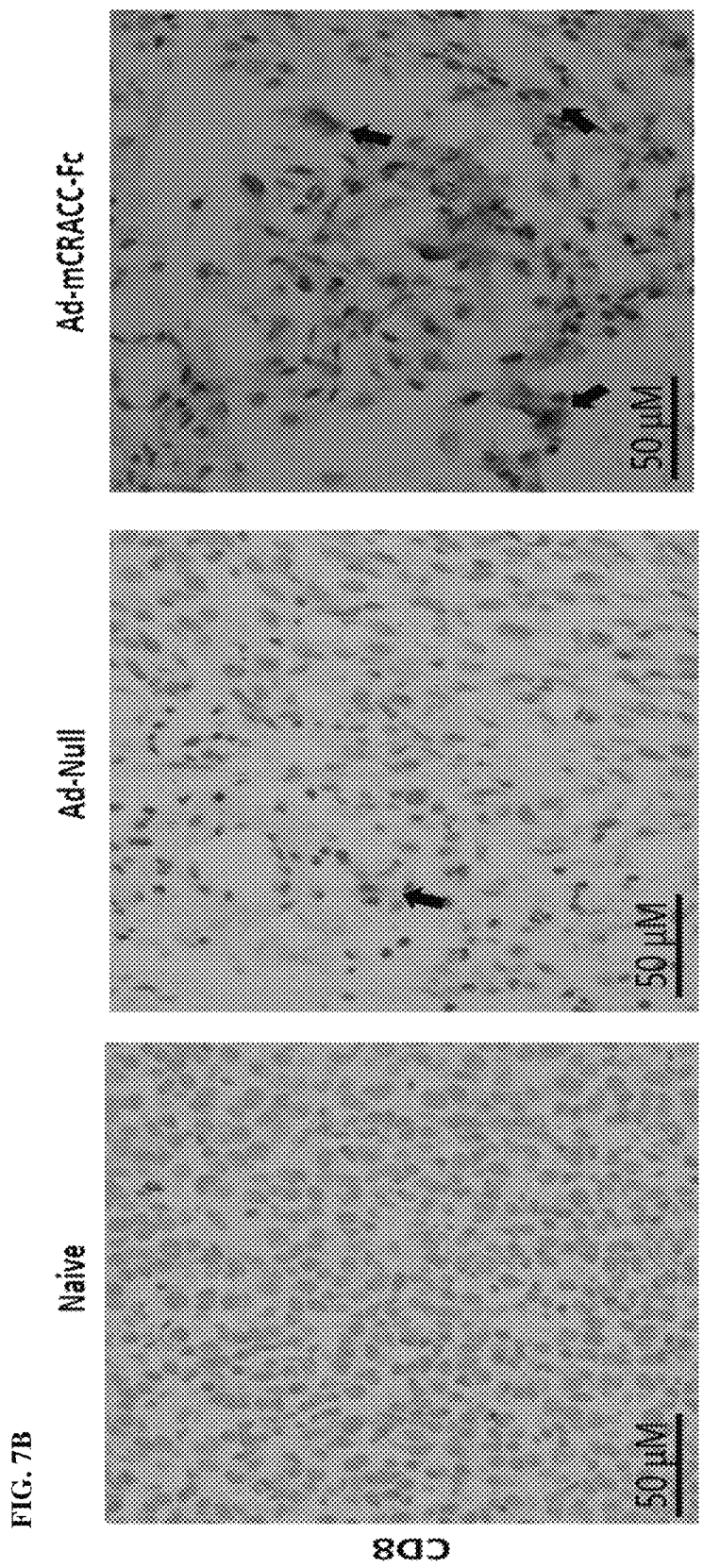

FIG. 7, contains two panels, FIG. 7A and FIG. 7B depicting CD3 and CD8 immunohistochemical analysis of tumors. Tumors from naïve (n=1), Ad-Null (n=3) and Ad-mCRACC-Fc (n=3) vaccinated mice were collected and fixed at the end of the study (day 41 post tumor challenge). Immunohistochemistry for CD3 and CD8 was performed. FIG. 7A depicts representative images of CD3 stained tumor slides, with images taken using 10× magnification. FIG. 7B depicts representative images of CD8 stained tumor sections, with arrows pointing at CD8+ cells. Images were taken using 20× magnification.

Figure 8:
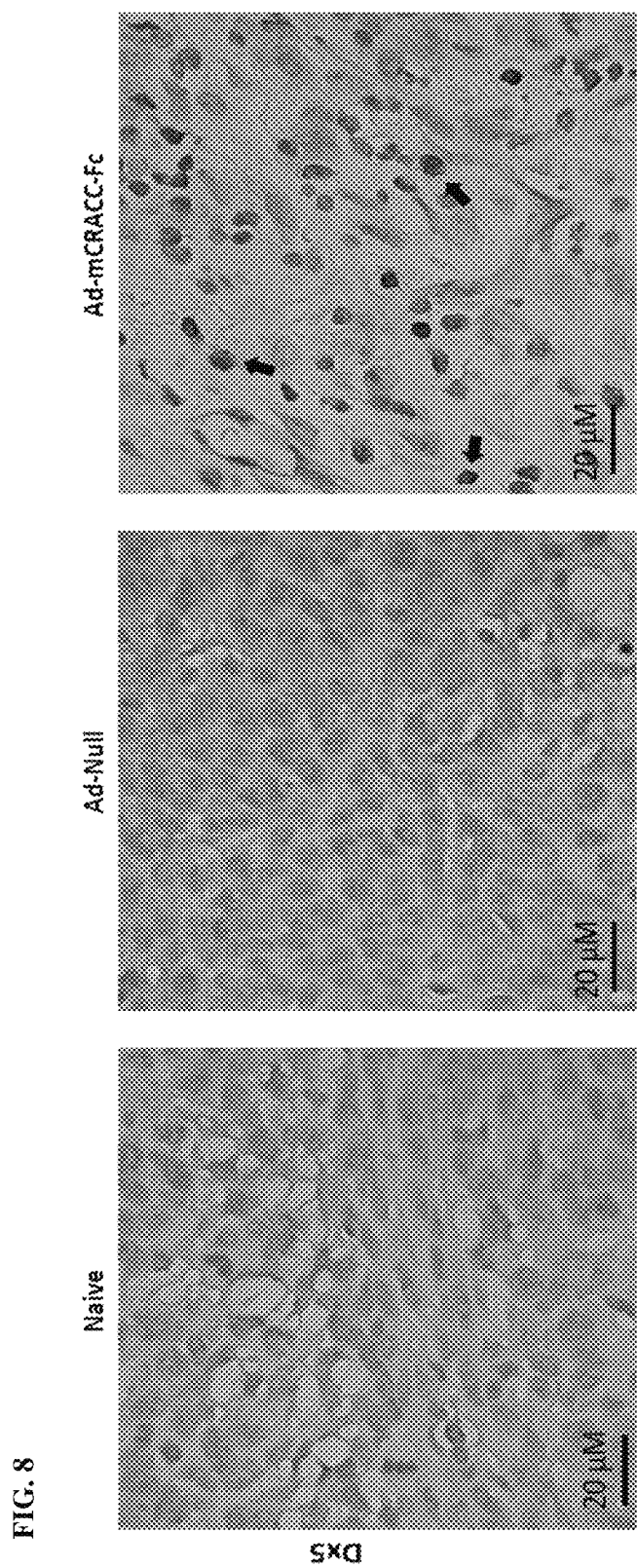

FIG. 8 depicts DX5 immunohistochemical analysis of tumors. Tumors from naïve, Ad-Null and Ad-mCRACC-Fc vaccinated mice (all n=1) were collected and fixed at the end of the study (Day 40 post tumor challenge). Immunohistochemistry for Dx5 was performed. Images were taken using 40× magnification. Representative images of DX5 stained tumor slides, with arrows pointing at DX5+ cells.

Note that for every figure containing a histogram, the bars from left to right for each discreet measurement correspond to the figure boxes from top to bottom in the figure legend as indicated.

DETAILED DESCRIPTION

I. Definitions

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

The articles "a" and "an" are used herein to refer to one or to more than one (i.e., to at least one) of the gra more than one element. mmatical object of the article. By way of example, "an element" means one element or more than one element.

As used herein, "adenoviruses" are DNA viruses with a 36-kb genome. There are 51 human adenovirus serotypes that have been distinguished on the basis of their resistance to neutralization by antisera to other known adenovirus serotypes. Adenoviruses as used herein encompass non-human or any adenovirus serotype developed as a gene transfer vector. Non-human adenovirus comprises an adenovirus selected from chimp, equine, bovine, mouse, chicken, pig, dog, or any mammalian or non-mammalian species. Although the majority of adenoviral vectors are derived from serotypes 2 and 5, other serotypes may also be used. The wild type adenovirus genome is divided into early (E1 to E4) and late (L1 to L5) genes, e.g., E1A, E1B, E2A, E2B, E3, E4, L1, L2, L3, L4, or L5. Adenovirus vectors can be prepared to be either replication competent or non-replicating. Replication defective adenoviral vectors may comprise at lease one deletion of any of the E1 to E4 or L1 to L5 genes. Replication deficient adenovirus based vectors are described in Hartman Z C et al. (2008) *Virus Res.* 132:1-14. In some embodiments, the replication defective adenovirus comprises deletions of the E1 and E3 genes. Foreign genes can be inserted into three areas of the adenovirus genome (E1, E3, or E4) as well as behind the major late promoter. The ability of the adenovirus genome to direct production of adenoviruses is dependent on sequences in E1.

Adenovirus vectors transduce large fragments of DNA into a wide range of cells in order to synthesize proteins in vivo, and gene expression can be modulated and even localized to specific cell types. Unlike other types of viral delivery systems, DNA delivered by adenovirus vectors does not integrate into the genome and thus circumvents the danger of insertional mutagenesis (Aldhamen Y A et al. (2011) *Front. Immun.* 2:1-12). Additionally, adenovirus vectors can be produced cost-efficiently in high abundance. Importantly, adenovirus vectors are currently being used in human clinical trials world-wide (Fukazawa T et al. (2010) *Int. J. Mol. Med.* 25:3-10).

The term "adjuvant" is used in its broadest sense as any substance or composition which enhances, increases, upwardly modulates or otherwise facilitates an immune response to an antigen be it added exogenously or already present such as a tumor associated antigen. The immune response may be measured by any convenient means such as antibody titer or level of cell-mediated response.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a one embodiment, body fluids are restricted to blood-related fluids, including whole blood, serum, plasma, and the like.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer is generally associated with uncontrolled cell growth, invasion of such cells to adjacent tissues, and the spread of such cells to other organs of the body by vascular and lymphatic menas. Cancer invasion occurs when cancer cells intrude on and cross the normal boundaries of adjacent tissue, which can be measured by assaying cancer cell migration, enzymatic destruction of basement membranes by cancer cells, and the like. In some embodiments, a particular stage of cancer is relevant and such stages can include the time period before and/or after angiogenesis, cellular invasion, and/or metastasis. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the present invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of melanoma and its subtypes.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison. In one embodiment, the control comprises obtaining a "control sample" from which expression product levels are detected and compared to the expression product levels from the test sample. Such a control sample may comprise any suitable sample, including but not limited to a sample from a control cancer patient or healthy patient (can be stored sample or previous sample measurement) with a known outcome; normal tissue or cells isolated from a subject, such as a healthy patient or the cancer patient, cultured primary cells/tissues isolated from a subject such as a normal subject or the cancer patient, adjacent normal cells/tissues obtained from the same organ or body location of the cancer patient, a tissue or cell sample isolated from a healthy subject, or a primary cells/tissues obtained from a depository. In another embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention.

Examples of diseases or conditions wherein enhancement of a protective immune response is desired includes, but are not limited to viral, pathogenic, protozoal, bacterial, or fungal infections and cancer.

Viral infectious diseases include human papilloma virus (HPV), hepatitis A Virus (HAV), hepatitis B Virus (HBV), hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, influenza virus, Hepatitis A and B, FIV, lentiviruses, pestiviruses, West Nile Virus, measles, smallpox, cowpox, ebola, coronavirus, retrovirus, herpesvirus, potato S virus, simian Virus 40 (SV40), Mouse Mammary Tumor Virus (MMTV) promoter, Moloney virus, ALV, Cytomegalovirus (CMV), Epstein Barr Virus (EBV), or Rous Sarcoma Virus (RSV). In addition, bacterial, fungal and other pathogenic diseases are included, such as *Aspergillus, Brugia, Candida, Chikungunya, Chlamydia, Coccidia, Cryptococcus, Dengue, Dirofilaria, Gonococcus, Histoplasma, Leishmania, Mycobacterium, Mycoplasma, Paramecium, Pertussis, Plasmodium, Pneumococcus, Pneumocystis, P. vivax* in *Anopheles* mosquito vectors, *Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis*, Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonasfoetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A compositions, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B compositions, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C compositions, such as nipah virus, hantaviruses, yellow fever in *Aedes* mosquitoes, and multidrug-resistant tuberculosis; helminths, such as *Schistosoma* and *Taenia*; and protozoa, such as *Leishmania* (e.g., *L. mexicana*) in sand flies, *Plasmodium*, Chagas disease in assassin bugs.

Other bacterial pathogens include, but are not limited to, bacterial pathogenic gram-positive cocci, which include but are not limited to: pneumococci; staphylococci; and streptococci. Pathogenic gram-negative cocci include: meningococci; and gonococci. Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirilum; Listeria monocytogenes; erysipelothrix rhusiopathiae; diphtheria; cholera; anthrax; and donovanosis (granuloma inguinale). Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of mycoplasma and chlamydial infections include: Mycoplasma pneumoniae; lymphogranuloma venereum; psittacosis; and perinatal chlamydial infections. Pathogenic protozoans and helminths and infections eukaryotes thereby include: amebiasis; malaria; leishmaniasis; trypanosomiasis; toxoplasmosis; Pneumocystis carinii; giardiasis; trichinosis; filariasis; schistosomiasis; nematodes; trematodes or flukes; and cestode (tapeworm) infections. While not a disease or condition, enhancement of a protective immune response is also beneficial in a vaccine or as part of a vaccination regimen as is described herein.

As used herein, a disease, disorder, condition, and/or illness associated with inflammation can include, but not limited to, septic shock, obesity-related inflammation, Parkinson's Disease, Crohn's Disease, Alzheimer's Disease (AD), cardiovascular disease (CVD), inflammatory bowel disease (IBD), chronic obstructive pulmonary disease, an allergic reaction, an autoimmune disease, blood inflammation, joint inflammation, arthritis, asthma, ulcerative colitis, hepatitis, psoriasis, atopic dermatitis, pemphigus, glomerulonephritis, atherosclerosis, sarcoidosis, rheumatoid arthritis, psoriatic arthritis, ankylosing spondylitis, Wegner's syndrome, Goodpasture's syndrome, giant cell arteritis, polyarteritis nodosa, idiopathic pulmonary fibrosis, acute lung injury, post-influenza pneumonia, SARS, tuberculosis, malaria, sepsis, cerebral malaria, Chagas disease, schistosomiasis, bacteria and viral meningitis, cystic fibrosis, multiple sclerosis, encephalomyelitis, sickle cell anemia, pancreatitis, transplantation, systemic lupus erythematosis, autoimmune diabetes, thyroiditis, and radiation pneumonitis, respiratory inflammation, or pulmonary inflammation.

The terms "enhance", "promote" or "stimulate" in terms of an immune response includes an increase, facilitation, proliferation, for example a particular action, function or interaction associated with an immune response.

The term "homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' (SEQ ID NO: 29) and a region having the nucleotide sequence 5'-TATGGC-3' (SEQ ID NO: 30) share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "host cell" is intended to refer to a cell into which any of the nucleotide sequence of the one or more cyclic di-nucleotide synthetase enzyme, or fragment thereof, such as a recombinant vector (e.g., gene therapy vector) of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "immunotherapeutic composition" can include any molecule, peptide, antibody or other composition which can stimulate a host immune system to generate an immune response to a tumor or cancer in the subject.

As used herein, the term "inhibit" includes the decrease, limitation, or blockage, of, for example a particular action, function, or interaction. For example, a pathogenic infection or cancer is "inhibited" if at least one symptom of the pathogenic infection or cancer, such as hyperproliferative growth, is alleviated, terminated, slowed, or prevented. As used herein, cancer is also "inhibited" if recurrence or metastasis of the cancer is reduced, slowed, delayed, or prevented.

As used herein, the term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules. Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

A "kit" is any manufacture (e.g., a package or container) comprising at least one reagent (e.g., gene therapy vector of the present invention, an extracellular Ag) for use in stimulating or enhancing an immune response when administered. The kit may be promoted, distributed, or sold as a unit for performing the methods of the present invention.

The term "modulate" includes up-regulation and down-regulation, e.g., enhancing or inhibiting a response.

The term "sample" is typically whole blood, plasma, serum, saliva, urine, stool (e.g., feces), tears, and any other bodily fluid (e.g., as described above under the definition of "body fluids"), or a tissue sample such as a small intestine, colon sample, or surgical resection tissue. In certain instances, the method of the present invention further comprises obtaining the sample from the individual prior to detecting or determining the presence or level of at least one marker in the sample.

The term "synergistic effect" refers to the combined effect of two or more compositions of matter of the present invention that is greater than the sum of the separate effects of the compositions of matter alone.

The term "mammal" refers to any healthy animal, subject or human, or any animal, mammal or human afflicted with a condition of interest (e.g., pathogenic infection or cancer). The term "subject" is interchangeable with "patient."

The term "purity" as used herein, refers to any of compositions or matter described herein which is substantially free of impurities or artifacts that may interfere in the efficacy of the composition when administered. Impurities or artifacts may include interfering antibody, polypeptide, peptide or fusion protein. In one embodiment, the language "purity of at least 75%, 80%, 85%, 90%, 95%, 98%, or 99%" includes preparations of vectors (e.g., gene therapy vectors), or pharmaceutical compositions, vaccines, adjuvants, combination vaccines (e.g., vector combined with an additional therapeutic agent), or the like, having less than about 30%, 20%, 15%, 10%, 5% (by dry weight) of impurities and/or artifacts. The terms "treatment" "treat" and "treating" encompasses alleviation, cure or prevention of at least one symptom or other aspect of a infection, disorder, disease, illness or other condition (e.g., pathogenic infections, cancer, etc.), or reduction of severity of the condition, and the like. A composition of matter of the invention, or combination, need not affect a complete cure, or eradicate every symptom or manifestation of a disease, to constitute a viable therapeutic composition. As is recognized in the pertinent field, drugs employed as therapeutic compositions may reduce the severity of a given disease state, but need not abolish every manifestation of the disease to be regarded as useful therapeutic compositions. Beneficial or desired clinical results include, but are not limited to, alleviation of symptoms, diminishment of extent of disease, stabilization (i.e., not worsening) of disease, delay or slowing of disease progression, amelioration or palliation of the disease state, remission (whether partial or total, whether detectable or undetectable) and prevention of relapse or recurrence of disease. Similarly, a prophylactically administered treatment need not be completely effective in preventing the onset of a condition in order to constitute a viable prophylactic composition. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

"Treatment" can also mean prolonging survival as compared to expected survival if not receiving treatment. In one embodiment, an indication that a therapeutically effective amount of a composition has been administered to the patient is a sustained improvement over baseline of an indicator that reflects the severity of the particular disorder.

By a "therapeutically effective amount" of a composition of the invention is meant an amount of the composition which confers a therapeutic effect on the treated subject, at a reasonable benefit/risk ratio applicable to any medical treatment. The therapeutic effect is sufficient to "treat" the patient as that term is used herein.

As used herein, a vaccine is a composition that provides protection against a pathogenic infection (e.g., protozoal, viral, or bacterial infection), cancer or other disorder or treatment for a pathogenic infection, cancer or other disorder. Protection against a pathogenic infection, cancer or other disorder will either completely prevent infection or the tumor or other disorder or will reduce the severity or duration of infection, tumor or other disorder if subsequently infected or afflicted with the disorder. Treatment will cause an amelioration in one or more symptoms or a decrease in severity or duration. For purposes herein, a vaccine results from infusion of injection (either concomitantly, sequentially or simultaneously) of any composition of matter, or combination, produced by the methods herein. As used herein, amelioration of the symptoms of a particular disorder by administration of a particular composition refers to any lessening, whether permanent or temporary, lasting or transient that can be attributed to or associated with administration of the compositions of matter described herein.

As used herein a "vaccination regimen" means a treatment regimen wherein a vaccine comprising an antigen and/or any of the gene therapy-vectors (alone or in combination) described herein, as an adjuvant, is administered to a subject in combination, simultaneously, in either separate or combined formulations, or sequentially at different times separated by minutes, hours or days, but in some way act together to provide the desired enhanced immune response to the vaccine in the subject as compared to the subject's immune response in the absence of a composition in accordance with the invention. In some embodiments of the methods described herein, the "antigen" is not delivered but is already present in the subject, such as those antigens which are associated with tumors. In some embodiments of the compositions described herein, the gene therapy vectors can have activity that is independent of their adjuvant properties.

As used herein, the term "vector", used interchangeably with "construct", refers to a nucleic acid capable of transporting another nucleic acid to which it has been linked. One type of vector is a "plasmid", which refers to a circular double stranded DNA loop into which additional DNA segments may be ligated. Another type of vector is a viral vector (e.g., replication defective adenovirus, retroviruses, or lentivirus), wherein additional DNA segments may be ligated into the viral genome. Viral vectors may also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors." In general, expression vectors of utility in recombinant DNA techniques are often in the form of plasmids. In the present specification, "plasmid" and "vector" may be used interchangeably as the plasmid is the most commonly used form of vector. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. Also included are DNA-based vectors, which can be delivered "naked" or formulated with liposomes to help the uptake of naked DNA into cells.

The term "CRACC" stands for "CD2-like receptor activating cytotoxic cell" receptor. The CRACC receptor is a member of the signaling lymphocytic activation molecules (SLAM) family receptors, that is expressed on NK cells, macrophages, dendritic cells and activated T and B cells (Bouchon A et al. *J Immunol*. 2001; 167(10):5517-21; Calpe S et al. *Adv Immunol*. 2008; 97:177-250; Cruz-Munoz M E et al. *Nat Immunol*. 2009; 10(3):297-305; Tassi I et al. *J Immunol*. 2005; 175(12):7996-8002). CRACC is also known in the art as SLAM Family Member 7; Membrane Protein FOAP-12; CD2 Subset 1; Protein 19A; CS1; Novel LY9 (Lymphocyte Antigen 9) Like Protein; 19A24 Protein; CD319 Antigen; Novel Ly9; CD319; and 19A. CRACC is a homotypic receptor that exclusively interacts with the Ewing's sarcoma-associated transcript 2 (EAT2) adaptor protein, which interacts with the cytoplasmic phosphorylated immunoreceptor tyrosine-based switch motifs (ITSMs) on CRACC protein via its Src homology 2 domain (SH2) (Cruz-Munoz M E et al. *Nat Immunol.* 2009; 10(3):297-305). In the presence of EAT2 adaptor protein, engagement of CRACC receptor generally results in immune cell activation, while in its absence, CRACC activation has inhibitory effects as has been shown in EAT2 negative NK cells (Guo H et al. *Mol Cell Biol.* 2015; 35(1):41-51), and antigen-specific T cells (Cruz-Munoz M E et al. *Nat Immunol.* 2009; 10(3):297-305). Therefore, manipulation of CRACC activation can potentially be used as an anti-tumor therapy and as an adjuvant for cancer and infectious diseases vaccines.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a protein or polypeptide of the present invention (or any portion thereof) can be used to derive the protein or polypeptide amino acid sequence, using the genetic code to translate the DNA or RNA into an amino acid sequence. Likewise, for a protein or polypeptide amino acid sequence, corresponding nucleotide sequences that can encode the protein or polypeptide can be deduced from the genetic code (which, because of its redundancy, will produce multiple nucleic acid sequences for any given amino acid sequence). Thus, description and/or disclosure herein of a nucleotide sequence which encodes a protein or polypeptide should be considered to also include description and/or disclosure of the amino acid sequence encoded by the nucleotide sequence. Similarly, description and/or disclosure of a protein or polypeptide amino acid sequence herein should be considered to also include description and/or disclosure of all possible nucleotide sequences that can encode the amino acid sequence.

Finally, nucleic acid and amino acid sequence information for any CRACC are well known in the art and readily available on publicly available databases, such as the National Center for Biotechnology Information (NCBI).

For example, exemplary CRACC nucleic acid and amino acid sequences derived from publicly available sequence databases are provided below.

TABLE 1

CRACC amino acid sequences

SEQ ID NO: 1 is an exemplary amino acid sequence for a full-length, human CRACC polypeptide. (NP_067004.3) (ECD corresponds to amino acid 23 to 226)
MAGSPTCLTL IYILWQLTGS AASGPVKELV GSVGGAVTFP LKSKVKQVDS IVWTFNTTPL VTIQPEGGTI IVTQNRNRER VDFPDGGYSL KLSKLKKNDS GIYYVGIYSS SLQQPSTQEY VLHVYEHLSK PKVTMGLQSN KNGTCVTNLT CCMEHGEEDV IYTWKALGQA ANESHNGSIL PISWRWGESD MTFICVARNP VSRNFSSPIL ARKLCEGAADDPDSSMVLLC LLLVPLLLSL FVLGLFLWFL KRERQEEYIE EKKRVDICRE TPNICPHSGE NTEYDTIPHT NRTILKEDPA NTVYSTVEIP KKMENPHSLL TMPDTPRLFA YENVI SEQ ID NO: 3 is an exemplary amino acid sequence for a full-length CRACC polypeptide expressed by *Rhesus macaque.* (ECD corresponds to amino acid 23 to 226)
MAGSPTCFTF IYILWQLTGS TASGSVKELV GSIGGAVTFP LKSEVKQVDS IVWTFNTTTL VTIQPEGGPM IVTQNRNKER VHFPDGGYSL KLSKLKKNDS GIYNVEIYSS SLQDPFTRKY VLRVYEHLSK PKVTMGLQSN KNGTCVTNLT CHMEHGEEDV IYTWKALGQA VNESHNGSIL PISWRWGESD MTFICTVRNP VSSNSSSPIL ARKLCEGAAD DSDSSMVLLC LLLVPLLLSL FVLGLFLWFL KRETQEESIE EKKRADICRE TPNICPYSGE NTEYDTIPYT NRTIPMEDAA NTLYSTVEIP KKIENPHSLL TMPDTPRLFA YENVI TABLE 1-continued CRACC amino acid sequences SEQ ID NO: 4 is an exemplary amino acid sequence
for a full-length CRACC polypeptide expressed by
Chimpanzee. (ECD corresponds to amino acid 23 to
226)
MAGSPTCLTL IYILWQLTGS AA**SGPVRELV GSVGGAVTFP
LKSKVKQVDS IVWTFNTTPL VTIQPEGGTI IVTQNRNKER
VDFPDGGYSL KLSKLKKNDS GIYYVGIYSS SLQQPSTQKY
VLHVYEHLSK PKVTMGLQSN KNGTCVTNLT CCMEHGEEDV
IYTWKALGQA ANESHNGSIL PISWRWGESD MTFICVARNP
VSSNFSSPIL ARKLCEGAAD DPDSSM**VLLC LLLVPLLLSL
FVLGLFLWFL KRERQEESIE EKKRADICRE TPNICPHSGE
NTEYDTIPHT NRTILKEDPA NTVYSTVEIP KKMENPHSLL
TMPDTPRLFA YENVI SEQ ID NO: 5 is an exemplary amino acid sequence
for a full-length, murine CRACC polypeptide.
(ECD corresponds to amino acid 23 to 223)
MARFSTYIIF TSVLCQLTVT AA**SGTLKKVA GALDGSVTFT
LNITEIKVDY VVWTFNTFFL AMVKKDGVTS QSSNKERIVF
PDGLYSMKLS QLKKNDSGAY RAEIYSTSSQ ASLIQEYVLH
VYKHLSRPKV TIDRQSNKNG TCVINLTCST DQDGENVTYS
WKAVGQGDNQ FHDGATLSIA WRSGEKDQAL TCMARNPVSN
SFSTPVFPQK LCEDAATDLT SLRGILYILC FSAVLILFAV**
LLTIPHTTWI KKGKGCEEDK KRVDRHQEMP DLCPHLEENA
DYDTIPYTEK RRPEEDAPNT FYSTVQIPKV VKSPSSLPAK
PLVPRSLSFE NVI SEQ ID NO: 7 is an exemplary amino acid sequence
for a full-length, canine CRACC polypeptide.
(XP_852458.2) (ECD corresponds to amino acid 23
to 226)
MLVPPAHFTIFFLLFQLTGPVT**SGALKELVGDLGGSVTFPLTLPGIQIDSI
VWTFNTTPLITIQPRTPDRQANVIVTHSHNKKRVDFLHGNYSLKLSKLNKS
DSGDYYVVIYSSSFKEPFSQRYGLRVYEHLSKPKVTMGLQNKENGTCVTNL
TCFVDQGGEDVTYSWESLGQAANKSYNGSILPISWRLGKGGMTFICVARNP
ISSNSSNPVFAWKLCEGAADDS**ESSVVLYFLGALLFMLTAFTLVPFILFMR
RERRKESIEEKKGMDTHQEILNYYPPSGETPVYDTISCVNNCIPEENSANT
LYFSVQIPPKMEKPHSPPTSPDTPKSFAYENVI SEQ ID NO: 8 is an exemplary amino acid sequence
for a full-length CRACC polypeptide expressed by
bos taurus (cattle).
MLGAPACFIF LLCQLTGPAA **SGIPKKLVGA IGGSVIFPLN
LSVNLVDSII WVFNSTTLVT IQPKTAGKKA LVIVTQKRNL
ERVNFPHEGY SLKLSRLKKN DSGIYRVEIH SSTLQDPLTQ
EYELHVYEYL SKPKVVIGLQ ENKNGTCVTN LTCSMEHGEE
DVTYSWKSLD QTTNESHRGS ILPISWRWEK SDMTFICMAS
NPISSNSSNP IFAQNLCEGA AGGQ**APYVVL YVLLSFFLLC
SLALVLIIFI IQRERKKEII EEKKELDTHQ KTLPFPPIPE
EMPEYDTIST FNGTIPEENP ANTIYSTVHI APKVTEPYSL
PMLSDTPTAS IYNNVM SEQ ID NO: 9 is an exemplary amino acid sequence
for a full-length CRACC polypeptide expressed
by rat.
MARFSTHIIF TSVLCQLTVT AA**SGTPKEVA GALDGSVTFT
LNTTEVKVDS VVWTFKTLFL AIINKNGTIK SQSYEERIVF
LDRHSMKLSQ LKKNDSGDYR AEIHIASNSL SSPFMQEYVL
HVHEHLSRPK VNTDSQSSKD GTCILNLTCS VERGGENVTY
SWKAVGQTVD EFHDSANLSI SWRLGEKDKT TCITARNPVS
SSSSTPLLAQ KLCKDAAKDL NSPRVLKYIL** CVTLVLVLFC
ILLVTILIRW IPKGKGFEED KKRVDGHQEM SNSCPHLENT
DYDTIPYTEK TRPEEDAPNT LYSTVQIPKV DAGSKSFGAY
MMIPHSRMPD TELQGLRLSA RF Noted in bolded and underlined are the amino acid sequences
coding for the ECD.

Included in Table 1, are variations of 1, 2, 3, 4, 5, 6, 7, 8, 9, 10, 11, 12, 13, 14, 15, 16, 17, 18, 19, 20, or more amino acids on the 5' end, on the 3' end, or on both the 5' and 3' ends, of the amino acid sequences.

Included in Table 1 are orthologs of the proteins, as well as polypeptide molecules comprising, consisting essentially of, or consisting of:

1) an amino acid sequence having at least 30%, 35%, 40%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NOs: 1, 3-5, and 7-9, or a biologically active fragment thereof;

2) an amino acid sequence having at least 30%, 35%, 40%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NOs: 1, 3-5, and 7-9, or a biologically active fragment thereof, comprising at least one or more (e.g., one, two, three, four, five, six, seven, eight, nine, ten or more) amino acid mutations, substitutions, insertions, or deletions, within CRACC;

3) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids;

4) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids, comprising at least one or more (e.g., one, two, three, four, five, six, seven, eight, nine, ten or more) amino acid mutations, substitutions, insertions, or deletions, within CRACC;

5) a biologically active fragment of an amino acid sequence of SEQ ID NOs: 1, 3-5, and 7-9 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids; or 6) a biologically active fragment of an amino acid sequence of SEQ ID NOs: 1, 3-5, and 7-9 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids, comprising at least one or more (e.g., one, two, three, four, five, six, seven, eight, nine, ten or more) amino acid mutations, substitutions, insertions, or deletions, within CRACC.

Also included in Table 1 are the ECD of CRACC, including, but no limited to, the sequences set forth in GENBANK accession numbers and corresponding species noted in parentheticals. In some embodiments the ECDs are linked to an Fc portion, wherein the Fc portion may comprise the IgG1, IgG2, IgG3, or IgG4 Fc portion, such as the amino acid sequence set forth in SEQ ID Nos: 19 and 20.

NP_067004.3 (*Homo sapiens*); CAB81950.2 (*Homo sapiens*; BAF84837.1 (*Homo sapiens*); XP_001172275.1 (*Pan troglodytes*); XP_011508130.1 (*Homo sapiens*); XP_003811917.1 (*Pan paniscus*); XP_002809957.1 (*Pongo abelii*); XP_004027770.1 (*Gorilla gorilla gorilla*);

XP_018880924.1 (Gorilla gorilla gorilla); XP_009434007.1 (Pan troglodytes); XP_007974659.1 (Chlorocebus sabaeus); XP_010359033.1 (Rhinopithecus roxellana); XP_011813004.1 (Colobus angolensis palliatus); XP_023070033.1 (Piliocolobus tephrosceles); XP_018880930.1 (Gorilla gorilla gorilla); XP_017720379.1 (Rhinopithecus bieti); XP_011922987.1 (Cercocebus atys); EHH15425.1 (Macaca mulatta); XP_011822576.1 (Mandrillus leucophaeus); XP_001117618.1 (Macaca mulatta); XP_011768403.1 (Macaca nemestrina); EHH50443.1 ((Macaca fascicularis); XP_023070032.1 (Piliocolobus tephrosceles); XP_003892984.1 (Papio anubis); XP_007974662.1 (Chlorocebus sabaeus); XP_003938007.1 (Saimiri boliviensis boliviensis); XP_011922989.1 (Cercocebus atys); XP_017359080.1 (Cebus capucinus imitator); XP_002760223.1 (Callithrix jacchus); XP_012305077.1 (Aotus nancymaae); XP_009183245.1 (Papio anubis); XP_012494986.1 (Propithecus coquereli); XP_024304525.1 (Homo sapiens); XP_012604679.1 (Microcebus murinus); XP_011234591.1 (Ailuropoda melanoleuca); XP_008698899.1 (Ursus maritimus); XP_024427117.1 (Desmodus rotundus); XP_003795231.1 (Otolemur garnettii); XP_006168878.1 (Tupaia chinensis); XP_019505131.1 (Hipposideros armiger); XP_006744483.1 (Leptonychotes weddellii); XP_008262433.1 (Oryctolagus cuniculus); XP_006174052.1 (Camelus ferus); XP_008839019.1 (Nannospalax galili); XP_020029915.1 (Castor canadensis); XP_016071185.1 (Miniopterus natalensis); XP_004775937.1 (Mustela putorius furo); XP_019573711.1 (Rhinolophus sinicus); XP_023580883.1 (Trichechus manatus latirostris); XP_022346408.1 (Enhydra lutris kenyoni); XP_005857819.1 (Myotis brandtii); XP_007171812.1 (Balaenoptera acutorostrata scammoni); XP_008056895.1 (Carlito syrichta); XP_019505133.1 (Hipposideros armiger); XP_015104500.1 (Vicugna pacos); XP_012932920.1 (Heterocephalus glaber); XP_017531813.1 Manis javanica); XP_005663244.1 (Sus scrofa); XP_020744990.1 (Odocoileus virginianus texanus); XP_003466724.1 (Cavia porcellus); XP_012039881.1 (Ovis aries); XP_008152457.1 (Eptesicus fuscus); XP_006990658.1 (Peromyscus maniculatus bairdii); XP_005677263.2 (Capra hircus); XP_019573714.1 (Rhinolophus sinicus); XP_023555617.1 (Octodon degus); XP_023580885.1 (Trichechus manatus latirostris); XP_005368660.1 (Microtus ochrogaster); XP_010836158.1 (Bison bison bison); NP_001178287.1 (Bos taurus); XP_005400274.1 (Chinchilla lanigera); XP_021054326.1 (Mus pahari); XP_005962536.1 (Pantholops hodgsonii); XP_021023820.1 (Mus caroli); XP_006060355.1 (Bubalus bubalis); XP_013377985.1 (Chinchilla lanigera); XP_005962535.1 (Pantholops hodgsonii); XP_012783532.1 (Ochotona princeps); XP_005903954.1 (Bos mutus); XP_021087570.1 (Mesocricetus auratus); BAE43122.1 (Mus musculus); NP_653122.2 (Mus musculus); Q8BHK6.2 (Mus musculus); EDL39061.1 (Mus musculus); XP_015347479.1 (Marmota marmota marmota); XP_021519928.1 (Meriones unguiculatus); XP_012384301.1 (Dasypus novemcinctus); XP_023555618.1 (Octodon degus); XP_006060356.1 (Bubalus bubalis); XP_010836159.1 (Bison bison bison); XP_005203614.1 (Bos taurus); XP_003500301.1 (Cricetulus griseus); XP_006250312.1 (Rattus norvegicus); XP_008542384.1 (Equus przewalskii); XP_014652549.1 (Ceratotherium simum simum); XP_005610012.1 (Equus caballus); XP_014703853.1 (Equus asinus); XP_007092438.1 (Panthera tigris altaica); XP_022415228.1 (Delphinapterus leucas); XP_022415227.1 (Delphinapterus leucas); XP_024613396.1 (Neophocaena asiaeorientalis asiaeorientalis); XP_024613389.1 (Neophocaena asiaeorientalis asiaeorientalis); XP_007467206.1 (Lipotes vexillifer); XP_019788177.1 (Tursiops truncatus); XP_004329466.1 (Tursiops truncatus); XP_024613413.1 (Neophocaena asiaeorientalis asiaeorientalis); XP_024613404.1 (Neophocaena asiaeorientalis asiaeorientalis); XP_023409943.1 (Loxodonta africana); XP_010593337.1 (Loxodonta africana); XP_852458.2 (Canis lupus familiaris); XP_012393951.1 (Orcinus orca); XP_021537504.1 (Neomonachus schauinslandi); XP_008056897.1 (Carlito syrichta); XP_006943097.2 (Felis catus); XP_010614947.1 (Fukomys damarensis); XP_014931739.1 (Acinonyx jubatus); XP_007124139.2 (Physeter catodon); KFO18140.1 (Fukomys damarensis); XP_023409944.1 (Loxodonta africana); XP_023580891.1 (Trichechus manatus latirostris); NP_001178479.1 (Rattus norvegicus); XP_015347485.1 (Marmota marmota marmota); XP_011234596.1 (Ailuropoda melanoleuca); XP_003775565.1 (Pongo abelii); XP_003258763.1 (Nomascus leucogenys); XP_001172059.1 (Pan troglodytes); XP_003811921.1 (Pan paniscus); NP_003865.1 (Homo sapiens); XP_012305084.1 (Aotus nancymaae); XP_017720366.1 (Rhinopithecus bieti); XP_011822675.1 (Mandrillus leucophaeus); XP_011768390.1 (Macaca nemestrina); XP_011813021.1 (Colobus angolensis palliatus); XP_005541301.1 (Macaca fascicularis); XP_002809960.3 (Pongo abelii); XP_011813020.1 (Colobus angolensis palliatus); XP_012366465.1 (Nomascus leucogenys); XP_023070024.1 (Piliocolobus tephrosceles); XP_001117595.1 (Macaca mulatta); XP_011923001.1 (Cercocebus atys); XP_003258764.1 (Nomascus leucogenys); PNI19763.1 (Pan troglodytes); XP_024782290.1 (Pan paniscus); NP_001317671.1 (Homo sapiens); EHH50442.1 (Macaca fascicularis); XP_003775566.2 (Pongo abelii); CAG46645.1 (Homo sapiens); XP_003938004.1 (Saimiri boliviensis boliviensis); PNI119762.1 (Pan troglodytes); XP_003811922.1 (Pan paniscus); NP_001171808.1 (Homo sapiens); XP_011813019.1 (Colobus angolensis palliatus); XP_007974675.1 (Chlorocebus sabaeus); EHH15422.1 (Macaca mulatta); XP_011822665.1 (Mandrillus leucophaeus); XP_017359088.1 (Cebus capucinus imitator); XP_003892974.1 (Papio anubis); XP_011822659.1 (Mandrillus leucophaeus); XP_008982989.1 (Callithrix jacchus); XP_008982988.1 (Callithrix jacchus); XP_013004653.1 (Cavia porcellus); XP_021017968.1 (Mus caroli); XP_020740644.1 (Odocoileus virginianus texanus); XP_022346497.1 (Enhydra lutris kenyoni); AAN63159.1 (Mus musculus); XP_011237177.1 (Mus musculus); AAN63158.1 (Mus musculus); BAE96340.1 (Mus musculus); AAN63160.1 (Mus musculus); XP_011234598.1 (Ailuropoda melanoleuca); XP_011234592.1 (Ailuropoda melanoleuca); XP_007945983.1 (Orycteropus afer afer); XP_022346622.1 (Enhydra lutris kenyoni); XP_022346620.1 (Enhydra lutris kenyoni); XP_008698906.1 (Ursus maritimus); XP_011234597.1 (Ailuropoda melanoleuca); XP_012420502.1 (Odobenus rosmarus divergens); XP_006922950.1 (Pteropus alecto); XP_011371360.1 (Pteropus vampyrus); XP_016070307.1 (Miniopterus natalensis); XP_013852321.1 (Sus scrofa); ELK03350.1 (Pteropus alecto); XP_011768394.1 (Macaca nemestrina); XP_011768392.1 (Macaca nemestrina); XP_011768395.1 (Macaca nemestrina); XP_023070020.1 (Piliocolobus tephrosceles); XP_023070019.1 (Piliocolobus tephrosceles); XP_011768393.1 (Macaca nemestrina); XP_023070018.1 (Piliocolobus tephrosceles); XP_007974678.1 (Chlorocebus sabaeus); XP_021017987.1 (Mus caroli); XP_021017978.1 (Mus caroli); XP_007974679.1 (Chlorocebus sabaeus); XP_023070013.1 (Piliocolobus tephrosceles); XP_021781469.1 (Papio anubis); XP_005541304.1 (Macaca fascicularis); XP_021781472.1 (Papio anubis); XP_023070015.1 (Piliocolobus tephrosceles); XP_005541305.1 (Macaca fascicularis); XP_011825757.1 (Mandrillus leucophaeus); XP_011923010.1 (Cercocebus atys); XP_011923007.1 (Cercocebus atys); XP_011825759.1 (Mandrillus leucophaeus): XP_011923008.1 (Cercocebus atys); XP_001117577.1 (Macaca mulatta); XP_014969025.1 (Macaca mulatta); XP_021781491.1 (Papio anubis); XP_021781489.1 (Papio anubis); EHH15421.1 (Macaca mulatta); XP_011923011.1 (Cercocebus atys); XP_007460005.1 (Lipotes vexillifer); CAB76561.1 (Homo sapiens); XP_023580882.1 (Trichechus manatus latirostris); XP_019573712.1 (Rhinolophus sinicus); XP_006922946.1 (Pteropus alecto); XP_011371352.1 (Pteropus vampyrus); XP_015995141.1 (Rousettus aegyptiacus); XP_023616470.1 (Myotis lucifugus); XP_023580884.1 (Trichechus manatus latirostris); ELR50448.1 (Bos mutus); XP_021054325.1 (Mus pahari); XP_008839020.1 (Nannospalax galili); XP_006861821.1 (Chrysochloris asiatica); XP_016285757.1 (Monodelphis domestica); XP_019843286.1 (Bos indicus); XP_005203570.1 (Bos taurus); XP_023555588.1 (Octodon degus); XP_019843275.1 (Bos indicus); XP_019288877.1 (Panthera pardus); XP_019288876.1 PREDICTED: SLAM family member 6 isoform X1 [Panthera pardus]; XP_019677876.2 (Felis catus); XP_007092434.1 (Panthera tigris altaica); XP_023555589.1 (Octodon degus); XP_004775933.1 (Mustela putorius furo); XP_006943100.4 (Felis catus); XP_014703843.1 (Equus asinus); XP_022346496.1 (Enhydra lutris kenyoni); XP_004448462.1 (Dasypus novemcinctus); XP_008518682.1 (Equus przewalskii); XP_015397631.1 (Panthera tigris altaica); XP_004775931.1 (Mustela putorius furo); XP_014931695.1 (Acinonyx jubatus); XP_008698900.1 (Ursus maritimus); XP_022415229.1 (Delphinapterus leucas); XP_022415230.1 (Delphinapterus leucas); XP_013004662.1 (Cavia porcellus); XP_020945224.1 (Sus scrofa); XP_023409945.1 (Loxodonta africana); XP_021591670.1 (Ictidomys tridecemlineatus); XP_010359039.1 (Rhinopithecus roxellana); XP_015310273.1 (Macaca fascicularis); XP_011923000.1 (Cercocebus atys); XP_001928499.4 (Sus scrofa); XP_021781435.1 (Papio anubis); XP_020945225.1 (Sus scrofa); XP_011923002.1 (Cercocebus atys); XP_021781448.1 (Papio anubis); XP_021023812.1 (Mus caroli); XP_004775934.1 (Mustela putorius furo); XP_012974580.1 (Mesocricetus auratus); XP_013852322.1 (Sus scrofa); XP_013966758.1 (Canis lupus familiaris); XP_014703845.1 (Equus asinus); XP_019573703.1 (Rhinolophus sinicus); XP_005610018.1 (Equus caballus); XP_019573702.1 (Rhinolophus sinicus); XP_019573704.1 (Rhinolophus sinicus); XP_023190022.1 (Xiphophorus maculatus); ELV10575.1 (Tupaia chinensis); XP_020744991.1 (Odocoileus virginianus texanus); XP_015104560.1 (Vicugna pacos); XP_010953949.1 (Camelus bactrianus); XP_010991392.1 (Camelus dromedarius); XP_008698907.1 (Ursus maritimus); XP_005640941.1 (Canis lupus familiaris); XP_010359040.1 (Rhinopithecus roxellana); XP_021054337.1 (Mus pahari); XP_019288894.1 (Panthera pardus); XP_021054336.1 (Mus pahari); XP_010614956.1 (Fukomys damarensis); XP_006943099.1 (Felis catus); XP_015397629.1 (Panthera tigris altaica); XP_014931696.1 (Acinonyx jubatus); XP_017359089.1 (Cebus capucinus imitator); XP_012885997.1 (Dipodomys ordii); XP_006168883.1 (Tupaia chinensis); XP_024606457.1 (Neophocaena asiaeorientalis asiaeorientalis); XP_007171816.1 (Balaenoptera acutorostrata scammoni); XP_024606440.1 (Neophocaena asiaeorientalis asiaeorientalis); XP_004858763.1 (Heterocephalus glaber); XP_022414971.1 (Delphinapterus leucas); XP_022414970.1 (Delphinapterus leucas); XP_007171817.1 (Balaenoptera acutorostrata scammoni); XP_019788217.1 (Tursiops truncatus); XP_024606464.1 (Neophocaena asiaeorientalis asiaeorientalis); XP_008590914.1 (Galeopterus variegatus); XP_008590913.1 (Galeopterus variegatus); XP_008590912.1 (Galeopterus variegatus); XP_016046970.1 (Erinaceus europaeus); XP_011768396.1 (Macaca nemestrina); XP_005541307.1 (Macaca fascicularis); XP_009183158.1 (Papio anubis); XP_023070021.1 (Piliocolobus tephrosceles); XP_008982987.1 (Callithrix jacchus); NP_443163.1 (Homo sapiens); XP_008982986.1 (Callithrix jacchus); XP_008982986.1 (Piliocolobus tephrosceles); NP_001171643.1 (Homo sapiens); XP_012305083.2 (Aotus nancymaae); XP_014969030.1 (Macaca mulatta); XP_012305082.2 (Aotus nancymaae); XP_005400268.1 (Chinchilla lanigera); XP_003811924.1 (Pan paniscus); XP_009433939.1 (Pan troglodytes); XP_004858764.1 (Heterocephalus glaber); XP_001171991.1 (Pan troglodytes); XP_008982985.1 (Callithrix jacchus); XP_011813024.1 (Colobus angolensis palliatus); XP_008962516.1 (Pan paniscus); XP_009433933.1 (Pan troglodytes); XP_011813025.1 (Colobus angolensis palliatus); XP_008982984.1 (Callithrix jacchus); XP_003466721.2 (Cavia porcellus); XP_018880877.1 (Gorilla gorilla gorilla); XP_018880872.1 (Gorilla gorilla gorilla); XP_016285011.1 (Monodelphis domestica); XP_017720358.1 (Rhinopithecus bieti); XP_017720359.1 (Rhinopithecus bieti); XP_010359044.1 (Rhinopithecus roxellana); XP_009240369.1 (Pongo abelii); XP_017359086.1 (Cebus capucinus imitator); XP_010359045.1 (Rhinopithecus roxellana); XP_016785983.1 (Pan troglodytes); XP_002809963.1 (Pongo abelii); XP_017720362.1 (Rhinopithecus bieti); XP_017359085.1 (Cebus capucinus imitator); XP_017359087.1 (Cebus capucinus imitator); XP_012384327.1 (Dasypus novemcinctus); XP_019505153.1 (Hipposideros armiger); XP_012366500.1 (Nomascus leucogenys); XP_003258760.1 (Nomascus leucogenys); XP_017720363.1 (Rhinopithecus bieti); XP_008056926.2 (Carlito syrichta); XP_007543067.1 (Poecilia formosa); XP_007543066.1 (Poecilia formosa); XP_023357849.1 (Sarcophilus harrisii); BAE42226.1 (Mus musculus); Q18PI6.1 (Mus musculus); NP_001276399.1 (Mus musculus); AAI44737.1 (Mus musculus); NP_038517.1 (Mus musculus); BAE96317.1 (Mus musculus); XP_021023261.1 (Mus caroli); XP_021023255.1 (Mus caroli); XP_007481701.1 (Monodelphis domestica); XP_005903958.2 (Bos mutus); XP_023357855.1 (Sarcophilus harrisii); XP_016830056.1 (Cricetulus griseus); XP_004775927.1 (Mustela putorius furo); XP_006036136.2 (Alligator sinensis); XP_006036137.2 (Alligator sinensis); XP_004775926.1 (Mustela putorius furo); XP_024606207.1 (Neophocaena asiaeorientalis asiaeorientalis); XP_024606214.1 (Neophocaena asiaeorientalis asiaeorientalis); XP_021170601.1 (Fundulus heteroclitus);

XP_007481697.2 (Monodelphis domestica); XP_006168929.1 (Tupaia chinensis); ELR50445.1 (Bos mutus); XP_014652515.1 (Ceratotherium simum simum); (Cavia porcellus); XP_013004655.1 (Cavia porcellus); XP_005640947.1 (Canis lupus familiaris); XP_005640948.1 (Canis lupus familiaris); XP_005640948.1 (Canis lupus familiaris); XP_021023829.1 (Mus caroli); XP_021054327.1 (Mus pahari); NP_001334113.1 (Mus musculus); XP_011371361.1 (Pteropus vampyrus); XP_014402848.1 (Myotis brandtii); XP_014402829.1 (Myotis brandtii); XP_014402839.1 (Myotis brandtii); XP_011234972.1 (Ailuropoda melanoleuca); XP_005981780.1 (Pantholops hodgsonii); XP_020024133.1 (Castor canadensis); XP_020024132.1 (Castor canadensis); XP_022271050.1 (Canis lupus familiaris); XP_005640946.1 (Canis lupus familiaris); XP_014166798.1 (Geospiza fortis); XP_014051129.1 (Salmo salar); XP_008589400.1 (Galeopterus variegatus); XP_012420516.1 (Odobenus rosmarus divergens); XP_012039887.1 (Ovis aries); XP_012807300.1 (Jaculus jaculus); XP_020945226.1 (Sus scrofa); XP_006047616.1 (Bubalus bubalis); XP_019843418.1 (Bos indicus); XP_007064709.1 (Chelonia mydas); XP_014703847.1 (Equus asinus); XP_008518686.1 (Equus przewalskii); XP_004448461.1 (Dasypus novemcinctus); XP_019333836.1 (Alligator mississippiensis); XP_014457221.1 (Alligator mississippiensis); XP_012384326.1 (Dasypus novemcinctus); XP_023372218.1 (Otolemur garnettii); XP_006497074.1 (Mus musculus); XP_012807302.1 (Jaculus jaculus); XP_012604649.1 (Microcebus murinus); XP_012604652.1 (Microcebus murinus); XP_020945227.1 (Sus scrofa); XP_006129452.2 (Pelodiscus sinensis); XP_017586644.1 (Corvus brachyrhynchos); XP_017586643.1 (Corvus brachyrhynchos); XP_018086989.1 (Xenopus laevis); XP_005640940.1 (Canis lupus familiaris); XP_020835231.1 (Phascolarctos cinereus); XP_020835228.1 (Phascolarctos cinereus); XP_020835234.1 (Phascolarctos cinereus); XP_007171807.1 (Balaenoptera acutorostrata scammoni); XP_022415384.1 (Delphinapterus leucas); XP_022415385.1 (Delphinapterus leucas); XP_024612931.1 (Neophocaena asiaeorientalis asiaeorientalis); XP_024612936.1 (Neophocaena asiaeorientalis asiaeorientalis); XP_007171806.1 (Balaenoptera acutorostrata scammoni); XP_007171808.1 (Balaenoptera acutorostrata scammoni); XP_019787995.1 (Tursiops truncatus); XP_024612923.1 (Neophocaena asiaeorientalis asiaeorientalis); XP_019787989.1 (Tursiops truncatus); XP_024612934.1 (Neophocaena asiaeorientalis asiaeorientalis); XP_007467166.1 (Lipotes vexillifer); XP_017586645.1 (Corvus brachyrhynchos); XP_011825761.1 (Mandrillus leucophaeus); NP_001171644.1 (Homo sapiens); XP_016855705.1 (Homo sapiens); XP_011813026.1 (Colobus angolensis palliatus); BAG64907.1 (Homo sapiens); XP_003811925.1 (Pan paniscus); XP_010359046.1 (Rhinopithecus roxellana); XP_004027766.1 (Gorilla gorilla gorilla); XP_002809964.1 (Pongo abelii); XP_018086990.1 (Xenopus laevis); XP_003258761.1 (Nomascus leucogenys); XP_023971762.1 (Physeter catodon); XP_019788157.1 (Tursiops truncatus); XP_020835229.1 (Phascolarctos cinereus); XP_012494972.1 (Propithecus coquereli); XP_020835226.1 (Phascolarctos cinereus); XP_012604664.1 (Microcebus murinus); XP_012604667.1 (Microcebus murinus); XP_012604665.1 (Microcebus murinus); XP_012604663.1 (Microcebus murinus); XP_022271051.1 (Canis lupus familiaris); XP_005610015.1 (Equus caballus); XP_003795233.1 (Otolemur garnettii); XP_014703849.1 (Equus asinus); XP_023580905.1 (Trichechus manatus latirostris); XP_023580904.1 (Trichechus manatus latirostris); XP_005610014.1 (Equus caballus); XP_014703848.1 (Equus asinus); XP_012039867.1 (Ovis aries); XP_012013962.1 (Ovis aries musimon); XP_004003766.2 (Ovis aries); XP_012013961.1 (Ovis aries musimon); XP_008262436.1 (Oryctolagus cuniculus); XP_005677269.2 (Capra hircus); XP_008767977.1 (Rattus norvegicus); XP_008767979.1 (Rattus norvegicus); XP_014652548.1 (Ceratotherium simum simum); XP_008767975.1 (Rattus norvegicus); XP_014652547.1 (Ceratotherium simum simum); XP_008767978.1 (Rattus norvegicus); NP_001178935.1 (Rattus norvegicus); XP_012863743.1 (Echinops telfairi); XP_015414139.1 (Myotis davidii); XP_006752907.1 (Myotis davidii); XP_010801104.1 (Bos taurus); XP_006047614.1 (Bubalus bubalis); XP_023972011.1 (Physeter catodon); XP_010845208.1 (Bison bison bison); XP_023972010.1 (Physeter catodon); XP_023972009.1 (Physeter catodon); XP_012039857.1 (Ovis aries); XP_012013960.1 (Ovis aries musimon); XP_004589149.1 (Ochotona princeps); EFB27748.1 (Ailuropoda melanoleuca); XP_005368642.1 (Microtus ochrogaster); XP_004589148.1 (Ochotona princeps); XP_014947204.1 (Ovis aries); XP_017525245.1 (Manis javanica); XP_004589147.1 (Ochotona princeps); ELK26146.1 (Myotis davidii); XP_016855704.1 (Homo sapiens); XP_021517989.1 (Meriones unguiculatus); EHB13660.1 (Heterocephalus glaber); XP_019573705.1 (Rhinolophus sinicus); XP_016070886.1 (Miniopterus natalensis); XP_006895600.1 (Elephantulus edwardii); XP_022415389.1 (Delphinapterus leucas); XP_015310289.1 (Macaca fascicularis); XP_019788005.1 (Tursiops truncatus); XP_022415387.1 (Delphinapterus leucas); XP_013852309.1 (Sus scrofa); XP_001925632.2 (Sus scrofa); XP_024612940.1 (Neophocaena asiaeorientalis asiaeorientalis); XP_005640937.1 (Canis lupus familiaris); XP_014402831.1 (Myotis brandtii); XP_014402856.1 (Myotis brandtii); XP_015995086.1 (Rousettus aegyptiacus); XP_013966756.1 (Canis lupus familiaris); XP_023394076.1 (Pteropus vampyrus); XP_001928602.1 (Sus scrofa); XP_022414974.1 (Delphinapterus leucas); XP_012664021.1 (Otolemur garnettii); XP_008542385.1 (Equus przewalskii); XP_020835227.1 (Phascolarctos cinereus); XP_019573708.1; (Rhinolophus sinicus); XP_006060357.1 (Bubalus bubalis); XP_006060359.1 (Bubalus bubalis); XP_014402867.1 (Myotis brandtii); XP_013966757.1 (Canis lupus familiaris); XP_019573706.1 (Rhinolophus sinicus); XP_005640943.1 (Canis lupus familiaris); XP_010953947.1 (Camelus bactrianus); XP_014417656.1 (Camelus ferus); XP_014417655.1 (Camelus ferus); XP_010991393.1 (Camelus dromedarius); XP_005640945.1 (Canis lupus familiaris); XP_005640944.1 (Canis lupus familiaris); XP_013966770.1 (Canis lupus familiaris); XP_014417660.1 (Camelus ferus); XP_010991394.1 (Camelus dromedarius); XP_010953948.1 (Camelus bactrianus); XP_007974663.1 (Chlorocebus sabaeus); XP_015310241.1 (Macaca fascicularis); XP_011768404.1 (Macaca nemestrina); XP_009183246.1 (Papio anubis); XP_023580887.1 (Trichechus manatus latirostris); XP_014969055.1 (Macaca mulatta); XP_009322221.1 (Pygoscelis adeliae); XP_011813005.1 (Colobus angolensis palliatus); XP_011822581.1 (Mandrillus leucophaeus);

XP_019573716.1 (*Rhinolophus sinicus*); XP_023971915.1 (*Physeter catodon*); XP_013852311.1 (*Sus scrofa*); XP_013852310.1 (*Sus scrofa*); XP_015414151.1 (*Myotis davidii*); XP_017720360.1 (*Rhinopithecus bieti*); XP_021087566.1 (*Mesocricetus auratus*); XP_014454476.1 (*Alligator mississippiensis*); XP_008283876.1 (*Stegastes partitus*); XP_008283878.1 (*Stegastes partitus*); XP_008283875.1 (*Stegastes partitus*); XP_019331566.1 (*Alligator mississippiensis*); XP_010614950.1 (*Fukomys damarensis*); XP_008962506.1 (*Pan paniscus*); PNI19771.1 (*Pan troglodytes*); XP_009240306.1 (*Pongo abelii*); XP_020835233.1 (*Phascolarctos cinereus*); XP_020835233.1 (*Phascolarctos cinereus*); XP_013852323.1 (*Sus scrofa*); XP_015414158.1 (*Myotis davidii*); XP_006168884.1 (*Tupaia chinensis*); XP_018941649.1 (*Cyprinus carpio*); XP_007543071.1 (*Poecilia formosa*); XP_013985041.1 (*Salmo salar*); XP_013225469.1 (*Columba livia*); XP_013985042.1 (*Salmo salar*); XP_013985043.1 (*Salmo salar*); XP_014373071.1 (*Alligator sinensis*); XP_010565948.1 (*Haliaeetus leucocephalus*); XP_009911139.1 (*Haliaeetus albicilla*); XP_021470526.1 (*Oncorhynchus mykiss*); XP_011581572.1 (*Aquila chrysaetos canadensis*); NP_001269521.1 (*Homo sapiens*); XP_003811918.1 (*Pan paniscus*); PNI19778.1 (*Pan troglodytes*); XP_011508131.1 (*Homo sapiens*); XP_002809958.1 (*Pongo abelii*); XP_007974661.1 (*Chlorocebus sabaeus*); XP_010359034.1 (*Rhinopithecus roxellana*); XP_017720381.1 (*Rhinopithecus bieti*); XP_003938008.1 (*Saimiri boliviensis boliviensis*); XP_012305078.1 (*Aotus nancymaae*); XP_008982992.1 (*Callithrix jacchus*); XP_017359081.1 (*Cebus capucinus imitator*); XP_021568382.1 (*Carlito syrichta*); EDL94662.1 (*Rattus norvegicus*); XP_014439787.1 (*Tupaia chinensis*); XP_014417665.1 (*Camelus ferus*); XP_010991395.1 (*Camelus dromedarius*); XP_010991395.1 (*Falco cherrug*); XP_020835877.1 (*Phascolarctos cinereus*); XP_017901855.1 (*Capra hircus*); AAD04232.1 (*Homo sapiens*); XP_020945215.1 (*Sus scrofa*); XP_003125709.1 (*Sus scrofa*); XP_011923004.1 (*Cercocebus atys*); XP_021781456.1 (*Papio anubis*); XP_019061941.1 (*Fukomys damarensis*); XP_023680218.1 (*Paramormyrops kingsleyae*); XP_010614951.1 (*Fukomys damarensis*); AAH11154.1 (*Mus musculus*); XP_021087572.1 (*Mesocricetus auratus*); XP_020760145.1 (*Odocoileus virginianus texanus*); XP_018875530.1 (*Gorilla gorilla gorilla*); XP_006990659.1 (*Peromyscus maniculatus bairdii*); XP_023580908.1 (*Trichechus manatus latirostris*); XP_006080977.1 (*Bubalus bubalis*); XP_005892145.1 (*Bos mutus*); XP_019813884.1 (*Bos indicus*); XP_021537573.1 (*Neomonachus schauinslandi*); XP_015864364.1 (*Peromyscus maniculatus bairdii*); XP_008698897.1 (*Ursus maritimus*); XP_004442859.1 (*Ceratotherium simum simum*); XP_017531823.1 (*Manis javanica*); XP_019333848.1 (*Alligator mississippiensis*); XP_019412329.1 (*Crocodylus porosus*); XP_005466533.2 (*Oreochromis niloticus*); XP_007543068.1 (*Poecilia formosa*); XP_020512419.1 (*Labrus bergylta*); XP_007543070.1 (*Poecilia formosa*); XP_020516659.1 (*Labrus bergylta*); XP_016333239.1 (*Sinocyclocheilus anshuiensis*); XP_020515109.1 (*Labrus bergylta*); XP_020515648.1 (*Labrus bergylta*); XP_020514064.1 (*Labrus bergylta*); XP_020516832.1 (*Labrus bergylta*); XP_016404370.1 (*Sinocyclocheilus rhinocerous*); KYO22596.1 (*Alligator mississippiensis*); XP_024229211.1 (*Oncorhynchus tshawytscha*); OCT58277.1 (*Xenopus laevis*); KYO22595.1 (*Alligator mississippiensis*); XP_020359665.1 (*Oncorhynchus kisutch*); XP_016395978.1 (*Sinocyclocheilus rhinocerous*); XP_009945591.1 (*Leptosomus discolor*); NP_001289596.1 (*Callithrix jacchus*); XP_007945984.1 (*Orycteropus afer afer*); XP_012305085.1 (*Aotus nancymaae*); XP_015347473.1 (*Marmota marmota marmota*); XP_015347474.1 (*Marmota marmota marmota*); XP_023409942.1 (*Loxodonta africana*); XP_022415390.1 (*Delphinapterus leucas*); XP_009240361.1 (*Pongo abelii*); XP_008962514.1 (*Pan paniscus*); PNI19764.1 (*Pan troglodytes*); NP_001171810.1 (*Homo sapiens*); XP_017359090.1 (*Cebus capucinus imitator*); XP_014969047.1 (*Macaca mulatta*); XP_006215798.1 (*Vicugna pacos*); XP_008982991.1 (*Callithrix jacchus*); XP_011822683.1 (*Mandrillus leucophaeus*); XP_012393963.1 (*Orcinus orca*); XP_011768391.1 (*Macaca nemestrina*); XP_005541302.1 (*Macaca fascicularis*); XP_011813022.1 (*Colobus angolensis palliatus*); AAA92623.1 (*Homo sapiens*); XP_004027777.1 (*Gorilla gorilla gorilla*); XP_004027776.1 (*Gorilla gorilla gorilla*); NP_001248385.1 (*Homo sapiens*); XP_011923005.1 (*Cercocebus atys*); EAW52696.1 (*Homo sapiens*); AAG14995.1 (*Homo sapiens*); NP_002339.2 (*Homo sapiens*); XP_016856790.1 (*Homo sapiens*); XP_006744488.1 (*Leptonychotes weddellii*); XP_012393964.1 (*Orcinus orca*); XP_006895597.1 (*Elephantulus edwardii*); XP_012393962.1 (*Orcinus orca*); XP_007974676.1 (*Chlorocebus sabaeus*); XP_002809956.2 (*Pongo abelii*); PNJ57044.1 (*Pongo abelii*); PNJ57047.1 (*Pongo abelii*); XP_003775564.2 (*Pongo abelii*); XP_004407986.1 (*Odobenus rosmarus divergens*); XP_004407986.1 (*Papio anubis*); XP_003949665.2 (*Pan troglodytes*); XP_001172413.2 (*Pan troglodytes*); XP_009434044.2 (*Pan troglodytes*); XP_009434054.2 (*Pan troglodytes*); XP_016786048.2 (*Pan troglodytes*); XP_016786062.2 (*Pan troglodytes*); XP_003811915.1 (*Pan paniscus*); XP_016786047.2 (*Pan troglodytes*); XP_003811916.1 (*Pan paniscus*); XP_008982954.2 (*Callithrix jacchus*); XP_017902030.1 (*Capra hircus*); XP_019573707.1 (*Rhinolophus sinicus*); XP_005462585.2 (*Oreochromis niloticus*); XP_019214968.1 (*Oreochromis niloticus*); XP_019214970.1 (*Oreochromis niloticus*); XP_019214969.1 (*Oreochromis niloticus*); XP_012039927.1 (*Ovis aries*); XP_004002724.1 (*Ovis aries*); XP_012039930.1 (*Ovis aries*); XP_016146291.1 (*Sinocyclocheilus grahami*); XP_020346965.1 (*Oncorhynchus kisutch*); XP_023496647.1 (*Equus caballus*); XP_017720380.1 (*Rhinopithecus bieti*); XP_015310251.1 (*Macaca fascicularis*); XP_020029922.1 (*Castor canadensis*); XP_020029924.1 (*Castor canadensis*); XP_020041104.1 (*Castor canadensis*); XP_010953956.1 (*Camelus bactrianus*); XP_010991383.1 (*Camelus dromedarius*); XP_019288817.1 (*Panthera pardus*); XP_006174053.1 (*Camelus ferus*); XP_011813001.1 (*Colobus angolensis palliatus*); XP_011813000.1 (*Colobus angolensis palliatus*); XP_017720383.1 (*Rhinopithecus bieti*); XP_017720382.1 (*Rhinopithecus bieti*); XP_023070031.1 (*Piliocolobus tephrosceles*); XP_005311297.2 (*Chrysemys picta bellii*); XP_024606222.1 (*Neophocaena asiaeorientalis asiaeorientalis*); OCT69321.1 (*Xenopus laevis*); XP_015347484.1 (*Marmota marmota marmota*); OPJ66522.1 (*Patagioenas fasciata monilis*); EFB22045.1 (*Ailuropoda melanoleuca*); XP_020029926.1 (*Castor canadensis*); XP_020029925.1 (*Castor canadensis*); XP_004718131.1 (*Echinops telfairi*); XP_010953960.1 (*Camelus bactrianus*); XP_008056922.1 (*Carlito syrichta*); XP_007171809.1 (*Balaenoptera acutorostrata scammoni*); XP_017370630.1 (*Cebus capucinus imitator*); XP_017370628.1 (*Cebus capucinus imitator*);

XP_017370627.1 (Cebus capucinus imitator); XP_017370626.1 (Cebus capucinus imitator); XP_010991386.1 (Camelus dromedarius); XP_020945216.1 (Sus scrofa); XP_020945217.1 (Sus scrofa); XP_020945220.1 (Sus scrofa); XP_015104577.1 (Vicugna pacos); XP_014417692.1 (Camelus ferus); XP_012403448.1 (Sarcophilus harrisii); XP_014703854.1 (Equus asinus); XP_023496627.1 (Equus caballus); ELV10576.1 (Tupaia chinensis); BAC41061.1 (Mus musculus); XP_008839079.2 (Nannospalax galili); XP_012403468.1 (Sarcophilus harrisii); XP_012584360.1 (Condylura cristata); XP_023955649.1 (Chrysemys picta bellii); XP_008943056.1 (Merops nubicus); XP_006036148.1 (Alligator sinensis); XP_019214976.1 (Oreochromis niloticus); XP_016430881.1 (Sinocyclocheilus rhinocerous); XP_017544283.1 (Pygocentrus nattereri); XP_008925947.2 (Manacus vitellinus); ELK03349.1 (Pteropus alecto); XP_021576808.1 (Ictidomys tridecemlineatus); NP_001289586.1 (Pan troglodytes); PNI19703.1 (Pan troglodytes); XP_006744491.1 (Leptonychotes weddellii); OWK04929.1 (Cervus elaphus hippelaphus); NP_001289585.1 (Pan paniscus); XP_010953958.1 (Camelus bactrianus); ELR58996.1 (Bos mutus); NP_001289591.1 (Bos taurus); NP_001289590.1 (Ovis aries); XP_010836168.1 (Bison bison bison); XP_010836166.1 (Bison bison bison); XP_010836163.1 (Bison bison bison); XP_010836161.1 (Bison bison bison); XP_010836162.1 (Bison bison bison); XP_015104576.1 (Vicugna pacos); XP_016856793.1 (Homo sapiens); XP_012305073.1 (Aotus nancymaae); XP_012305072.1 (Aotus nancymaae); EAW52698.1 (Homo sapiens); EAW52700.1 (Homo sapiens); EAW52697.1 (Homo sapiens); XP_006096972.1 (Myotis lucifugus); XP_016856788.1 (Homo sapiens); XP_011507851.1 (Homo sapiens); XP_014417690.1 (Camelus ferus); XP_016856789.1 (Homo sapiens); XP_011507850.1 (Homo sapiens); XP_011507854.1 (Homo sapiens); XP_016856787.1 (Homo sapiens); XP_011507852.1 (Homo sapiens); XP_016856786.1 (Homo sapiens); XP_019843266.1 (Bos indicus); XP_019843256.1 (Bos indicus); XP_012584421.1 (Condylura cristata); XP_012393965.1 (Orcinus orca); XP_010845171.1 (Bison bison bison); XP_010801071.1 (Bos taurus); XP_005203568.1 (Bos taurus); XP_010801069.1 (Bos taurus); XP_010801068.1 (Bos taurus); XP_005203567.1 (Bos taurus); XP_020835264.1 (Phascolarctos cinereus); XP_012028310.1 (Ovis aries); EMP31355.1 (Chelonia mydas); XP_006922951.1 (Pteropus alecto); XP_023394074.1 (Pteropus vampyrus); XP_021781503.1 (Papio anubis); XP_021781478.1 (Papio anubis); XP_005233216.1 (Falco peregrinus); OXB70583.1 (Colinus virginianus); XP_005515144.2 (Columba livia); XP_021138498.1 (Columba livia); NP_001269519.1 (Homo sapiens); BAF84786.1 (Homo sapiens); PNI19777.1 (Pan troglodytes); NP_001269523.1 (Homo sapiens); PNI19772.1 (Pan troglodytes); XP_009240297.1 (Pongo abelii); XP_008962504.1 (Pan paniscus); XP_009240301.1 (Pongo abelii); XP_008962505.1 (Pan paniscus); XP_012367033.1 (Nomascus leucogenys); XP_012367032.1 (Nomascus leucogenys); NP_001269520.1 (Homo sapiens); XP_009240320.1 (Pongo abelii); XP_011822605.1 (Mandrillus leucophaeus); XP_008962509.1 (Pan paniscus); XP_012367035.1 (Nomascus leucogenys); XP_011822598.1 (Mandrillus leucophaeus); XP_011822619.1 (Mandrillus leucophaeus); XP_010359041.1 (Rhinopithecus roxellana); XP_015397637.1 (Panthera tigris altaica); XP_015397638.1 (Panthera tigris altaica); XP_015397639.1 (Panthera tigris altaica); XP_007092439.1 (Panthera tigris altaica); XP_012604650.1 (Microcebus murinus); XP_019288813.1 (Panthera pardus); XP_019288812.1 (Panthera pardus); XP_019288811.1 (Panthera pardus); XP_019288810.1 (Panthera pardus); XP_019288814.1 (Panthera pardus); XP_014336332.1 (Bos mutus); XP_014336333.1 (Bos mutus); XP_015310282.1 (Macaca fascicularis); XP_017720384.1 (Rhinopithecus bieti); XP_017720385.1 (Rhinopithecus bieti); XP_011923003.1 (Cercocebus atys); XP_012604651.1 (Microcebus murinus); BAG64457.1 (Homo sapiens); XP_021502756.1 (Meriones unguiculatus); XP_008698898.1 (Ursus maritimus); XP_012604653.1 (Microcebus murinus); XP_021781450.1 (Papio anubis); XP_011813002.1 (Colobus angolensis palliatus); NP_001248386.1 (Homo sapiens); XP_014931700.1 (Acinonyx jubatus); XP_014931698.1 (Acinonyx jubatus); XP_009434069.1 (Pan troglodytes); XP_001172348.2 (Pan troglodytes); XP_016786077.1 (Pan troglodytes); XP_016786072.1 (Pan troglodytes); XP_011822716.1 (Mandrillus leucophaeus); XP_006943095.1 (Felis catus); XP_003811914.1 (Pan paniscus); XP_003775563.2 (Pongo abelii); XP_019677869.1 (Felis catus); XP_006943094.1 (Felis catus); PNJ57046.1 (Pongo abelii); XP_019677870.1 (Felis catus); XP_021794464.1 (Papio anubis); XP_004089893.2 (Nomascus leucogenys); XP_011922986.1 (Cercocebus atys); XP_005545217.1 (Macaca fascicularis); EHB13659.1 (Heterocephalus glaber); XP_014968783.1 (Macaca mulatta); XP_005962534.1 (Pantholops hodgsonii); OCA27161.1 (Xenopus tropicalis); XP_017952176.1 (Xenopus tropicalis); XP_006115307.1 (Pelodiscus sinensis); XP_016333238.1 (Sinocyclocheilus anshuiensis); XP_010614946.1 (Fukomys damarensis); XP_016430879.1 (Sinocyclocheilus rhinocerous); XP_010614948.1 (Fukomys damarensis); NP_001178602.1 (Rattus norvegicus); XP_008767954.1 (Rattus norvegicus); KFO18142.1 (Fukomys damarensis); XP_010614957.1 (Fukomys damarensis); XP_014703856.1 (Equus asinus); XP_005610010.2 (Equus caballus); XP_023496629.1 (Equus caballus); XP_008542382.1 (Equus przewalskii); XP_024606449.1 (Neophocaena asiaeorientalis asiaeorientalis); XP_019505130.1 (Hipposideros armiger); XP_019505129.1 (Hipposideros armiger); EDL39066.1 (Mus musculus); XP_014426752.1 (Pelodiscus sinensis); XP_023103234.1 (Felis catus); XP_015393945.1 (Panthera tigris altaica); XP_019288711.1 (Panthera pardus); XP_016355521.1 (Sinocyclocheilus anshuiensis); XP_016355523.1 (Sinocyclocheilus anshuiensis); XP_005141108.2 (Melopsittacus undulatus); XP_006861823.1 (Chrysochloris asiatica); XP_007171813.1 (Balaenoptera acutorostrata scammoni); XP_022415231.1 (Delphinapterus leucas); EPY88990.1 (Camelus ferus); XP_020835235.1 (Phascolarctos cinereus); XP_017370632.1 (Cebus capucinus imitator); XP_023580910.1 (Trichechus manatus latirostris); XP_023580912.1 (Trichechus manatus latirostris); and EFB22049.1 Ailuropoda melanoleuca).

TABLE 2

CRACC nucleic acid sequences
Noted in bolded and underlined are the
nucleotide sequences coding for the ECD SEQ ID NO: 12 is an exemplary nucleic acid sequence for a full-length, human CRACC.
(ECD corresponds to nucleotides 69 to 678)
atggctggtt cccccaacatg cctcacccctc atctatatcc tttggcagct cacagggtca gcagcctctg gacccgtgaa agagctggtc ggttccgttg gtggggccgt gactttcccc ctgaagtcca aagtaaagca agttgactct attgtctgga ccttcaacac aaccccctctt gtcaccatac agccagaagg gggcactatc atagtgaccc aaaatcgtaa tagggagaga gtagacttcc cagatggagg ctactccctg aagctcagca aactgaagaa gaatgactca gggatctact atgtggggat atacagctca tcactccagc agccctccac ccaggagtac gtgctgcatg tctacgagca cctgtcaaag cctaaagtca ccatgggtct gcagagcaat aagaatggca cctgtgtgac caatctgaca tgctgcatgg aacatgggga agaggatgtg atttatacct ggaaggccct ggggcaagca gccaatgagt cccataatgg gtccatcctc cccatctcct ggagatgggg agaaagtgat atgaccttca tctgcgttgc caggaaccct gtcagcagaa acttctcaag ccccatcctt gccaggaagc tctgtgaagg tgctgctgat gacccagatt cctccatggt cctcctgtgt ctcctgttgg tgcccctcct gctcagtctc tttgtactgg ggctatttct ttggtttctg aagagagaga gacaagaaga gtacattgaa gagaagaaga gagtggacat ttgtcgggaa actcctaaca tatgcccca ttctggagag aacacagagt acgacacaat ccctcacact aatagaacaa tcctaaagga gatccagca aatacggttt actccactgt ggaaataccg aaaaagatgg aaaatcccca ctcactgctc acgatgccag acacaccaag gctatttgcc tatgagaatg ttatctag SEQ ID NO: 13 is an exemplary nucleic acid sequence for a full-length, *Rhesus
macaque* CRACC. (ECD corresponds to nucleotides 69 to 678)
atggctggtt cccccaacatg cttcacccttc atctatatcc tttggcagct cacagggtca acagcctctg gatccgtgaa agagctggtc ggttccattg gtggggctgt gactttcccc ctgaagtctg aagtaaagca agttgactct attgtctgga ccttcaacac aaccactctt gtcaccatac agccagaagg gggccctatg atagtgaccc aaaatcgtaa taaggagaga gtacacttcc cagatggagg ctattccctg aagctcagca aactgaagaa gaatgactca gggatctaca atgtggagat atacagctca tccctccagg atcccttcac ccggaagtat gtgctgcgtg tctacgagca cctgtcaaag cctaaagtca ccatgggtct acagagtaat aagaatggca cctgtgtgac caatctgaca tgccacatgg aacatgggga agaggatgtg atttatacct ggaaggccct ggggcaagca gtcaatgagt cccataatgg gtccatccta cccatctcct ggagatgggg agaaagtgat atgaccttca tctgcactgt caggaaccct gtcagcagca actcctcaag ccccatcctt gccaggaagc tctgtgaagg tgctgctgat gactcagatt cctccatggt cctcctgtgt ctcctgttgg tgcccctcct gctcagtctc tttgtactgg ggctatttct ttggtttctg aagagagaga cacaagaaga gtccattgaa gagaagaaga gagcggacat ttgtcgggaa actcctaaca tatgcccta ttctggagag aacacagagt atgacacaat cccttacact aatagaacta tcccaatgga agacgcagca aatacacttt attccactgt ggaaatacca aaaaagattg aaaatcccca ctcactgctc acgatgccag acacaccaag gctatttgcc tatgagaatg ttatctag SEQ ID NO: 14 is an exemplary nucleic acid sequence for a full-length,
Chimpanzee CRACC. (ECD corresponds to nucleotides 69 to 678)
atggctggtt cccccaacatg cctcacccctc atctatatcc tttggcagct cacagggtca gcagcctctg gacctgtgag agagctggtc ggttccgttg gtggggccgt gactttcccc ctgaagtcca aagtaaagca agttgactct attgtctgga ccttcaacac aaccccctctt gtcaccatac agccggaagg gggcactatc atagtgaccc aaaatcgtaa taggagaga gtagacttcc cagatggagg ctactccctg aagctcagca aactgaagaa gaatgactca gggatctact atgtggggat atacagctca tcactccagc agccctccac ccagaagtac gtgctgcatg tctacgagca cctgtcaaag cctaaagtca ccatgggtct gcagagcaat aagaatggca cctgtgtgac caatctgaca tgctgcatgg aacatgggga agaggatgtg atttatacct ggaaggccct

TABLE 2-continued

CRACC nucleic acid sequences
Noted in bolded and underlined are the
nucleotide sequences coding for the ECD ggggcaagca gccaacgagt cccataatgg gtccatcctc cccatctcct ggagatgggg agaaagtgat atgaccttca tctgcgttgc caggaaccct gtcagcagca acttctcaag ccccatcctt gccaggaagc tctgtgaagg tgctgctgat gacccagatt cctccatggt cctcctgtgt ctcctgttgg tgccctcct gctcagtctc tttgtactgg ggctatttct ttggtttctg aagagagaga gacaagaaga gtccattgaa gagaagaaga gagcagacat ttgtcgggaa actcctaaca tatgccccca ttctggagag aacacagagt acgacacaat ccctcacact aatagaacaa tcctaaagga agatccagca aatacagttt actccactgt ggaaatacca aaaaagatgg aaaatcccca ctcactgctc acgatgccag acacaccaag gctatttgcc tatgagaatg ttatctag SEQ ID NO: 15 is an exemplary nucleic acid sequence for a full-length, murine
CRACC. (ECD corresponds to nucleotides 69 to 678)
atggctcgtt tctcaacgta catcatcttt acctctgtcc tctgtcagct aacagtcaca gcagcttctg gaactctgaa gaaggtggcc ggtgcccttg atggatctgt gacattcact ctgaatatca ctgaaataaa ggttgactat gttgtatgga cgttcaacac attctttctt gccatggtaa aaaaagacgg cgttacatca caaagtagta acaaagaaag gatagtcttt ccagatggac tctactccat gaagctcagc caattgaaga agaatgactc tggagcctac cgtgcagaga tttacagtac atcgagtcag gcttccttaa tccaggagta tgcgctgcat gtctacaagc atttgtcaag gcccaaggtc accatagatc ggcaaagcaa caagaatggc acctgcgtaa tcaatctgac atgttccacg gatcaggacg gggagaatgt aacctacagc tggaaagctg tggggcaggg ggacaatcag tttcatgatg gtgccaccct ctccatcgcc tggagatcag gagagaaaga ccaggcctta acatgcatgg ccaggaatcc agtcagcaac agtttctcaa ccccgtctt tccccagaag ctctgtgaag atgctgccac ggatctaact tcactcaggg gcatcctata catcctgtgc ttctcagcag tgctcatcct atttgctgtc ttgctgacta tttttcatac tatgtggata agaaaggaa aaggatgtga ggaagacaag aagagagtgg acaggcacca ggaaatgccc gacttgtgcc ctcacttaga ggagaacgca gactatgaca caatcccctta cacggaaaaa agaagaccag aagaagatgc accaaacaca ttttattcca ctgtgcagat ccccaaagtg gtaagaagct gtccagctga gcatcatctt acttgccaac cccttttccct ggatcatgct cgggctcaga tttcttag SEQ ID NO: 16 is an exemplary nucleic acid sequence for a full-length, canine
CRACC. (ECD corresponds to nucleotides 69 to 678)
atgcttgttc ccccagcgca cttcaccatt ttctttctcc tcttcagct cacagggcca gtaacctctg gagctctgaa ggagctagtt ggtgaccttg gtgggtctgt gactttccct ctgacgctcc caggaattca gattgacagc attgtctgga ccttcaacac aaccccctc atcaccatac aaccaagaac gccagacaga caagccaatg tcatagtgac ccacagtcat aataagaaaa gggtggattt cctacatgga aactactccc tgaagctcag caaactgaat aagagtgact cgggtgacta ctacgtggtg atatacagct cttccttcaa agagcccttc agccagcggt atgggctgcg tgtctatgag cacctatcaa agcccaaggt taccatgggt ctgcagaaca aagagaatgg cacctgtgtg actaatttga cctgcttcgt ggaccaggga ggagaggatg tgacctacag ctgggagtcc ctggggcagg cagccaataa gtcctataat ggctccatcc tccccatatc ctggaggctg gggaaagggg gcatgacctt catctgcgtg gccaggaacc ccatcagcag caattcttca aatcctgtct ttgcctggaa gctctgtgaa ggtgctgctg atgactccga atcctccgtg gtcctgtact tcctgggggc gttgctcttc atgctcactg cctttaccct ggtgccattt attctgtta tgcggagaga aagaagaaa gagtccattg aagagaagaa gggaatggat actcatcagg aaattcttaa ctactatccc ccttctggag agacccccagt gtatgacaca atcagttgtg ttaataactg tattccagaa gaaaattctg caaatacact ttatttctct gtgcaaatac ccccaaagat ggagaaaccc cactctcccc ccacatcacc agacacacca aagtcatttg cctatgagaa cgtcatctaa TABLE 2-continued CRACC nucleic acid sequences
Noted in bolded and underlined are the
nucleotide sequences coding for the ECD SEQ ID NO: 17 is an exemplary amino acid sequence for a full-length, bos taurus
(cattle) CRACC. (ECD corresponds to nucleotides 63 to 672)
atgcttggtg ccccagcatg cttcatcttt ctcctctgcc agctcacagg gccagcagcc tctggaatcc caaagaagct ggttggtgcc attggtgggt ctgtgattt ccctctgaat ctctcagtaa atctagttga cagcattatc tgggtcttca attcaaccac tctcgttacc atacagccaa aaacagcagg caaaaaagcc cttgtcatag tgacccaaaa gcgtaacttg gaaagagtga atttcccaca tgaaggctac tccctgaagc tcagcagact gaagaagaac gactcaggta tctaccgtgt ggagatacac agctcaaccc tccaggatcc cctcacccag gagtatgagc tgcatgtcta tgagtacctg tcaaagccca aagtcgtcat aggtctgcag gagaataaga atggcacctg tgtaaccaat ctcacatgtt ccatggaaca tggagaagag gatgtaactt acagctggaa gtctctggac cagacaacca atgaatccca cagggctcc attctcccca tatcctggag gtgggagaaa agtgacatga ccttcatctg catggccagt aaccccatca gcagcaactc ctcaaaccct atctttgccc agaatctctg tgaaggtgct gctgggggcc aggctcccta cgtggtcctc tacgtcctgt tgtcgttctt cctgctctgt tccctcgcac tggtgttaat tatttttatc atacaaagag aaagaaaaaa agagatcatt gaagagaaga aggaactgga cactcatcag aaaactcttc ccttccctcc cattcctgaa gagatgcccg agtatgatac aatctctact tttaatggca ctattccaga ggaaaaccca gccaatacca tctattccac tgtgcacata gccccaaagg taacagaacc ctactccctg cccatgttgt cagatacacc aacggcatct atctataaca atgtcatgta a SEQ ID NO: 18 is an exemplary amino acid sequence for a full-length, rat CRACC.
(ECD corresponds to nucleotides 69 to 678)
atggctcgtt tctcgacaca catcatcttt acctctgtcc tctgccagct aacagtcaca gcagcttctg gaacgccaaa ggaggtggcc ggtgcccttg atggatctgt gacattcact ctgaatacta ctgaagtaaa agttgacagt gttgtatgga ccttcaagac actctttctt gccataataa ataaaaatgg taccatcaaa tcacaaagtt atgaagaaag gatagtcttt ttagatagac actccatgaa gctcagccag ctgaagaaga atgactctgg agactaccgt gcagagattc acattgcgtc aaattcactt tcatctccct tcatgcagga gtacgtgctg catgtccatg agcacctgtc aaggcccaag gtcaacacag attcgcaaag cagcaaggac ggcacctgca tcttaaatct gacatgttcc gtggaacggg gaggagagaa tgtgacatac agctggaaag ctgtgggaca gacagtcgat gagtttcatg acagtgccaa cctctccatc tcctggagac tgggagagaa agacaagacc ataatctgca cagccaggaa tccagtcagc agcagttcct caacccact cctcgcccag aagctctgta aagatgctgc caaggaccta aattcaccca gggtcctcaa atacattctg tgcgtcacac tagtgctcgt cctgttctgt atcctgctgg tgactattct ttttaggtgg ataccgaaag gaaaaggctt tgaggaagac aagaagagag tggacggcca ccaggaaatg tccaactctt gccctcactt ggagaacaca gactatgaca caatcccctta cacagaaaaa acgagaccag aagaagatgc gccaaacaca ctttattcca ctgtgcagat ccccaaagtg gatgcagggt ccaaatcctt tggagcttac atgatgatac cacatagcag gatgccagat acggagcttc aaggcttacg tctctctgcc aggttctga Included in Table 2 are variations of 1, 2, 3, 4, 5, 6, 7, 8, 9, 10, 11, 12, 13, 14, 15, 16, 17, 18, 19, 20, or more nucleotides on the 5' end, on the 3' end, or on both the 5' and 3' ends, of the nucleic acid sequences.

Included in Table 2 are RNA nucleic acid molecules (e.g., thymines replaced with uredines), nucleic acid molecules encoding orthologs of the encoded proteins, as well as DNA or RNA, nucleic acid molecules comprising, consisting essentially of, or consisting of:

1) a nucleotide sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NOs: 12-18, or a biologically active or inactive fragment thereof;

2) a nucleotide sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NOs: 12-18, or a biologically active or inactive fragment thereof, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within CRACC;

3) a nucleotide sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleotides;

4) a nucleotide sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within CRACC;

5) a biologically active fragment of an nucleotide sequence of SEQ ID NOs: 12-18 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids; or 6) a biologically active or inactive fragment of an nucleotide sequence of SEQ ID NOs: 12-18 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within CRACC.

Also included in Table 2 are the ECD of CRACC including, but no limited to, the sequences set for in the following GENBANK accession numbers. In some embodiments the ECDs are linked to an Fc portion, wherein the Fc portion may comprise the IgG1, IgG2, IgG3, or IgG4 Fc portion, such as the nucleotide sequence set forth in SEQ ID Nos: 24 and 25. NM_021181.4 (*Homo sapiens*); AY358512.1 (*Homo sapiens*); AF390894.1 (*Homo sapiens*); AF291815.1 (*Homo sapiens*); AB027233.1 (*Homo sapiens*); AK292148.1 (*Homo sapiens*); AJ276429.2 (*Homo sapiens*); XM_003811869.2 (*Pan paniscus*); XM_001172275.5 (*Pan troglodytes*); XM_004027721.2 (*Gorilla gorilla gorilla*); XM_002809911.4 (*Pongo abelii*); XM_007976468.1 (*Chlorocebus sabaeus*); XM_012067597.1 (*Cercocebus atys*); XM_005541237.2 (*Macaca fascicularis*); XM_001117618.3 (*Macaca mulatta*); XM_011770101.1 (*Macaca nemestrina*); XM_011957614.1 (*Colobus angolensis palliatus*); XM_010360731.1 (*Rhinopithecus roxellana*); XM_017864890.1 (*Rhinopithecus bieti*); XM_011967186.1 (*Mandrillus leucophaeus*); XM_003892935.4 (*Papio anubis*); XM_023214265.1 (*Piliocolobus tephrosceles*); XM_007976472.1 (*Chlorocebus sabaeus*); XM_012449654.2 (*Aotus nancymaae*); XM_003937958.2 (*Saimiri boliviensis boliviensis*); XM_002760177.3 (*Callithrix jacchus*); XM_017503591.1 (*Cebus capucinus*); XM_024448757.1 (*Homo sapiens*); XM_011509828.1 (*Homo sapiens*); XM_019025379.1 (*Gorilla gorilla gorilla*); XM_023214264.1 (*Piliocolobus tephrosceles*); XM_012639532.1 (*Propithecus coquereli*); XM_012749225.2 (*Microcebus murinus*); XM_008058704.1 (*Carlito syrichta*); AL121985.13 (human); XM_019649586.1 (*Hipposideros armiger*); XM_019718152.1 (*Rhinolophus sinicus*); XM_003795183.3 (*Otolemur garnettii*); XM_005857757.2 (*Myotis brandtii*); XM_022490700.1 (*Enhydra lutris kenyoni*); XM_004775880.2 (*Mustela putorius* furo); AK350925.1 (*Sus scrofa*); XM_005663187.3 (*Sus scrofa*); XM_007171750.1 (*Balaenoptera acutorostrata scammoni*); XM_006744420.1 (*Leptonychotes weddellii*); XM_008700677.1 (*Ursus maritimus*); XM_011236289.2 (*Ailuropoda melanoleuca*); XM_005609955.3 (*Equus caballus*); XM_008544162.1 (*Equus przewalskii*); XM_014797063.1 (*Ceratotherium simum simum*); XM_022559520.1 (*Delphinapterus leucas*); XM_022559519.1 (*Delphinapterus leucas*); XM_012538497.1 (*Orcinus orca*); XM_007467144.1 (*Lipotes vexillifer*); XM_004329418.2 (*Tursiops truncatus*); XM_022559522.1 (*Delphinapterus leucas*); XM_019932618.1 (*Tursiops truncatus*); XM_024757628.1 (*Neophocaena asiaeorientalis asiaeorientalis*); XM_024757621.1 (*Neophocaena asiaeorientalis asiaeorientalis*); XM_007124077.2 (*Physeter catodon*); XM_017676324.1 (*Manis javanica*); XM_010993087.1 (*Camelus dromedarius*); XM_010955650.1 (*Camelus bactrianus*); XM_015249014.1 (*Vicugna pacos*); XM_847365.4 (*Canis lupus familiaris*); XM_016930551.2 (*Pan troglodytes*); XM_019718154.1 (*Rhinolophus sinicus*); XM_019718153.1 (*Rhinolophus sinicus*); XM_011770102.2 (*Macaca nemestrina*); XM_015454755.1 (*Macaca fascicularis*); XM_009184982.3 (*Papio anubis*); XM_023640879.1 (*Equus caballus*); LT160000.1 (*Macaca fascicularis*); AC211795.5 (*Macaca mulatta*); XM_022559521.1 (*Delphinapterus leucas*); XM_011373050.2 (*Pteropus vampyrus*); XM_006922884.3 (*Pteropus alecto*); XM_011236290.2 (*Ailuropoda melanoleuca*); XM_008700678.1 (*Ursus maritimus*); XM_007976470.1 (*Chlorocebus sabaeus*); XM_011957615.1 (*Colobus angolensis palliatus*); XM_011967191.1 (*Mandrillus leucophaeus*); NM_001282592.1 (*Homo sapiens*); AK290706.1 (*Homo sapiens*); BC027867.1 (*Homo sapiens*); AJ271869.1 (*Homo sapiens*); XM_003811870.2 (*Pan paniscus*); XM_011509829.1 (*Homo sapiens*); XM_008984744.2 (*Callithrix jacchus*); XM_002809912.4 (*Pongo abelii*); XM_017503592.1 (*Cebus capucinus*); XM_010360732.1 (*Rhinopithecus roxellana*); XM_017864892.1 (*Rhinopithecus bieti*); EU832487.1 (*Homo sapiens*); LT737458.1 (Human); KJ903014.1 (*Homo sapiens*); EU832567.1 (*Homo sapiens*); XM_009435732.2 (*Pan troglodytes*); XM_019025385.1 (*Gorilla gorilla gorilla*); XM_007976471.1 (*Chlorocebus sabaeus*);

XM_012067599.1 (*Cercocebus atys*); XM_009184981.3 (*Papio anubis*); XM_019718155.1 (*Rhinolophus sinicus*); XM_011957616.1 (*Colobus angolensis palliatus*); XM_011967199.1 (*Mandrillus leucophaeus*); XM_016139655.1 (*Rousettus aegyptiacus*); XM_009435739.2 (*Pan troglodytes*); XM_007976473.1 (*Chlorocebus sabaeus*); XM_012449655.2 (*Aotus nancymaae*); XM_003937959.2 (*Saimiri boliviensis boliviensis*); XM_019718157.1 (*Rhinolophus sinicus*); XM_008544163.1 (*Equus przewalskii*); XM_012565062.1 (*Odobenus rosmarus divergens*); XM_008154235.1 (*Eptesicus fuscus*); XM_007171751.1 (*Balaenoptera acutorostrata scammoni*); XM_015454765.1 (*Macaca fascicularis*); XM_017864891.1 (*Rhinopithecus bieti*); XM_021712707.1 (*Carlito syrichta*); XM_015491993.1 (*Marmota marmota marmota*); NM_001282590.1 (*Homo sapiens*); AL834424.1 (*Homo sapiens*); AK292097.1 (*Homo sapiens*); XM_008964257.1 (*Pan paniscus*); XM_009242026.2 (*Pongo abelii*); XM_011957619.1 (*Colobus angolensis palliatus*); XM_011967215.1 (*Mandrillus leucophaeus*); NM_001282594.1 (*Homo sapiens*); AK301432.1 (*Homo sapiens*); XM_008964256.1 (*Pan paniscus*); XM_009242022.1 (*Pongo abelii*); XM_011957618.1 (*Colobus angolensis palliatus*); XM_011967208.1 (*Mandrillus leucophaeus*); AB590100.1 (*Homo sapiens*); AM392941.1 (*Homo sapiens*); XM_021089565.1 (*Sus scrofa*); XM_022559523.1 (*Delphinapterus leucas*); XM_019649588.1 (*Hipposideros armiger*); XM_005640883.2 (*Canis lupus familiaris*); NM_001282595.1 (*Homo sapiens*); XM_008964259.1 (*Pan paniscus*); XM_009242037.2 (*Pongo abelii*); XM_012511579.1 (*Nomascus leucogenys*); XM_012511578.1 (*Nomascus leucogenys*); XM_024757645.1 (*Neophocaena asiaeorientalis asiaeorientalis*); XM_024757636.1 (*Neophocaena asiaeorientalis asiaeorientalis*); XM_019718156.1 (*Rhinolophus sinicus*); NM_001282589.1 (*Homo sapiens*); AK298499.1 (*Homo sapiens*); XM_008964258.1 (*Pan paniscus*); XM_009242031.2 (*Pongo abelii*); XM_011967220.1 (*Mandrillus leucophaeus*); XM_011957620.1 (*Colobus angolensis palliatus*); XM_012951848.1 (*Jaculus jaculus*); XM_011957621.1 (*Colobus angolensis palliatus*); NM_001282596.1 (*Homo sapiens*); XM_008964260.1 (*Pan paniscus*); XM_009242042.2 (*Pongo abelii*); NM_001282591.1 (*Homo sapiens*); AK301438.1 (*Homo sapiens*); XM_009242045.2 (*Pongo abelii*); XM_008964261.1 (*Pan paniscus*); XM_011967229.1 (*Mandrillus leucophaeus*); XM_011957622.1 (*Colobus angolensis palliatus*); XM_012511580.1 (*Nomascus leucogenys*); NM_001282588.1 (*Homo sapiens*); AK298548.1 (*Homo sapiens*); XM_008964262.1 (*Pan paniscus*); XM_009242050.2 (*Pongo abelii*); XM_011957623.1 (*Colobus angolensis palliatus*); XM_012511581.1 (*Nomascus leucogenys*); XM_006752841.2 (*Myotis davidii*); NM_001282593.1 (*Homo sapiens*); AK301137.1 (*Homo sapiens*); XM_009242056.2 (*Pongo abelii*); XM_008964263.1 (*Pan paniscus*); XM_011957624.1 (*Colobus angolensis palliatus*); XM_015571559.1 (*Myotis davidii*); XM_012511582.1 (*Nomascus leucogenys*); XM_021712708.1 (*Carlito syrichta*); XM_005853069.1 (*Myotis brandtii*); XM_005853072.1 (*Myotis brandtii*); XM_021712710.1 (*Carlito syrichta*); and AL713801.1 (*Homo sapiens*).

As used herein "Fc region" or "Fc portion" refers to the Fc constant region or Fc constant portion. Such Fc regions or Fc portions may be derived from antibodies belonging to each of the immunoglobulin classes referred to as IgA, IgD, IgE, IgG (e.g., subclasses IgG1, IgG2, IgG3, and IgG4), and IgM. The choice of appropriate Fc regions is discussed in detail in U.S. Pat. Nos. 5,541,087, and 5,726,044, the disclosures of which are incorporated herein by reference in their entirety. Nucleic acid and amino acid sequence information for any Fc region are well known in the art and readily available on publicly available databases, such as the National Center for Biotechnology Information (NCBI).

For example, exemplary Fc region nucleic acid and amino acid sequences derived from publicly available sequence databases are provided below.

TABLE 3

| Fc constant region or Fc constant portion |
|---|
| SEQ ID NO: 19 is an exemplary amino acid sequence for a human IgG4 Fc constant region. ESKYGP PCPPCPAPEF EGGPSVFLFP PKPKDTLMIS RTPEVTCVVV DVSQEDPEVQ FNWYVDGVEV HNAKTKPREE QFNSTYRVVS VLTVLHQDWL NGKEYKCKVS NKGLPSSIEK TISKAKGQPR EPQVYTLPPS QEEMTKNQVS LTCLVKGFYP SDIAVEWESN GQPENNYKTT PPVLDSDGSF FLYSRLTVDK SRWQEGNVFS PSVMHEALHN HYTQKSLSLS LGK |
| SEQ ID NO: 20 is an exemplary amino acid sequence for a mouse IgG1 Fc constant region. GGCKPCICT VPEVSSVFIF PPKPKDVLTI TLTPKVTCVV VDISKDDPEV QFSWFVDDVE VHTAQTQPRE EQFNSTFRSV SELPIMHQDW LNGKEFKCRV NSAAFPAPIE KTISKTKGRP KAPQVYTIPP PKEQMAKDKV SLTCMITDFF PEDITVEWQW NGQPAENYKN TQPIMDTDGS YFVYSKLNVQ KSNWEAGNTF TCSVLHEGLH NHHTEKSLSH SPGK |
| Human IgG1 Fc comprising the amino acid sequence of: TCPPCPAPELLGGPSVFLFPPKPKDTLMISRTPEVTCVVVDVSH EDPEVKFNWYVDGVEVHNAKTKPREEQYNSTYRVVSVLTVLHQD WLNGKEYKCKVSNKALPAPIEKTISKAKGQPREPQVYTLPPSRD ELTKNQVSLTCLVKGFYPSDIAVEWESNGQPENNYKTTPPVLDS DGPFFLYSKLTVDKSRWQQGNVFSCSVMHEALHNHYTQKSLSLS PGK (Genbank AF150959.1) |
| AF150959.1 *Homo sapiens* immunoglobulin G1 Fc fragment mRNA comprising the nucleotide sequence of: ACATGCCCACCGTGCCCAGCACCTGAACTCCTGGGGGACCGTC AGTCTTCCTCTTCCCCCCAAAACCCAAGGACACCCTCATGATCT CCCGGACCCCTGAGGTCACATGCGTGGTGGTGGACGTGAGCCAC GAAGACCCTGAGGTCAAGTTCAACTGGTACGTGGACGGCGTGGA GGTGCATAATGCCAAGACAAAGCCGCGGGAGGAGCAGTACAACA GCACGTACCGTGTGGTCAGCGTCCTCACCGTCCTGCACCAGGAC TGGCTGAATGGCAAGGAGTACAAGTGCAAGGTCTCCAACAAAGC CCTCCCAGCCCCCATCGAGAAAACCATCTCCAAAGCCAAAGGGC AGCCCCGAGAACCACAGGTGTACACCCTGCCCCCATCCCGGGAT |

TABLE 3-continued

Fc constant region or Fc constant portion

GAGCTGACCAAGAACCAGGTCAGCCTGACCTGCCTGGTCAAAGG

CTTCTATCCCAGCGACATCGCCGTGGAGTGGGAGAGCAATGGGC

AGCCGGAGAACAACTACAAGACCACGCCTCCCGTGCTGGACTCC

GACGGCCCCTTCTTCCTCTACAGCAAGCTCACCGTGGACAAGAG

CAGGTGGCAGCAGGGGAACGTCTTCTCATGCTCCGTGATGCATG

AGGCTCTGCACAACCACTACACGCAGAAGAGCCTCTCCCTGTCT

CCGGGTAAA

Included in Table 3 are variations of 1, 2, 3, 4, 5, 6, 7, 8, 9, 10, 11, 12, 13, 14, 15, 16, 17, 18, 19, 20, or more amino acids on the 5' end, on the 3' end, or on both the 5' and 3' ends, of the amino acid sequences.

Included in Table 3 are orthologs of the proteins, as well as polypeptide molecules comprising, consisting essentially of, or consisting of:
1) an amino acid sequence having at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NOs: 19-20, or a biologically active fragment thereof;
2) an amino acid sequence having at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NOs: 19-20, or a biologically active fragment thereof, comprising at least one or more (e.g., one, two, three, four, five, six, seven, eight, nine, ten or more) amino acid mutations, substitutions, insertions, or deletions, within the Fc region;
3) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids;
4) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids, comprising at least one or more (e.g., one, two, three, four, five, six, seven, eight, nine, ten or more) amino acid mutations, substitutions, insertions, or deletions, within the Fc region;
5) a biologically active fragment of an amino acid sequence of SEQ ID NOs: 19-20 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids; or
6) a biologically active fragment of an amino acid sequence of SEQ ID NOs: 19-20 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids, comprising at least one or more (e.g., one, two, three, four, five, six, seven, eight, nine, ten or more) amino acid mutations, substitutions, insertions, or deletions, within the Fc region.

TABLE 4

Fc constant region or Fc constant portion

SEQ ID NO: 24 is an exemplary nucleotide sequence for a human IgG4 Fc constant region.

SEQ ID NO: 25 is an exemplary nucleotide sequence for a mouse IgG1 Fc constant region.

Human IgG4 FC comprising the nucleotide sequence of:
TCTGGTCCTGTGAAGGAACTGGTCGGCTCCGTGGGAGGAGCTGTGACCT

TCCCCCTGAAGAGCAAGGTGAAGCAGGTGGACTCCATCGTGTGGACCTT

CAACACCACACCACTGGTCACCATCCAGCCCGAGGGCGGCACAATCATC

GTGACCCAGAACCGGAATAGGGAGAGAGTGGACTTCCCTGATGGCGGCT

ACTCCCTGAAGCTGTCTAAGCTGAAGAAGAATGATTCTGGCATCTACTA

TGTGGGCATCTATAGCTCCTCTCTGCAGCAGCCCAGCACACAGGAGTAC

GTGCTGCACGTGTATGAGCACCTGAGCAAGCCTAAGGTCACCATGGGCC

TGCAGTCCAACAAGAATGGCACCTGCGTGACAAACCTGACCTGCTGCAT

GGAGCACGGCGAGGAGGACGTGATCTACACATGGAAGGCTCTGGGCCAG

GCCGCTAACGAGAGCCACAATGGCTCCATCCTGCCTATCTCTTGGCGGT

GGGGCGAGAGCGATATGACCTTCATCTGCGTGGCCCGGAACCCTGTGAG

CAGGAACTTCAGCTCCCCAATCCTGGCTAGAAAGCTGTGCGAGGGAGCT

GCTGACGATCCAGACTCTAGCATG

Mouse IgG1 FC comprising the nucleotide sequence of:
GGGTGTAAACCATGCATCTGTACTGTCCCCGAAGTGTCAAGCGTCTTCA

TTTTTCCCCCTAAGCCCAAAGACGTGCTGACTATCACCCTGACACCTAA

GGTCACCTGTGTGGTCGTGGATATTTCAAAAGACGATCCTGAGGTGCAG

TTCAGCTGGTTTGTCGACGATGTCGAAGTGCACACAGCTCAGACTCAGC

CAAGGGAGGAACAGTTCAATTCCACCTTTCGCTCAGTGAGCGAGCTGCC

CATCATGCATCAGGACTGGCTGAATGGCAAGGAGTTCAAGTGCAGAGTG

AACTCTGCAGCCTTTCCAGCCCCCATCGAGAAGACCATTAGTAAGACAA

AAGGGAGGCCCAAAGCTCCTCAGGTGTACACAATTCCACCCCCTAAGGA

ACAGATGGCAAAGGATAAAGTGAGCCTGACTTGTATGATCACCGACTTC

TTTCCCGAGGATATTACCGTGGAATGGCAGTGGAACGGGCAGCCTGCAG

TABLE 4-continued

Fc constant region or Fc constant portion

```
AGAACTATAAGAATACACAGCCAATCATGGACACTGATGGAAGCTACTT

CGTGTATTCCAAGCTGAACGTCCAGAAAAGCAATTGGGAAGCCGGCAAC

ACTTTTACCTGCTCCGTGCTGCACGAGGGGCTGCACAACCACCATACCG

AGAAAAGTCTGAGTCATTCACCTGGGAAG
```

Included in Table 4 are variations of 1, 2, 3, 4, 5, 6, 7, 8, 9, 10, 11, 12, 13, 14, 15, 16, 17, 18, 19, 20, or more nucleotides on the 5' end, on the 3' end, or on both the 5' and 3' ends, of the nucleic acid sequences.

Included in Table 4 are RNA nucleic acid molecules (e.g., thymines replaced with uredines), nucleic acid molecules encoding orthologs of the encoded proteins, as well as DNA or RNA, nucleic acid molecules comprising, consisting essentially of, or consisting of:

1) a nucleotide sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NOs: 24-25, or a biologically active or inactive fragment thereof;

2) a nucleotide sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NOs: 24-25, or a biologically active or inactive fragment thereof, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within the Fc region;

3) a nucleotide sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleotides;

4) a nucleotide sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within the Fc region;

5) a biologically active fragment of an nucleotide sequence of SEQ ID NOs: 24-25 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids; or 6) a biologically active or inactive fragment of an nucleotide sequence of SEQ ID NOs: 24-25 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within the Fc region.

As used herein, "fusion protein of CRACC" or "CRACC fusion" proteins refers to all or part of a CRACC ECD (see above) and a heterologous moiety. The heterologous moiety can be, or include, for example, the Fc portion of an immunoglobulin, i.e., the carboxyl-terminal portion of an immunoglobulin heavy chain constant region, or an analog or portion thereof capable of binding an Fc receptor. Each immunoglobulin heavy chain constant region comprises four or five domains. The domains are named sequentially as follows: CH1-hinge-CH2-CH3, and optionally, CH4. CH4 is present in IgM, which has no hinge region. The immunoglobulin heavy chain constant region useful in the practice of the invention can comprise an immunoglobulin hinge region, and preferably also includes a CH3 domain. The immunoglobulin heavy chain constant region can comprise an immunoglobulin hinge region, a CH2 domain and a CH3 domain. As used herein, the term immunoglobulin "hinge region" is understood to mean an entire immunoglobulin hinge region or at least a portion of the immunoglobulin hinge region sufficient to form one or more disulfide bonds with a second immunoglobulin hinge region.

Representative fusion CRACC proteins, including amino acid and nucleotide sequences are set forth in Tables 5 and 6 below.

TABLE 5

CRACC fusion proteins
Noted in bolded and underlined are the
amino acids corresponding to the ECD.

SEQ ID NO: 10 is an exemplary amino acid sequence
for a fusion protein comprising human CRACC ECD
and a human IgG4 Fc constant region.

SGPVKELVGS VGGAVTFPLK SKVKQVDSIV WTFNTTPLVT

IQPEGGTIIV TQNRNRERVD FPDGGYSLKL SKLKKNDSGI

YYVGIYSSSL QQPSTQEYVL HVYEHLSKPK VTMGLQSNKN

GTCVTNLTCC MEHGEEDVIY TWKALGQAAN ESHNGSILPI

SWRWGESDMT FICVARNPVS RNFSSPILAR KLCEGAADDP

DSSMESKYGP PCPPCPAPEF EGGPSVFLFP PKPKDTLMIS

RTPEVTCVVV DVSQEDPEVQ FNWYVDGVEV HNAKTKPREE

QFNSTYRVVS VLTVLHQDWL NGKEYKCKVS NKGLPSSIEK

TABLE 5-continued

CRACC fusion proteins
Noted in bolded and underlined are the
amino acids corresponding to the ECD.

TISKAKGQPR EPQVYTLPPS QEEMTKNQVS LTCLVKGFYP

SDIAVEWESN GQPENNYKTT PPVLDSDGSF FLYSRLTVDK

SRWQEGNVFS PSVMHEALHN HYTQKSLSLS LGK

SEQ ID NO: 11 is an exemplary amino acid sequence
for a fusion protein comprising murine CRACC ECD
and a murine IgG1 Fc constant region.
SGTLKKVAGA LDGSVTFTLN ITEIKVDYVV WTFNTFFLAM

VKKDGVTSQS SNKERIVFPD GLYSMKLSQL KKNDSGAYRA

EIYSTSSQAS LIQEYVLHVY KHLSRPKVTI DRQSNKNGTC

VINLTCSTDQ DGENVTYSWK AVGQGDNQFH DGATLSIAWR

SGEKDQALTC MARNPVSNSF STPVFPQKLC EDAATDLTSL

RGGCKPCICT VPEVSSVFIF PPKPKDVLTI TLTPKVTCVV

VDISKDDPEV QFSWFVDDVE VHTAQTQPRE EQFNSTFRSV

SELPIMHQDW LNGKEFKCRV NSAAFPAPIE KTISKTKGRP

KAPQVYTIPP PKEQMAKDKV SLTCMITDFF PEDITVEWQW

NGQPAENYKN TQPIMDTDGS YFVYSKLNVQ KSNWEAGNTF

TCSVLHEGLH NHHTEKSLSH SPGK

In SEQ ID NO: 11 of Table 5, the murine ECD portion of the polypeptide is in bold and underline. The remaining amino acid sequence corresponds to the murine IgG1 Fe portion of the fusion protein. In SEQ ID NO: 10 of Table 5, the human ECD portion of the polypeptide is in bold and underline. The remaining amino acid sequence corresponds to the human IgG4 Fc portion of the fusion protein, wherein the Fe constant regions comprises two substitutions: S228P and L235E. Included in Table 5 are fusion proteins containing a signal peptide, e.g., an IL-12 signal peptide having the amino acid sequence: MYRMQLLSCIALSLALVTNS (SEQ ID NO:26).

Included in Table 5 are variations of 1, 2, 3, 4, 5, 6, 7, 8, 9, 10, 11, 12, 13, 14, 15, 16, 17, 18, 19, 20, or more amino acids on the 5' end, on the 3' end, or on both the 5' and 3' ends, of the amino acid sequences.

Included in Table 5 are orthologs of the proteins, as well as polypeptide molecules comprising, consisting essentially of, or consisting of:
1) an amino acid sequence having at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NOs: 10-11, or a biologically active fragment thereof;
2) an amino acid sequence having at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NOs: 10-11, or a biologically active fragment thereof, comprising at least one or more (e.g., one, two, three, four, five, six, seven, eight, nine, ten or more) amino acid mutations, substitutions, insertions, or deletions, within the CRACC fusion;
3) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids;
4) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids, comprising at least one or more (e.g., one, two, three, four, five, six, seven, eight, nine, ten or more) amino acid mutations, substitutions, insertions, or deletions, within the CRACC fusion;
5) a biologically active fragment of an amino acid sequence of SEQ ID NOs: 10-11 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids; or
6) a biologically active fragment of an amino acid sequence of SEQ ID NOs: 10-11 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, or more amino acids, or any range in between, inclusive such as between 100 and 200 amino acids, comprising at least one or more (e.g., one, two, three, four, five, six, seven, eight, nine, ten or more) amino acid mutations, substitutions, insertions, or deletions, within the CRACC fusion.

TABLE 6

CRACC fusion nucleotide sequences

SEQ ID NO: 27 is an exemplary nucleotide sequence
for a CRACC fusion comprising human CRACC ECD and
a human IgG4 Fc constant region.

SEQ ID NO: 28 is an exemplary nucleotide sequence
for a CRACC fusion comprising murine CRACC ECD
and a murine IgG1 Fc constant region.

Human IgG4 FC comprising the nucleotide
sequence of:
TCTGGTCCTGTGAAGGAACTGGTCGGCTCCGTGGGAGGAGCTGTGACCT

TCCCCCTGAAGAGCAAGGTGAAGCAGGTGGACTCCATCGTGTGGACCTT

CAACACCACACCACTGGTCACCATCCAGCCCGAGGGCGGCACAATCATC

GTGACCCAGAACCGGAATAGGGAGAGAGTGGACTTCCCTGATGGCGGCT

ACTCCCTGAAGCTGTCTAAGCTGAAGAAGAATGATTCTGGCATCTACTA

TGTGGGCATCTATAGCTCCTCTCTGCAGCAGCCCAGCACACAGGAGTAC

GTGCTGCACGTGTATGAGCACCTGAGCAAGCCTAAGGTCACCATGGGCC

TGCAGTCCAACAAGAATGGCACCTGCGTGACAAACCTGACCTGCTGCAT

GGAGCACGGCGAGGAGGACGTGATCTACACATGGAAGGCTCTGGGCCAG

TABLE 6-continued

CRACC fusion nucleotide sequences

GCCGCTAACGAGAGCCACAATGGCTCCATCCTGCCTATCTCTTGGCGGT

GGGGCGAGAGCGATATGACCTTCATCTGCGTGGCCCGGAACCCTGTGAG

CAGGAACTTCAGCTCCCCAATCCTGGCTAGAAAGCTGTGCGAGGGAGCT

GCTGACGATCCAGACTCTAGCATG

Mouse IgG1 FC comprising the nucleotide
sequences of:
GGGTGTAAACCATGCATCTGTACTGTCCCCGAAGTGTCAAGCGTCTTCA

TTTTTCCCCCTAAGCCCAAAGACGTGCTGACTATCACCCTGACACCTAA

GGTCACCTGTGTGGTCGTGGATATTTCAAAAGACGATCCTGAGGTGCAG

TTCAGCTGGTTTGTCGACGATGTCGAAGTGCACACAGCTCAGACTCAGC

CAAGGGAGGAACAGTTCAATTCCACCTTTCGCTCAGTGAGCGAGCTGCC

CATCATGCATCAGGACTGGCTGAATGGCAAGGAGTTCAAGTGCAGAGTG

AACTCTGCAGCCTTTCCAGCCCCCATCGAGAAGACCATTAGTAAGACAA

AAGGGAGGCCCAAAGCTCCTCAGGTGTACACAATTCCACCCCCTAAGGA

ACAGATGGCAAAGGATAAAGTGAGCCTGACTTGTATGATCACCGACTTC

TTTCCCGAGGATATTACCGTGGAATGGCAGTGGAACGGGCAGCCTGCAG

AGAACTATAAGAATACACAGCCAATCATGGACACTGATGGAAGCTACTT

CGTGTATTCCAAGCTGAACGTCCAGAAAAGCAATTGGGAAGCCGGCAAC

ACTTTTACCTGCTCCGTGCTGCACGAGGGGCTGCACAACCACCATACCG

AGAAAAGTCTGAGTCATTCACCTGGGAAG

Included in Table 6 are variations of 1, 2, 3, 4, 5, 6, 7, 8, 9, 10, 11, 12, 13, 14, 15, 16, 17, 18, 19, 20, or more nucleotides on the 5' end, on the 3' end, or on both the 5' and 3' ends, of the nucleic acid sequences.

Included in Table 6 are RNA nucleic acid molecules (e.g., thymines replaced with uredines), nucleic acid molecules encoding orthologs of the encoded proteins, as well as DNA or RNA, nucleic acid molecules comprising, consisting essentially of, or consisting of:
1) a nucleotide sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NOs: 27-28, or a biologically active or inactive fragment thereof;
2) a nucleotide sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NOs: 27-28, or a biologically active or inactive fragment thereof, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within the CRACC fusion;
3) a nucleotide sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleotides;
4) a nucleotide sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within the CRACC fusion;
5) a biologically active fragment of an nucleotide sequence of SEQ ID NOs: 27-28 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids; or
6) a biologically active or inactive fragment of an nucleotide sequence of SEQ ID NOs: 27-28 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, or more nucleic acids, or any range in between, inclusive such as between 200 and 600 nucleic acids, comprising at least one or more (e.g., one, two, three, four, five, six, seven, eight, nine, ten, eleven, twelve, thirteen, fourteen, fifteen, sixteen, seventeen, eighteen, nineteen, twenty, or more) nucleotide mutations, substitutions, insertions, or deletions, within the CRACC fusion.

"Polypeptide," "peptide," and "protein" are used interchangeably and mean any peptide-linked chain of amino acids, regardless of length or post-translational modification. As noted below, the polypeptides described herein can be, e.g., wild-type proteins, functional fragments of the wild-type proteins, or variants of the wild-type proteins or fragments. Variants, in accordance with the disclosure, can contain amino acid substitutions, deletions, or insertions. The substitutions can be conservative or non-conservative. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST software. Appropriate parameters for measuring alignment, including any algorithms needed to achieve maximal alignment over the full-length of the sequences being compared can be determined by known methods.

II. Compositions of Matter—Vectors, Pharmaceutical Compositions, Vaccine, and Adjuvants Comprising CRACC Provided herein are compositions comprising CRACC. Such compositions (e.g., vectors, pharmaceutical compositions, adjuvants, vaccines) may comprise any CRACC genes (e.g., CRACC, fragments, variants, and fusions) that encode CRACC polypeptides listed herein, the Tables 1-6, the Figures, and the Examples, or any subset thereof. Such CRACC compositions may be provided in a vector in combination with any therapeutic agent, and are useful for the prevention and treatment of diseases, conditions, or disorders, for which an upregulation of an immune response would be beneficial. For example, the compositions or combinations may be used in the prevention or treatment of pathogenic infections, such as viral, protozoal, fungal, or bacterial infections, or cancers. Such compositions may comprise a CRACC alone, or in combination with any therapeutic agent (e.g., another vaccine, an immunomodulatory drug, a checkpoint inhibitor, or a small molecule inhibitor). In some embodiments, the compositions are provided alone or in combined with antigens (e.g., epitopes, tumor-associated antigens, or pathogen associated antigens) to enhance, stimulate, and/or increase an immune response.

CRACC Polypeptides, Fragment, or Variants Thereof

In some embodiments, the CRACC composition comprises, or consists of, all or a portion of a CRACC polypeptide (e.g., the extracellular domain (ECD) of a CRACC polypeptide), wherein the portion retains the ability to inhibit the interaction between two CRACC polypeptides. The following is an exemplary amino acid sequence for a full-length human CRACC protein:

(SEQ ID NO: 1)
MAGSPTCLTLIYILWQLTGSAASGPVKELVGSVGGAVTFPLKSKVKQVD

SIVWTFNTTPLVTIQPEGGTIIVTQNRNRERVDFPDGGYSLKLSKLKKN

DSGIYYVGIYSSSLQQPSTQEYVLHVYEHLSKPKVTMGLQSNKNGTCVT

NLTCCMEHGEEDVIYTWKALGQAANESHNGSILPISWRWGESDMTFICV

ARNPVSRNFSSPILARKLCEGAADDPDSSM*VLLCLLLVPLLLSLFVLGL*

*FLWFLKRERQEEYIEEKKRVDICRETPNICPHSGENTEYDTIPHTNRTI*

LKEDPANTVYSTVEIPKKMENPHSLLTMPDTPRLFAYENVI
(UniProt identifier: Q9NQ25).

The signal sequence of the protein consists of the first 22 amino acids and is underlined. The extracellular domain (ECD) of the human CRACC protein (amino acids 23-226) is in bold. The protein also includes a transmembrane domain, amino acids 227-247, the amino acid sequence of which is in italics. The remaining amino acids (248-335) constitute the cytoplasmic domain of this exemplary CRACC protein sequence. The Ig-G like domain spans from amino acid 103 to 206 of SEQ ID NO: 1. An exemplary amino acid for the human CRACC ECD is as follows:

(SEQ ID NO: 2)
SGPVKELVGSVGGAVTFPLKSKVKQVDSIVWTFNTTPLVTIQPEGGTII

VTQNRNRERVDFPDGGYSLKLSKLKKNDSGIYYVGIYSSSLQQPSTQEY

VLHVYEHLSKPKVTMGLQSNKNGTCVTNLTCCMEHGEEDVIYTWKALGQ

AANESHNGSILPISWRWGESDMTFICVARNPVSRNFSSPILARKLCEGA

ADDPDSSMAANESHNGSILPISWRWGESDMTFICVARNPVSRNFSSPIL

ARKLCEGAADDPDSSM.

The following is an exemplary amino acid sequence for a full-length CRACC protein from Rhesus macaque:

(SEQ ID NO: 3)
MAGSPTCFTFIYILWQLTGSTASGSVKELVGSIGGAVTFPLKSEVKQVD

SIVWTFNTTTLVTIQPEGGPMIVTQNRNKERVHFPDGGYSLKLSKLKKN

DSGIYNVEIYSSSLQDPFTRKYVLRVYEHLSKPKVTMGLQSNKNGTCVT

NLTCHMEHGEEDVIYTWKALGQAVNESHNGSILPISWRWGESDMTFICT

VRNPVSSNSSSPILARKLCEGAADDSDSSM*VLLCLLLVPLLLSLFVLGL*

FLWFLKRETQEESIEEKKRADICRETPNICPYSGENTEYDTIPYTNRTI

PMEDAANTLYSTVEIPKKIENPHSLLTMPDTPRLFAYENVI
(UniProt identifier: F7HQ72).

The signal sequence of the protein is underlined. The extracellular domain (ECD) of the rhesus CRACC protein (amino acids 23-226) is in bold. The protein also includes a transmembrane domain, amino acids 227-247, the amino acid sequence of which is in italics. The remaining amino acids constitute the cytoplasmic domain of this exemplary CRACC protein sequence.

The following is an exemplary amino acid sequence for a full-length CRACC protein from chimpanzee:

(SEQ ID NO: 4)
MAGSPTCLTLIYILWQLTGSAASGPVRELVGSVGGAVTFPLKSKVKQVD

SIVWTFNTTPLVTIQPEGGTIIVTQNRNKERVDFPDGGYSLKLSKLKKN

DSGIYYVGIYSSSLQQPSTQKYVLHVYEHLSKPKVTMGLQSNKNGTCVT

NLTCCMEHGEEDVIYTWKALGQAANESHNGSILPISWRWGESDMTFICV

ARNPVSSNFSSPILARKLCEGAADDPDSSM*VLLCLLLVPLLLSLFVLGL*

*FLWFLKRERQEESIEEKKRADICRETPNICPHSGENTEYDTIPHTNRTI*

LKEDPANTVYSTVEIPKKMENPHSLLTMPDTPRLFAYENVI
(UniProt identifier: H2Q0F0).

The signal sequence of the protein is underlined. The extracellular domain (ECD) of the chimpanzee CRACC protein (amino acids 23-226) is in bold. The protein also includes a transmembrane domain, amino acids 227-247, the amino acid sequence of which is in italics. The remaining amino acids constitute the cytoplasmic domain of this exemplary CRACC protein sequence.

The following is an exemplary amino acid sequence for a full-length, murine CRACC protein:

(SEQ ID NO: 5)
MARFSTYIIFTSVLCQLTVTAASGTLKKVAGALDGSVTFTLNITEIKVD

YVVWTFNTFFLAMVKKDGVTSQSSNKERIVFPDGLYSMKLSQLKKNDSG

-continued

AYRAEIYSTSSQASLIQEYVLHVYKHLSRPKVTIDRQSNKNGTCVINLT

CSTDQDGENVTYSWKAVGQGDNQFHDGATLSIAWRSGEKDQALTCMARN

PVSNSFSTPVFPQKLCEDAATDLTSLRG*ILYILCFSAVLILFAVLLTIF*

HTTWIKKGKGCEEDKKRVDRHQEMPDLCPHLEENADYDTIPYTEKRRPE

EDAPNTFYSTVQIPKVVKSPSSLPAKPLVPRSLSFENVI
(UniProt identifier: Q8BHK6).

The signal sequence of the protein is underlined. The extracellular domain (ECD) of the murine CRACC protein (amino acids 23-224) is in bold. The protein also includes a transmembrane domain, amino acids 225-245, which are in italics. The remaining amino acids constitute the cytoplasmic domain of this exemplary murine CRACC protein sequence. An exemplary amino acid sequence for a murine CRACC ECD is as follows:

(SEQ ID NO: 9)
SGTLKKVAGALDGSVTFTLNITEIKVDYVVWTFNTFFLAMVKKDGVTSQ

SSNKERIVFPDGLYSMKLSQLKKNDSGAYRAEIYSTSSQASLIQEYVLH

VYKHLSRPKVTIDRQSNKNGTCVINLTCSTDQDGENVTYSWKAVGQGDN

QFHDGATLSIAWRSGEKDQALTCMARNPVSNSFSTPVFPQKLCEDAATD

LTSLRG.

In some embodiments, the CRACC composition comprises a variant CRACC ECD polypeptide comprising an amino sequence that is at least 90 (e.g., at least 91, 92, 93, 94, 95, 96, 97, 98, or 99) % identical to the amino acid sequence depicted in SEQ ID NO:2. In some embodiments, the CRACC composition comprises a variant CRACC ECD polypeptide comprising an amino sequence that is at least 90 (e.g., at least 91, 92, 93, 94, 95, 96, 97, 98, or 99) % identical to the ECD amino acid sequence depicted in SEQ ID NOs:1, 3, 4, 5, 7, 8, or 9.

In some embodiments, the CRACC composition comprises a variant CRACC ECD polypeptide comprising an amino acid sequence that has one or more amino acid substitutions, insertions, or deletions, relative to the amino acid sequence depicted in SEQ ID NOs:2 or 6. In some embodiments, the CRACC composition comprises a variant CRACC ECD polypeptide comprising an amino acid sequence that has one or more amino acid substitutions, insertions, or deletions, relative to the ECD amino acid sequence depicted in Table 1 (e.g., SEQ ID NOs:1, 3, 4, 5, 7, 8, or 9). In some embodiments, the variant CRACC ECD polypeptide has at least two (e.g., at least three, four, five, six, seven, eight, nine, 10, 11, 12, 13, 14, 15, 16, 17, 18, 19, 20, 21, 22, 23, 24, 25, 30, 35, 40, 45, or 50) amino acid substitutions, insertions, or deletions relative to the amino acid sequence depicted in SEQ ID NOs:2 or 6. In some embodiments, the variant CRACC ECD polypeptide has at least two (e.g., at least three, four, five, six, seven, eight, nine, 10, 11, 12, 13, 14, 15, 16, 17, 18, 19, 20, 21, 22, 23, 24, 25, 30, 35, 40, 45, or 50) amino acid substitutions, insertions, or deletions relative to the ECD amino acid sequence depicted in Table 1 (e.g., SEQ ID NOs:1, 3, 4, 5, 7, 8, or 9). In some embodiments, the variant CRACC ECD polypeptide has no more than 60 (e.g., no more than 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, insertions or deletions, relative to the amino acid sequence depicted in SEQ ID NOs:2 or 6. In some embodiments, the variant CRACC ECD polypeptide has no more than 60 (e.g., no more than 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, insertions or deletions, relative to the ECD amino acid sequence depicted in Table 1 (e.g., SEQ ID NOs:1, 3, 4, 5, 7, 8, or 9). The substitutions can be conservative, non-conservative, or a mixture of both.

In some embodiments, an inhibitory portion of a CRACC polypeptide retains at least 10 (e.g., at least 15, 20, 25, 30, 35, 40, 45, 50, 55, 60, 65, 70, 75, 80, 85, 90, 95, or 100) % of the ability of the full-length, wild-type CRACC ECD from the same species from which the portion was derived to inhibit an interaction between two CRACC polypeptides. Methods for measuring the interaction between two polypeptides, as well as inhibition of that interaction, are well known in the art. For example, a first CRACC protein can be bound to a solid surface (the surface of a well in an assay plate or a chip) and then contacted with a detectably-labeled second CRACC protein in the presence or absence of an agent. The surface is then, optionally, washed to remove unbound material. Detection of the signal produced by the detectably-labeled second CRACC protein bound to the first CRACC protein follows. Decreased binding of the second CRACC protein (as a function of a reduction in signal from the detectable label) in the presence of the agent as compared to binding of the second CRACC protein in the absence of the agent indicates the agent inhibits the interaction between the CRACC proteins. Suitable methods for detecting or measuring the interaction between two CRACC proteins are described herein.

In some embodiments, the CRACC compositions described herein can be modified. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the CRACC compositions can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO:21)), polyhistidine (6-His; HHHHHH (SEQ ID NO:22), hemagglutinin (HA; YPYDVPDYA (SEQ ID NO:23)), glutathione-S-transferase (GST), or maltose-binding protein (MBP)) for use in purifying a polypeptide. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., a portion (e.g. ECD region) of a CRACC polypeptide and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of a protein agent. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the CRACC compositions can be modified, e.g., with a moiety that improves the stabilization and/or retention of the antibodies in circulation, e.g., in blood, serum, or other tissues. For example, a CRACC composition comprising the ECD of a CRACC polypeptide can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387 (1-2): 110-119). The stabilization moiety can improve the stability, or retention of, the CRACC composition by at least 1.5 (e.g., at least 2, 5, 10, 15, 20, 25, 30, 40, or 50 or more) fold.

CRACC Fusions

Provided herein are CRACC fusions comprising an ECD of CRACC linked to an Fc portion. In some embodiments, the ECD is set forth in SEQ ID NOs 2 and 6. In some embodiments, the ECD is set forth in Table 1 (e.g., SEQ ID Nos: 1, 3-5, and 7-9). In some embodiments, the Fc portion may comprise the IgG1, IgG2, IgG3, or IgG4 Fc portion, such as the amino acid sequence set forth in SEQ ID Nos:19 and 20, or any of the amino acid sequences set forth in Table 3. In some embodiments, the CRACC fusion may comprise any of the CRACC fusion amino acid sequences set forth in Table 5.

It may be useful, in some circumstances, to modify the immunoglobulin heavy chain constant region, for example, by mutation, deletion or other changes mediated by genetic engineering or other approaches, so that certain activities, such as complement fixation or stimulation of antibody-dependent cell-mediated cytotoxicity (ADCC) are reduced or eliminated, while preferably preserving the Fc regions' ability to bind an Fe receptor (e.g., FcRn). In some embodiments, the Fc constant region can be altered in a way such that it does not homodimerize with another Fc constant region.

In some embodiments, the Fc region (including those of an antibody or antigen-binding fragment described herein) can be an altered Fc constant region having reduced (or no) effector function relative to its corresponding unaltered constant region. Effector functions involving the Fc constant region may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent. For example, an altered Fc constant region that displays modulated ADCC and/or CDC activity may exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the Fc constant region. An altered Fc region described herein may exhibit reduced or no measurable ADCC and/or CDC activity.

In certain embodiments, the altered constant region has at least one amino acid substitution, insertion, and/or deletion, compared to a native sequence constant region or to the unaltered constant region, e.g. from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity to the sequences set forth in Table 3 (e.g., SEQ ID Nos 19 or 20). The altered constant region may also contain one or more amino acid deletions or insertions. Additionally, the altered constant region may contain one or more amino acid substitutions, deletions, or insertions that results in altered post-translational modifications, including, for example, an altered glycosylation pattern (e.g., the addition of one or more sugar components, the loss of one or more sugar components, or a change in composition of one or more sugar components relative to the unaltered constant region).

Altered Fc constant regions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, $2^{nd}$ Edition," Cold Spring Harbor Laboratory Press, Cold Spring Harbor, N.Y.; PCT publication no. WO 06/53301; and U.S. Pat. No. 7,704,497, the disclosures of each of which are incorporated herein by reference in their entirety.

Altered Fc constant regions having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. According to these embodiments, the Fc constant region comprises a substitution to an alanine at position 234 or a mutation to an alanine at position 235. Additionally, the altered constant region may contain a double mutation: a mutation to an alanine at position 234 and a second mutation to an alanine at position 235. In one embodiment, the Fc constant region comprises an IgG4 framework, wherein the Ala-Ala mutation would describe a mutation(s) from phenylalanine to alanine at position 234 and/or a mutation from leucine to alanine at position 235. In another embodiment, the Fc constant region comprises an IgG1 framework, wherein the Ala-Ala mutation would describe a mutation(s) from leucine to alanine at position 234 and/or a mutation from leucine to alanine at position 235. An Fc constant region may alternatively or additionally carry other mutations, including the point mutation K322A in the CH2 domain (Hezareh et al. (2001) *J Virol* 75:12161-12168).

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR" of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an altered Fc constant region (e.g., an altered human Fc constant region) can bind to neonatal Fc receptor (FcRn) with greater affinity than that of the native Fc constant region from which the altered or variant Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. See, e.g., Hinton et al. (2004) *J Biol Chem* 279:6213-6216 and Datta-Mannan et al. (2007) *Drug Metab Dispos* 35:1-9. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., Datta-Mannan et al. (2007) *J Biol Chem* 282(3): 1709-1717; International Publication No. WO 98/23289; International Publication No. WO 97/34631; and U.S. Pat. No. 6,277,375, the disclosures of each of which are incorporated herein by reference in their entirety.

Substitutions that enhance the binding affinity of an antibody Fc constant region for FcRn are known in the art and include, e.g., (1) the M252Y/S254T/TT256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376. In some embodiments, the altered or variant Fc constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine, or histidine for aspartic acid at position 312; lysine, or arginine for leucine at position 314; alanine, or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid, or histidine for glycine at position 385; proline for glutamine at position 386; glutamic acid for proline at position 387; alanine, or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

CRACC Fusion Containing Vectors or Constructs

In some embodiments, vectors and/or host cells are further provided. One aspect of the present invention pertains to the use of recombinant vectors (e.g., adenoviral vectors), containing at least one nucleic acid encoding at least one CRACC fusion listed herein, the Figures, the Tables 5 or 6, and the Examples, or any subset thereof, or a portion or ortholog thereof. Another aspect of the present invention pertains to the use of recombinant vectors (e.g., adenoviral vectors), containing at least one nucleic acid encoding at least one CRACC ECD set forth in Table 1 linked to at least one nucleic acid encoding at least one Fc region set forth in Table 3. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of recombinant vectors (e.g., viral vectors, replication defective adenoviruses, any human or non-human adenovirus, AAV, DNA-based vector, retroviruses, or lentiviruses), which serve equivalent functions. In one embodiment, vectors comprising a CRACC fusion are used. In one embodiment, adenoviral vectors comprising CRACC fusion are used.

The recombinant vectors (e.g., adenoviral vectors) of the present invention comprise any of the nucleic acid encoding a CRACC fusion listed herein, the Figures, Tables 5 or 6, and the Examples, or any subset thereof, or a portion or ortholog thereof, in a form suitable for expression of the nucleic acid in a host cell. In some embodiments, the recombinant vectors (e.g., adenoviral vectors) of the present invention comprise any of at least one nucleic acid encoding at least one CRACC ECD set forth in Table 1 linked to at least one nucleic acid encoding at least one Fc region set forth in Table 3. In some embodiments, the recombinant vectors (e.g., adenoviral vectors) of the present invention comprise any of at least one nucleic acid of CRACC ECD set forth in Table 2 linked to at least one nucleic acid of an Fc region set forth in Table 4. This means that the recombinant vectors include one or more regulatory sequences, selected on the basis of the host cells to be used for expression, which is operatively linked to the nucleic acid sequence to be expressed. Within a recombinant vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the recombinant vector (e.g., adenoviral vector) can depend on such factors as the choice of the host cell to be transformed, the level of expression of protein desired, etc. The recombinant vectors (e.g., adenoviral vectors) of the present invention can be introduced into host cells to thereby produce CRACC fusions listed herein, the Figures, the Tables, and the Examples, or any subset thereof, or a portion or ortholog thereof, encoded by nucleic acids as described herein.

The recombinant vectors of the present invention comprising any of the nucleic acid encoding a CRACC fusion listed herein, the Figures, and the Examples, or any subset thereof, or a portion or ortholog thereof, can be designed for expression of the desired CRACC fusion, in prokaryotic or eukaryotic cells. For example, a CRACC fusion can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant vector can be transcribed and translated in vitro, for example using T7 promoter regulatory sequences and T7 polymerase. Examples of suitable inducible non-fusion *E. coli* vectors include pTrc (Amann et al., (1988) *Gene* 69:301-315) and pET11d (Studier et al., *Gene Expression Technology: Methods in Enzymology* 185, Academic Press, San Diego, Calif. (1990) 60-89). Examples of suitable yeast vectors include pYepSecl (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Examples of suitable baculovirus vectors useful for insect cell hosts include the pAc series (Smith et al. (1983) *Mol. Cell Biol.* 3:2156-2165) and the pVL series (Lucklow and Summers (1989) *Virology* 170:31-39). Examples of suitable mammalian vectors include CMV-containing vectors, such as pCDM8 (Seed, B. (1987) *Nature* 329:840), and pMT2PC (Kaufman et al. (1987) *EMBO J.* 6:187-195).

In another embodiment, the recombinant vector (e.g., adenoviral vector) comprising any of the nucleic acid encoding a CRACC fusion, listed herein, the Figures, the Tables, and the Examples, or any subset thereof, or a portion or ortholog thereof, is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters such as in melanoma cancer cells are well-known in the art (see, for example, Pleshkan et al. (2011) *Acta Nat.* 3:13-21).

The present invention further provides a recombinant vector (e.g., adenoviral vector) comprising any of the nucleic acid encoding a CRACC fusion listed herein, the Figures, and the Examples, or any subset thereof, or a portion or ortholog thereof, cloned into the recombinant vector (e.g., adenoviral vector) in an antisense orientation. That is, the DNA molecule is operatively linked to a regulatory sequence in a manner which allows for expression (by transcription of the DNA molecule) of an RNA molecule which is antisense to a CRACC fusion, mRNA described herein. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the present invention pertains to host cells into which a recombinant vector comprising any of the nucleic acid encoding a CRACC fusion, listed herein, the Figures, the Tables, and the Examples, or any subset thereof, or a portion or ortholog thereof has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the CRACC fusion can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989), and other laboratory manuals.

A cell culture includes host cells, media and other byproducts. Suitable media for cell culture are well known in the art. A CRACC fusion may be secreted and isolated from a mixture of cells and medium containing the polypeptide. Alternatively, a CRACC fusion, may be retained cytoplasmically and the cells harvested, lysed and the protein or protein complex isolated. A CRACC fusion polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of a CRACC fusion, or a fragment thereof. In other embodiments, heterologous tags can be used for purification purposes (e.g., epitope tags and FC fusion tags), according to standards methods known in the art.

Thus, a nucleotide sequence encoding all or a selected portion of a CRACC fusion may be used to produce a recombinant form of the protein via microbial or eukaryotic cellular processes. Ligating the sequence into a polynucleotide construct, such as an recombinant vector (e.g., adenoviral vector), and transforming or transfecting into hosts, either eukaryotic (yeast, avian, insect or mammalian) or prokaryotic (bacterial cells), are standard procedures. Similar procedures, or modifications thereof, may be employed to prepare recombinant cyclic di-nucleotide synthetase enzyme polypeptides, or fragments thereof, by microbial means or tissue-culture technology in accord with the subject invention.

A host cell of the present invention, such as a prokaryotic or eukaryotic host cell in culture, can be used to produce (i.e., express) CRACC fusion protein. Accordingly, the invention further provides methods for producing CRACC fusion protein using the host cells of the present invention. In one embodiment, the method comprises culturing the host cell of invention (into which a recombinant vector encoding a CRACC fusion has been introduced) in a suitable medium until CRACC fusion protein is produced. In another embodiment, the method further comprises isolating the CRACC fusion protein from the medium or the host cell.

The host cells of the present invention can also be used to produce nonhuman transgenic animals. The nonhuman transgenic animals can be used in screening assays designed to identify compositions or compounds, e.g., drugs, pharmaceuticals, etc., which are capable of modulation (e.g., upregulating) an immune response. For example, in one embodiment, a host cell of the present invention is a fertilized oocyte or an embryonic stem cell into which CRACC fusion encoding sequences, or fragments thereof, have been introduced. Such host cells can then be used to create non-human transgenic animals. Such animals are useful for studying the function and/or activity of CRACC fusion, and for identifying and/or evaluating modulators of CRACC fusion activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal.

A transgenic animal of the present invention can be created by introducing nucleic acids encoding a CRACC fusion into the male pronuclei of a fertilized oocyte, e.g., by microinjection, retroviral infection, and allowing the oocyte to develop in a pseudopregnant female foster animal. Human CRACC fusion sequences can be introduced as a transgene into the genome of a nonhuman animal. Alternatively, a nonhuman homologue of the human CRACC fusion can be used as a transgene. Intronic sequences and polyadenylation signals can also be included in the transgene to increase the efficiency of expression of the transgene. A tissue-specific regulatory sequence(s) can be operably linked to the CRACC fusion transgene to direct expression of CRACC fusion protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the CRACC fusion mRNA in tissues or cells of the animals. A transgenic founder animal can then be used to breed additional animals carrying the transgene. Moreover, transgenic animals carrying a transgene encoding a CRACC fusion can further be bred to other transgenic animals carrying other transgenes.

III. Biological Samples and Sample Collection

Suitable biological samples for use in the methods described herein include, e.g., any biological fluid. A biological sample can be, for example, a specimen obtained from a subject (e.g., a mammal such as a human) or can be derived from such a subject. A biological sample can also be a biological fluid such as urine, whole blood or a fraction thereof (e.g., plasma or serum), saliva, semen, sputum, cerebrospinal fluid, tears, or mucus. A biological sample can be further fractionated, if desired, to a fraction containing particular analytes (e.g., proteins) of interest. For example, a whole blood sample can be fractionated into serum or into fractions containing particular types of proteins. If desired, a biological sample can be a combination of different biological samples from a subject such as a combination of two different fluids.

Biological samples suitable for the invention may be fresh or frozen samples collected from a subject, or archival samples with known diagnosis, treatment and/or outcome history. The biological samples can be obtained from a subject, e.g., a subject having, suspected of having, or at risk of developing, a cancer or an infection (e.g., a viral infection). Any suitable methods for obtaining the biological samples can be employed, although exemplary methods include, e.g., phlebotomy, swab (e.g., buccal swab), lavage, or fine needle aspirate biopsy procedure. Biological samples can also be obtained from bone marrow or spleen.

In some embodiments, a protein extract may be prepared from a biological sample. In some embodiments, a protein extract contains the total protein content. Methods of protein extraction are well known in the art. See, e.g., Roe (2001) "Protein Purification Techniques: A Practical Approach", 2nd Edition, Oxford University Press. Numerous different and versatile kits can be used to extract proteins from bodily fluids and tissues, and are commercially-available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.).

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of Methods in molecular biology, Humana Press; Masters (2000) "Animal cell culture: a practical approach," volume 232 of Practical approach series, Oxford University Press; and Jones (1996) "Human cell culture protocols," volume 2 of Methods in molecular medicine, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

IV. Pharmaceutical Compositions and Formulations

Another aspect, the present invention provides pharmaceutically acceptable compositions, adjuvants, and vaccines which comprise a therapeutically-effective amount of any of the aforementioned recombinant vectors (e.g., adenoviral vector comprising any of the CRACC fusions). In some embodiments, the pharmaceutical compositions comprise a recombinant vector (e.g., adenoviral vector) comprising at least one CRACC fusion set listed herein, the Figures, the Tables 5 or 6, and the Examples, or any subset thereof, or fragment thereof, which increases or enhances immune response levels and/or activity, formulated together with one or more pharmaceutically acceptable carriers (additives) and/or diluents. In some embodiments, the pharmaceutical compositions, adjuvants, and vaccines comprises a first gene therapy vector (e.g., adenoviral vector)) comprising at least one CRACC fusion set listed herein, the Figures, the Tables 5 or 6, and the Examples, or any subset thereof, or fragment thereof, in combination with a extracellular antigen, epitope, or peptide (naked or provided in an gene therapy vector). In some embodiments, the pharmaceutical compositions, adjuvants, and vaccines can be combined with any immune modulating, anti-viral, anti-bacterial, anti-cancer, chemotherapeutic, or immunotherapeutic compositions.

Immunotherapeutic compositions, include, but are not limited to, ipilimumab (Yervoy®), trastuzumab (Herceptin®), rituximab (Rituxan®), bevacizumab (Avastin®), pertuzumab (Omnitarg®), tositumomab (Bexxar®), edrecolomab (Panorex®), and G250. Compounds of the present invention can also be combined with, or used in combination with, anti-TNF-α antibodies. Large molecule active compositions may be administered in the form of anti-cancer vaccines. For example, compositions that secrete, or cause the secretion of, cytokines such as IL-2, G-CSF, and GM-CSF can be used in the methods, pharmaceutical compositions, and kits provided herein. See, e.g., Emens, L. A., et al., Curr. Opinion Mol. Ther. 3(1):77-84 (2001).

Second active compositions that are small molecules can also be used to in combination with the compositions of the present invention. Examples of small molecule second active compositions include, but are not limited to, anti-cancer compositions, antibiotics, antivirals, immunosuppressive compositions, and steroids.

In some embodiments, well known "combination chemotherapy" regimens can be used. In one embodiment, the combination chemotherapy comprises a combination of two or more of cyclophosphamide, hydroxydaunorubicin (also known as doxorubicin or adriamycin), oncovorin (vincristine), and prednisone. In another embodiment, the combination chemotherapy comprises a combination of cyclophsophamide, oncovorin, prednisone, and one or more chemotherapeutics selected from the group consisting of anthracycline, hydroxydaunorubicin, epirubicin, and motixantrone.

Examples of other anti-cancer compositions include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; β-lactam derivatives; β-alethine; betaclamycin B; betulinic acid; bFGF inhibitor; bicalutamide; bisantrene; bisaziridinylspermine; bisnafide; bistratene A;

bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cyclosporin A; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer composition; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer. Specific second active compositions include, but are not limited to, chlorambucil, fludarabine, dexamethasone (Decadron®), hydrocortisone, methylprednisolone, cilostamide, doxorubicin (Doxil®), forskolin, rituximab, cyclosporin A, cisplatin, vincristine, PDE7 inhibitors such as BRL-50481 and IR-202, dual PDE4/7 inhibitors such as IR-284, cilostazol, meribendan, milrinone, vesnarionone, enoximone and pimobendan, Syk inhibitors such as fostamatinib disodium (R406/R788), R343, R-112 and Excellair® (ZaBeCor Pharmaceuticals, Bala Cynwyd, Pa.).

Antiviral, antifungal, and/or antibacterial compositions, include but not limited, cidofovir and interleukin-2, Cytarabine (also known as ARA-C), isoniazid, rifampicin, pyrazinamide, ethambutol, streptomycin, kanamycin, amikacin, capreomycin, ofloxacin, levofloxacin, moxifloxacin, cycloserine, para-aminosaicylic acid, ethioamide, prothionamide, thioacetazone, clofazimine, amoxicilin with clavulanate, imipenem, linezolid, clarithromycin, thioridazine, bicyclic nitroimidazoles (e.g., (S)-6,7-dihydro-2-nitro-6-[[4-(trifluoromethoxy)phenyl]methoxy]-5H-imidazo[2,1-b][1,3] oxazine (PA-824) and TBA-354, available from TB Alliance), bedaquiline (TMC-207), delamanid (OPC67683), oxazolidinone, 2-[(2S)-2-methyl-1,4-dioxa-8-azaspiro[4.5] decan-8-yl]-8-nitro-6-trifluoromethyl-4H-1,3-benzothiazin-4-one (BTZ043), imidazopyridines (e.g., Q201, available from Quro Science Inc.), anti-interleukin 4 neutralizing antibodies, high-dose intravenous immunoglobulin, 16a-bromoepiandosterone (HE2000), RUTI® vaccine, DNA vaccine with HSP65, Ag85, MPT-64, and MPT-83, dzherelo (plant extracts from the Ukraine), cytokines (such as Interleukin 2, Interleukin 7, Interleukin 15, Interleukin 27, Interleukin 12, Interferon γ, corticosteroids, thalidomide, etanercept, steroids, prednisone, (NNRTIs), such as efavirenz (Sustiva), etravirine (Intelence) and nevirapine (Viramune); Nucleoside reverse transcriptase inhibitors (NRTIs), such as Abacavir (Ziagen), and the combination drugs emtricitabine and tenofovir (Truvada), and lamivudine and zidovudine (Combivir); Protease inhibitors (Pis), such as atazanavir (Reyataz), darunavir (Prezista), fosamprenavir (Lexiva) and ritonavir (Norvir); Entry or fusion inhibitors, such enfuvirtide (Fuzeon) and maraviroc (Selzentry); and Integrase inhibitors, such as Raltegravir (Isentress).

The CRACC compositions described herein can be formulated as a pharmaceutical solution, e.g., for administration to a subject for modulating (e.g., enhancing) an immune response to an antigen. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filtered sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions described herein are administered in an aqueous solution by parenteral injection. The disclosure features pharmaceutical compositions comprising an effective amount of the CRACC composition (e.g., adenoviral vector comprising CRACC fusion) and optionally include pharmaceutically acceptable diluents, preservatives, solubilizers, emulsifiers, adjuvants and/or carriers. Such compositions include sterile water, buffered saline (e.g., Tris-HCl, acetate, phosphate), pH and ionic strength; and optionally, additives such as detergents and solubilizing agents (e.g., TWEEN® 20, TWEEN 80, Polysorbate 80), anti-oxidants (e.g., ascorbic acid, sodium metabisulfite), and preservatives (e.g., thimersol, benzyl alcohol) and bulking substances (e.g., lactose, mannitol). The formulations may be sterilized, e.g., using filtration, incorporating sterilizing agents into the compositions, by irradiating the compositions, or by heating the compositions.

The CRACC compositions (e.g., adenoviral vector comprising CRACC fusions) can be formulated at a concentration of between about 10 mg/mL to 100 mg/mL (e.g., between about 9 mg/mL and 90 mg/mL; between about 9 mg/mL and 50 mg/mL; between about 10 mg/mL and 50 mg/mL; between about 15 mg/mL and 50 mg/mL; between about 15 mg/mL and 110 mg/mL; between about 15 mg/mL and 100 mg/mL; between about 20 mg/mL and 100 mg/mL; between about 20 mg/mL and 80 mg/mL; between about 25 mg/mL and 100 mg/mL; between about 25 mg/mL and 85 mg/mL; between about 20 mg/mL and 50 mg/mL; between about 25 mg/mL and 50 mg/mL; between about 30 mg/mL and 100 mg/mL; between about 30 mg/mL and 50 mg/mL; between about 40 mg/mL and 100 mg/mL; between about 50 mg/mL and 100 mg/mL; or between about 20 mg/mL and 50 mg/mL). In some embodiments, compositions can be formulated at a concentration of greater than 5 mg/mL and less than 50 mg/mL. Methods for formulating a protein in an aqueous solution are known in the art and are described in, e.g., U.S. Pat. No. 7,390,786; McNally and Hastedt (2007), "Protein Formulation and Delivery," Second Edition, *Drugs and the Pharmaceutical Sciences*, Volume 175, CRC Press; and Banga (1995), "Therapeutic peptides and proteins: formulation, processing, and delivery systems," CRC Press. In some embodiments, the aqueous solution has a neutral pH, e.g., a pH between, e.g., 6.5 and 8 (e.g., between and inclusive of 7 and 8). In some embodiments, the aqueous solution has a pH of about 6.6, 6.7, 6.8, 6.9, 7, 7.1, 7.2, 7.3, 7.4, 7.5, 7.6, 7.7, 7.8, 7.9, or 8.0. In some embodiments, the aqueous solution has a pH of greater than (or equal to) 6 (e.g., greater than or equal to 6.1, 6.2, 6.3, 6.4, 6.5, 6.6, 6.7, 6.8, 6.9, 7, 7.1, 7.2, 7.3, 7.4, 7.5, 7.6, 7.7, 7.8, or 7.9), but less than pH 8.

As noted above, nucleic acids encoding a therapeutic polypeptide (e.g., CRACC fusion) as set forth in Table 6 can be incorporated into a gene construct to be used as a part of a gene therapy protocol to deliver nucleic acids that can be used to express and produce CRACC fusions within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or CaPO$_4$ precipitation (see, e.g., WO04/060407) carried out in vivo. Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc. Natl. Acad. Sci. USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). As noted above, suitable adenoviral vectors derived from the adenovirus strain Ad type 5 d1324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

In some embodiments, CRACC composition (e.g., adenoviral vector comprising CRACC fusion) can be formulated with one or more additional therapeutic agents, e.g., additional agents for stimulating an immune response in a subject, e.g., adjuvants and excipients. In some embodiments, the compositions can be formulated with an inhibitor of the interaction between PD-1 and one its natural ligands, such as PD-L1 or PD-L2. Exemplary PD-1/PD-L1 inhibitors (e.g., anti-PD-1 and/or anti-PD-L1 antibodies) are known in the art and described in, e.g., International Patent Application Publication Nos. WO 2010036959 and WO 2013/079174, as well as U.S. Pat. Nos. 8,552,154 and 7,521,051, the disclosures of each of which as they relate to the antibody descriptions are incorporated herein by reference in their entirety.

When CRACC compositions (e.g., adenoviral vector comprising CRACC fusions) are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times (see below).

V. Applications

The CRACC compositions (e.g., adenoviral vector comprising CRACC fusion) can be used in a number of in vitro, ex vivo, and in vivo applications. In some embodiments, the CRACC compositions can be contacted to cultured cells in vitro or in vivo, or administered to a subject (e.g., a mammal, such as a human) to modulate the activation of an immune cell and/or modulate an immune response to an antigen of interest. For example, in the presence of an antigen of interest (or more than one antigen of interest), contacting an immune cell with an effective amount of a CRACC composition to thereby modulate activation of the immune cell by the antigen. The effective amount of the CRACC compositions (e.g., adenoviral vector comprising CRACC fusions) is the amount required to modulate the activation of the immune cell by the antigen, that is, to produce an enhanced or reduced activation level in response to the antigen as compared to the level of activation produced by the immune cell in response to the antigen in the absence of the CRACC composition.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the immune cell is a T cell (e.g., a CD8$^+$ T cell, a CD3$^+$CD8$^+$ T cell, a naïve T cell, or an NK cell). In some embodiments, the immune cell is a macrophage or a dendritic cell. Naïve T cells are mature T cells which have not yet encountered their cognate antigen within the periphery.

As used herein, the term "immune response" refers to the biological functions of immune cells (including macromolecules produced by such immune cells or the liver, such as antibodies, cytokines, and complement proteins) that result in selective damage to, destruction of, or elimination from the human body of invading pathogens, cells or tissues infected with pathogens, cancerous cells, or, in cases of autoimmunity or pathological inflammation, normal human cells or tissues. In some embodiments, the immune response is an innate immune response. In some embodiments, the immune response is a T cell response, e.g., a memory T cell response. In some embodiments, the immune response is a humoral immune response.

Immune cell activation (e.g., T cell activation) or like grammatical terms refers to one or more cellular responses of the subject immune cell, such as proliferation, maturation, differentiation, cytokine secretion, cytotoxic effector molecule release, cytotoxic activity, and expression of activation or differentiation markers. Suitable methods to measure activation of an immune cell (e.g., T cell activation, NK activation, or dendritic cell maturation) are known in the art and described in the working examples.

An antigen is any substance that will induce a detectable (or measurable) immune response (e.g., humoral and/or cellular) when administered to a mammal. For example, an antigen may be capable of inducing a measurable antibody response by the mammal to which the antigen is administered. An effective amount of an antigen is one that is sufficient to activate an immune cell in culture and/or, in the in vivo setting, capable of inducing a measurable immune response by a mammal to the antigen. Representative antigens include peptides, proteins, polysaccharides, saccharides, lipids, nucleic acids, or combinations thereof. The antigen can be derived from a tumor or from a transformed cell such as a cancer or leukemic cell and can be a whole cell or immunogenic component thereof, e.g., cell wall components or molecular components thereof.

Suitable antigens are known in the art and are available from commercial sources. The antigens may be purified or partially purified polypeptides derived from tumors or other sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids. An antigen can have one or more epitopes, each of which being capable of inducing an immune response. In some embodiments, the antigen is an attenuated or killed microorganism, or a protein (or antigenic fragment thereof) derived from a microorganism. While in no way limiting, exemplary antigens can include proteins, carbohydrates, or lipids from any one of the following: viruses (e.g., HIV, rotavirus, influenza, parainfluenza, herpes (e.g., VZV, HSV-1, HAV-6, HSV-II, CMV, and Epstein Barr virus) Chicken pox, small pox, rabies, polio, Hepatitis A, Hepatitis B, Hepatitis C, measles, Dengue, mumps, Coxsackie virus, flaviviruses, adenoviruses, distemper, reovirus, respiratory syncytial virus, ebola, hanta virus, papillomavirus, and parvovirus), bacteria (e.g., *Bordetella pertussis, Brucella abortis, Escherichia coli, Salmonella* species, *Streptococci, Cholera, Shigella, Pseudomonas, Tuberculosis, Pertussis,* pneumonococci, meningococci, *Klebsiella proteus, legionella,* anthrax, leptospirosis), parasites (e.g., *Plasmodium, falciparum, P. vivax, P. malariae, Entamoeba histolvytica, Balantidium coli, Naegleriafowleri, Acanthamoeba* sp., *Giardia lambia, Cryptosporidium* sp., *Pneumocystis carinii, Plasmodium rivax, Babesia microti, Trypanosoma brucei, Trypanosoma cruzi, Leislunania donovani, Toxoplasma gondi,* and *Nippostrongylus brasiliensis*), or *Candida* (e.g., *albicans, krusei, glabrata,* or *tropicalis*), *Cryptococcus neoformans, Aspergillus* (e.g., *fumigatus* or *niger*), *Mucorales* (e.g., *mucor, absidia, rhizophus*), *Sporothrix schenkii, Blastomyces dermatitidis, Paracoccidioides brasiliensis, Coccidioides immitis,* or *Histoplasma capsulatum*). Antigens also include Sporozoan antigens, *Plasmodium* antigens, such as all or a portion of Circumsporozoite protein, a Sporozoite surface protein, a liver stage antigen, an apical membrane associated protein, or a Merozoite surface protein. It is understood that a mammal described herein can, in some embodiments, be one infected with any of the foregoing microorganisms.

In some embodiments, the antigen is a tumor antigen, including: alpha-actinin-4, Bcr-Abl, Casp-8, beta-catenin, cdc27, cdk4, cdkn2a, coa-1, dek-can, EF2, ETV6-AML1, LDLR-fucosyltransferaseAS, HLA-A2, HLA-All, hsp70-2, KIAAO205, Mart2, Mum-1, 2, and 3, neo-PAP, myosin class I, OS-9, pm1-RARα, PTPRK, K-ras, N-ras, Triosephosphate isomerase. Bage-1. Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (PmeI 17), tyrosinase, TRP-1, TRP-2, MAGE-1, MAGE-3, BAGE, GAGE-1, GAGE-2, p15(58), CEA, RAGE, NY-ESO (LAGE). SCP-1, Hom/Mel-40, PRAME, p53. H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1. PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein/cyclophilin C-associated protein), TAAL6, TAG72, TLP, and TPS.

In some embodiments, the CRACC compositions (e.g., adenoviral vector comprising CRACC fusions) can be contacted to a plurality of immune cells, which plurality comprises T cells (e.g., CD8$^+$ T cells) and antigen presenting cells. For example, the plurality can be a population of splenocytes or peripheral blood mononuclear cells (PBMCs). The contacting can occur in the presence of one or more antigens of interest.

In some embodiments, the immune cell or plurality of immune cells is obtained from a mammal who has been exposed to the antigen or antigens of interest prior to the cells being obtained and, optionally, such prior exposure to the antigen resulted in the production of a measurable immune response to the antigen or antigens, e.g., the production of antibodies against the antigen or antigens. In some embodiments, the immune cell or plurality of cells is obtained from a patient known to be infected with a virus, such as HIV-1. In some embodiments, the immune cell or plurality of immune cells is obtained from a patient with a cancer (e.g., a colon, brain, stomach, liver, pancreatic, skin, ocular, stomach, lung, esophageal, or hematologic cancer).

In some embodiments, the contacting can occur in the further presence of an agent that interferes with the interaction between PD-1, PD-L1, and PD-L2. Such agents are known in the art and discussed supra.

Methods for Modulating an Immune Response

The above-described CRACC compositions (e.g., adenoviral vector comprising CRACC fusion) are also useful to modulate (e.g., enhance) an immune response in a mammal. For example, an effective amount of an antigen and an effective amount of CRACC compositions (e.g., adenoviral vector comprising CRACC fusions) can be administered to a mammal, wherein the immune response to the antigen by the mammal is enhanced in the presence of the CRACC composition. In some embodiments, the CRACC composition is administered first in time and the antigen is administered second in time. In some embodiments, the antigen is administered first in time and the CRACC composition is administered second in time. In some embodiments, the CRACC composition and antigen are administered to the mammal by different medical professionals. In some embodiments, the CRACC composition and the antigen are administered to the mammal by the same medical professional (e.g., at the same time). In some embodiments, the CRACC composition and the antigen are administered to the mammal at different times (optionally by different routes of administration), but not more than 30 (e.g., not more than 29, 28, 27, 26, 25, 24, 23, 22, 21, 20, 19, 18, 17, 16, 15, 14, 13, 12, 11, 10, 9, 8, 7, 6, 5, 4, 3, 2, or 1) day(s) apart. In some embodiments, the CRACC composition and antigen are administered at different times, but within 48 (e.g., 40, 36, 30, 24, 20, 18, 16, 14, 12, 11, 10, 9, 8, 7, 6, 5, 4, 3, 2, or 1) hour(s) of each other.

In some embodiments, more than one dose of the CRACC composition is administered to the mammal. In some embodiments, more than one dose of the antigen is administered to the mammal. In some embodiments, more than one dose of the CRACC composition and more than one dose of the antigen are administered to the mammal.

In some embodiments, the antigen and CRACC compositions (e.g., adenoviral vector comprising CRACC fusions) can be administered to the mammal using different routes of administration. For example, the antigen can be administered subcutaneously or intramuscularly and the CRACC composition can be administered intravenously.

As used herein, a mammal can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the mammal is an infant (e.g., a human infant).

As used herein, a subject mammal "in need of prevention," "in need of treatment," or "in need thereof," refers to one, who by the judgment of an appropriate medical practitioner (e.g., a doctor, a nurse, or a nurse practitioner in the case of humans; a veterinarian or zoologist in the case of non-human mammals), would reasonably benefit from a given treatment (e.g., vaccination with an antigen of interest in conjunction with a CRACC compositions (e.g., adenoviral vector comprising CRACC fusions)).

The term "preventing" is art-recognized, and when used in relation to a condition, is well understood in the art, and includes administration of a composition which reduces the frequency of, or delays the onset of, symptoms of a medical condition in a subject mammal relative to a subject which does not receive the composition. Preventing also includes reducing the likelihood of becoming productively infected by a microorganism against which the subject was immunized (e.g., by administration of an antigen from the microorganism in conjunction with an agent that inhibits an interaction between two CRACC proteins, such as a CRACC composition (e.g., adenoviral vector comprising CRACC fusion)).

In some embodiments, the mammal is one who has, is suspected of having, or is at risk for developing a cancer or an infection.

As used herein, a subject "at risk for developing" a cancer is a subject having one or more (e.g., two, three, four, five, six, seven, or eight or more) risk factors for developing a cancer. For example, a subject at risk of developing a cancer may have a predisposition to develop a cancer (i.e., a genetic predisposition to develop a cancer such as a mutation in a tumor suppressor gene (e.g., mutation in BRCA1, p53, RB, or APC) or has been exposed to conditions that can result in the condition. Thus, a subject can be one "at risk of developing a cancer when the subject has been exposed to mutagenic or carcinogenic levels of certain compounds (e.g., carcinogenic compounds in cigarette smoke such as acrolein, arsenic, benzene, benz[a]anthracene, benzo[a]pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer.

Similarly, a mammal at risk for developing an infection is one having one or more risk factors that increase the likelihood of exposure to a pathogenic microorganism.

A subject "suspected of having" a cancer or an infection is one having one or more symptoms of the cancer or infection. It should be understood that mammal at risk for developing, or suspected of having, a cancer or an infection does not include all mammals within the species of interest.

In some embodiments, the methods include determining whether the subject mammal has a cancer or an infection.

In some embodiments, the mammal is afflicted with a persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. In addition, bacterial, fungal and other pathogenic infections are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and Vibriocholerae. Exemplary species include *Neisseria gonorrhea, Mycobacterium tuberculosis, Candida albicans, Candida tropicalis, Trichomonas vaginalis, Haemophilus vaginalis,* Group B *Streptococcus* sp., Microplasma *hominis, Hemophilus ducreyi, Granuloma inguinale, Lymphopathia venereum, Treponema pallidum,*

*Brucella abortus. Brucella melitensis, Brucella suis, Brucella canis, Campylobacter fetus, Campylobacter fetus* intestinalis, *Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium*.

As described in the working examples, the inventors have discovered that patients afflicted with a viral infection (e.g., HIV-1 infection) have a higher concentration of CRACC-expressing immune cells than non-infected humans. Thus, the disclosure also features methods for enhancing an immune response in mammals afflicted with an infection (e.g., a viral, bacterial, or parasitic infection) or cancer (or in mammals at risk of developing a cancer or an infection, e.g., a viral infection, such as HIV-1, herpes, papillomavirus, or hepatitis infection) by administering to the mammal an effective amount of an agent that inhibits the interaction between a first and second CRACC protein, such as a CRACC composition (e.g., adenoviral vector comprising CRACC fusion). Suitable CRACC compositions may also include, e.g., an anti-CRACC siRNA, an anti-CRACC antibody, or antigen-binding fragment thereof, and a fusion protein comprising all or part of a CRACC ECD.

In some embodiments, T cells (e.g., $CD8^+$ T cells) from the infected (or cancer-carrying) mammals express higher levels of a CRACC polypeptide than T cells of the same histological type from a mammal that is not infected (or cancer carrying). In some embodiments, the cells express at least 5 (e.g., at least 10, 15, 20, 25, 30, 35, 40, 45, 50, 60, 70, 80, 90, or 100) % greater levels of a CRACC polypeptide, relative to cells of the same histological type from a healthy mammal of the same species. In some embodiments, the immune cells express at least 2 (e.g., at least 3, 4, 5, 6, 7, 8, 9, 10, 15, 20, 25, 30, 50, or 100) times the amount of a CRACC polypeptide relative to cells of the same histological type from a healthy mammal of the same species. In some embodiments, the methods can include measuring the level of expression (e.g., mRNA or protein expression) of a CRACC polypeptide by cells from the subject mammal. In some embodiments, the methods include administering the CRACC composition (e.g., adenoviral vector comprising CRACC fusion) to a mammal afflicted with an infection or cancer, wherein the mammal is one who has immune cells that overexpress a CRACC polypeptide. Suitable methods for measuring the expression level of an mRNA or protein are well known in the art.

In some embodiments, the mammal is infected with HIV-1.

In some embodiments, the methods can include monitoring a mammal (e.g., a human patient) for modulation (e.g., enhancement) of an immune response to an antigen of interest. In some embodiments, for example, embodiments in which the mammal has an infection or a cancer, the methods can include evaluating the mammal for a change in a disease parameter, e.g., an improvement in one or more symptoms of a given disorder. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer or an infection.

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect (e.g., modulate (e.g., enhance) an immune response to an antigen. The precise dosage will vary according to a variety of factors such as subject-dependent variables (e.g., age, immune system health, etc.), the disease, and the treatment being effected. Therapeutically effective amounts of the CRACC compositions disclosed herein enhance an immune response by a mammal to a target antigen.

Suitable human doses of any of the antibodies or fragments thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of cancer, vaccination, or infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. CRACC compositions that exhibits a high therapeutic index are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site.

In some embodiments of any of the methods described herein, a CRACC composition can be administered to a mammal in conjunction with one or more additional therapeutic agents (e.g., therapeutic agents for treating an infection or treating cancer).

Nutritional supplements that enhance immune responses, such as vitamin A, vitamin E, vitamin C, and the like, are well known in the art (see, for example, U.S. Pat. Nos. 4,981,844 and 5,230,902 and PCT Publ. No. WO 2004/004483) can be used in the methods described herein.

Similarly, compositions and therapies other than immunotherapy or in combination thereof can be used with in combination with the compositions of the present invention to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well known in the art.

In one embodiment, chemotherapy is used. Chemotherapy includes the administration of a chemotherapeutic composition. Such a chemotherapeutic composition may be, but is not limited to, those selected from among the following groups of compounds: platinum compounds, cytotoxic antibiotics, antimetabolities, anti-mitotic compositions, alkylating compositions, arsenic compounds, DNA topoisomerase inhibitors, taxanes, nucleoside analogues, plant alkaloids, and toxins; and synthetic derivatives thereof. Exemplary compounds include, but are not limited to, alkylating compositions: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic compositions: halichondrin, colchicine, and rhizoxin. Compositions comprising one or more chemotherapeutic compositions (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of β-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. (2003) *Experimental Hematology,* 31(6):446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. *Proc Natl Acad Sci USA* 94:7303-7307; Schreiber V et al. (2006) *Nat Rev Mol Cell Biol* 7:517-528; Wang Z Q, et al. (1997) *Genes Dev* 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) *Nature* 434:913-917; Farmer H, et al. (2005) *Nature* 434:917-921). The foregoing examples of chemotherapeutic compositions are illustrative, and are not intended to be limiting. Additional examples of chemotherapeutic and other anti-cancer compositions are described in US Pat. Publs. 2013/0239239 and 2009/0053224.

In still another embodiment, the term "targeted therapy" refers to administration of compositions that selectively interact with a chosen biomolecule to thereby treat cancer. For example, bevacizumab (Avastin®) is a humanized monoclonal antibody that targets vascular endothelial growth factor (see, for example, U.S. Pat. Publ. 2013/0121999, WO 2013/083499, and Presta et al. (1997) *Cancer Res.* 57:4593-4599) to inhibit angiogenesis accompanying tumor growth. In some cases, targeted therapy can be a form of immunotherapy depending on whether the target regulates immunomodulatory function.

The term "untargeted therapy" refers to administration of compositions that do not selectively interact with a chosen biomolecule yet treat cancer. Representative examples of untargeted therapies include, without limitation, chemotherapy, gene therapy, and radiation therapy.

Regarding irradiation, a sublethal dose of irradiation is generally within the range of 1 to 7.5 Gy whole body irradiation, a lethal dose is generally within the range of 7.5 to 9.5 Gy whole body irradiation, and a supralethal dose is within the range of 9.5 to 16.5 Gy whole body irradiation.

Depending on the purpose and application, the dose of irradiation may be administered as a single dose or as a fractionated dose. Similarly, administering one or more doses of irradiation can be accomplished essentially exclusively to the body part or to a portion thereof, so as to induce myeloreduction or myeloablation essentially exclusively in the body part or the portion thereof. As is widely recognized in the art, a subject can tolerate as sublethal conditioning ultra-high levels of selective irradiation to a body part such as a limb, which levels constituting lethal or supralethal conditioning when used for whole body irradiation (see, for example, Breitz (2002) *Cancer Biother Radiopharm.* 17:119; Limit (1997) *J. Nucl. Med.* 38:1374; and Dritschilo and Sherman (1981) *Environ. Health Perspect.* 39:59). Such selective irradiation of the body part, or portion thereof, can be advantageously used to target particular blood compartments, such as specific lymph nodes, in treating hematopoietic cancers.

The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

The following examples are intended to illustrate, not to limit, this disclosure.

EXAMPLES

This invention is further illustrated by the following examples, which should not be construed as limiting.

Strategies targeting immune cell inhibitory and/or co-stimulatory molecules have been successfully used to treat multiple cancer types in humans, however, there is a need to develop novel cancer immunotherapies. The immune-cell receptor, CD2-like receptor activating cytotoxic cell (CRACC), is a member of the signaling lymphocytic activation molecules (SLAM) family of receptors that plays a critical role in immune cell regulation. As described herein, an adenovirus gene-transfer vector is constructed that expresses a murine CRACC-Fc fusion protein (rAd5-mCRACC-Fc) for use as an immunomodulating agent against established CT26 colon adenocarcinoma tumors. Compared to controls, administration of rAd5-mCRACC-Fc into mice increased CD69 and IFN-$\gamma$ expression in splenic natural killer cells. Enhanced CD86 expression on splenic dendritic cells and macrophages of rAd5-mCRACC-Fc-treated mice was also noted. These responses were associated with robust type I interferon (IFN) gene expression and IL-12 production in rAd5-mCRACC-Fc vaccinated mice, compared to controls. Upon CT26 tumor challenge, intratumoral administration of rAd5-mCRACC-Fc reduced tumor growth and increased survival of CT26 tumor-bearing mice. Vaccinations with rAd5-mCRACC-Fc in conjunction with CT26 tumor lysates resulted in enhanced CT26-specific B- and T-cell memory responses and antibody-dependent cell-mediated cytotoxicity (ADCC). Additionally, rAd5-mCRACC-Fc enhanced T- and NK-cell infiltrations of the tumors compared to rAd5-Null-injected controls.

Despite expression of tumor-associated antigens (TAA), the immunosuppressive tumor microenvironment (TME) prevents the development of strong anti-tumor immune responses (1). Tumor immunosuppressive mechanisms include inhibition of T cells via soluble factors or reduction of co-stimulation signals from antigen presenting cells (APCs) (1-3). Blockade of T cell inhibitory receptors, such as CTLA-4 (4), PD-1 (5), Tim-3 (6), and others, have been proven to be effective anti-tumor therapies. Furthermore, agonistic antibodies against co-stimulatory molecules, such as CD134 (OX40) (7), CD137 (4-1BB) (8), and CD27 (9), are promising tumor immunotherapies. Additionally, combination of multiple immune checkpoint inhibitors has been shown to be superior to mono-therapies (10,11), allowing for a strengthened immune response against tumors and potentially preventing tumor relapse in the future. Therefore, developing potent cancer immunotherapies that augment anti-tumor responses, either as a stand-alone therapy or in combination with other agents, is of importance.

The CD2-like receptor activating cytotoxic cell (CRACC) receptor (CD317, CS-1, SLAMF7) is a member of the signaling lymphocytic activation molecules (SLAM) family of receptors, that is expressed on NK cells, macrophages, dendritic cells, and activated T and B cells (12-15). CRACC is a homotypic receptor that interacts with the Ewing's sarcoma-associated transcript 2 (EAT-2) adaptor protein via the phosphorylated cytoplasmic immunoreceptor tyrosine-based switch motifs (ITSMs) of CRACC protein via its Src homology 2 (SH2) domain (14). In the presence of EAT-2 adaptor protein, engagement of CRACC receptor generally results in immune cell activation, while in its absence, CRACC activation has inhibitory effects as has been shown in EAT-2 negative NK cells (16), and T cells (14).

Specific targeting of CRACC, using CRACC-Fc protein during vaccination allows for blockade of the CRACC receptor and significantly enhanced NK cell activation, DC maturation, and antigen-specific CD8+ T cell responses (17). It was hypothesized that CRACC-Fc fusion protein would make an effective and potent anti-tumor therapeutic by simultaneously activating the innate and adaptive arms of the immune system, thus allowing for enhanced tumor cell killing via simultaneous activation of APCs and enhancement of NK cell and cytotoxic T lymphocyte (CTL) immune responses. To test the ability of mCRACC-Fc to augment innate and adaptive immune responses within the TME, an adenovirus-based platform was generated (18), and its anti-tumor activity was tested in a well-established murine CT26 colon adenocarcinoma tumor model. It was shown that transduction of mCRACC-Fc gene using adenovirus was successful and that expression of mCRACC-Fc resulted in augmented IL-12 production, enhanced activation of NK cells, and increased maturation and activation of APCs. The robust innate immune activation observed in response to mCRACC-Fc overexpression was accompanied by dramatic elevation of IFN-β and Interferon Stimulated Gene (ISG) responses in the spleens of rAd5-mCRACC-Fc treated mice. During CT26 tumor challenge, intratumoral administration of rAd5-mCRACC-Fc allowed for reduced tumor growth and decreased mortality of CT26 tumor-bearing mice. Additionally, serial vaccinations against CT26 colon adenocarcinoma using combination of whole CT26 tumor lysate and rAd5-mCRACC-Fc allowed for development of enhanced CT26 tumor-specific humoral and T cell responses. Tumors derived from rAd5-mCRACC-Fc vaccinated mice developed enhanced lymphocyte infiltration. Finally, antibodies derived from rAd5-mCRACC-Fc-treated mice showed an enhanced tumor killing via antibody-mediated cellular-cytotoxicity (ADCC). Together, this data suggests that overexpression of mCRACC-Fc in TME is a novel cancer immunotherapy strategy that augment both innate and adaptive anti-tumor immune responses.

Example 1. Materials and Methods

Animal Procedures

Adult male wild type Balb/c mice were purchased from Taconic Farms. Care for mice was provided in accordance with Michigan State University (MSU) Institutional Animal Care and Use Committee (IACUC) (http://iacuc.msu.edu-.proxyl.cl.msu.edu/), covered by AUF: 09-14-166-00. All procedures were reviewed and approved by the MSU Institutional Biosafety Committee (IBC) and Environmental Health and Safety (EHS).

Adenovirus Generation and Production

The rAd-5-Null (an adenovirus construct encoding no additional exogenous protein and used as a control in the experiments) viruses were constructed, amplified and purified as previously described (Aldhamen Y A et al. *Vaccine* 2016; 34(27):3109-18). rAd-5-mCRACC-Fc was engineered as follows. rAd5-Null was constructed and purified, as previously described (19). For rAd5-mCRACC-Fc vector, the CRACC extracellular domain (ECD) (NCBI Reference Sequence: NM_144539.5 (http://www.ncbi.nlm.nih.gov/nuccore/NM 144539.5)) was fused to mIgG1-Fc portion and cloned into pShuttle CMV. The rAd5-mCRACC-Fc vector was constructed and purified, as described.

Adenovirus Vector Construction

CRACC-ECD/mIgG1-Fc was excised using primers flanked by EcoRI and HindIII restriction endonucleases (NEB, Ipswich, Mass.) from a plasmid (Biomatik, Delaware, USA) and sub-cloned into the pShuttle vector, which contains a CMV expression cassette. The resulting pShuttle-mCRACC-Fc plasmid was linearized with PmeI restriction enzyme and homologously recombined with the pAdEasyI Ad5 vector genome yielding pAd-mCRACC-Fc. HEK293 cells were transfected with PacI linearized plasmid and viable virus was obtained and amplified after several rounds of expanding infection. rAd5-mCRACC-Fc virus was purified using a $CsCl_2$ gradient. To confirm that rAd5-mCRACC-Fc vector expresses mCRACC-Fc transgene, qRT-PCR analysis was performed to validate the expression of mCRACC-Fc following rAd5-mCRACC-Fc or rAd5-Null infection. All viruses were found to be replication competent adenovirus (RCA)-free by both RCA PCR (E1 region amplification) and direct sequencing methods.

Tumor Challenge

Intratumoral study: 6 weeks old male Balb/c mice were injected subcutaneously (S.Q.) into the flank with 150,000 CT26 cells in 100 µL of PBS. 8 days later, once visible tumors formed, mice were split randomly into 3 groups and were either injected intratumorally (I.T.) with $10^{10}$ v.p. of Ad-Null (n=15), Ad-mCRACC-Fc (n=15), or not injected (n=14). Mice were monitored every 2-3 days and their tumor width and lengths were measured. Using formula ½* (Length×Width²), tumor volumes were calculated. Tumor volume of 2,000 mm³ or presence of ulcerations on the tumors were used as humane end-point. 1 naïve, 4 ad-null and 3 Ad-mCRACC injected mice completely resolved their tumors. At the completion of the intatumoral injections challenge these mice were re-challenged with CT26 tumors cells via S.Q. injection of 300,000 cells into the flank. These mice were followed for 3 months and observed no visible tumor formation.

Pre-vaccination using cell lysate and adenoviruses: 6-weeks-old Balb/c male mice were given three doses of 200 µg of CT26 tumor lysate and $10^{10}$ v.p. of Ad-Null (n=8), or Ad-mCRACC-Fc (n=9) intraperitoneally (I.P.), or not injected (unvaccinated, n=9) over a period of 5 weeks. $2^{nd}$ dose—3 weeks after the first, $3^{rd}$ dose—12 days after $2^{nd}$ dose. On the same day as the dose 3, mice were injected with 250,000 CT26 tumor cells. Mice were monitored every 2-3 days starting on day 5 post tumor challenge. Measurements and humane end point were the same as above.

Cell Culture

CT26 colon adenocarcinoma cells were purchased from ATCC and cultured in complete RPMI 1640 media (10% heat inactivated FBS, and 1% penicillin, streptomycin and fungizone). C7 cells were cultured in complete RPMI 1640 media.

For killing assay, tumor free mice in remission from the intratumoral injections study were sacrificed and their spleens were collected. CT26 cells were stained with 5 µM of CFSE in PBS at RT for 12 minutes, washed twice with 5% FBS and plated at 50,000 cells/well in round U-bottom 96-well plates. Splenocytes were added at an effector to target ratio of 10:1 in presence of 1 ng/mL of mouse IL-2. All wells were infected with Ad-mCRACC-Fc at measure of infectivity (MOI—number of viral particles per cell) of 5,000. Cell were left in the incubator for 40 hours, after which cells were trypsinized with 0.25% trypsin for 5 minutes at 37° C., washed, stained with 2 µL of Propidium Iodide for 2 minutes, and flow sorted on BD LSR II instrument.

Innate Immune Study 6-weeks-old Balb/c male mice were injected intravenously (I.V.) with $10^{10}$ viral particles (v.p.) of Ad-Null (n=6), Ad-mCRACC-Fc (n=6) or not injected—naïve (n=3). After 10 hours, plasma and spleens were collected for Bioplex and Flow cytometry analysis.

Cytokine and Chemokine Analysis

Mouse 27-plex multiplex-based assay was used to determine cytokine/chemokine plasma concentrations via Luminex 100 per manufacturer's protocol.

Cell Staining and Flow Cytometry

Splenocytes were processed and stained as described previously (Aldhamen Y A et al. *PLoS One.* 2013; 8(7):

e69539). Briefly, for surface staining, 2 million cells were incubated with Fcγ block (BD Biosciences) and incubated on ice with the appropriate antibodies for 45 minutes and washed twice with FACS buffer. List of antibodies used: mix 1: PE-Cy7—CD11c (BD Biosciences), APC-Cy7—CD11b (BD Biosciences), PE—F4/80 (eBioscience), V450—CD86 (BD Horizon), FITC—CD40 (eBioscience), PerCP-Cy5.5—CD107 (CCR7) (BD Pharmigen); mix 2: APC-Cy7—CD3e (BD Pharmigen), Alexa Fluor 700—CD8(BD Pharmigen), PerCP-Cy5.5—CD19 (BD Pharmigen), PE-Cy7—CD49b clone Dx5 (eBioscience), FITC—CD69 (BD Pharmigen, eFluor450—CD107a (eBioscience); mix 3: APC—CD3, Alexa Fluor 700—CD8a (BD Pharmigen), PE-Cy7—CD49b clone Dx5 (eBioscience), Alexa Fluor 488—IFN-γ (BD Pharmigen), eFluor450—CD107a (eBioscience).

For surface staining, 2 million cells were incubated with Fcγ block (BD Biosciences) and appropriate antibodies on ice for 45 minutes and washed twice with FACS buffer. List of antibodies used: mix 1: PE-Cy7—CD11c (BD Biosciences), APC-Cy7—CD11b (BD Biosciences), PE—F4/80 (eBioscience), V450—CD86 (BD Horizon), FITC—CD40 (eBioscience), PerCP-Cy5.5—CD107 (CCR7) (BD Pharmigen); mix 2: APC-Cy7—CD3e (BD Pharmigen), Alexa Fluor 700—CD8 (BD Pharmigen), PerCP-Cy5.5—CD19 (BD Pharmigen), PE-Cy7—CD49b clone Dx5 (eBioscience), FITC—CD69 (BD Pharmigen, eFluor450—CD107a (eBioscience); mix 3: APC—CD3 (BD Pharmigen), Alexa Fluor 700—CD8a (BD Pharmigen), PE-Cy7—CD49b clone Dx5 (eBioscience), Alexa Fluor 488—IFN-γ (BD Pharmigen), eFluor450—CD107a (eBioscience).

For intracellular staining, after surface staining, cells were washed with FACS buffer, and fixed with BD Cytofix/Cytoperm Fixation/Permeabilization kit (BD Biosciences) per manufacturer's protocol. Cells were stained on ice for 1 hour and washed twice with FACS buffer, after which they were flow sorted on BD LSR II instrument and analyzed using FlowJo software (Tree Star).

Anti-IgG ELISA

100 μg of CT26 lysate was plated per well in a high-binding 96-well flat-bottom plate and incubated at 4° C. overnight. Following incubation, plates were washed with wash buffer (PBS containing 0.05% Tween) and incubated with blocking buffer (PBS containing 3% bovine serum albumin) for an hour at room temperature. Plasma was plated at 1:10, 1:50, 1:100, 1:200, 1:500 and 1:1000 dilutions. After incubation, wells were washed with wash buffer 5 times. Wells were coated with 100 μL of horseradish peroxidase (HRP)-conjugated goat anti-mouse anti IgG antibody (Bio-Rad) diluted 1:7,000 and incubated for 1 hour at RT. After washing wells with wash buffer 5 times, 100 μL of Tetramethylbenzidine (TMB) substrate (Sigma-Aldrich) was added to each well to initiate the spectrophotometric reaction, which was stopped with 50 μL of 2 N sulfuric acid after 30 minutes of incubation. Plates were analyzed using an automatic microplate reader at 450 nm absorbance.

ELISA Analysis

Following incubation of high-binding with CT26 lysate, plates were washed with PBS, containing 0.05% Tween (Sigma-Aldrich) and incubated with blocking buffer (PBS containing 3% bovine serum albumin) for 1 hour at room temperature. Plasma was plated at 1:10, 1:50, 1:100, 1:200, 1:500 and 1:1000 dilutions. After incubation, wells were washed with wash buffer 5 times. Wells were coated with 100 μL of horseradish peroxidase (HRP)-conjugated goat anti-mouse anti IgG antibody (Bio-Rad) diluted 1:7,000 and incubated for 1 hour at RT. After washing wells with wash buffer 5 times, 100 μL of Tetramethylbenzidine (TMB) substrate (Sigma-Aldrich) was added to each well to initiate the spectrophotometric reaction, which was stopped with 50 μL of 2 N sulfuric acid after 30 minutes of incubation. Plates were analyzed using an automatic microplate reader at 450 nm absorbance.

ELISPOT Analysis

Splenocytes were incubated with media alone (unstimulated), media containing 20 g/mL of whole CT26 tumor lysate, or with $10^{10}$ v.p. of heat inactivate rAd5-Null. Plates were then incubated for 18 h in a 37° C., 5% C02 incubator. Plates were stained and developed using Ready-set Go IFN-γ kit (eBioscience) per the manufacturer's protocol. Spots were counted and photographed by an automated ELISPOT reader system (Cellular Technology).

RT-PCR Analysis 6-weeks-old Balb/c male mice were injected intravenously (I.V.) with $10^{10}$ viral particles (v.p.) of Ad-Null (n=6), Ad-mCRACC-Fc (n=6) or not injected—naïve (n=3). After 6 hours, mice were sacrificed, and their spleens were snap frozen in liquid nitrogen and stored at −80° C. RNA was extracted using the Trizol reagent (Life Technologies), per manufacturer's protocol. cDNA was generated using SuperStrand First Strand Synthesis Kit III (Invitrogen) per the manufacturer's protocol. Quantitative RT-PCR was performed using SYBR green PCR Mastermix (Life Technologies) and analyzed on a QuantStudio7 system (Thermofisher). The following primers were used:

```
IL-15:
Forward
                                (SEQ ID NO: 31)
5'GTGACTTTCATCCCAGTTGC3', Reverse
                                (SEQ ID NO: 32)
5'TTCCTTGCAGCCAGATTCTG3';

ISG15:
Forward
                                (SEQ ID NO: 33)
5'GGTGTCCGTGACTAACTCCAT3', Reverse
                                (SEQ ID NO: 34)
5'TGGAAAGGGTAAGACCGTCCT'3;

OAS2:
Forward
                                (SEQ ID NO: 35)
5'TTGAAGAGGAATACATGCGGAAG3', Reverse
                                (SEQ ID NO: 36)
5'GGGTCTGCATTACTGGCACTT3';

Irf9:
Forward
                                (SEQ ID NO: 37)
5'GCCGAGTGGTGGGTAAGAC3', Reverse
                                (SEQ ID NO: 38)
5'GCAAAGGCGCTGAACAAAGAG3'.
```

HEK-293 derived C7 cells were plated at $2*10^6$/mL in 12-well plates in 500 μL of complete RPMI media. Ad-Null and Ad-mCRACC viruses were added at 1,000 MOI per well in 10 μL. Mock treated cells were treated with 10 μL of PBS.

Cells were incubated overnight. After 12 hours of incubation, RNA was extracted using Trizol method. Primers used:

```
mCRACC-Fc:
Forward
                            (SEQ ID NO: 39)
5'GGCACATGCGTGATCAATCT3', Reverse
                            (SEQ ID NO: 40)
5'ATCGCCAAGCGATACTCAGA3'.
```

To measure relative gene expression, GAPDH (glyceraldehyde-3-phosphate dehydrogenase) gene measurement and the comparative threshold cycle method were used for all samples. Induction of gene expression was calculated as the relative change from the level of mock-treated cell transcripts to the level of recombinant Ad5-treated cell transcripts.

Quantitative RT-PCR Analysis cDNA was generated using SuperStrand First Strand Synthesis Kit III (Invitrogen) from Reizol isolated RNA per the manufacturer's protocol. Quantitative RT-PCR was performed using SYBR green PCR Mastermix (Life Technologies) and analyzed on a QuantStudio7 system (Thermofisher). The following primers were used:

```
IL-15:
For
5'GTGACTTTCATCCCAGTTGC3',

Rev
5'TTCCTTGCAGCCAGATTCTG3';

ISG15:
For
5'GGTGTCCGTGACTAACTCCAT3',

Rev
5'TGGAAAGGGTAAGACCGTCCT'3;

OAS2:
For
5'TTGAAGAGGAATACATGCGGAAG3',

Rev
5'GGGTCTGCATTACTGGCACTT3';

IFNa:
For:
5'GCCTTGACACTCCTGGTACAAATGAG3',

Rev:
5'CAGCACATTGGCAGAGGAAGACAG3';

IFNb:
For:
5'TGGGTGGAATGAGACTATTGTTG3',

Rev:
5'CTCCCACGTCAATCTTTCCTC3';

IL-6:
For:
5'TAGTCCTTCCTACCCCAATTTCC3',

Rev:
5'TTGGTCCTTAGCCACTCCTTC3';

IL-12p40:
For:
5'TGGTTTGCCATCGTTTTGCTG3',

Rev:
5'ACAGAGGTTCACTGTTTCT3';

IP10:
For:
5'CCAAGTGCTGCCGTCATTTTC3',

Rev:
5'GGCTCGCAGGGATGATTTCAA3';

GM-CSF:
For:
5'GGCCTTGGAAGCATGTAGAGG3',

Rev:
5'GGAGAACTCGTTAGAGACGACTT3';

Socs1:
For:
5'CTGCGGCTTCTATTGGGGAC'3,

Rev:
5'AAAAGGCAGTCGAAGGTCTCG'3;

mGAPDH:
For:
3'AGAACATCATCCCTGCATCC3',

Rev:
5'CACATTGGGGGTAGGAACAC3'.
```

HEK-293 derived C7 cells were plated at $2*10^6$/mL in 12-well plates in 500 μL of complete RPMI (GIBCO) media. rAd5-Null and rAd5-mCRACC viruses were added at multiplicity of infectivity (MOI) of 1,000 v.p. per cell per well in 10 μL. Mock treated cells were treated with 10 μL of PBS. Cells were incubated overnight. After 12 hours of incubation, RNA was extracted using Trizol. Primers used:

```
mCRACC-Fc:
For:
5'GGCACATGCGTGATCAATCT3',

Rev:
5'ATCGCCAAGCGATACTCAGA3'.

hGAPDH:
For:
5'GGGTGTGAACCATGAGAAGTATGAC3',

Rev:
5'GCCATCCACAGTCTTCTGGGT3'.
```

To measure relative gene expression, GAPDH gene measurement and the comparative threshold cycle method were used for all samples. Induction of gene expression was calculated as the relative change from the level of mock-treated cell transcripts to the level of recombinant Ad5-treated cell transcripts.

Western Blot

Spleens from Mock, rAd5-Null and rAD5-mCRACC-Fc intravenously injected mice 6 hours post injections were harvested, snap frozen and stored at −80° C. For cell lysate preparation, spleens were homogenized in ice-cold lysis buffer containing 1% NP-40 Lysis Buffer (Life Technologies), protease inhibitor (Sigma-Aldrich) and phosphatase inhibitors (ThermoFisher Scientific). The concentrations of cell lysates were determined by a BCA assay (ThermoFisher Scientific). 50 μg of total protein was loaded onto 12% gel Mini-Protean TGX Precast Gels (Bio-Rad). The proteins were transferred to nitrocellulose membrane (Amersham Protran) for 1 hour at room temperature. The membrane was blocked for 1 hour in Odyssey Blocking Buffer (Licor Biosciences), then incubated for overnight at room temperature with primary monoclonal rabbit anti-human anti-STAT- 1-P (1:200, R&D, cat #1086B) or anti-mouse anti-β-actin (1:3000; Abcam, cat #8224). The blot was washed with TBS-T three times and then incubated with IRDye anti-mouse (926-32210; Licor) or anti-rabbit (925-68070) secondary Ab diluted in blocking buffer (1:10,000) for 1 h at room temperature. The blotted membrane was washed and developed on the Licor Odyssey (Licor). Once, the nictro-cellulose paper was scanned and analyzed for STAT1-P, it was stripped using NewBolt IR Stripping Buffer (Licor) and re-blotted and analyzed for β-actin. Densitometric analysis was done using ImageJ software.

Immunohistochemistry—CD3, CD8 & Integrin Alpha-2 (DX5) Primary Antibodies

Specimens were fixed in 10% Neutral Buffered Formalin, processed, embedded in paraffin and sectioned on a rotary microtome at 4μ's. Sections were placed on positively charged slides and dried at 56° C. overnight. The slides were subsequently deparaffinized in Xylene and hydrated through descending grades of ethyl alcohol to distilled water. Slides were placed in Tris Buffered Saline (TBS) pH 7.4 (Scytek Labs—Logan, Utah) for 5 minutes for pH adjustment. Following TBS, slides for CD8 and DX5 staining underwent heat induced epitope retrieval in a steamer or pressure cooker utilizing Scytek Citrate Plus Retrieval pH 6.0 (Table 7), followed by rinses in several changes of distilled water. Endogenous Peroxidase was blocked utilizing 3% Hydrogen Peroxide/Methanol bath for 30 minutes followed by running tap and distilled water rinses. Following pretreatments standard micro-polymer complex staining steps were performed at room temperature on the IntelliPath™ Flex Autostainer. All staining steps are followed by rinses in TBS Autowash buffer (Biocare Medical). After blocking for non-specific protein with Rodent Block M (Biocare) for 10 or 20 minutes (Table 7); sections were incubated with specific primary antibodies (Table 7) in normal antibody diluent (NAD-Scytek) and incubated for 60 minutes. Micro-Polymer (Biocare) reagents were subsequently applied for specified incubations (Table 7) followed by reaction development with Romulin AEC™ (Biocare) (Table 7) and counterstained with Cat Hematoxylin (Table 7).

TABLE 7

Specifications of antibodies used for immunohistochemistry

| Primary Antibody | Ab Vendor: | Pretreatment: | Primary: | Staining System (BioCare Medical): |
|---|---|---|---|---|
| Rabbit anti - CD3 Polyclonal | Abcam #GR3194253-3 Cambridge, MA | Heat Retrieval - Citrate Buffer pH 6.0 - Pascal Pressure Cooker - 125° C. for 15 sec, 80° C. for 1 min, room temperature with lid off for 30 min | 1:450 in NAD - 1 Hour | Rodent Block M - 20 minutes ProMark Rabbit on Rodent HRP Polymer ™ - 35 minutes AEC Chromogen - 5 minutes CATHE Hematoxylin 1:10 - 1 minute |
| Rat anti - CD8 Monoclonal | Dianova #DIA-808 Hamburg, Germany | Heat Retrieval - Citrate Buffer pH 6.0 - Steamer for 30 min, room temperature with lid off for 10 min | 1:100 in NAD - 1 Hour | Rodent Block M - 10 minutes ProMark Rat on Mouse HRP Probe ™ - 10 minutes ProMark Rat on Mouse HRP Polymer ™ - 10 minutes AEC Chromogen - 5 minutes CATHE Hematoxylin 1:10 - 1 minute |
| Rabbit anti - Integrin Alpha 2 (DX5) Monoclonal | Abcam #GR196223-25 Cambridge, MA | No Pretreatment | 1:100 in NAD - 1 Hour | Rodent Block M - 20 minutes ProMark Rabbit on Rodent HRP Polymer ™ - 20 minute AEC Chromogen - 5 minutes CATHE Hematoxylin 1:10 - 1 minute |

Statistical Analysis

The statistical significance of all data with exception of percent survival analysis was determined using one-way ANOVA with Tukey post hoc analysis. Data in all graphs is presented as mean±standard error. Statistical analysis of the percent survival in tumor challenges mice was determined using log-rank test. All statistical analysis was performed using GraphPad Prism 7 software.

Example 2: CRACC-Fc-Expressing Ad5 Vectors Successfully Infects Cells and Induces mCRACC-Fc Expression Previously, CRACC-Fc fusion protein was previously constructed and composed of CRACC extracellular domain fused to murine IgG1 Fc domain (Aldhamen Y A et al. Vaccine 2016; 34(27):3109-18). This protein's ability to interact with CRACC receptor in a dose-dependent manner was successfully validated, and discovered its ability to enhance activity of NK cells, maturity of DC cells and T cell responses (Aldhamen Y A et al. Vaccine 2016; 34(27):3109-18), making it a suitable candidate for anti-tumor therapy. To further study this protein as anti-cancer immunogen, an adenovirus platform was utilized instead of purified protein due to cost-effectiveness and scalability of using adenovirus vector system (Sharon D et al. Biotechnol Bioeng. 2018; 115(1):25-40).

An Adenovirus (Ad5) vector expressing mCRACC-Fc protein was constructed and mCRACC-Fc production was confirmed by infecting modified HEK 293—C7 cell lines.

Figure 1A:
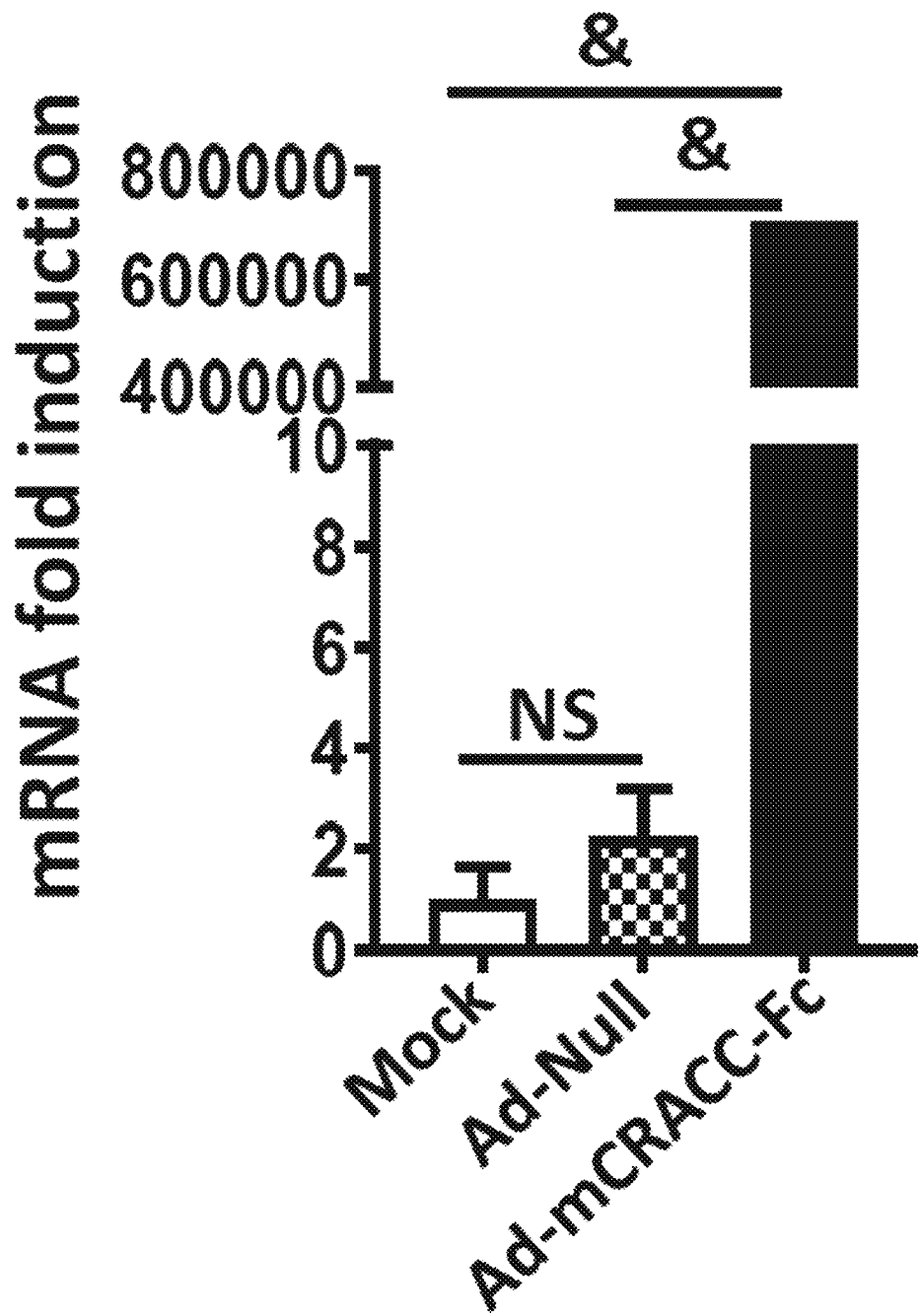
FIG. 1A shows mRNA fold induction compared to mock is graphed as a mean+/−SEM. 6 weeks old Balb/c male were injected I.V, with $10^{10}$ v.p. of Ad-null or Ad-mCRACC-Fc. 10 hours post injection spleens were collected from injected (n=6) and naïve mice (n=3), processed, stained and analyzed by Flow cytometry.
Figure 1B:
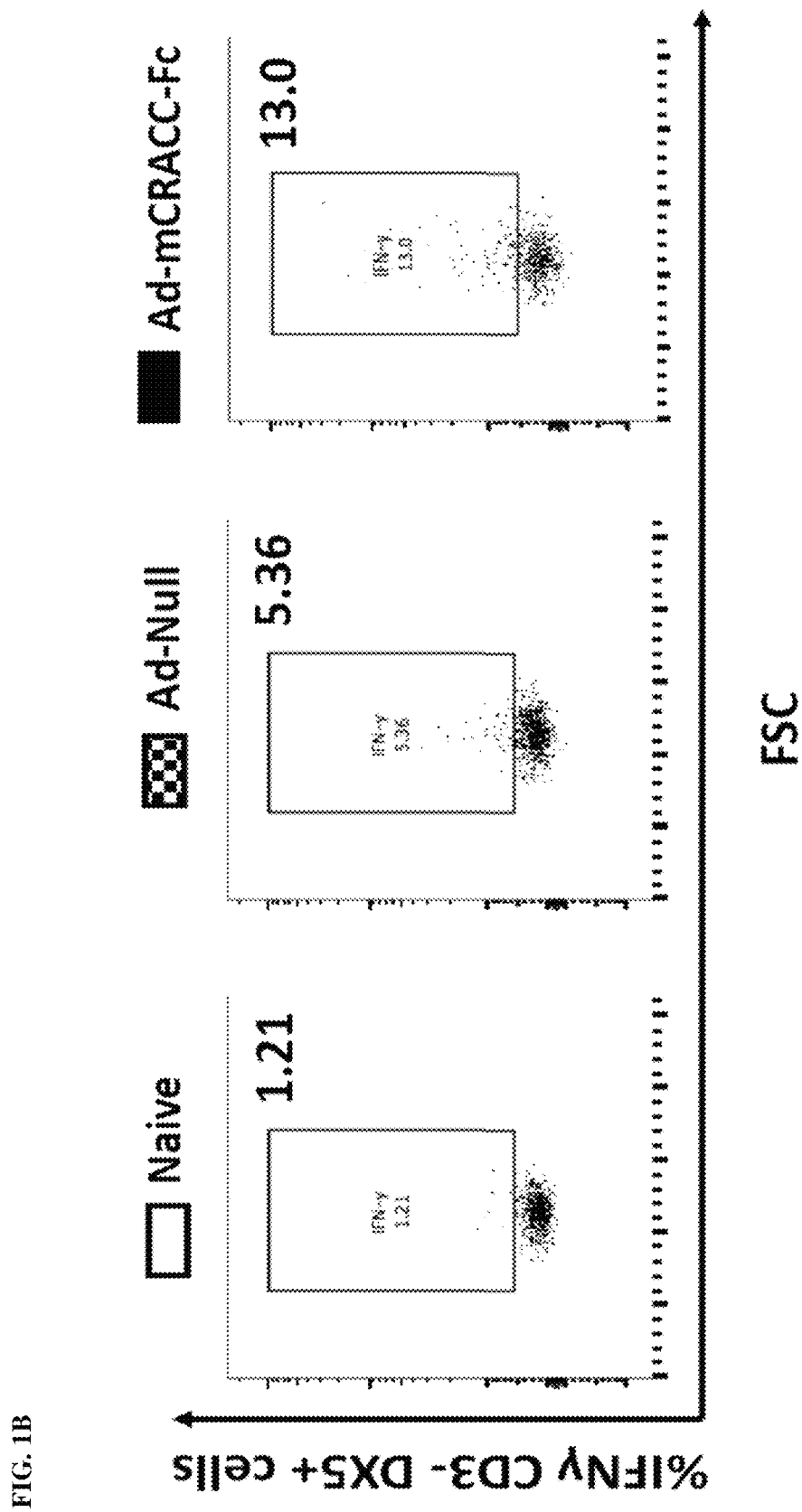
FIG. 1B depicts representative histograms showing percent of intracellular IFNγ+CD3-Dx5$^+$ NK cells.
Figure 1C:
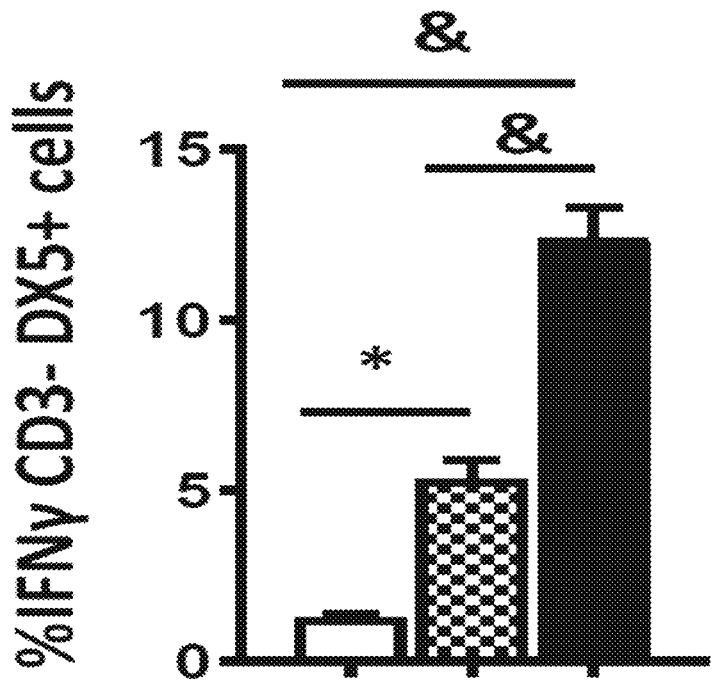
FIG. 1C shows a graph representing percent of intracellular IFNγ+CD3-Dx5$^+$ NK cells.
Figure 1D:
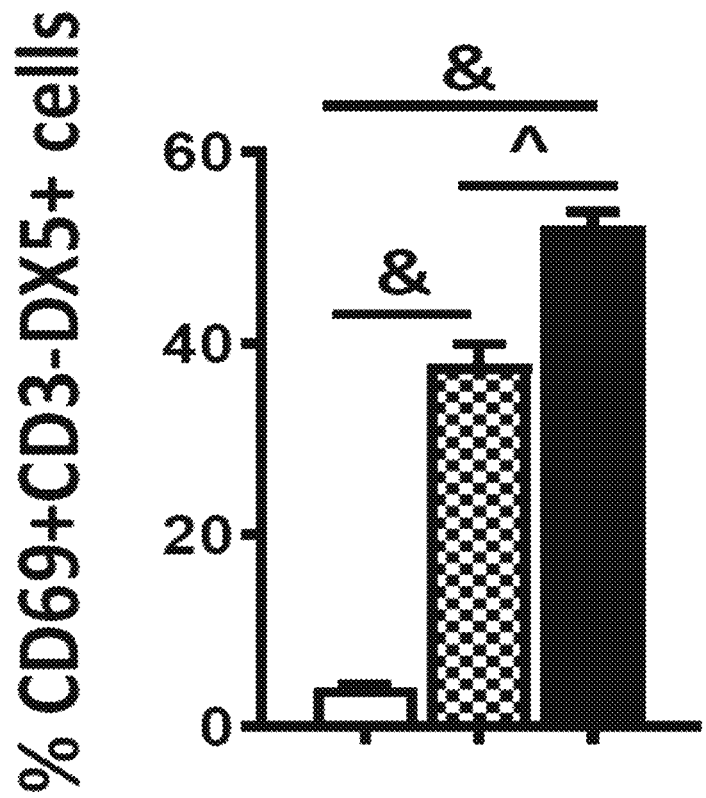
FIG. 1D depicts graphed surface levels of CD69 activation marker on CD3-Dx5$^+$ NK cells. 6 weeks old Balb/c male were injected I.V, with $10^{10}$ v.p. of Ad-Null or Ad-mCRACC-Fc. 6 hours post injection spleens were collected from injected (n=6) and naïve mice (n=3), flash frozen in liquid nitrogen and stored at −80 C for RNA analysis. mRNA fold induction over naïve mice is graphed for the following genes: IFNβ (FIG. 1E), IFNα (FIG. 1F), IL-15 (FIG. 1G), ISG15 (FIG. 1H), and OAS2 (FIG. 1I).
Figure 1E:
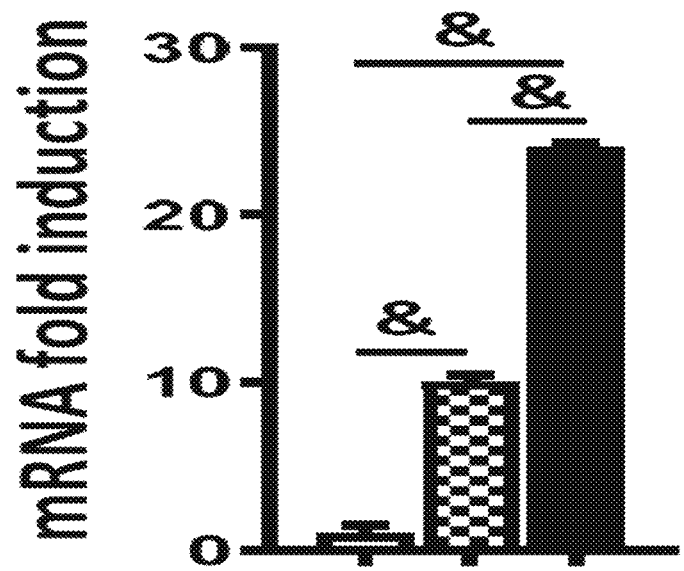
FIG. 1, contains ten panels FIG. 1A-FIG. 1J, depicting the effect of mCRACC-Fc overexpression on NK cell activity and function. C7 cells (n=3) were mock treated (PBS) or infected with MOI 1,000 of Ad-Null or Ad-mCRACC-Fc virus overnight. Trizol method was used for mRNA isolation from cells as described in methods. CRACC gene expression levels were normalized compared to GAPDH gene.
FIG. 1J shows expression of mCRACC-Fc in Ct26 cells. CT26 cells (n=3) were mock treated (PBS) or infected with MOI 1,000 of rAd5-Null or rAd5-mCRACC-Fc virus overnight. Trizol was used for mRNA isolation from cells as described in methods. CRACC gene expression levels were normalized compared to GAPDH gene and graphed in (FIG. 1A). All graphs represent mean+/−SEM. Statistical analysis was performed using One-way ANOVA with Tukey's post hoc test, where *—$p<0.05$, #—$p<0.01$, ˆ—$p<0.001$, & —$p<0.0001$, and NS—not significant.
Figure 1F:
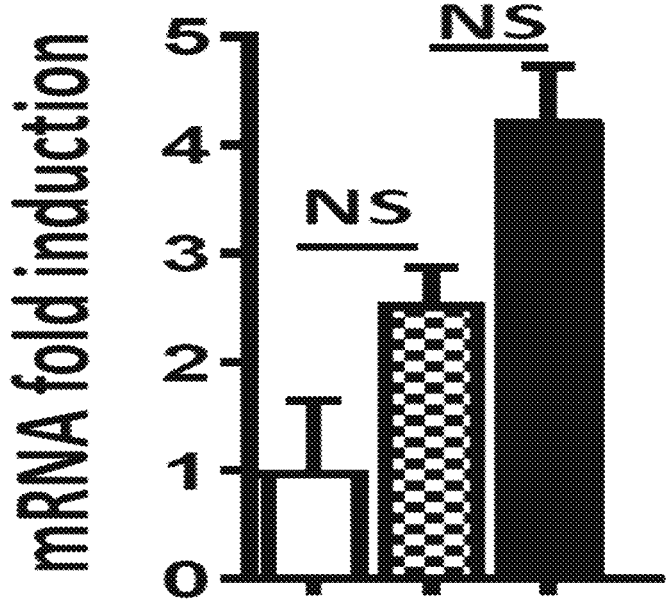
Figure 1G:
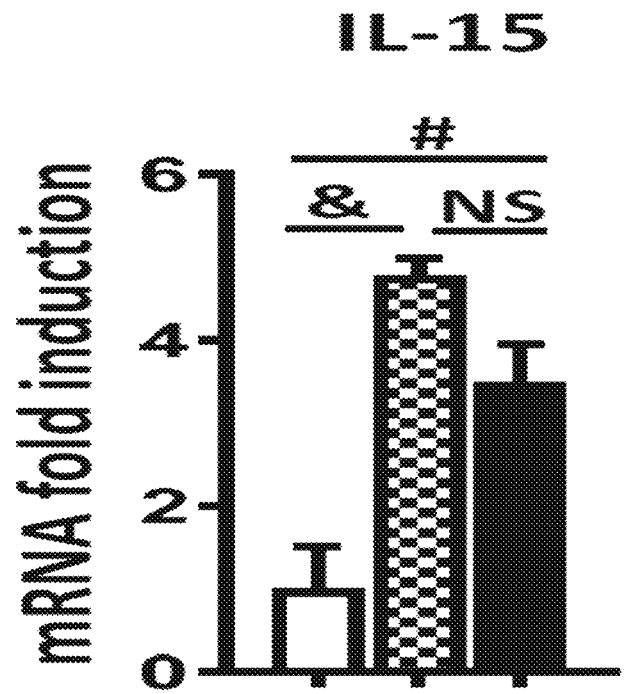
Figure 1H:
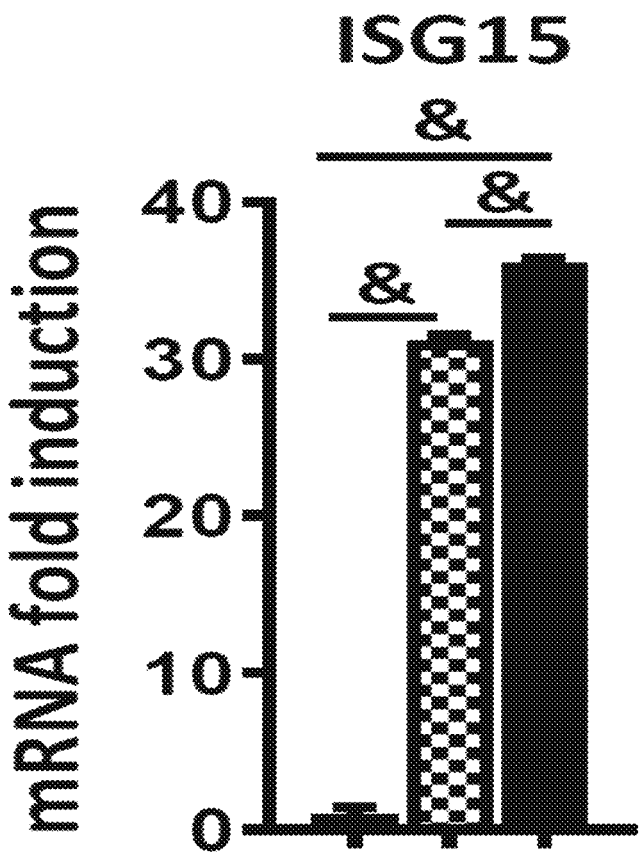
Figure 1I:
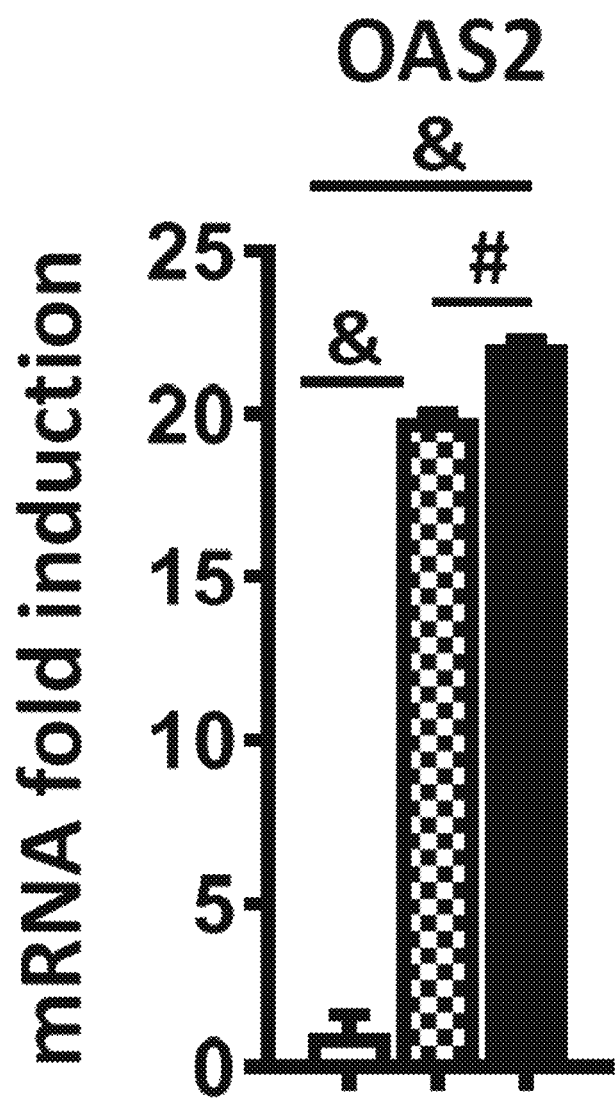
Figure 1J:
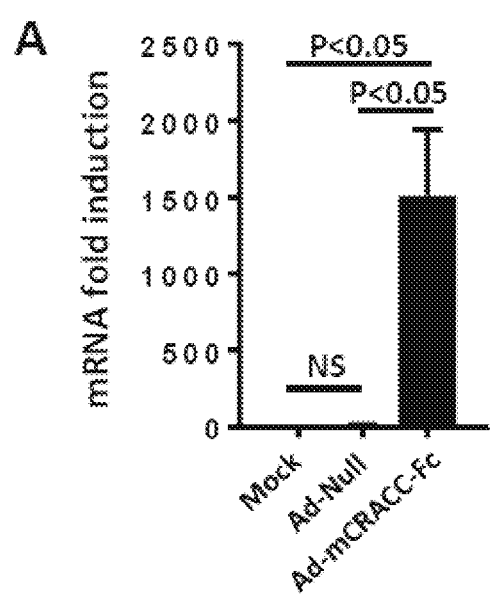

Ad-mCRACC-Fc infection at 1,000 MOI over 12 hours showed an over 600,000-fold induction of mCRACC-Fc (FIG. 1A), proving effective transduction and robustness of utilizing adenovirus as a vector for gene transfer. This proves effective transduction and robustness of utilizing Ad5 as a vector for expressing mCRACC-Fc gene. Similarly, CT26 cells infected with rAd5-mCRACC-Fc, had significantly (p<0.05) increased mcRACC-Fc gene expression over controls (FIG. 1J).

Example 3. Overexpression of mCRACC-Fc Results in Increased Expression of Type I IFNs and Activation of NK Cells Previously, it was shown that co-administration of CRACC-Fc protein and rAd5-Null vector resulted in activation of multiple arms of the innate immune system. Namely, an increased IFNγ secretion by NK cells 12 hours post injection was observed (Aldhamen Y A et al. *Vaccine* 2016; 34(27):3109-18). To investigate if mCRACC-Fc overexpression activates NK cells, mice were injected with rAd5-mCRACC-Fc, or rAd5-Null controls, and NK cells activation was evaluated. It was confirmed that administration of rAd5-mCRACC-Fc resulted in increased percent IFN-γ+NK cells in the spleen, 10 hours after injection (FIG. 1B, FIG. C). In addition, an increased percent of activated CD69+NK cells was observed (FIG. 1D). Type I interferons (IFNs) have been shown to be important in NK cell function and tumor cell killing (Muller L et al. *Front Immunol.* 2017; 8:304), so type I IFN response following rAd5-mCRACC-Fc injection was evaluated. Spleens for type I IFN gene expression was evaluated 6 hours post rAd5-mCRACC-Fc injection and a dramatic increase (20 fold) in IFN-α (p<0.01) and IFN-β (p<0.0001) genes compared to rAd5-Null and naive mice was observed (FIG. 1F, FIG. 1E).

In addition, upon evaluation of ISGs, a significant induction of IL-15 gene expression in Ad-Null (p<0.0001) and Ad-mCRACC-Fc (p<0.01) was observed injected mice compared to naïve animals. IL-15 is one of the most important genes for NK cells differentiation, maturation and function (Wu Y et al. *Front Immunol.* 2017; 8:930). An increased induction of ISG15 gene in Ad-Null (p<0.0001) and Ad-mCRACC-Fc (p<0.0001) injected mice compared to naïve mice was observed. Similarly, an increased expression of OAS2 gene in Ad-Null (p<0.0001) and Ad-mCRACC-Fc (p<0.0001) challenged mice compared to naïve was observed. The mCRACC-Fc expression resulted in significantly higher induction of ISG15 (p<0.0001) and OAS2 (p<0.01) gene expression compared to Ad-Null injected mice. All of the above suggests that mCRACC-Fc expression induces type I interferon gene activation and downstream ISG activation, which have been shown to be important in anti-tumor immune responses (Muller L et al. *Front Immunol.* 2017; 8:304; Honda K et al. *Immunity* 2006; 25(3):349-60). Consistent with increased IFN-β expression, enhanced ISG15 (p<0.0001) and OAS2 (p<0.01) expression was observed in the spleens of rAd5-mCRACC-Fc treated mice, compared to rAd5-Null-injected mice. Significant upregulation of these genes upon rAd5-mCRACC-Fc infections suggested that mCRACC-Fc expression induced type I interferon gene activation and downstream ISG activation.

Figure 2A:
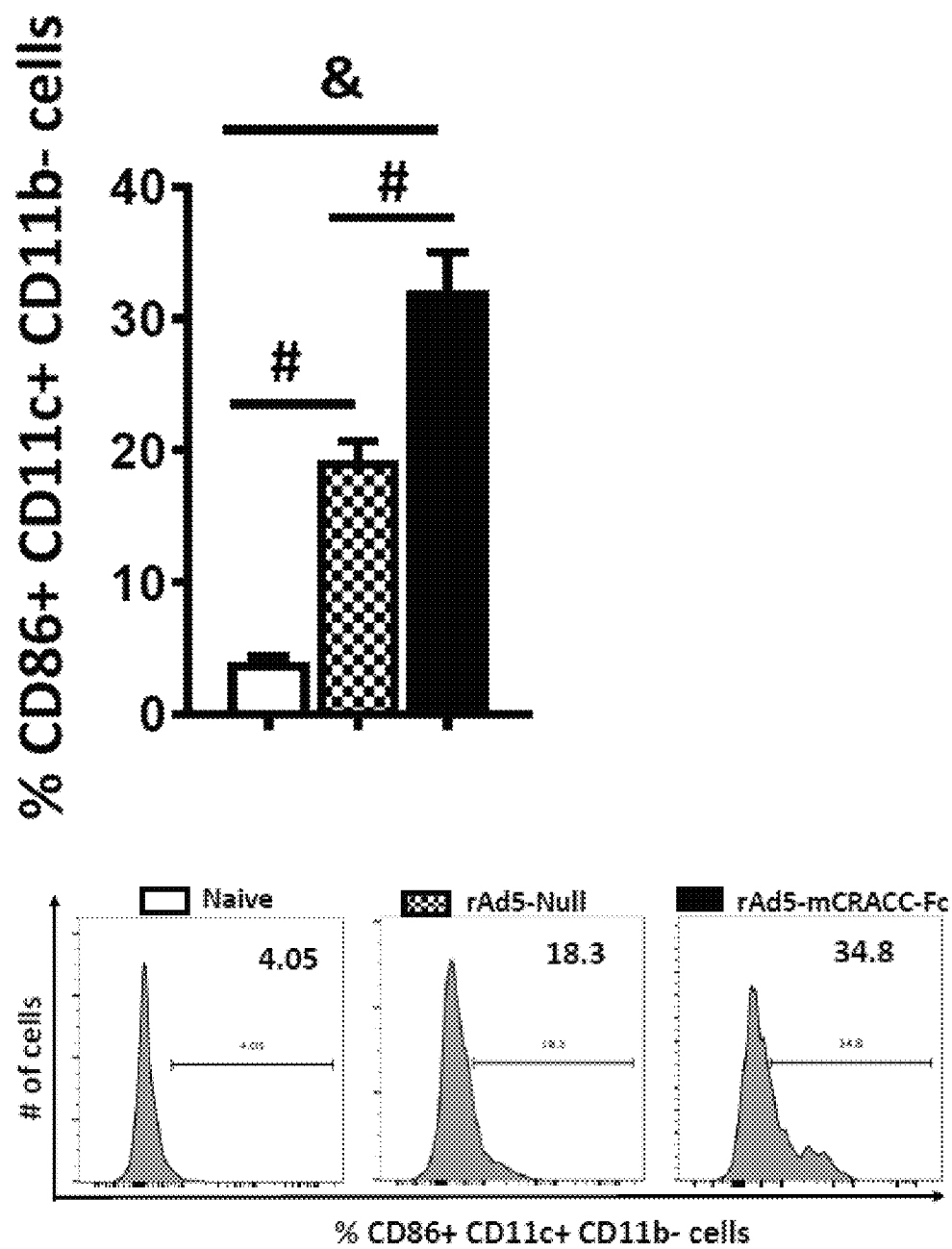
FIG. 2A shows the graphed and histogram of percent CD86+CD11c+ CD11b− dendritic cells.
Figure 2B:
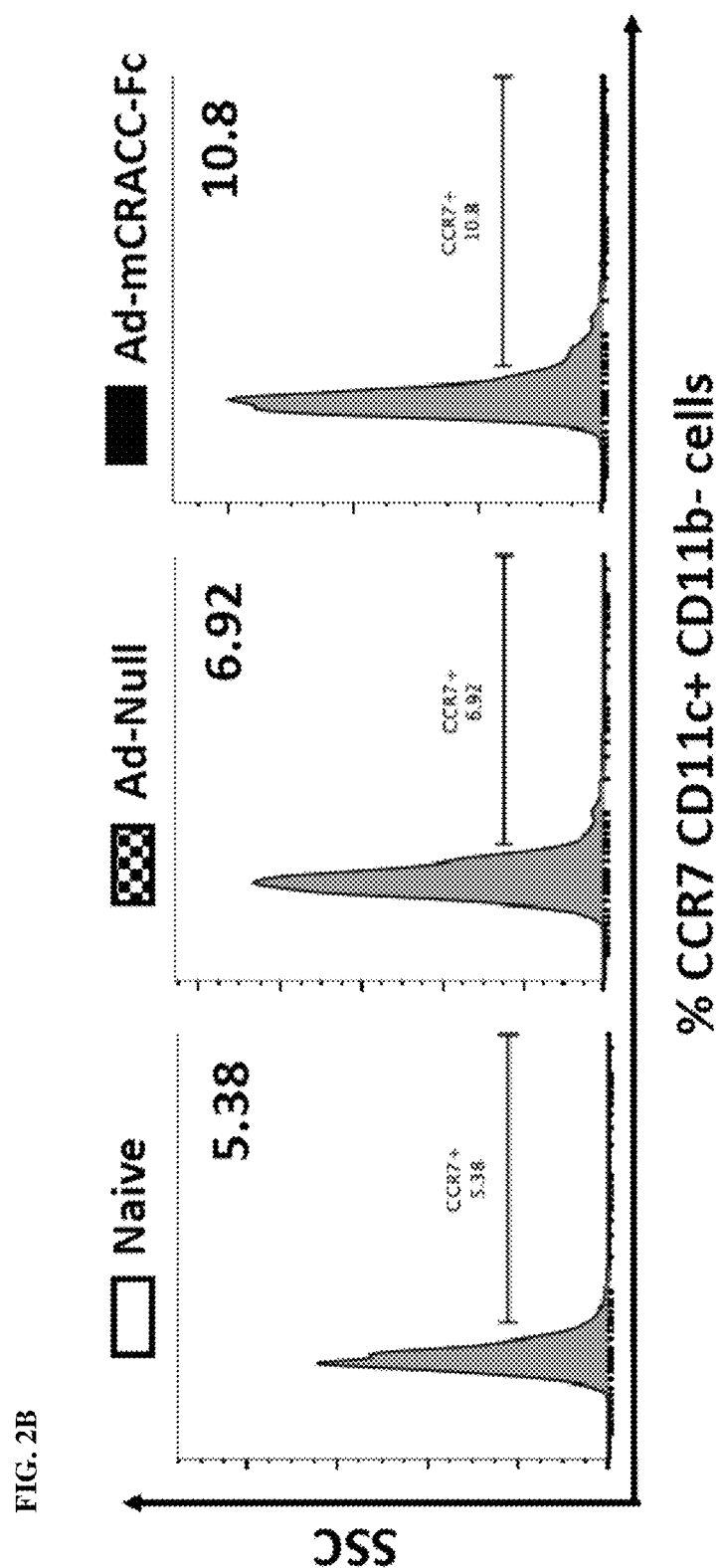
FIG. 2B shows representative histograms of CCR7+CD11c+CD11b− dendritic cells.
Figure 2C:
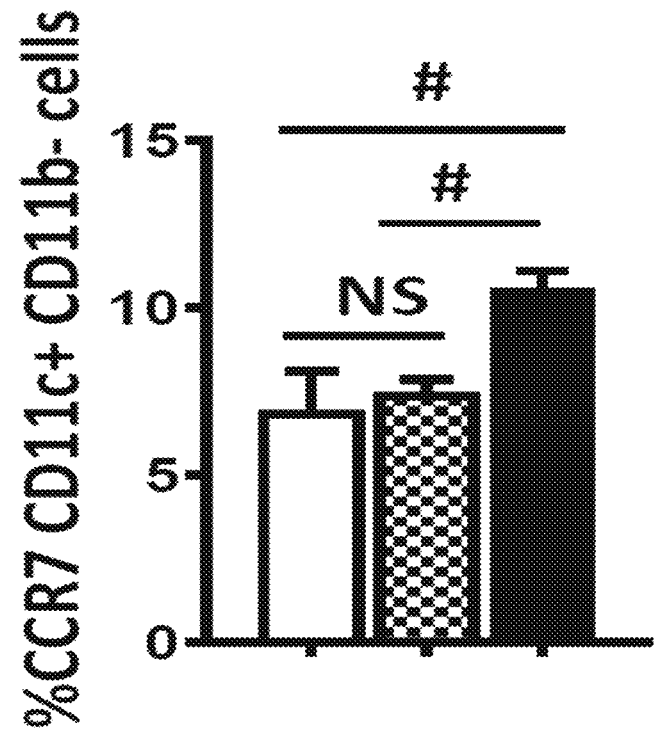
FIG. 2C shows a graph representing CCR7+CD11c+CD11b− dendritic cells.
Figure 2D:
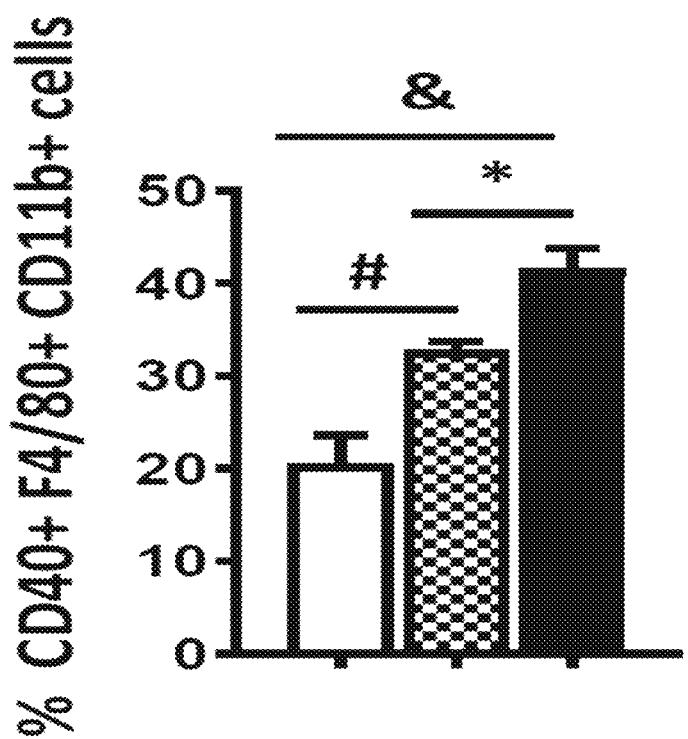
FIG. 2D depicts frequency of CD40+F4/80+ CD11b+ macrophages graphed.
Figure 2E:
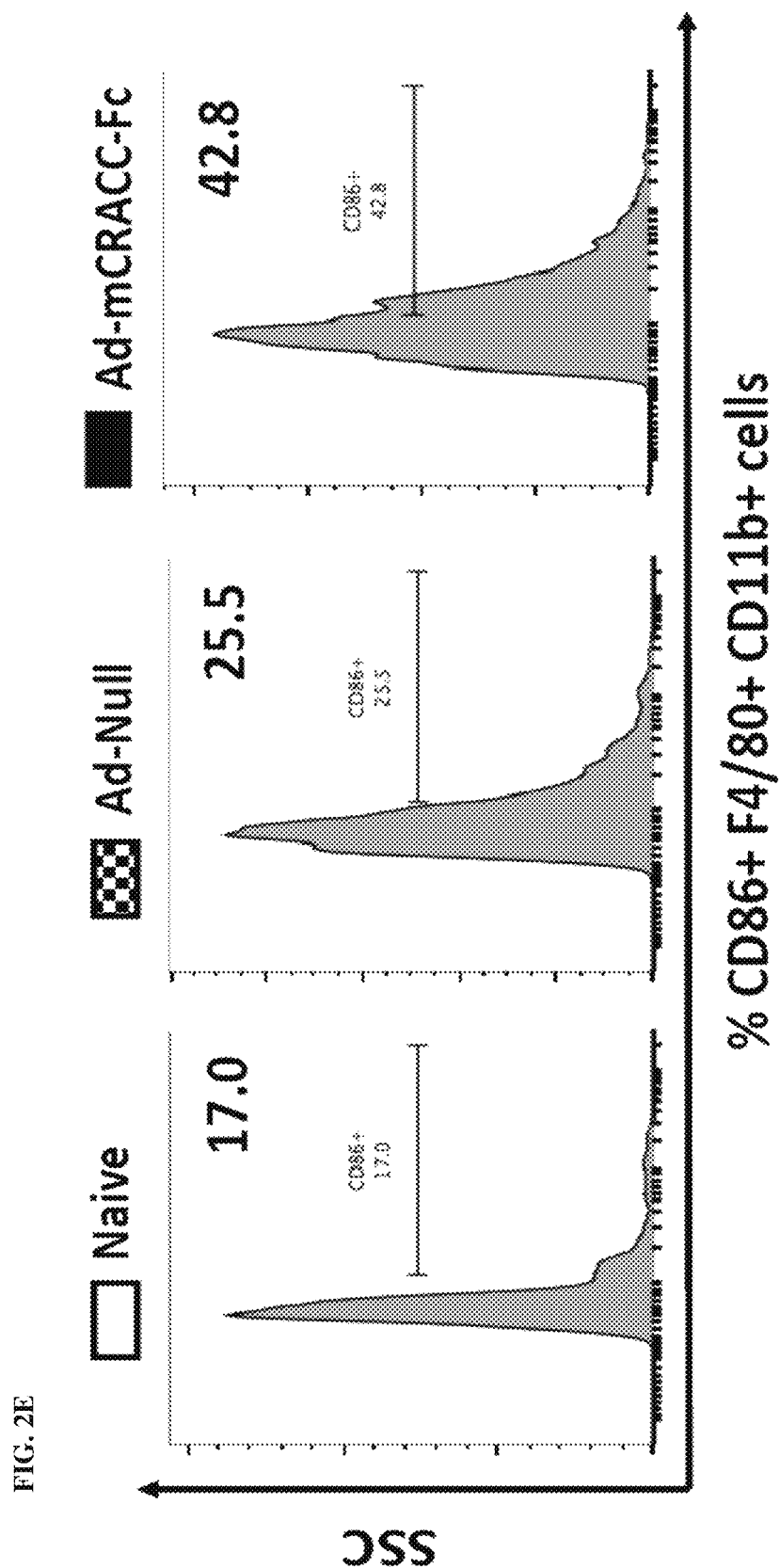
FIG. 2E depicts representative histogram images of CD86+F4/80+CD11b+ macrophages, with graphed values in (FIG. 2F). All graphs represent mean+/−SEM. Statistical analysis was performed using One-way ANOVA with Tukey's post hoc test, where *—$p<0.05$, #—$p<0.01$, ˆ—$p<0.001$, & —$p<0.0001$, and NS—not significant.
Figure 2F:
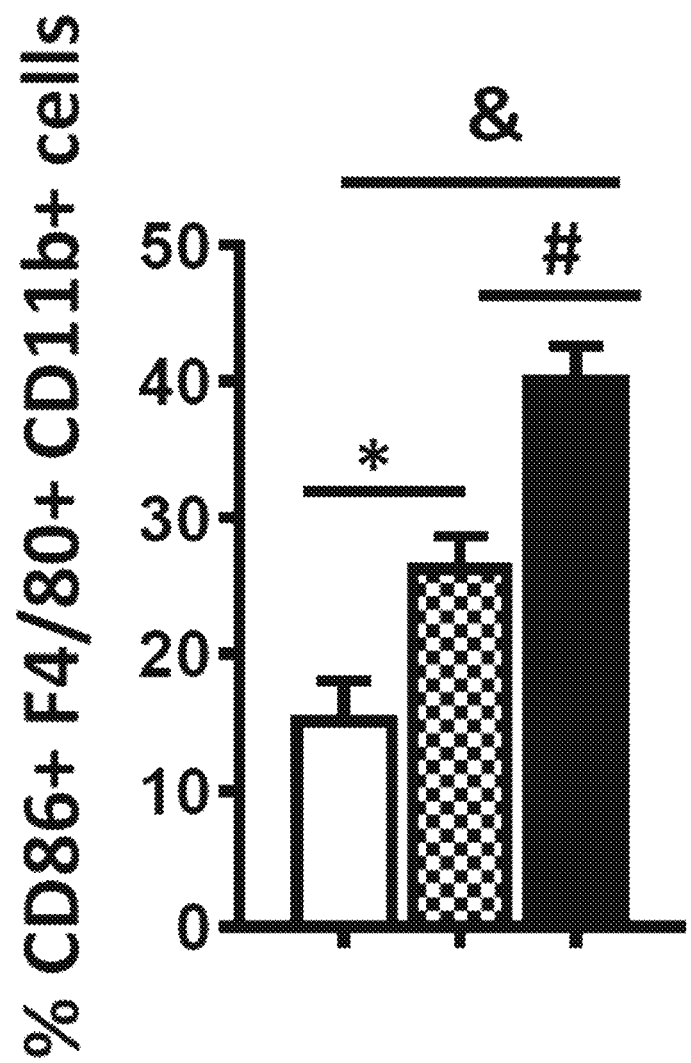
FIG. 2, contains six panels FIG. 2A-FIG. 2F, depicting a flow cytometry analysis of dendritic cells and macrophage activation in response to mCRACC-Fc overexpression. 6 weeks old Balb/c male were injected I.V, with $10^{10}$ v.p. of Ad-null or Ad-mCRACC-Fc. 10 hours post injection spleens were collected from injected (n=6) and naïve mice (n=3), processed, stained and analyzed by Flow cytometry.

Example 4. Overexpression of mCRACC-Fc Results in Dendritic Cell and Macrophage Activation It was previously showed that CRACC-Fc fusion protein injections in conjunction with rAd5-Null virus induced maturation and activation of dendritic cells after 12 hours (Aldhamen Y A et al. *Vaccine* 2016; 34(27):3109-18). Here, mice were injected with rAd5-Null or rAd5-mCRACC-Fc viruses and innate immune cells from spleen were evaluated via flow cytometry to determine the effect of mCRACC-Fc protein expression on innate immune cell activation. An enhanced expression (p<0.01) of surface CD86 co-stimulatory molecule on CD11c+ dendritic cells from rAd5-mCRACC-Fc injected mice was observed, as compared to rAd5-null and mock infected mice (p<0.0001) (FIG. 2A). In addition, an increased percent of CCR7 positive dendritic cells was observed in rAd5-mCRACC-Fc injected mice compared Ad-Null (p<0.01) and mock infected animals (p<0.01) (FIG. 2B, FIG. 2C), suggesting increased activation of dendritic cells in response to mCRACC-Fc expression. There was also significant difference in CD40 activation marker levels upon Ad-mCRACC-Fc infection (p<0.001) compared to naïve mice [data not shown]. A survey of splenocytes was conducted and showed that the macrophages had a significant increase in CD40 expression in Ad-mCRACC-Fc injected, compared to Ad-Null injected mice (p<0.05) and compared to naïve mice (p<0.0001) (FIG. 2D). In addition, a significantly increased percent of CD86 positive F4/80+CD11b- macrophages in the spleens of Ad-mCRACC-Fc injected mice compared to Ad-Null (p<0.01) and naive (p<0.0001) mice was observed (FIG. 2E, FIG. 2F). A significant differences in the CCR7 expression on macrophages upon Ad-mCRACC-Fc expression was not observed [data not shown]. All the above confirmed an enhanced activation and maturation of innate cells in response to Ad-mCRACC-Fc injection.

Example 5. Overexpression of mCRACC-Fc Results in Cytokine and Chemokine Upregulation In addition to innate immune cell activation and maturation, increases in the proinflammatory cytokine upregulation in the spleens of Ad-mCRACC-Fc injected mice 10 hours after injection were observed, where mRNA levels of IL-6 (p<0.0001 over mock and p<0.01 over Ad-Null) and IL-12 (p<0.0001 over mock and Ad-Null) were significantly increased. IP-10 (CXCL10) chemokine was also significantly upregulated in the spleens of Ad-mCRACC-Fc injected animals compared to naïve (p<0.0001), however, was significantly lower compared to Ad-Null injected mice (p<0.0001) (FIG. 3C). Gene expression levels of the granulocyte-macrophage colony-stimulating factor (GM-CSF), which is known to be an important growth factor for granulocyte and monocyte differentiation, were also significantly upregulated in Ad-mCRACC-Fc injected mice compared to naïve (p<0.001), but not Ad-Null injected mice (FIG. 3D). Increased protein levels of IL-12p40 (p<0.05), MIP1β (CCL4) (p<0.001) cytokines and RANTES (CCL5) (p<0.05) and KC (CXCL1) (p<0.01) chemokines were found to be significantly increased in the plasma of Ad-mCRACC-Fc injected mice compared to Ad-Null as determined by the BioPlex analysis (FIG. 3G-3J).

To discern the signaling pathway responsible for increased proinflammatory cytokine production and innate cell activation, mRNA levels were evaluated of MyD88, Tyk2, Jak1, STAT1, TRAF6 and NF-kB, but observed no significant differences in the levels of these genes in response to Ad-mCRACC-Fc injection [data not shown]. However, an increased upregulation of Irf7 gene was observed in Ad-mcRACC-Fc (p<0.0001) injected compared to naïve mice (FIG. 3F). Irf7 is known to be important for upregulation of IFNβ gene expression (Maniatis T et al.

Cold Spring Harb Symp Quant Biol. 1998; 63:609-20; Panne D et al. Cell 2007; 129(6):1111-23), which in turn induces transcription of IFNα and other IFNα-stimulated genes (Honda K et al. Immunity 2006; 25(3):349-60). Additionally, an increased gene expression of Irf9 (p<0.01) was detected in Ad-mCRACC-Fc injected mice compared to naïve. Irf9 is an important factor downstream of type I interferon signaling, which is required for ISG responses (Stark G R et al. Immunity 2012; 36(4):503-14). All of the above suggests that injection with Ad-mCRACC-Fc stimulated type I IFN release and its downstream effects, which have been shown to be important in anti-tumor immunity (Muller L et al. Front Immunol. 2017; 8:304; Cheon H et al. Semin Oncol. 2014; 41(2):156-73).

To discern the signaling pathway responsible for increased proinflammatory cytokine production and innate cell activation, mRNA levels of MyD88, Tyk2, Jak1, TRAF6, and NF-kB were evaluated. Significant induction 6 hours post rAd5-Null or rAd5-mCRACC-Fc injections was not observed. An increased upregulation of Irf7, Irf9, Socs1, and STAT1 upon rAd5-mCRACC-Fc injection was observed, and mRNA transcript levels of these genes were not significantly higher than in rAd5-Null 6 hours after injection. To investigate if the enhanced type I IFN signaling and ISG upregulation in response to mCRACC-Fc overexpression is associated with increased STAT1 activation, WB analysis was performed for STAT1 phosphorylation. Compared to spleen lysates of rAd5-Null-treated mice, lysates of rAd5-mCRACC-Fc-treated mice showed an increased STAT1 phosphorylation [FIG. 3L, M].

Example 6. Intratumoral Ad-mCRACC-Fc Administration Allows for Reduced Tumor Growth and Increased Survival of CT26 Challenged Mice The efficacy of Ad-mCRACC-Fc virus as an intratumoral agent in the CT26 colon adenocarcinoma cancer model was tested. 6 weeks-old Balb/c mice were S.Q. injected with 150,000 CT26 cells (ATCC) and allowed for tumors to develop. On day 8 after the CT26 cells injection, when the tumors became 150-200 mm$^3$, mice were injected intratumorally with $10^{10}$ v.p. of Ad-Null, Ad-mCRACC-Fc or not injected (untreated). Mice were monitored every 1-3 days for presence of ulcerations and their tumors were measured as described in methods. Mice were sacrificed upon reaching a humane end-point or reaching a tumor volume of 2,000 mm$^3$ or when they developed ulcerations on the tumor surface. Log rank test showed a significantly increased (p<0.05) survival of Ad-mCRACC-Fc injected mice (85% survival) compared to untreated (43%) and Ad-Null (46%) injected mice (FIG. 4A). Ad-mCRACC-Fc vaccination resulted in significantly reduced tumor volumes compared to untreated mice starting on day 10 (p<0.01) till day 21 and continuing through day 23 (p<0.05) (FIG. 4B). However, Ad-mCRACC-Fc intratumoral treatment was not significantly superior to the Ad-Null treatment, and Ad-Null treatment resulted in significantly reduced tumor volume on days 10 through 19 compared to naive mice (p<0.05) (FIG. 4A). The efficacy of Ad-Null in reducing tumor volumes is not surprising as it is a double stranded DNA virus which can activate innate immune responses via TLR2 and TLR9 pathogen recognition receptors and induce downstream signaling despite it being a non-replicating virus (Appledorn D M et al. J Immunol. 2008; 181(3):2134-44). Although, the differences between tumor volume were not significant with One-way ANOVA analysis, tumor volumes from Ad-mCRACC-Fc treated mice showed a strong trend of smaller volumes compared to Ad-Null and exhibited less variability in tumor sizes.

rAd5-mCRACC-Fc treated mice, which were able to completely resolve their tumors, were re-challenged with 300,000 CT26 cells S.Q., at day 60, and monitored for 3 months for development of tumors. None of the re-challenged mice developed tumors [data not shown]. The memory T cell responses by measuring killing efficacy of the CT26 tumor cells by the splenocytes from the tumor-free mice in remission was analyzed. Splenocytes from the re-challenged mice were isolated and incubated the splenocytes with CFSE labeled CT26 tumors cells at 1:10 effector to target ratio for 48 hours in the presence of Ad-mCRACC-Fc virus. A significantly higher killing of the CT26 cells by the splenocytes from Ad-mCRACC-Fc treated mice compared to naïve (p<0.0001) and Ad-Null (p<0.05) treated animals was observed (FIG. 4C). The same non-significant trend without addition of adenovirus to the cell culture was observed [data not shown].

Example 7. Ad-mCRACC-Fc Administration Enhances Adaptive Immune Responses

Type I interferons are known to elicit antitumor effects due to its ability of stimulating innate and adaptive immune responses (Le Bon A et al. J Immunol. 2006; 176(4):2074-8; Santini S M et al. J Exp Med. 2000; 191(10):1777-88). In addition to stimulating NK cells maturation and cytolytic activity, type IFNs induce DC activation and maturation which indirectly stimulates the adaptive arm of the immune system via antigen cross-presentation to T and B cells, as well due to direct effects on effector T cells, regulatory T cells, and B cells (Le Bon A et al. J Immunol. 2006; 176(4):2074-8; Santini S M et al. J Exp Med. 2000; 191(10):1777-88). Since mCRACC-Fc expression induced dramatic upregulation of IFNβ, and activation of DCs, MCs and NK cells, the adaptive immune responses was assessed as well. Balb/c mice were injected I.V, with Ad-Null, Ad-mCRACC-Fc or not injected (naïve) and after 10 hours, their spleens were harvested, stained and analyzed by flow cytometry. A significant upregulation (p<0.001) of activation marker CD69 on CD19+CD3− B cells, CD3+CD8− (CD4 T cells) and CD3+CD8+ T cells was detected, compared to Ad-Null injected and naïve mice, suggesting enhanced early activation of the adaptive immune cells due to mCRACC-Fc overexpression.

Example 8. Assessment of Adaptive Immune Responses Following Ad-mCRACC-Fc Administration rAd5-mCRACC-Fc Vaccination Enhances Adaptive Immune Responses to the Co-Administered Antigens.

In addition to activating innate immunity, type I IFNs are known to stimulate the adaptive arm of the immune system, both directly by impacting effector T-, regulatory T-, and B-cell responses, as well as indirectly by enhancing antigen cross-presentation to T and B cells (24,25). Balb/c mice were intravenously injected with rAd5-Null, rAd5-mCRACC-Fc, or not injected (naïve). Ten hours following rAd5 administration, splenocytes were isolated, stained, and analyzed by flow cytometry to assess the activation phenotype of the adaptive immune cells. Significantly (p<0.001) increased percentages of the CD69-expressing CD19+CD3− B− [FIG. 5A, B], CD3+CD8− T+ [FIG. 5C], and CD3+

CD8+ T-cells FIG. 5D was observed as compared to cells derived from rAd5-Null injected mice.

The ability of rAd5-mCRACC-Fc to induce memory B- and T-cell responses by utilizing CT26 tumor cell lysates was evaluated. Balb/c mice were vaccinated twice over a period of one month with either CT26 tumor lysate alone, or combination of tumor lysates+ rAd5-Null or tumor lysates+ rAd5-mCRACC-Fc vectors. Splenocytes were harvested and cultured for 48 hours in the presence of CT26 tumor lysates to stimulate memory responses against tumor-associated antigen (TAAs). In this assay significantly ($p<0.01$) increased activation of CD3+CD8+ T cells from rAd5-mCRACC-Fc/CT26 lysate co-vaccinated mice was observed, as compared to rAd5-Null/CT26 lysate, and lysate only groups [FIG. 5E]. Similar trends in CD3+CD8-T cells were also observed. Additionally, a number of, CT26-derived, TAA-specific IFN-γ-producing memory T cells via ELISPOT assay were evaluated. Significantly increased ($p<0.05$) number of CT26-specific IFN-γ+ T cells in rAd5-mCRACC-Fc/CT26 lysate co-vaccinated mice was observed compared to naive and lysate only vaccinated groups [FIG. 5F]. Similarly, a significantly increased number of Ad5-specific IFN-γ+ T cells in rAd5-mCRACC-Fc/CT26 lysate-vaccinated mice was observed, as compared to naive ($p<0.01$) and lysate only ($p<0.05$) groups [FIG. 5G]. The data suggests that overexpression of mCRACC-Fc enhances the early activation of the adaptive immune cells and induces memory T cell responses to the co-administered antigens.

Example 9. Adenovirus and Tumor Lysate Vaccinations Allow for Reduced Tumor Growth and Increased Survival Upon CT26 Tumor Challenge Compared to Unvaccinated Mice Strategies using agents that can enhance innate immune responses (Coffman R L et al. *Immunity* 2010; 33(4):492-503) or block inhibitory immune pathways have proven to be useful as vaccine adjuvants by increasing vaccine immunogenicity (Koff W C et al. *Science* 2013; 340(6136): 1232910; Pardoll D M et al. *Nat Rev Cancer.* 2012; 12(4): 252-64). Since robust increases in the innate and adaptive immune activation in response to Ad-mCRACC-Fc injections was shown herein, the efficacy of mCRACC-Fc as a vaccine adjuvant in preventing tumor formation was tested. 6 weeks old Balb/c mice were vaccinated with 200 ag of CT26 tumor lysates and Ad-Null (CT26/Ad-Null) or Ad-mCRACC-Fc (CT26/Ad-mCRACC-Fc) three times in a period of 5 week, after which, vaccinated and unvaccinated mice were injected with 250,000 CT26 cells S.Q. Starting on day 5 post tumor challenge tumors every 2-3 days were measured, and the mice were sacrificed once they reached the humane end-point of 2,000 mm$^3$ tumor volume or developed tumor ulcerations. Percent survival at the completion of the study was significantly increased ($p<0.05$) in Ad-Null (67%) and Ad-mCRACC-Fc (63%) pre-vaccinated mice compared to unvaccinated mice (11%) (FIG. 6A). On days 22, 26 and 28 the tumor volumes were significantly reduced ($p<0.01$) in Ad-mCRACC-Fc pre-vaccinated mice compared to unvaccinated (FIG. 6B). Ad-Null pre-vaccinated mice also developed significantly reduced tumor sizes compared to unvaccinated mice on days 22 ($p<0.01$), 26 ($p<0.05$) and 28 ($p<0.01$) (FIG. 6B). There was no significant difference in the tumors volumes between Ad-Null and Am-mCRACC-Fc pre-vaccinated animals, showing the robustness in adenovirus-based vaccines in activating the immune system and anti-tumor responses that developed after three doses of combined tumor lysate and virus injections.

To evaluate the tumor antigen specific memory response developed by the vaccinated mice, levels of the total IgG antibody were quantified against tumor lysate in the vaccinated mice using ELISA. Multiple dilutions of plasma were performed to dilute down the signal and be able to discern differences between the three groups of mice. While both viruses significantly increased tumor-specific antibody production, at dilutions 1:100 and 1:500 it was evident that Ad-mCRACC-Fc produced significantly ($p<0.01$ and $p<0.05$, respectively) more robust tumor-specific antibody response, compared to Ad-Null treated group (FIG. 6C).

Based on the fact that Fc region of IgG antibodies can bind to CD16 receptor on NK cells and activate ADCC (28), killing of CT26 tumor cells was evaluated in the presence of plasma from co-vaccinated and unvaccinated mice. Splenocytes or isolated NK cells from naïve animals were incubated with CFSE-labeled CT26 tumor cells in the presence of plasma from unvaccinated, rAd5-Null or rAd5-mCRACC-Fc vaccinated mice for 18 hours, after which killing of tumors cells was assessed by flow cytometry as described in Methods. Interestingly, plasma from rAd5-mCRACC-Fc/CT26 lysate co-vaccinated mice significantly enhanced CT26 tumor killing by both total splenocytes ($p<0.01$) [FIG. 6D] and isolated NK cells ($p<0.05$) [FIG. 6E], as compared to plasma-derived from unvaccinated mice. rAd5-Null/CT26 lysate co-vaccination did not induce significantly higher killing by splenocytes or NK cells compared to unvaccinated mice [FIG. 6D, E]. The above data suggests that combination rAd5-mCRACC-Fc and CT26 lysate is an approach that improves tumor killing via enhanced ADCC activity.

Example 10. Ad-mCRACC-Fc Expression Induces CD8 T and NK Cell Recruitment to the Tumor Upon completion of the tumor lysate vaccination study, the tumors from each of the three study groups with CT26 tumors were harvested and immunohistochemistry were performed to evaluate their tumors for the presence of tumor infiltrating lymphocytes (TILs). Anti-CD3 antibody staining was remarkably high in the tumors from Ad-mCRACC-Fc pre-vaccinated mice and was especially pronounced in the peripheral aspects of the tumors. Tumors from the unvaccinated and Ad-Null-vaccinated mice had visibly less pronounced and sparsely distributed CD3+ staining throughout the tumors (FIG. 7A). In addition, anti-CD8 and anti-Dx5 staining were performed to evaluate for presence of CTLs and NK cells in the tumors. While evidence of CD8+ staining in the tumors from the Ad-Null and Ad-mCRACC-FC pre-vaccinated animals were observed, none were observed in the unvaccinated group (FIG. 7B). Interestingly, only Ad-mCRACC-Fc group showed signs of NK cell infiltration in the tumors (FIG. 8).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope

DISCUSSION

, A specific immune receptor that has not been evaluated in solid-tumor models previously was studied. The self-ligand CRACC receptor mediates both positive and negative signals in immune cells, a function that is governed by the presence or absence of the EAT-2 adaptor (15,31). A gene therapy approach was developed that targets the CRACC pathway using recombinant Ad5 as a vector. Overexpression of mCRACC-Fc by adenoviral vector allowed for enhanced production of critical, Th-1-skewed cytokines, as well as early activation of innate and adaptive immune cells. Additionally, serial injections of tumor antigen in combination with rAd5-mCRACC-Fc enhanced TAAs-specific memory T- and B-cell responses, as well as infiltrations of tumors by leukocytes. Most importantly, intratumoral administration of rAd5-mCRACC-Fc vector reduced tumor growth and improved survival rate in mice with established CT26 colon adenocarcinoma tumors.

While the molecular mechanism of rAd5-mCRACC-Fc is not fully defined, dramatic upregulation was observed of type I IFNs, especially IFNβ, in response to mCRACC-Fc overexpression. Type I IFNs are known to play an important role in mediating anti-tumor immune responses (23). In addition to preventing malignant cellular transformation, via maintaining p53 tumor suppressor gene expression (32) and triggering apoptosis of certain cancers (33), type I IFN-mediated anti-tumor activity is thought to be mainly indirect, via the activation of other immune cells (34). For example, type I IFNs increase APC survival and antigen cross-presentation, thereby promoting CD8+ T cell survival, and inhibiting regulatory T cell responses (21,23). Additionally, type I IFNs are known to play a particularly important role in driving NK cell anti-tumor activity by directly promoting NK cells maturation and activation, and indirectly via IL-15 secretion by type I IFN-activated conventional DCs (21). It is known that delivery of a strong type I IFN signal specifically into tumors and combination of type I IFN targeted strategies with immune checkpoint inhibitors allows for the development of robust anti-cancer responses (34,35). Therefore, the enhanced NK cell, APC, and T cell activation following rAd5-mCRACC-Fc administration may be the result of upregulation of type I interferon and its downstream effects. Interestingly, this suggests that targeting CRACC pathway, may prove to be a useful strategy for promoting interferon induced responses.

Expression of mCRACC-Fc via adenovirus platform resulted in enhanced NK cell activation and increased IFN-γ production early after rAd5-mCRACC-Fc administration, an NK cell phenotype that is important for the development of Th-1-skewing innate and adaptive immune responses (36,37). This finding is very important because NK cells are vital for tumor cell killing and prevention of metastasis (38). Additionally, Th-1 skewed immune responses promote anti-tumor immunity (39). While the exact mechanism responsible for the enhanced NK activity by rAd5-mCRACC-Fc is not completely defined, it was noted that administration of rAd5-mCRACC-Fc induced higher levels of IL-12 production, early after administration, which is important for NK cell activity and induction of Th-1 responses (40). Therefore, it is possible that the enhanced NK cells activation and IFN-γ production is mediated by IL-12 release (40). Moreover, mice serially vaccinated with CT26 tumor lysate and rAd5-mCRACC-Fc developed increased levels of tumor-specific IgG antibodies, and as a result, showed increased killing of tumor cells by activating ADCC response ex-vivo. ADCC is an important mechanism in tumor-killing, (28), which is exploited in anti-tumor immunotherapy approaches (41,42). Ability of rAd5-mCRACC-Fc to enhance tumor-specific antibody production with an enhanced ADCC-inducing ability is another feature that makes CRACC receptor a favorable target for immune-modulation.

In addition to NK cell activation, it was also noted that CRACC modulation enhanced the maturation and activation of CD11c+ conventional DCs, a phenotype that might also be mediated by the increased IFN-γ production from NK cells (43). These data suggest that CRACC could function as an inhibitory receptor in DCs and monocytes, and that blockade of CRACC-CRACC self-ligation by the use of CRACC-Fc-producing rAd5 vectors enhances DC- and macrophage-mediated innate immune responses. Consistent with this, activation of human monocytes with LPS, has been shown to reduce EAT-2 levels, while activation of CRACC-receptor resulted in reduced TNF-α and IL12p70 production (44). These findings suggest that in LPS treated monocytes CRACC has an inhibitory function due to loss of EAT-2.

Anti-cancer treatments are generally highly immunosuppressive, especially toward the adaptive immune cells (45). Preclinical data suggests that enhancement of innate immune responses can ensure the development of long-lasting adaptive anti-cancer immune responses (41). It is therefore thought that strategies that enhance both the innate and adaptive immune responses might allow for the development of more effective and long-lasting anti-tumor immunity. As shown herein, it was observed that overexpression of mCRACC-Fc resulted in increased activation of DCs and macrophages as evidenced by upregulation of CD86 activation receptor. CD86 is a co-stimulatory molecule that binds to B7 receptor, which upon stimulation, induces T cell activation (46). Increased surface levels of maturation markers on DCs and macrophages, suggests that CRACC-Fc overexpression enhances the activation of the adaptive arm of the immune system via antigen cross-presentation (46). Consistent with this, serial vaccinations with tumor lysate and rAd5-mCRACC-Fc enhanced tumor specific adaptive immune responses, as was evidenced by enhanced production of tumor-specific antibodies and IFNγ-expressing T cells.

Recently, a small phase Ib clinical trial reported an improved response in patients with metastatic melanoma to combined intralesional injection of modified human herpes simplex virus and systemic anti-PD-1 (30). This was accompanied by conversion of cold (non-inflamed) tumors to hot (inflamed) tumors, as was evidenced by enhanced T cells infiltrations into the tumors in response to therapy. Additionally, it is evident that increased infiltration of tumors by CD3+ and CD8+ T-cells is associated with better prognosis and increased survival in patients affected by various solid tumors (29). Increased infiltration of CD3+, CD8+, and Dx5+ TILs, suggests that increased lymphocyte recruitment to the tumors may, at least in part, may be the mechanism responsible for the increased survival rates and reduced tumor growth in CT26 challenged mice following rAD5-mCRACC-Fc intratumoral administration. Interestingly, it was observed an increased stimulation of MIP-1β secretion in response to rAd5-mCRACC-Fc administration, a chemokine that has been shown to reduce tumor size and survival in CT26 challenged mice via the recruitment of T- and NK-cells to tumors (47).

In effort to test the efficacy of combined tumor antigens and rAd5-mCRACC-Fc as a preventative vaccine against CT26 colon adenocarcinoma, mice were subjected to three doses of combination vaccines containing tumor lysate prior to CT26 challenge as a proof of principle. rAd5-mCRACC-Fc group was able to control tumor growth, and it was noted differences between rAd5-Null and rAd5-mCRACC-Fc treatments in terms of tumor sizes and survival rates. Tumor volumes from rAd5-mCRACC-Fc treated mice showed a trend of smaller volumes compared to rAd5-Null and exhibited less variability in tumor sizes. Ad5 can also enhance adaptive immune responses (49). It is likely that the robust immune activation induced by three-dose vaccination of rAd5 vectors potentially masked some of the beneficial effects of mCRACC-Fc overexpression. Additionally, tumor lysates alone have low immunogenicity (50), therefore use of more immunogenic epitopes along with rAd5-mCRACC-Fc vaccine would likely result in more impressive responses. rAd5-mCRACC-Fc and tumor lysates co-vaccination triggered enhanced CT26 tumor-specific antibody production and ADCC responses.

REFERENCES

1. Adler A J. Mechanisms of T cell tolerance and suppression in cancer mediated by tumor-associated antigens and hormones. Curr Cancer Drug Targets 2007; 7:3-14
2. Gabrilovich D I, Ostrand-Rosenberg S, Bronte V. Coordinated regulation of myeloid cells by tumours. Nat Rev Immunol 2012; 12:253-68
3. Juneja V R, McGuire K A, Manguso R T, LaFleur M W, Collins N, Haining W N, et al. PD-L1 on tumor cells is sufficient for immune evasion in immunogenic tumors and inhibits CD8 T cell cytotoxicity. J Exp Med 2017; 214:895-904
4. Hodi F S, O'Day S J, McDermott D F, Weber R W, Sosman J A, Haanen J B, et al. Improved survival with ipilimumab in patients with metastatic melanoma. N Engl J Med 2010; 363:711-23
5. Topalian S L, Hodi F S, Brahmer J R, Gettinger S N, Smith D C, McDermott D F, et al. Safety, activity, and immune correlates of anti-PD-1 antibody in cancer. N Engl J Med 2012; 366:2443-54
6. Anderson A C, Joller N, Kuchroo V K. Lag-3, Tim-3, and TIGIT: Co-inhibitory Receptors with Specialized Functions in Immune Regulation. Immunity 2016; 44:989-1004
7. Weinberg A D, Morris N P, Kovacsovics-Bankowski M, Urba W J, Curti B D. Science gone translational: the OX40 agonist story. Immunol Rev 2011; 244:218-31
8. Ascierto P A, Simeone E, Sznol M, Fu Y X, Melero I. Clinical experiences with anti-CD137 and anti-PD1 therapeutic antibodies. Semin Oncol 2010; 37:508-16
9. Roberts D J, Franklin N A, Kingeter L M, Yagita H, Tutt A L, Glennie M J, et al. Control of established melanoma by CD27 stimulation is associated with enhanced effector function and persistence, and reduced PD-1 expression of tumor infiltrating CD8(+) T cells. J Immunother 2010; 33:769-79
10. Larkin J, Chiarion-Sileni V, Gonzalez R, Grob J J, Cowey C L, Lao C D, et al. Combined Nivolumab and Ipilimumab or Monotherapy in Untreated Melanoma. N Engl J Med 2015; 373:23-34
11. Moynihan K D, Opel C F, Szeto G L, Tzeng A, Zhu E F, Engreitz J M, et al. Eradication of large established tumors in mice by combination immunotherapy that engages innate and adaptive immune responses. Nat Med 2016; 22:1402-10
12. Bouchon A, Cella M, Grierson H L, Cohen J I, Colonna M. Activation of NK cell-mediated cytotoxicity by a SAP-independent receptor of the CD2 family. J Immunol 2001; 167:5517-21
13. Calpe S, Wang N, Romero X, Berger S B, Lanyi A, Engel P, et al. The SLAM and SAP gene families control innate and adaptive immune responses. Adv Immunol 2008; 97:177-250
14. Cruz-Munoz M E, Dong Z, Shi X, Zhang S, Veillette A. Influence of CRACC, a SLAM family receptor coupled to the adaptor EAT-2, on natural killer cell function. Nat Immunol 2009; 10:297-305
15. Tassi I, Colonna M. The cytotoxicity receptor CRACC (CS-1) recruits EAT-2 and activates the PI3K and phospholipase Cgamma signaling pathways in human NK cells. J Immunol 2005; 175:7996-8002
16. Guo H, Cruz-Munoz M E, Wu N, Robbins M, Veillette A. Immune cell inhibition by SLAMF7 is mediated by a mechanism requiring src kinases, CD45, and SHIP-1 that is defective in multiple myeloma cells. Mol Cell Biol 2015; 35:41-51
17. Aldhamen Y A, Rastall D P W, Chen W, Seregin S S, Pereira-Hicks C, Godbehere S, et al. CRACC-targeting Fc-fusion protein induces activation of NK cells and DCs and improves T cell immune responses to antigenic targets. Vaccine 2016; 34:3109-18
18. Sharon D, Kamen A. Advancements in the design and scalable production of viral gene transfer vectors. Biotechnol Bioeng 2018; 115:25-40
19. Aldhamen Y A, Seregin S S, Schuldt N J, Rastall D P, Liu C J, Godbehere S, et al. Vaccines expressing the innate immune modulator EAT-2 elicit potent effector memory T lymphocyte responses despite pre-existing vaccine immunity. J Immunol 2012; 189:1349-59
20. Alyaqoub F S, Aldhamen Y A, Koestler B J, Bruger E L, Seregin S S, Pereira-Hicks C, et al. In Vivo Synthesis of Cyclic-di-GMP Using a Recombinant Adenovirus Preferentially Improves Adaptive Immune Responses against Extracellular Antigens. J Immunol 2016; 196:1741-52
21. Muller L, Aigner P, Stoiber D. Type I Interferons and Natural Killer Cell Regulation in Cancer. Front Immunol 2017; 8:304
22. Zhu J, Huang X, Yang Y. A critical role for type I IFN-dependent NK cell activation in innate immune elimination of adenoviral vectors in vivo. Mol Ther 2008; 16:1300-7
23. Cheon H, Borden E C, Stark G R. Interferons and their stimulated genes in the tumor microenvironment. Semin Oncol 2014; 41:156-73
24. Le Bon A, Thompson C, Kamphuis E, Durand V, Rossmann C, Kalinke U, et al. Cutting edge: enhancement of antibody responses through direct stimulation of B and T cells by type I IFN. J Immunol 2006; 176:2074-8
25. Santini S M, Lapenta C, Logozzi M, Parlato S, Spada M, Di Pucchio T, et al. Type I interferon as a powerful adjuvant for monocyte-derived dendritic cell development and activity in vitro and in Hu-P BL-SCID mice. J Exp Med 2000; 191:1777-88
26. Coffman R L, Sher A, Seder R A. Vaccine adjuvants: putting innate immunity to work. Immunity 2010; 33:492-503
27. Pardoll D M. The blockade of immune checkpoints in cancer immunotherapy. Nat Rev Cancer 2012; 12:252-64

28. Kobayashi M, Fitz L, Ryan M, Hewick R M, Clark S C, Chan S, et al. Identification and purification of natural killer cell stimulatory factor (NKSF), a cytokine with multiple biologic effects on human lymphocytes. J Exp Med 1989; 170:827-45
29. Gooden M, Lampen M, Jordanova E S, Leffers N, Trimbos J B, van der Burg S H, et al. HLA-E expression by gynecological cancers restrains tumor-infiltrating CD8 (+) T lymphocytes. Proc Natl Acad Sci USA 2011; 108:10656-61
30. Haanen J. Converting Cold into Hot Tumors by Combining Immunotherapies. Cell 2017; 170:1055-6
31. Veillette A. SLAM-family receptors: immune regulators with or without SAP-family adaptors. Cold Spring Harb Perspect Biol 2010; 2:a002469
32. Takaoka A, Hayakawa S, Yanai H, Stoiber D, Negishi H, Kikuchi H, et al. Integration of interferon-alpha/beta signalling to p53 responses in tumour suppression and antiviral defence. Nature 2003; 424:516-23
33. Yang Y, Shaffer A L, 3rd, Emre N C, Ceribelli M, Zhang M, Wright G, et al. Exploiting synthetic lethality for the therapy of ABC diffuse large B cell lymphoma. Cancer Cell 2012; 21:723-37
34. Zitvogel L, Galluzzi L, Kepp O, Smyth M J, Kroemer G. Type I interferons in anticancer immunity. Nat Rev Immunol 2015; 15:405-14
35. Sokolowska O, Nowis D. STING Signaling in Cancer Cells: Important or Not? Arch Immunol Ther Exp (Warsz) 2018; 66:125-32
36. Martin-Fontecha A, Thomsen L L, Brett S, Gerard C, Lipp M, Lanzavecchia A, et al. Induced recruitment of NK cells to lymph nodes provides IFN-gamma for T(H)1 priming. Nat Immunol 2004; 5:1260-5
37. Reid-Yu S A, Small C L, Coombes B K. CD3(-)NK1.1 (+) cells aid in the early induction of a Th1 response to an attaching and effacing enteric pathogen. Eur J Immunol 2013; 43:2638-49
38. Kim S, Iizuka K, Aguila H L, Weissman I L, Yokoyama W M. In vivo natural killer cell activities revealed by natural killer cell-deficient mice. Proc Natl Acad Sci USA 2000; 97:2731-6
39. Xu H M. Th1 cytokine-based immunotherapy for cancer. Hepatobiliary Pancreat Dis Int 2014; 13:482-94
40. Wu Y, Tian Z, Wei H. Developmental and Functional Control of Natural Killer Cells by Cytokines. Front Immunol 2017; 8:930
41. Goldberg J L, Sondel P M. Enhancing Cancer Immunotherapy Via Activation of Innate Immunity. Semin Oncol 2015; 42:562-72
42. Boyerinas B, Jochems C, Fantini M, Heery C R, Gulley J L, Tsang K Y, et al. Antibody-Dependent Cellular Cytotoxicity Activity of a Novel Anti-PD-L1 Antibody Avelumab (MSB0010718C) on Human Tumor Cells. Cancer Immunol Res 2015; 3:1148-57
43. Piccioli D, Sbrana S, Melandri E, Valiante N M. Contact-dependent stimulation and inhibition of dendritic cells by natural killer cells. J Exp Med 2002; 195:335-41
44. Kim J R, Horton N C, Mathew S O, Mathew P A. CS1 (SLAMF7) inhibits production of proinflammatory cytokines by activated monocytes. Inflamm Res 2013; 62:765-72
45. Whiteside T L. Inhibiting the inhibitors: evaluating agents targeting cancer immunosuppression. Expert Opin Biol Ther 2010; 10:1019-35
46. van Vliet S J, den Dunnen J, Gringhuis S I, Geijtenbeek T B, van Kooyk Y. Innate signaling and regulation of Dendritic cell immunity. Curr Opin Immunol 2007; 19:435-40
47. Luo X, Yu Y, Liang A, Xie Y, Liu S, Guo J, et al. Intratumoral expression of MIP-1beta induces antitumor responses in a pre-established tumor model through chemoattracting T cells and NK cells. Cell Mol Immunol 2004; 1:199-204
48. Appledorn D M, Patial S, McBride A, Godbehere S, Van Rooijen N, Parameswaran N, et al. Adenovirus vector-induced innate inflammatory mediators, MAPK signaling, as well as adaptive immune responses are dependent upon both TLR2 and TLR9 in vivo. J Immunol 2008; 181: 2134-44
49. Aldhamen Y A, Seregin S S, Amalfitano A. Immune recognition of gene transfer vectors: focus on adenovirus as a paradigm. Front Immunol 2011; 2:40
50. Win S J, Ward V K, Dunbar P R, Young S L, Baird M A. Cross-presentation of epitopes on virus-like particles via the MHC I receptor recycling pathway. Immunol Cell Biol 2011; 89:681-8

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the present invention described herein. Such equivalents are intended to be encompassed by the following claims.

What we claim is:

1. A method for treating or preventing cancer in a subject in need thereof comprising administering to the subject an effective amount of at least one CRACC composition, said composition comprising a non-naturally occurring vector comprising a nucleic acid sequence encoding the amino acid sequence of at least one CD2-like receptor activating cytotoxic cell gene (CRACC) fusion, which has at least 65% sequence identity to the amino acid sequence set forth in Table 5, to thereby treat or prevent cancer in the subject.

2. The method of claim 1, wherein the immune response is induced or enhanced, or stimulated in the mammal.

3. The method of claim 1, further comprising administering one or more additional compositions or therapies that upregulates an immune response or treats the condition selected from the group consisting of anti-viral therapy, immunotherapy, chemotherapy, radiation, and surgery.

4. The method of claim 1, wherein the at least one CRACC fusion has at least two, three, four, five, six, seven, eight, nine, ten, or more mutations, wherein the at least one mutation is a non-naturally occurring mutation.

5. The method of claim 1, wherein the non-naturally occurring vector is selected from the group consisting of adenovirus, adeno-associated virus (AAV), retrovirus, and lentivirus.

6. The method of claim 5, wherein the adenovirus is human adenovirus serotype 5.

7. The method of claim 6, wherein the adenovirus has at least one mutation or deletion in at least one adenoviral gene.

8. The method of claim 7, wherein the adenoviral gene is selected from the group consisting of E1A, E1B, E2A, E2B, E3, E4, L1, L2, L3, L4, and L5.

9. The method of claim 7, wherein the adenovirus has a deletion of at least on adenoviral gene selected from the group consisting of E1A, E1B, and E3, or any combination thereof.

10. The method of claim 1, wherein the at least one CRACC fusion is operatively linked to a transcriptional and translational regulatory sequences.

11. The method of claim 1, wherein the at least one CRACC fusion has at least 70%, 75%, 80%, 85%, 90%, or 95% sequence identity to the amino acid or nucleotide sequences set forth in Tables 1-6.

12. The method of claim 1, wherein the CRACC fusion is set forth in SEQ ID NO: 10.

13. The method of claim 1, wherein the CRACC fusion is set forth in SEQ ID NO: 11.

14. The method of claim 1, wherein the cancer is selected from the group consisting of acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hypopharyngeal cancer, intraocular melanoma, islet cell tumors (endocrine pancreas), Kaposi sarcoma, Langerhans cell histiocytosis, laryngeal cancer, leukemia, lung cancer, non-small cell lung cancer, small cell lung cancer, Hodgkin lymphoma, lymphoma, medulloblastoma, medulloepithelioma, melanoma, mesothelioma, mouth cancer, multiple myeloma, nasopharyngeal cancer, neuroblastoma, non-Hodgkin lymphoma, oral cancer, oropharyngeal cancer, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm, pleuropulmonary blastoma, primary central nervous system lymphoma, prostate cancer, rectal cancer, renal cell (kidney) cancer, rhabdomyosarcoma, salivary gland cancer, sarcoma, Ewing sarcoma family of tumors, sarcoma, Sezary syndrome, skin cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

15. The method of claim 1, wherein the at least one CRACC composition increases or stimulates the secretion of cytokines and chemokines.

16. The method of claim 1, wherein the at least one CRACC composition increases or stimulates an immune response selected from the group consisting of DC maturation, NK cell response, T-cell response, and B-cell response, or combination thereof.

17. The method of claim 1, wherein the effective amount is from about $1 \times 10^6$ vp to about $5 \times 10^{11}$ vp.

18. A method for treating or preventing a pathogenic infection in a subject in need thereof comprising administering to the subject an effective amount of at least one CRACC composition, said composition comprising a non-naturally occurring vector comprising
 a nucleic acid sequence encoding the amino acid sequence of at least one CRACC fusion, which has at least 65% sequence identity to the amino acid sequence set forth in Table 5,
 to thereby treat or prevent a pathogenic infection in the subject.

19. A method of treating a subject having a condition that would benefit from upregulation of an immune response comprising administering to the subject an effective amount of at least one CRACC composition, said composition comprising a non-naturally occurring vector comprising
 a nucleic acid sequence encoding the amino acid sequence of at least one CRACC fusion, which has at least 65% sequence identity to the amino acid sequence set forth in Table 5,
 to thereby modulate a CRACC-dependent pathway such that the condition that would benefit from upregulation of an immune response is treated.

20. The method of claim 19, wherein the condition that would benefit from upregulation of an immune response is selected from the group consisting septic shock, obesity-related inflammation, Parkinson's Disease, Crohn's Disease, Alzheimer's Disease (AD), cardiovascular disease (CVD), inflammatory bowel disease (IBD), chronic obstructive pulmonary disease, an allergic reaction, an autoimmune disease, blood inflammation, joint inflammation, arthritis, asthma, ulcerative colitis, hepatitis, psoriasis, atopic dermatitis, pemphigus, glomerulonephritis, atherosclerosis, sarcoidosis, rheumatoid arthritis, psoriatic arthritis, ankylosing spondylitis, Wegner's syndrome, Goodpasture's syndrome, giant cell arteritis, polyarteritis nodosa, idiopathic pulmonary fibrosis, acute lung injury, post-influenza pneumonia, SARS, tuberculosis, malaria, sepsis, cerebral malaria, Chagas disease, schistosomiasis, bacteria and viral meningitis, cystic fibrosis, multiple sclerosis, encephalomyelitis, sickle cell anemia, pancreatitis, transplantation, systemic lupus erythematosis, autoimmune diabetes, thyroiditis, and radiation pneumonitis, respiratory inflammation, and pulmonary inflammation.

* * * * *

SEQUENCE LISTING

```
<160> NUMBER OF SEQ ID NOS: 61

<210> SEQ ID NO 1
<211> LENGTH: 335
<212> TYPE: PRT
<213> ORGANISM: Homo sapiens

<400> SEQUENCE: 1

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
```

```
                20                  25                  30
Val Gly Gly Ala Val Thr Phe Pro Leu Lys Ser Lys Val Lys Gln Val
            35                  40                  45

Asp Ser Ile Val Trp Thr Phe Asn Thr Thr Pro Leu Val Thr Ile Gln
50                  55                  60

Pro Glu Gly Gly Thr Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
                100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
            130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
                180                 185                 190

Phe Ile Cys Val Ala Arg Asn Pro Val Ser Arg Asn Phe Ser Ser Pro
            195                 200                 205

Ile Leu Ala Arg Lys Leu Cys Glu Gly Ala Ala Asp Asp Pro Asp Ser
            210                 215                 220

Ser Met Val Leu Leu Cys Leu Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
            275                 280                 285

His Thr Asn Arg Thr Ile Leu Lys Glu Asp Pro Ala Asn Thr Val Tyr
            290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 2
<211> LENGTH: 261
<212> TYPE: PRT
<213> ORGANISM: Homo sapiens

<400> SEQUENCE: 2

Ser Gly Pro Val Lys Glu Leu Val Gly Ser Val Gly Gly Ala Val Thr
1               5                   10                  15

Phe Pro Leu Lys Ser Lys Val Lys Gln Val Asp Ser Ile Val Trp Thr
                20                  25                  30

Phe Asn Thr Thr Pro Leu Val Thr Ile Gln Pro Glu Gly Gly Thr Ile
            35                  40                  45

Ile Val Thr Gln Asn Arg Asn Arg Glu Arg Val Asp Phe Pro Asp Gly
            50                  55                  60
```

```
Gly Tyr Ser Leu Lys Leu Ser Lys Leu Lys Lys Asn Asp Ser Gly Ile
 65                  70                  75                  80

Tyr Tyr Val Gly Ile Tyr Ser Ser Ser Leu Gln Gln Pro Ser Thr Gln
                 85                  90                  95

Glu Tyr Val Leu His Val Tyr Glu His Leu Ser Lys Pro Lys Val Thr
            100                 105                 110

Met Gly Leu Gln Ser Asn Lys Asn Gly Thr Cys Val Thr Asn Leu Thr
        115                 120                 125

Cys Cys Met Glu His Gly Glu Asp Val Ile Tyr Thr Trp Lys Ala
    130                 135                 140

Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
                165                 170                 175

Asn Pro Val Ser Arg Asn Phe Ser Ser Pro Ile Leu Ala Arg Lys Leu
            180                 185                 190

Cys Glu Gly Ala Ala Asp Asp Pro Asp Ser Ser Met Ala Ala Asn Glu
        195                 200                 205

Ser His Asn Gly Ser Ile Leu Pro Ile Ser Trp Arg Trp Gly Glu Ser
    210                 215                 220

Asp Met Thr Phe Ile Cys Val Ala Arg Asn Pro Val Ser Arg Asn Phe
225                 230                 235                 240

Ser Ser Pro Ile Leu Ala Arg Lys Leu Cys Glu Gly Ala Ala Asp Asp
                245                 250                 255

Pro Asp Ser Ser Met
            260

<210> SEQ ID NO 3
<211> LENGTH: 335
<212> TYPE: PRT
<213> ORGANISM: Rhesus macaque

<400> SEQUENCE: 3

Met Ala Gly Ser Pro Thr Cys Phe Thr Phe Ile Tyr Ile Leu Trp Gln
  1               5                  10                  15

Leu Thr Gly Ser Thr Ala Ser Gly Ser Val Lys Glu Leu Val Gly Ser
                 20                  25                  30

Ile Gly Gly Ala Val Thr Phe Pro Leu Lys Ser Glu Val Lys Gln Val
             35                  40                  45

Asp Ser Ile Val Trp Thr Phe Asn Thr Thr Leu Val Thr Ile Gln
 50                  55                  60

Pro Glu Gly Gly Pro Met Ile Val Thr Gln Asn Arg Asn Lys Glu Arg
 65                  70                  75                  80

Val His Phe Pro Asp Gly Gly Tyr Ser Leu Lys Leu Ser Lys Leu Lys
                 85                  90                  95

Lys Asn Asp Ser Gly Ile Tyr Asn Val Glu Ile Tyr Ser Ser Ser Leu
            100                 105                 110

Gln Asp Pro Phe Thr Arg Lys Tyr Val Leu Arg Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys His Met Glu His Gly Glu Glu Asp Val
145                 150                 155                 160

Ile Tyr Thr Trp Lys Ala Leu Gly Gln Ala Val Asn Glu Ser His Asn
                165                 170                 175
```

Gly Ser Ile Leu Pro Ile Ser Trp Arg Trp Gly Glu Ser Asp Met Thr
            180                 185                 190

Phe Ile Cys Thr Val Arg Asn Pro Val Ser Ser Asn Ser Ser Ser Pro
        195                 200                 205

Ile Leu Ala Arg Lys Leu Cys Glu Gly Ala Ala Asp Asp Ser Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Thr Gln Glu
                245                 250                 255

Glu Ser Ile Glu Glu Lys Lys Arg Ala Asp Ile Cys Arg Glu Thr Pro
            260                 265                 270

Asn Ile Cys Pro Tyr Ser Gly Glu Asn Thr Glu Tyr Asp Thr Ile Pro
        275                 280                 285

Tyr Thr Asn Arg Thr Ile Pro Met Glu Asp Ala Ala Asn Thr Leu Tyr
    290                 295                 300

Ser Thr Val Glu Ile Pro Lys Lys Ile Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 4
<211> LENGTH: 335
<212> TYPE: PRT
<213> ORGANISM: Pan troglodytes

<400> SEQUENCE: 4

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Arg Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Lys Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Lys Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Ser Asn Phe Ser Ser Pro
        195                 200                 205

Ile Leu Ala Arg Lys Leu Cys Glu Gly Ala Ala Asp Asp Pro Asp Ser

```
              210                 215                 220
Ser Met Val Leu Leu Cys Leu Leu Val Pro Leu Leu Ser Leu
225                 230                 235                 240

Phe Val Leu Gly Leu Phe Leu Trp Phe Leu Lys Arg Glu Gln Glu
                245                 250                 255

Glu Ser Ile Glu Glu Lys Lys Arg Ala Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 5
<211> LENGTH: 333
<212> TYPE: PRT
<213> ORGANISM: Mus musculus

<400> SEQUENCE: 5

Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
        35                  40                  45

Asp Tyr Val Val Trp Thr Phe Asn Thr Phe Phe Leu Ala Met Val Lys
    50                  55                  60

Lys Asp Gly Val Thr Ser Gln Ser Ser Asn Lys Glu Arg Ile Val Phe
65                  70                  75                  80

Pro Asp Gly Leu Tyr Ser Met Lys Leu Ser Gln Leu Lys Lys Asn Asp
                85                  90                  95

Ser Gly Ala Tyr Arg Ala Glu Ile Tyr Ser Thr Ser Ser Gln Ala Ser
            100                 105                 110

Leu Ile Gln Glu Tyr Val Leu His Val Tyr Lys His Leu Ser Arg Pro
        115                 120                 125

Lys Val Thr Ile Asp Arg Gln Ser Asn Lys Asn Gly Thr Cys Val Ile
    130                 135                 140

Asn Leu Thr Cys Ser Thr Asp Gln Asp Gly Glu Asn Val Thr Tyr Ser
145                 150                 155                 160

Trp Lys Ala Val Gly Gln Gly Asp Asn Gln Phe His Asp Gly Ala Thr
                165                 170                 175

Leu Ser Ile Ala Trp Arg Ser Gly Glu Lys Asp Gln Ala Leu Thr Cys
            180                 185                 190

Met Ala Arg Asn Pro Val Ser Asn Ser Phe Ser Thr Pro Val Phe Pro
        195                 200                 205

Gln Lys Leu Cys Glu Asp Ala Ala Thr Asp Leu Thr Ser Leu Arg Gly
    210                 215                 220

Ile Leu Tyr Ile Leu Cys Phe Ser Ala Val Leu Ile Leu Phe Ala Val
225                 230                 235                 240

Leu Leu Thr Ile Phe His Thr Thr Trp Ile Lys Lys Gly Lys Gly Cys
                245                 250                 255
```

Glu Glu Asp Lys Lys Arg Val Asp Arg His Gln Glu Met Pro Asp Leu
            260                 265                 270

Cys Pro His Leu Glu Glu Asn Ala Asp Tyr Asp Thr Ile Pro Tyr Thr
        275                 280                 285

Glu Lys Arg Arg Pro Glu Glu Asp Ala Pro Asn Thr Phe Tyr Ser Thr
    290                 295                 300

Val Gln Ile Pro Lys Val Val Lys Ser Pro Ser Leu Pro Ala Lys
305                 310                 315                 320

Pro Leu Val Pro Arg Ser Leu Ser Phe Glu Asn Val Ile
                325                 330

<210> SEQ ID NO 6
<211> LENGTH: 202
<212> TYPE: PRT
<213> ORGANISM: Mus musculus

<400> SEQUENCE: 6

Ser Gly Thr Leu Lys Lys Val Ala Gly Ala Leu Asp Gly Ser Val Thr
1               5                   10                  15

Phe Thr Leu Asn Ile Thr Glu Ile Lys Val Asp Tyr Val Val Trp Thr
            20                  25                  30

Phe Asn Thr Phe Phe Leu Ala Met Val Lys Lys Asp Gly Val Thr Ser
        35                  40                  45

Gln Ser Ser Asn Lys Glu Arg Ile Val Phe Pro Asp Gly Leu Tyr Ser
    50                  55                  60

Met Lys Leu Ser Gln Leu Lys Lys Asn Asp Ser Gly Ala Tyr Arg Ala
65                  70                  75                  80

Glu Ile Tyr Ser Thr Ser Ser Gln Ala Ser Leu Ile Gln Glu Tyr Val
                85                  90                  95

Leu His Val Tyr Lys His Leu Ser Arg Pro Lys Val Thr Ile Asp Arg
            100                 105                 110

Gln Ser Asn Lys Asn Gly Thr Cys Val Ile Asn Leu Thr Cys Ser Thr
        115                 120                 125

Asp Gln Asp Gly Glu Asn Val Thr Tyr Ser Trp Lys Ala Val Gly Gln
    130                 135                 140

Gly Asp Asn Gln Phe His Asp Gly Ala Thr Leu Ser Ile Ala Trp Arg
145                 150                 155                 160

Ser Gly Glu Lys Asp Gln Ala Leu Thr Cys Met Ala Arg Asn Pro Val
                165                 170                 175

Ser Asn Ser Phe Ser Thr Pro Val Phe Pro Gln Lys Leu Cys Glu Asp
            180                 185                 190

Ala Ala Thr Asp Leu Thr Ser Leu Arg Gly
        195                 200

<210> SEQ ID NO 7
<211> LENGTH: 339
<212> TYPE: PRT
<213> ORGANISM: Canis lupus familiaris

<400> SEQUENCE: 7

Met Leu Val Pro Pro Ala His Phe Thr Ile Phe Phe Leu Leu Phe Gln
1               5                   10                  15

Leu Thr Gly Pro Val Thr Ser Gly Ala Leu Lys Glu Leu Val Gly Asp
            20                  25                  30

Leu Gly Gly Ser Val Thr Phe Pro Leu Thr Leu Pro Gly Ile Gln Ile
        35                  40                  45

```
Asp Ser Ile Val Trp Thr Phe Asn Thr Thr Pro Leu Ile Thr Ile Gln
    50                  55                  60

Pro Arg Thr Pro Asp Arg Gln Ala Asn Val Ile Val Thr His Ser His
65                  70                  75                  80

Asn Lys Lys Arg Val Asp Phe Leu His Gly Asn Tyr Ser Leu Lys Leu
                85                  90                  95

Ser Lys Leu Asn Lys Ser Asp Ser Gly Asp Tyr Tyr Val Val Ile Tyr
            100                 105                 110

Ser Ser Ser Phe Lys Glu Pro Phe Ser Gln Arg Tyr Gly Leu Arg Val
        115                 120                 125

Tyr Glu His Leu Ser Lys Pro Lys Val Thr Met Gly Leu Gln Asn Lys
    130                 135                 140

Glu Asn Gly Thr Cys Val Thr Asn Leu Thr Cys Phe Val Asp Gln Gly
145                 150                 155                 160

Gly Glu Asp Val Thr Tyr Ser Trp Glu Ser Leu Gly Gln Ala Ala Asn
                165                 170                 175

Lys Ser Tyr Asn Gly Ser Ile Leu Pro Ile Ser Trp Arg Leu Gly Lys
            180                 185                 190

Gly Gly Met Thr Phe Ile Cys Val Ala Arg Asn Pro Ile Ser Ser Asn
        195                 200                 205

Ser Ser Asn Pro Val Phe Ala Trp Lys Leu Cys Glu Gly Ala Ala Asp
    210                 215                 220

Asp Ser Glu Ser Ser Val Val Leu Tyr Phe Leu Gly Ala Leu Leu Phe
225                 230                 235                 240

Met Leu Thr Ala Phe Thr Leu Val Pro Phe Ile Leu Phe Met Arg Arg
                245                 250                 255

Glu Arg Arg Lys Glu Ser Ile Glu Glu Lys Lys Gly Met Asp Thr His
            260                 265                 270

Gln Glu Ile Leu Asn Tyr Tyr Pro Pro Ser Gly Glu Thr Pro Val Tyr
        275                 280                 285

Asp Thr Ile Ser Cys Val Asn Asn Cys Ile Pro Glu Glu Asn Ser Ala
    290                 295                 300

Asn Thr Leu Tyr Phe Ser Val Gln Ile Pro Pro Lys Met Glu Lys Pro
305                 310                 315                 320

His Ser Pro Pro Thr Ser Pro Asp Thr Pro Lys Ser Phe Ala Tyr Glu
                325                 330                 335

Asn Val Ile

<210> SEQ ID NO 8
<211> LENGTH: 336
<212> TYPE: PRT
<213> ORGANISM: Bos taurus

<400> SEQUENCE: 8

Met Leu Gly Ala Pro Ala Cys Phe Ile Phe Leu Leu Cys Gln Leu Thr
1               5                   10                  15

Gly Pro Ala Ala Ser Gly Ile Pro Lys Lys Leu Val Gly Ala Ile Gly
                20                  25                  30

Gly Ser Val Ile Phe Pro Leu Asn Leu Ser Val Asn Leu Val Asp Ser
            35                  40                  45

Ile Ile Trp Val Phe Asn Ser Thr Leu Val Thr Ile Gln Pro Lys
    50                  55                  60

Thr Ala Gly Lys Lys Ala Leu Val Ile Val Thr Gln Lys Arg Asn Leu
65                  70                  75                  80
```

-continued

Glu Arg Val Asn Phe Pro His Glu Gly Tyr Ser Leu Lys Leu Ser Arg
                85                  90                  95

Leu Lys Lys Asn Asp Ser Gly Ile Tyr Arg Val Glu Ile His Ser Ser
            100                 105                 110

Thr Leu Gln Asp Pro Leu Thr Gln Glu Tyr Glu Leu His Val Tyr Glu
        115                 120                 125

Tyr Leu Ser Lys Pro Lys Val Val Ile Gly Leu Gln Glu Asn Lys Asn
    130                 135                 140

Gly Thr Cys Val Thr Asn Leu Thr Cys Ser Met Glu His Gly Glu Glu
145                 150                 155                 160

Asp Val Thr Tyr Ser Trp Lys Ser Leu Asp Gln Thr Thr Asn Glu Ser
                165                 170                 175

His Arg Gly Ser Ile Leu Pro Ile Ser Trp Arg Trp Glu Lys Ser Asp
            180                 185                 190

Met Thr Phe Ile Cys Met Ala Ser Asn Pro Ile Ser Ser Asn Ser Ser
        195                 200                 205

Asn Pro Ile Phe Ala Gln Asn Leu Cys Glu Gly Ala Ala Gly Gly Gln
    210                 215                 220

Ala Pro Tyr Val Val Leu Tyr Val Leu Leu Ser Phe Phe Leu Leu Cys
225                 230                 235                 240

Ser Leu Ala Leu Val Leu Ile Ile Phe Ile Ile Gln Arg Glu Arg Lys
                245                 250                 255

Lys Glu Ile Ile Glu Glu Lys Lys Glu Leu Asp Thr His Gln Lys Thr
            260                 265                 270

Leu Pro Phe Pro Pro Ile Pro Glu Glu Met Pro Glu Tyr Asp Thr Ile
        275                 280                 285

Ser Thr Phe Asn Gly Thr Ile Pro Glu Glu Asn Pro Ala Asn Thr Ile
    290                 295                 300

Tyr Ser Thr Val His Ile Ala Pro Lys Val Thr Glu Pro Tyr Ser Leu
305                 310                 315                 320

Pro Met Leu Ser Asp Thr Pro Thr Ala Ser Ile Tyr Asn Asn Val Met
                325                 330                 335

<210> SEQ ID NO 9
<211> LENGTH: 342
<212> TYPE: PRT
<213> ORGANISM: Rattus norvegicus

<400> SEQUENCE: 9

Met Ala Arg Phe Ser Thr His Ile Ile Phe Thr Ser Val Leu Cys Gln
1               5                   10                  15

Leu Thr Val Thr Ala Ala Ser Gly Thr Pro Lys Glu Val Ala Gly Ala
            20                  25                  30

Leu Asp Gly Ser Val Thr Phe Thr Leu Asn Thr Thr Glu Val Lys Val
        35                  40                  45

Asp Ser Val Val Trp Thr Phe Lys Thr Leu Phe Leu Ala Ile Ile Asn
    50                  55                  60

Lys Asn Gly Thr Ile Lys Ser Gln Ser Tyr Glu Glu Arg Ile Val Phe
65                  70                  75                  80

Leu Asp Arg His Ser Met Lys Leu Ser Gln Leu Lys Lys Asn Asp Ser
                85                  90                  95

Gly Asp Tyr Arg Ala Glu Ile His Ile Ala Ser Asn Ser Leu Ser Ser
            100                 105                 110

Pro Phe Met Gln Glu Tyr Val Leu His Val His Glu His Leu Ser Arg
        115                 120                 125

```
Pro Lys Val Asn Thr Asp Ser Gln Ser Lys Asp Gly Thr Cys Ile
    130                 135                 140
Leu Asn Leu Thr Cys Ser Val Glu Arg Gly Gly Glu Asn Val Thr Tyr
145                 150                 155                 160
Ser Trp Lys Ala Val Gly Gln Thr Val Asp Glu Phe His Asp Ser Ala
                165                 170                 175
Asn Leu Ser Ile Ser Trp Arg Leu Gly Glu Lys Asp Lys Thr Ile Ile
            180                 185                 190
Cys Thr Ala Arg Asn Pro Val Ser Ser Ser Ser Thr Pro Leu Leu
        195                 200                 205
Ala Gln Lys Leu Cys Lys Asp Ala Ala Lys Asp Leu Asn Ser Pro Arg
210                 215                 220
Val Leu Lys Tyr Ile Leu Cys Val Thr Leu Val Leu Val Leu Phe Cys
225                 230                 235                 240
Ile Leu Leu Val Thr Ile Leu Phe Arg Trp Ile Pro Lys Gly Lys Gly
                245                 250                 255
Phe Glu Glu Asp Lys Lys Arg Val Asp Gly His Gln Glu Met Ser Asn
                260                 265                 270
Ser Cys Pro His Leu Glu Asn Thr Asp Tyr Asp Thr Ile Pro Tyr Thr
            275                 280                 285
Glu Lys Thr Arg Pro Glu Glu Asp Ala Pro Asn Thr Leu Tyr Ser Thr
290                 295                 300
Val Gln Ile Pro Lys Val Asp Ala Gly Ser Lys Ser Phe Gly Ala Tyr
305                 310                 315                 320
Met Met Ile Pro His Ser Arg Met Pro Asp Thr Glu Leu Gln Gly Leu
                325                 330                 335
Arg Leu Ser Ala Arg Phe
            340

<210> SEQ ID NO 10
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Gly Pro Val Lys Glu Leu Val Gly Ser Val Gly Gly Ala Val Thr
1               5                   10                  15
Phe Pro Leu Lys Ser Lys Val Lys Gln Val Asp Ser Ile Val Trp Thr
                20                  25                  30
Phe Asn Thr Thr Pro Leu Val Thr Ile Gln Pro Glu Gly Gly Thr Ile
            35                  40                  45
Ile Val Thr Gln Asn Arg Asn Arg Glu Arg Val Asp Phe Pro Asp Gly
        50                  55                  60
Gly Tyr Ser Leu Lys Leu Ser Lys Leu Lys Asn Asp Ser Gly Ile
65                  70                  75                  80
Tyr Tyr Val Gly Ile Tyr Ser Ser Leu Gln Gln Pro Ser Thr Gln
                85                  90                  95
Glu Tyr Val Leu His Val Tyr Glu His Leu Ser Lys Pro Lys Val Thr
                100                 105                 110
Met Gly Leu Gln Ser Asn Lys Asn Gly Thr Cys Val Thr Asn Leu Thr
            115                 120                 125
Cys Cys Met Glu His Gly Glu Glu Asp Val Ile Tyr Thr Trp Lys Ala
```

```
        130                 135                 140
Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
                165                 170                 175

Asn Pro Val Ser Arg Asn Phe Ser Pro Ile Leu Ala Arg Lys Leu
            180                 185                 190

Cys Glu Gly Ala Ala Asp Asp Pro Asp Ser Ser Met Glu Ser Lys Tyr
                195                 200                 205

Gly Pro Pro Cys Pro Pro Cys Pro Ala Pro Glu Phe Glu Gly Gly Pro
            210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser Gln Glu Asp
                245                 250                 255

Pro Glu Val Gln Phe Asn Trp Tyr Val Asp Gly Val Glu Val His Asn
            260                 265                 270

Ala Lys Thr Lys Pro Arg Glu Glu Gln Phe Asn Ser Thr Tyr Arg Val
            275                 280                 285

Val Ser Val Leu Thr Val Leu His Gln Asp Trp Leu Asn Gly Lys Glu
            290                 295                 300

Tyr Lys Cys Lys Val Ser Asn Lys Gly Leu Pro Ser Ser Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Gln Glu Glu Met Thr Lys Asn Gln Val Ser Leu Thr
            340                 345                 350

Cys Leu Val Lys Gly Phe Tyr Pro Ser Asp Ile Ala Val Glu Trp Glu
            355                 360                 365

Ser Asn Gly Gln Pro Glu Asn Asn Tyr Lys Thr Thr Pro Pro Val Leu
            370                 375                 380

Asp Ser Asp Gly Ser Phe Phe Leu Tyr Ser Arg Leu Thr Val Asp Lys
385                 390                 395                 400

Ser Arg Trp Gln Glu Gly Asn Val Phe Ser Pro Ser Val Met His Glu
                405                 410                 415

Ala Leu His Asn His Tyr Thr Gln Lys Ser Leu Ser Leu Ser Leu Gly
            420                 425                 430

Lys

<210> SEQ ID NO 11
<211> LENGTH: 424
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Gly Thr Leu Lys Lys Val Ala Gly Ala Leu Asp Gly Ser Val Thr
1               5                   10                  15

Phe Thr Leu Asn Ile Thr Glu Ile Lys Val Asp Tyr Val Val Trp Thr
                20                  25                  30

Phe Asn Thr Phe Phe Leu Ala Met Val Lys Lys Asp Gly Val Thr Ser
            35                  40                  45

Gln Ser Ser Asn Lys Glu Arg Ile Val Phe Pro Asp Gly Leu Tyr Ser
```

```
            50                  55                  60
Met Lys Leu Ser Gln Leu Lys Asn Asp Ser Gly Ala Tyr Arg Ala
 65                  70                  75                  80

Glu Ile Tyr Ser Thr Ser Ser Gln Ala Ser Leu Ile Gln Glu Tyr Val
                 85                  90                  95

Leu His Val Tyr Lys His Leu Ser Arg Pro Lys Val Thr Ile Asp Arg
            100                 105                 110

Gln Ser Asn Lys Asn Gly Thr Cys Val Ile Asn Leu Thr Cys Ser Thr
            115                 120                 125

Asp Gln Asp Gly Glu Asn Val Thr Tyr Ser Trp Lys Ala Val Gly Gln
130                 135                 140

Gly Asp Asn Gln Phe His Asp Gly Ala Thr Leu Ser Ile Ala Trp Arg
145                 150                 155                 160

Ser Gly Glu Lys Asp Gln Ala Leu Thr Cys Met Ala Arg Asn Pro Val
                165                 170                 175

Ser Asn Ser Phe Ser Thr Pro Val Phe Pro Gln Lys Leu Cys Glu Asp
                180                 185                 190

Ala Ala Thr Asp Leu Thr Ser Leu Arg Gly Gly Cys Lys Pro Cys Ile
                195                 200                 205

Cys Thr Val Pro Glu Val Ser Ser Val Phe Ile Phe Pro Pro Lys Pro
210                 215                 220

Lys Asp Val Leu Thr Ile Thr Leu Thr Pro Lys Val Thr Cys Val Val
225                 230                 235                 240

Val Asp Ile Ser Lys Asp Asp Pro Glu Val Gln Phe Ser Trp Phe Val
                245                 250                 255

Asp Asp Val Glu Val His Thr Ala Gln Thr Gln Pro Arg Glu Glu Gln
                260                 265                 270

Phe Asn Ser Thr Phe Arg Ser Val Ser Glu Leu Pro Ile Met His Gln
                275                 280                 285

Asp Trp Leu Asn Gly Lys Glu Phe Lys Cys Arg Val Asn Ser Ala Ala
290                 295                 300

Phe Pro Ala Pro Ile Glu Lys Thr Ile Ser Lys Thr Lys Gly Arg Pro
305                 310                 315                 320

Lys Ala Pro Gln Val Tyr Thr Ile Pro Pro Lys Glu Gln Met Ala
                325                 330                 335

Lys Asp Lys Val Ser Leu Thr Cys Met Ile Thr Asp Phe Phe Pro Glu
                340                 345                 350

Asp Ile Thr Val Glu Trp Gln Trp Asn Gly Gln Pro Ala Glu Asn Tyr
                355                 360                 365

Lys Asn Thr Gln Pro Ile Met Asp Thr Asp Gly Ser Tyr Phe Val Tyr
            370                 375                 380

Ser Lys Leu Asn Val Gln Lys Ser Asn Trp Glu Ala Gly Asn Thr Phe
385                 390                 395                 400

Thr Cys Ser Val Leu His Glu Gly Leu His Asn His His Thr Glu Lys
                405                 410                 415

Ser Leu Ser His Ser Pro Gly Lys
                420
```

<210> SEQ ID NO 12
<211> LENGTH: 1008
<212> TYPE: DNA
<213> ORGANISM: Homo sapiens

<400> SEQUENCE: 12

```
atggctggtt ccccaacatg cctcaccctc atctatatcc tttggcagct cacagggtca    60
gcagcctctg gacccgtgaa agagctggtc ggttccgttg gtggggccgt gactttcccc   120
ctgaagtcca agtaaagca agttgactct attgtctgga ccttcaacac aaccctctt    180
gtcaccatac agccagaagg gggcactatc atagtgaccc aaaatcgtaa tagggagaga   240
gtagacttcc cagatggagg ctactccctg aagctcagca aactgaagaa gaatgactca   300
gggatctact atgtggggat atacagctca tcactccagc agccctccac ccaggagtac   360
gtgctgcatg tctacgagca cctgtcaaag cctaaagtca ccatgggtct gcagagcaat   420
aagaatggca cctgtgtgac caatctgaca tgctgcatgg aacatgggga agaggatgtg   480
atttatacct ggaaggccct ggggcaagca gccaatgagt cccataatgg gtccatcctc   540
cccatctcct ggagatgggg agaaagtgat atgaccttca tctgcgttgc caggaaccct   600
gtcagcagaa acttctcaag ccccatcctt gccaggaagc tctgtgaagg tgctgctgat   660
gacccagatt cctccatggt cctcctgtgt ctcctgttgg tgccctcct gctcagtctc   720
tttgtactgg ggctatttct ttggtttctg aagagagaga gacaagaaga gtacattgaa   780
gagaagaaga gagtggacat ttgtcgggaa actcctaaca tatgcccca ttctggagag   840
aacacagagt acgacacaat ccctcacact aatagaacaa tcctaaagga agatccagca   900
aatacggttt actccactgt ggaaataccg aaaaagatgg aaaatcccca ctcactgctc   960
acgatgccag acacaccaag gctatttgcc tatgagaatg ttatctag              1008
```

<210> SEQ ID NO 13
<211> LENGTH: 1008
<212> TYPE: DNA
<213> ORGANISM: Rhesus macaque

<400> SEQUENCE: 13

```
atggctggtt ccccaacatg cttcaccttc atctatatcc tttggcagct cacagggtca    60
acagcctctg gatccgtgaa agagctggtc ggttccattg gtggggctgt gactttcccc   120
ctgaagtctg aagtaaagca agttgactct attgtctgga ccttcaacac aaccactctt   180
gtcaccatac agccagaagg gggccctatg atagtgaccc aaaatcgtaa taaggagaga   240
gtacacttcc cagatggagg ctattccctg aagctcagca aactgaagaa gaatgactca   300
gggatctaca atgtggagat atacagctca tccctccagg atcccttcac ccggaagtat   360
gtgctgcgtg tctacgagca cctgtcaaag cctaaagtca ccatgggtct acagagtaat   420
aagaatggca cctgtgtgac caatctgaca tgccacatgg aacatgggga agaggatgtg   480
atttatacct ggaaggccct ggggcaagca gtcaatgagt cccataatgg gtccatccta   540
cccatctcct ggagatgggg agaaagtgat atgaccttca tctgcactgt caggaaccct   600
gtcagcagca actcctcaag ccccatcctt gccaggaagc tctgtgaagg tgctgctgat   660
gactcagatt cctccatggt cctcctgtgt ctcctgttgg tgccctcct gctcagtctc   720
tttgtactgg ggctatttct ttggtttctg aagagagaga cacaagaaga gtccattgaa   780
gagaagaaga gagcggacat ttgtcgggaa actcctaaca tatgccccta ttctggagag   840
aacacagagt atgacacaat cccttacact aatagaacta tcccaatgga agacgcagca   900
aatacacttt attccactgt ggaaatacca aaaaagattg aaaatcccca ctcactgctc   960
acgatgccag acacaccaag gctatttgcc tatgagaatg ttatctag              1008
```

<210> SEQ ID NO 14
<211> LENGTH: 1008

```
<212> TYPE: DNA
<213> ORGANISM: Pan troglodytes

<400> SEQUENCE: 14
atggctggtt ccccaacatg cctcaccctc atctatatcc tttggcagct cacagggtca    60
gcagcctctg gacctgtgag agagctggtc ggttccgttg gtggggccgt gactttcccc   120
ctgaagtcca agtaaagca  agttgactct attgtctgga ccttcaacac aaccctctt   180
gtcaccatac agccggaagg gggcactatc atagtgaccc aaaatcgtaa taaggagaga   240
gtagacttcc cagatggagg ctactccctg aagctcagca aactgaagaa gaatgactca   300
gggatctact atgtggggat atacagctca tcactccagc agccctccac ccagaagtac   360
gtgctgcatg tctacgagca cctgtcaaag cctaaagtca ccatgggtct gcagagcaat   420
aagaatggca cctgtgtgac caatctgaca tgctgcatgg aacatgggga agaggatgtg   480
atttatacct ggaaggccct ggggcaagca gccaacgagt cccataatgg gtccatcctc   540
cccatctcct ggagatgggg agaaagtgat atgaccttca tctgcgttgc caggaaccct   600
gtcagcagca acttctcaag ccccatcctt gccaggaagc tctgtgaagg tgctgctgat   660
gacccagatt cctccatggt cctcctgtgt ctcctgttgg tgcccctcct gctcagtctc   720
tttgtactgg ggctatttct ttggtttctg aagagagaga gacaagaaga gtccattgaa   780
gagaagaaga gagcagacat ttgtcgggaa actcctaaca tatgccccca ttctggagag   840
aacacagagt acgacacaat ccctcacact aatagaacaa tcctaaagga agatccagca   900
aatacagttt actccactgt ggaaatacca aaaaagatgg aaaatcccca ctcactgctc   960
acgatgccag acacaccaag gctatttgcc tatgagaatg ttatctag            1008

<210> SEQ ID NO 15
<211> LENGTH: 1008
<212> TYPE: DNA
<213> ORGANISM: Mus musculus

<400> SEQUENCE: 15
atggctcgtt tctcaacgta catcatcttt acctctgtcc tctgtcagct aacagtcaca    60
gcagcttctg gaactctgaa gaaggtggcc ggtgcccttg atggatctgt gacattcact   120
ctgaatatca ctgaaataaa ggttgactat gttgtatgga cgttcaacac attctttctt   180
gccatggtaa aaaagacgg  cgttacatca caaagtagta caaagaaag  gatagtcttt   240
ccagatggac tctactccat gaagctcagc caattgaaga agaatgactc tggagcctac   300
cgtgcagaga tttacagtac atcgagtcag gcttccttaa tccaggagta tgcgctgcat   360
gtctacaagc atttgtcaag gcccaaggtc accatagatc ggcaaagcaa caagaatggc   420
acctgcgtaa tcaatctgac atgttccacg gatcaggacg gggagaatgt aacctacagc   480
tggaaagctg tggggcaggg ggacaatcag tttcatgatg gtgccaccct ctccatcgcc   540
tggagatcag gagagaaaga ccaggcctta acatgcatgg ccaggaatcc agtcagcaac   600
agtttctcaa ccccgtctt  tccccagaag ctctgtgaag atgctgccac ggatctaact   660
tcactcaggg gcatcctata catcctgtgc ttctcagcag tgctcatcct atttgctgtc   720
ttgctgacta ttttcatac  tatgtggata aagaaaggaa aggatgtgaa ggaagacaag   780
aagagagtgg acaggcacca ggaaatgccc gacttgtgcc ctcacttaga ggagaacgca   840
gactatgaca caatccctta cacgaaaaaa agaagaccag aagaagatgc accaaacaca   900
ttttattcca ctgtgcagat ccccaaagtg gtaagaagct gtccagctga gcatcatctt   960
```
acttgccaac ccctttccct ggatcatgct cgggctcaga tttcttag      1008

<210> SEQ ID NO 16
<211> LENGTH: 1020
<212> TYPE: DNA
<213> ORGANISM: Canis lupus familiaris

<400> SEQUENCE: 16
atgcttgttc cccagcgca cttcaccatt ttctttctcc tcttccagct cacagggcca      60
gtaacctctg gagctctgaa ggagctagtt ggtgaccttg gtgggtctgt gactttccct     120
ctgacgctcc caggaattca gattgacagc attgtctgga ccttcaacac aaccccctc     180
atcaccatac aaccaagaac gccagacaga caagccaatg tcatagtgac ccacagtcat     240
aataagaaaa gggtggattt cctacatgga aactactccc tgaagctcag caaactgaat     300
aagagtgact cgggtgacta ctacgtggtg atatacagct cttccttcaa agagcccttc     360
agccagcggt atgggctgcg tgtctatgag cacctatcaa agcccaaggt taccatgggt     420
ctgcagaaca aagagaatgg cacctgtgtg actaatttga cctgcttcgt ggaccaggga     480
ggagaggatg tgacctacag ctgggagtcc ctggggcagg cagccaataa gtcctataat     540
ggctccatcc tccccatatc ctggaggctg gggaaagggg gcatgacctt catctgcgtg     600
gccaggaacc ccatcagcag caattcttca aatcctgtct ttgcctggaa gctctgtgaa     660
ggtgctgctg atgactccga atcctccgtg gtcctgtact tcctgggggc gttgctcttc     720
atgctcactg cctttaccct ggtgccattt attctgttta tgcggagaga aagaagaaaa     780
gagtccattg aagagaagaa gggaatggat actcatcagg aaattcttaa ctactatccc     840
ccttctggag agacccccagt gtatgacaca atcagttgtg ttaataactg tattccagaa     900
gaaaattctg caaatacact ttatttctct gtgcaaatac ccccaaagat ggagaaaccc     960
cactctcccc ccacatcacc agacacacca aagtcatttg cctatgagaa cgtcatctaa    1020

<210> SEQ ID NO 17
<211> LENGTH: 1011
<212> TYPE: DNA
<213> ORGANISM: Bos taurus

<400> SEQUENCE: 17
atgcttggtg cccagcatg cttcatcttt ctcctctgcc agctcacagg gccagcagcc      60
tctggaatcc caaagaagct ggttggtgcc attggtgggt ctgtgatttt ccctctgaat     120
ctctcagtaa atctagttga cagcattatc tgggtcttca attcaaccac tctcgttacc     180
atacagccaa aacagcagg caaaaaagcc cttgtcatag tgacccaaaa gcgtaacttg     240
gaaagagtga atttcccaca tgaaggctac tccctgaagc tcagcagact gaagaagaac     300
gactcaggta tctaccgtgt ggagatacac agctcaaccc tccaggatcc cctcacccag     360
gagtatgagc tgcatgtcta tgagtacctg tcaaagccca agtcgtcat aggtctgcag     420
gagaataaga atggcacctg tgtaaccaat ctcacatgtt ccatggaaca tggagaagag     480
gatgtaactt acagctggaa gtctctggac cagacaacca atgaatccca caggggctcc     540
attctcccca tatcctggag gtgggagaaa agtgacatga ccttcatctg catggccagt     600
aaccccatca gcagcaactc ctcaaaccct atctttgccc agaatctctg tgaaggtgct     660
gctgggggcc aggctcccta cgtggtcctc tacgtcctgt tgtcgttctt cctgctctgt     720
tccctcgcac tggtgttaat tattttttatc atacaaagag aaagaaaaaa agagatcatt     780
gaagagaaga aggaactgga cactcatcag aaaactcttc ccttccctcc cattcctgaa     840

```
gagatgcccg agtatgatac aatctctact tttaatggca ctattccaga ggaaaaccca    900
gccaatacca tctattccac tgtgcacata gccccaaagg taacagaacc ctactccctg    960
cccatgttgt cagatacacc aacggcatct atctataaca atgtcatgta a            1011
```

<210> SEQ ID NO 18
<211> LENGTH: 1029
<212> TYPE: DNA
<213> ORGANISM: Rattus norvegicus

<400> SEQUENCE: 18

```
atggctcgtt tctcgacaca catcatcttt acctctgtcc tctgccagct aacagtcaca     60
gcagcttctg gaacgccaaa ggaggtggcc ggtgcccttg atggatctgt gacattcact    120
ctgaatacta ctgaagtaaa agttgacagt gttgtatgga ccttcaagac actctttctt    180
gccataataa ataaaaatgg taccatcaaa tcacaaagtt atgaagaaag gatagtcttt    240
ttagatagac actccatgaa gctcagccag ctgaagaaga atgactctgg agactaccgt    300
gcagagattc acattgcgtc aaattcactt tcatctccct tcatgcagga gtacgtgctg    360
catgtccatg agcacctgtc aaggcccaag gtcaacacag attcgcaaag cagcaaggac    420
ggcacctgca tcttaaatct gacatgttcc gtggaacggg aggagagaa tgtgacatac     480 agctggaaag ctgtgggaca gacagtcgat gagtttcatg acagtgccaa cctctccatc    540
tcctggagac tgggagagaa agacaagacc ataatctgca cagccaggaa tccagtcagc    600
agcagttcct caaccccact cctcgcccag aagctctgta agatgctgc caaggaccta    660 aattcaccca gggtcctcaa atacattctg tgcgtcacac tagtgctcgt cctgttctgt    720
atcctgctgg tgactattct tttaggtgg ataccgaaag gaaaaggctt tgaggaagac    780
aagaagagag tggacggcca ccaggaaatg tccaactctt gccctcactt ggagaacaca    840
gactatgaca caatccctta cacagaaaaa acgagaccag aagaagatgc gccaaacaca    900
ctttattcca ctgtgcagat ccccaaagtg gatgcagggt ccaaatcctt tggagcttac    960
atgatgatac cacatagcag gatgccagat acggagcttc aaggcttacg tctctctgcc   1020
aggttctga                                                           1029
```

<210> SEQ ID NO 19
<211> LENGTH: 229
<212> TYPE: PRT
<213> ORGANISM: Homo sapiens

<400> SEQUENCE: 19

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110
```

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Pro Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 20
<211> LENGTH: 223
<212> TYPE: PRT
<213> ORGANISM: Mus musculus

<400> SEQUENCE: 20

Gly Gly Cys Lys Pro Cys Ile Cys Thr Val Pro Glu Val Ser Ser Val
1               5                   10                  15

Phe Ile Phe Pro Pro Lys Pro Lys Asp Val Leu Thr Ile Thr Leu Thr
            20                  25                  30

Pro Lys Val Thr Cys Val Val Val Asp Ile Ser Lys Asp Asp Pro Glu
        35                  40                  45

Val Gln Phe Ser Trp Phe Val Asp Asp Val Glu Val His Thr Ala Gln
    50                  55                  60

Thr Gln Pro Arg Glu Glu Gln Phe Asn Ser Thr Phe Arg Ser Val Ser
65                  70                  75                  80

Glu Leu Pro Ile Met His Gln Asp Trp Leu Asn Gly Lys Glu Phe Lys
                85                  90                  95

Cys Arg Val Asn Ser Ala Ala Phe Pro Ala Pro Ile Glu Lys Thr Ile
            100                 105                 110

Ser Lys Thr Lys Gly Arg Pro Lys Ala Pro Gln Val Tyr Thr Ile Pro
        115                 120                 125

Pro Pro Lys Glu Gln Met Ala Lys Asp Lys Val Ser Leu Thr Cys Met
    130                 135                 140

Ile Thr Asp Phe Phe Pro Glu Asp Ile Thr Val Glu Trp Gln Trp Asn
145                 150                 155                 160

Gly Gln Pro Ala Glu Asn Tyr Lys Asn Thr Gln Pro Ile Met Asp Thr
                165                 170                 175

Asp Gly Ser Tyr Phe Val Tyr Ser Lys Leu Asn Val Gln Lys Ser Asn
            180                 185                 190

Trp Glu Ala Gly Asn Thr Phe Thr Cys Ser Val Leu His Glu Gly Leu
        195                 200                 205

His Asn His His Thr Glu Lys Ser Leu Ser His Ser Pro Gly Lys
    210                 215                 220

<210> SEQ ID NO 21
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 21

Asp Tyr Lys Asp Asp Asp Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 22

His His His His His His
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Pro Tyr Asp Val Pro Asp Tyr Ala
1               5

<210> SEQ ID NO 24
<211> LENGTH: 612
<212> TYPE: DNA
<213> ORGANISM: Homo sapiens

<400> SEQUENCE: 24
tctggtcctg tgaaggaact ggtcggctcc gtgggaggag ctgtgacctt cccctgaag        60 agcaaggtga agcaggtgga ctccatcgtg tggaccttca acaccacacc actggtcacc      120
atccagcccg agggcggcac aatcatcgtg acccagaacc ggaatagggga gagagtggac    180 ttccctgatg gcggctactc cctgaagctg tctaagctga agaagaatga ttctggcatc     240
tactatgtgg gcatctatag ctcctctctg cagcagccca gcacacagga gtacgtgctg     300
cacgtgtatg agcacctgag caagcctaag gtcaccatgg gcctgcagtc caacaagaat     360
ggcacctgcg tgacaaacct gacctgctgc atggagcacg gcgaggagga cgtgatctac     420
acatggaagg ctctgggcca ggccgctaac gagagccaca atggctccat cctgcctatc     480
tcttggcggt ggggcgagag cgatatgacc ttcatctgcg tggcccggaa ccctgtgagc     540
aggaacttca gctccccaat cctggctaga aagctgtgcg agggagctgc tgacgatcca     600
gactctagca tg                                                         612

<210> SEQ ID NO 25
<211> LENGTH: 666
<212> TYPE: DNA
<213> ORGANISM: Mus musculus

<400> SEQUENCE: 25
gggtgtaaac catgcatctg tactgtcccc gaagtgtcaa gcgtcttcat ttttcccct      60 aagcccaaag acgtgctgac tatcaccctg acacctaagg tcacctgtgt ggtcgtggat    120
```

```
atttcaaaag acgatcctga ggtgcagttc agctggtttg tcgacgatgt cgaagtgcac      180
acagctcaga ctcagccaag ggaggaacag ttcaattcca cctttcgctc agtgagcgag      240
ctgcccatca tgcatcagga ctggctgaat ggcaaggagt tcaagtgcag agtgaactct      300
gcagcctttc cagcccccat cgagaagacc attagtaaga caaaagggag cccaaagct       360 cctcaggtgt acacaattcc accccctaag gaacagatgg caaaggataa agtgagcctg      420
acttgtatga tcaccgactt ctttcccgag gatattaccg tggaatggca gtggaacggg      480
cagcctgcag agaactataa gaatacacag ccaatcatgg acactgatgg aagctacttc      540
gtgtattcca agctgaacgt ccagaaaagc aattgggaag ccggcaacac ttttacctgc      600
tccgtgctgc acgaggggct gcacaaccac cataccgaga aaagtctgag tcattcacct      660
gggaag                                                                666
```

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Tyr Arg Met Gln Leu Leu Ser Cys Ile Ala Leu Ser Leu Ala Leu
1               5                   10                  15

Val Thr Asn Ser
            20

<210> SEQ ID NO 27
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
tctggtcctg tgaaggaact ggtcggctcc gtgggaggag ctgtgacctt cccctgaag       60 agcaaggtga gcaggtgga ctccatcgtg tggaccttca acaccacacc actggtcacc       120
atccagcccg agggcggcac aatcatcgtg acccagaacc ggaatagga gagagtggac      180 ttccctgatg gcggctactc cctgaagctg tctaagctga gaagaatga ttctggcatc      240 tactatgtgg gcatctatag ctcctctctg cagcagccca gcacacagga gtacgtgctg     300
cacgtgtatg agcacctgag caagcctaag gtcaccatgg gcctgcagtc caacaagaat     360
ggcacctgcg tgacaaacct gacctgctgc atggagcacg gcgaggagga cgtgatctac     420
acatggaagg ctctgggcca ggccgctaac gagagccaca atggctccat cctgcctatc     480
tcttggcggt ggggcgagag cgatatgacc ttcatctgcg tggcccggaa ccctgtgagc     540
aggaacttca gctccccaat cctggctaga aagctgtgcg agggagctgc tgacgatcca    600
gactctagca tg                                                         612
```

<210> SEQ ID NO 28
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gggtgtaaac catgcatctg tactgtcccc gaagtgtcaa gcgtcttcat ttttcccct      60
aagcccaaag acgtgctgac tatcaccctg acacctaagg tcacctgtgt ggtcgtggat    120
atttcaaaag acgatcctga ggtgcagttc agctggtttg tcgacgatgt cgaagtgcac    180
acagctcaga ctcagccaag ggaggaacag ttcaattcca cctttcgctc agtgagcgag    240
ctgcccatca tgcatcagga ctggctgaat ggcaaggagt tcaagtgcag agtgaactct    300
gcagcctttc cagcccccat cgagaagacc attagtaaga caaagggag gcccaaagct     360
cctcaggtgt acacaattcc accccctaag aacagatgg caaaggataa agtgagcctg     420
acttgtatga tcaccgactt ctttcccgag gatattaccg tggaatggca gtggaacggg    480
cagcctgcag agaactataa gaatacacag ccaatcatgg acactgatgg aagctacttc    540
gtgtattcca agctgaacgt ccagaaaagc aattgggaag ccggcaacac ttttacctgc    600
tccgtgctgc acgaggggct gcacaaccac cataccgaga aaagtctgag tcattcacct    660
gggaag                                                              666
```

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
attgcc                                                                6
```

<210> SEQ ID NO 30
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
tatggc                                                                6
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
gtgactttca tcccagttgc                                                20
```

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
ttccttgcag ccagattctg                                                20
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtgtccgtg actaactcca t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tggaaagggt aagaccgtcc t                                              21

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttgaagagga atacatgcgg aag                                            23

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggtctgcat tactggcact t                                              21

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccgagtggt gggtaagac                                                 19

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcaaaggcgc tgaacaaaga g                                              21

-continued

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggcacatgcg tgatcaatct                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atcgccaagc gatactcaga                                              20

<210> SEQ ID NO 41
<211> LENGTH: 223
<212> TYPE: PRT
<213> ORGANISM: Homo sapiens

<400> SEQUENCE: 41

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Pro Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 42
<211> LENGTH: 669
<212> TYPE: DNA

<213> ORGANISM: Homo sapiens

<400> SEQUENCE: 42

```
acatgcccac cgtgcccagc acctgaactc ctgggggac cgtcagtctt cctcttcccc    60
ccaaaaccca aggacaccct catgatctcc cggaccctg aggtcacatg cgtggtggtg   120
gacgtgagcc acgaagaccc tgaggtcaag ttcaactggt acgtggacgg cgtggaggtg   180
cataatgcca agacaaagcc gcgggaggag cagtacaaca gcacgtaccg tgtggtcagc   240
gtcctcaccg tcctgcacca ggactggctg aatggcaagg agtacaagtg caaggtctcc   300
aacaaagccc tcccagcccc catcgagaaa accatctcca aagccaaagg gcagccccga   360
gaaccacagg tgtacaccct gcccccatcc cgggatgagc tgaccaagaa ccaggtcagc   420
ctgacctgcc tggtcaaagg cttctatccc agcgacatcg ccgtggagtg ggagagcaat   480
gggcagccgg agaacaacta caagaccacg cctcccgtgc tggactccga cggcccttc    540
ttcctctaca gcaagctcac cgtggacaag agcaggtggc agcaggggaa cgtcttctca   600
tgctccgtga tgcatgaggc tctgcacaac cactacacgc agaagagcct ctccctgtct   660
ccgggtaaa                                                           669
```

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
tggaaagggt aagaccgtcc t                                              21
```

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
gccttgacac tcctggtaca aatgag                                         26
```

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
cagcacattg gcagaggaag acag                                           24
```

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
tgggtggaat gagactattg ttg                                            23
```

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctcccacgtc aatctttcct c                                              21

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tagtccttcc taccccaatt tcc                                            23

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttggtcctta gccactcctt c                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tggtttgcca tcgttttgct g                                              21

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acagaggttc actgtttct                                                 19

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccaagtgctg ccgtcatttt c                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggctcgcagg gatgatttca a                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggccttggaa gcatgtagag g                                              21

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggagaactcg ttagagacga ctt                                            23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctgcggcttc tattggggac                                                20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aaaaggcagt cgaaggtctc g                                              21

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agaacatcat ccctgcatcc                                                20

```
<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cacattgggg gtaggaacac                                                20

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gggtgtgaac catgagaagt atgac                                          25

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gccatccaca gtcttctggg t                                              21
```